(12) United States Patent
Hlubek et al.

(10) Patent No.: US 10,316,304 B2
(45) Date of Patent: Jun. 11, 2019

(54) CHIMERIC ENDONUCLEASES AND USES THEREOF

(75) Inventors: Andrea Hlubek, Quedlinburg (DE); Christian Biesgen, Quedlinburg (DE); Hans Wolfgang Höffken, Ludwigshafen (DE)

(73) Assignee: BASF PLANT SCIENCE COMPANY GMBH, Ludwigshafen (DE)

( * ) Notice: Subject to any disclaimer, the term of this patent is extended or adjusted under 35 U.S.C. 154(b) by 1139 days.

(21) Appl. No.: 13/512,202

(22) PCT Filed: Nov. 26, 2010

(86) PCT No.: PCT/IB2010/055452
§ 371 (c)(1),
(2), (4) Date: May 25, 2012

(87) PCT Pub. No.: WO2011/064750
PCT Pub. Date: Jun. 3, 2011

(65) Prior Publication Data
US 2012/0284877 A1    Nov. 8, 2012

Related U.S. Application Data

(60) Provisional application No. 61/264,715, filed on Nov. 27, 2009, provisional application No. 61/365,809, filed on Jul. 20, 2010.

(30) Foreign Application Priority Data

Nov. 27, 2009 (EP) .................................. 09177375
Jul. 20, 2010 (EP) .................................. 10170164

(51) Int. Cl.
| C12N 9/22 | (2006.01) |
| C12N 15/10 | (2006.01) |
| C07K 14/47 | (2006.01) |
| C12N 15/82 | (2006.01) |

(52) U.S. Cl.
CPC ............ *C12N 9/22* (2013.01); *C07K 14/4702* (2013.01); *C12N 15/102* (2013.01); *C12N 15/8213* (2013.01)

(58) Field of Classification Search
None
See application file for complete search history.

(56) References Cited

U.S. PATENT DOCUMENTS

| 7,008,780 B2 | 3/2006 | Pomerantz et al. |
| 7,951,925 B2 | 5/2011 | Ando et al. |
| 2010/0071083 A1 | 3/2010 | Smith et al. |

FOREIGN PATENT DOCUMENTS

| JP | 2009538141 A | 11/2009 |
| WO | WO-1996/20951 A1 | 7/1996 |
| WO | 98/36079 | * 8/1998 |
| WO | WO-2000/02996 A2 | 1/2000 |
| WO | WO-2001/038504 A2 | 5/2001 |
| WO | WO-2001/089283 A1 | 11/2001 |
| WO | WO-2002/24865 A2 | 3/2002 |
| WO | WO-2003/060133 A2 | 7/2003 |
| WO | WO-2003/62455 A2 | 7/2003 |
| WO | WO-2003/089452 A2 | 10/2003 |
| WO | WO-2004/031346 A2 | 4/2004 |
| WO | WO-2005/085417 A2 | 9/2005 |
| WO | WO-2005/105989 A1 | 11/2005 |
| WO | WO-2007/014275 A2 | 2/2007 |
| WO | WO-2007/034262 A1 | 3/2007 |
| WO | WO-2007/047859 A2 | 4/2007 |
| WO | WO-2007/093918 A2 | 8/2007 |
| WO | WO-2007/135022 A1 | 11/2007 |
| WO | WO-2008/076290 A2 | 6/2008 |
| WO | WO-2008/093249 A2 | 8/2008 |
| WO | WO-2008/102198 A1 | 8/2008 |
| WO | WO-2008/130629 A2 | 10/2008 |
| WO | WO-2008/152524 A2 | 12/2008 |
| WO | WO-2009/001159 A1 | 12/2008 |
| WO | WO-2009/042163 A2 | 4/2009 |
| WO | WO-2009/059195 A2 | 5/2009 |
| WO | WO-2009/074842 A1 | 6/2009 |
| WO | WO-2009/074873 A1 | 6/2009 |
| WO | WO-2009/076292 A2 | 6/2009 |
| WO | WO-2009/114321 A2 | 9/2009 |
| WO | WO-2009/131632 A1 | 10/2009 |
| WO | WO-2009/134714 A2 | 11/2009 |
| WO | WO-2010/001189 A1 | 1/2010 |
| WO | WO-2010/009147 A1 | 1/2010 |
| WO | WO-2011/064736 A1 | 6/2011 |
| WO | WO-2011/064751 A1 | 6/2011 |

OTHER PUBLICATIONS

Miller et al 2007 (Nature Biotechnology 25:7, p. 778-785).*
E. Nahon et al. "Targeting a Truncated Ho-Endonuclease of Yeast to Novel DNA Sites With Foreign Zinc Fingers", Nucleic Acids Research 26(5):1233-1239. (1998).*
B. Chevalier et al. "The LAGLIDADG Homing Endonuclease Family", Nucleic Acids and Molecular Biology 16:33-47 (2005).*
Wright, D.A., et al., "High-Frequency Homologous Recombination in Plants Mediated by Zinc-Finger Nucleases", The Plant Journal, vol. 44, (2005), pp. 693-705.
Langdon, R.C., et al, "A Chimeric Activator of Transcription That Uses Two DNA-Binding Domains to Make Simultaneous Contact with Pairs of Recognition Sites", Molecular Microbiology, vol. 41, No. 4, (2001), pp. 885-896.

(Continued)

*Primary Examiner* — Rebecca E Prouty
(74) *Attorney, Agent, or Firm* — Marshall, Gerstein & Borun LLP

(57) ABSTRACT

The invention relates to chimeric endonucleases, comprising a endonuclease and a heterologous DNA binding domain comprising one or more $Zn_2C_6$ zinc fingers, as well as methods of targeted integration, targeted deletion or targeted mutation of polynucleotides using chimeric endonucleases.

12 Claims, 15 Drawing Sheets

Specification includes a Sequence Listing.

(56) References Cited

OTHER PUBLICATIONS

Lippow, S.M., et al., "Creation of a Type IIS Restriction Endonuclease with a Long Recognition Sequence", Nucleic Acids Research, vol. 37, No. 9, (2009), pp. 3061-3073.
International Search Report for PCT/IB2010/055452, dated Mar. 17, 2011.
Cahuzac, et al., "The Solution Structure of an AlcR-DNA Complex Sheds Light onto the Unique Tight and Monomeric DNA Binding of a $Zn_2Cys_6$ Protein", Structure, 2001, vol. 9, pp. 827-836.
Paques, et al., "Meganucleases and DNA Double-Strand Break-Induced Recombination: Perspective for Gene Therapy", Current Gene Therapy, 2007, vol. 7, pp. 49-66.
Mori, et al., "Sandwiched Zinc-Finger Nucleases Harboring a Single-Chain FokI Dimer as a DNA-Cleavage Domain", Biochemical and Biophysical Research Communications, 2009, vol. 390, pp. 694-697.
International Preliminary Report on Patentability, PCT/IB2010/055452, dated May 30, 2012.
Belfort, M., et al., "Homing Endonucleases: Keeping the House in Order", Nucleic Acids Research, 1997, vol. 25, No. 17, pp. 3379-3388.
Yura, K., et al., "Zinc Finger Domains", Seitai no Kagaku, 2001, vol. 52, No. 5, pp. 394-395 with English Translation Attached.

\* cited by examiner

Figure 1: Model of a chimeric nuclease comprising I-SceI as N-terminal and AlcR (1-60) as a C-terminal domain Figure 3: Sequence alignment of different I-SceI homologs Figure 4: Sequence alignment of different I-CreI homologs
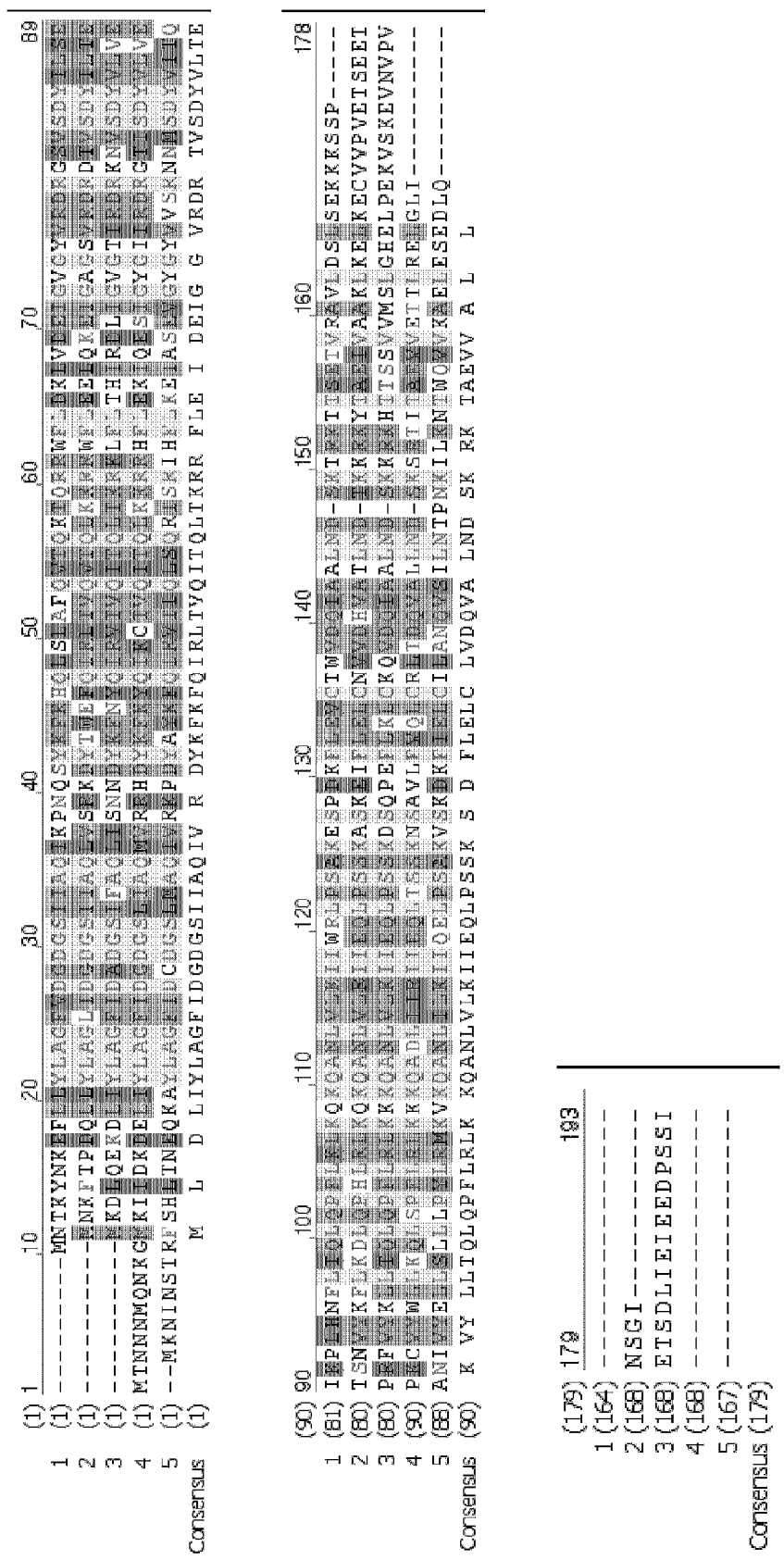

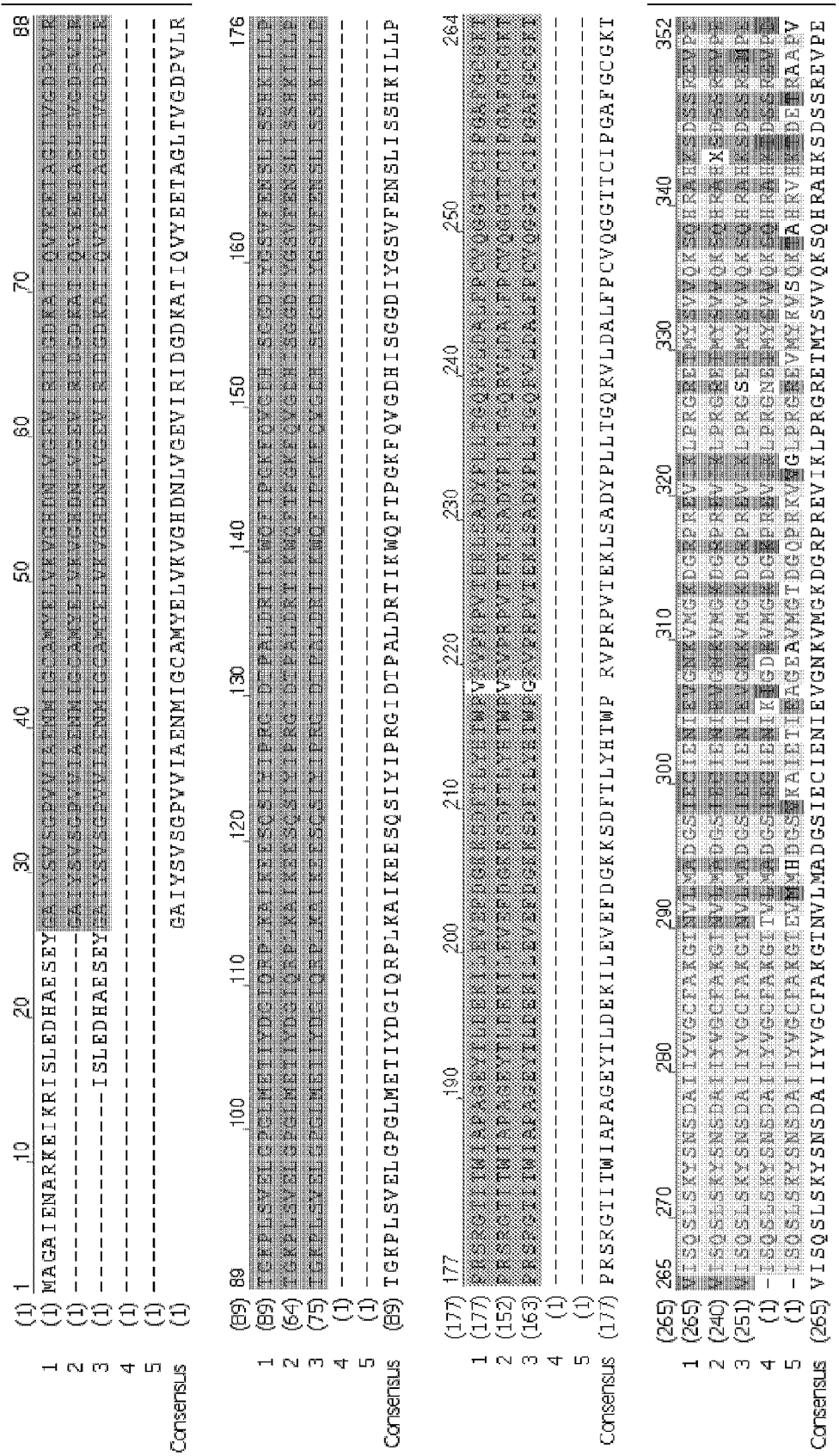
Figure 5a: Sequence alignment of different PI-SceI homologs

Figure 5b: Sequence alignment of different PI-SceI homologs

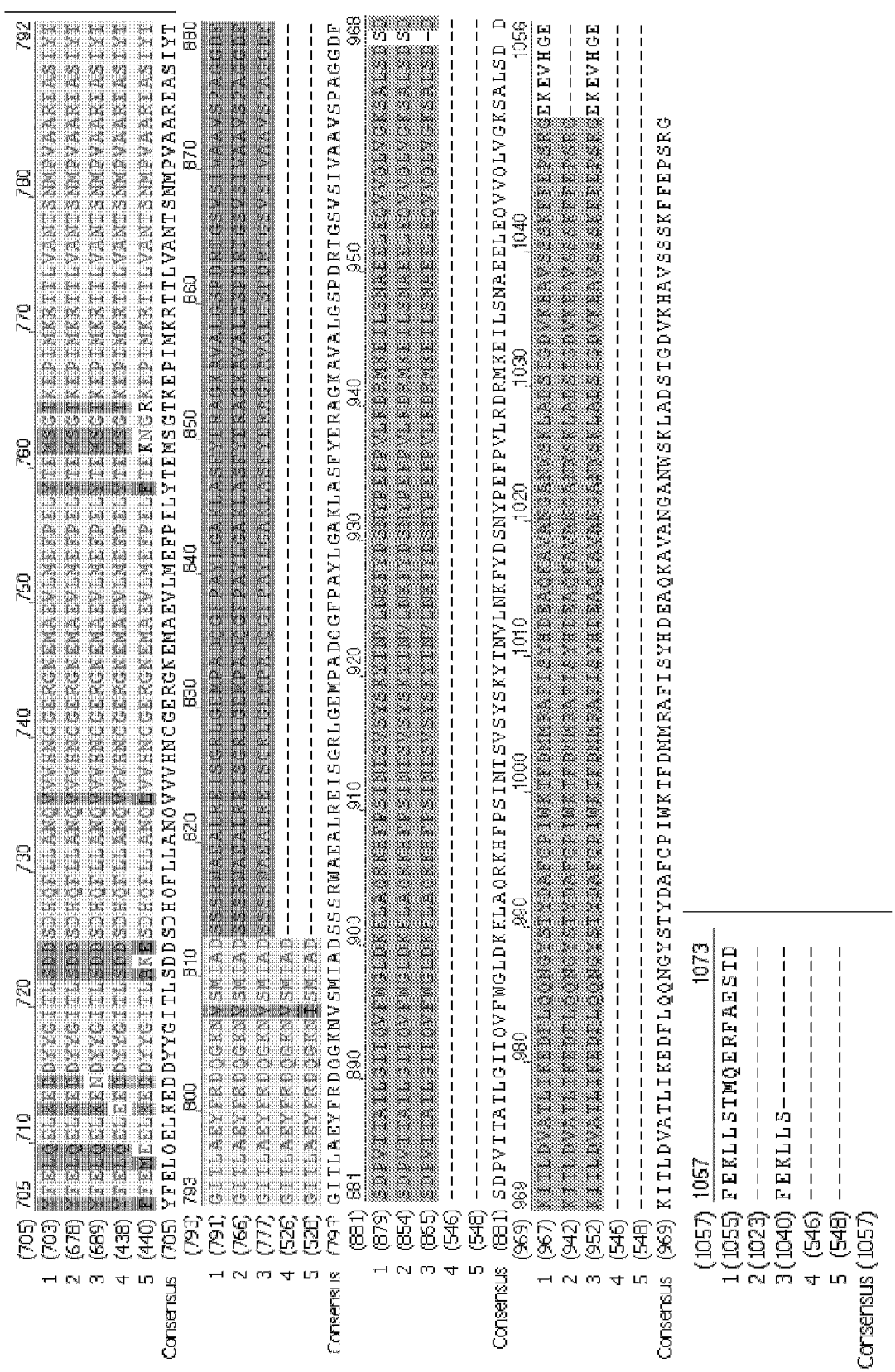
Figure 5c: Sequence alignment of different PI-SceI homologs

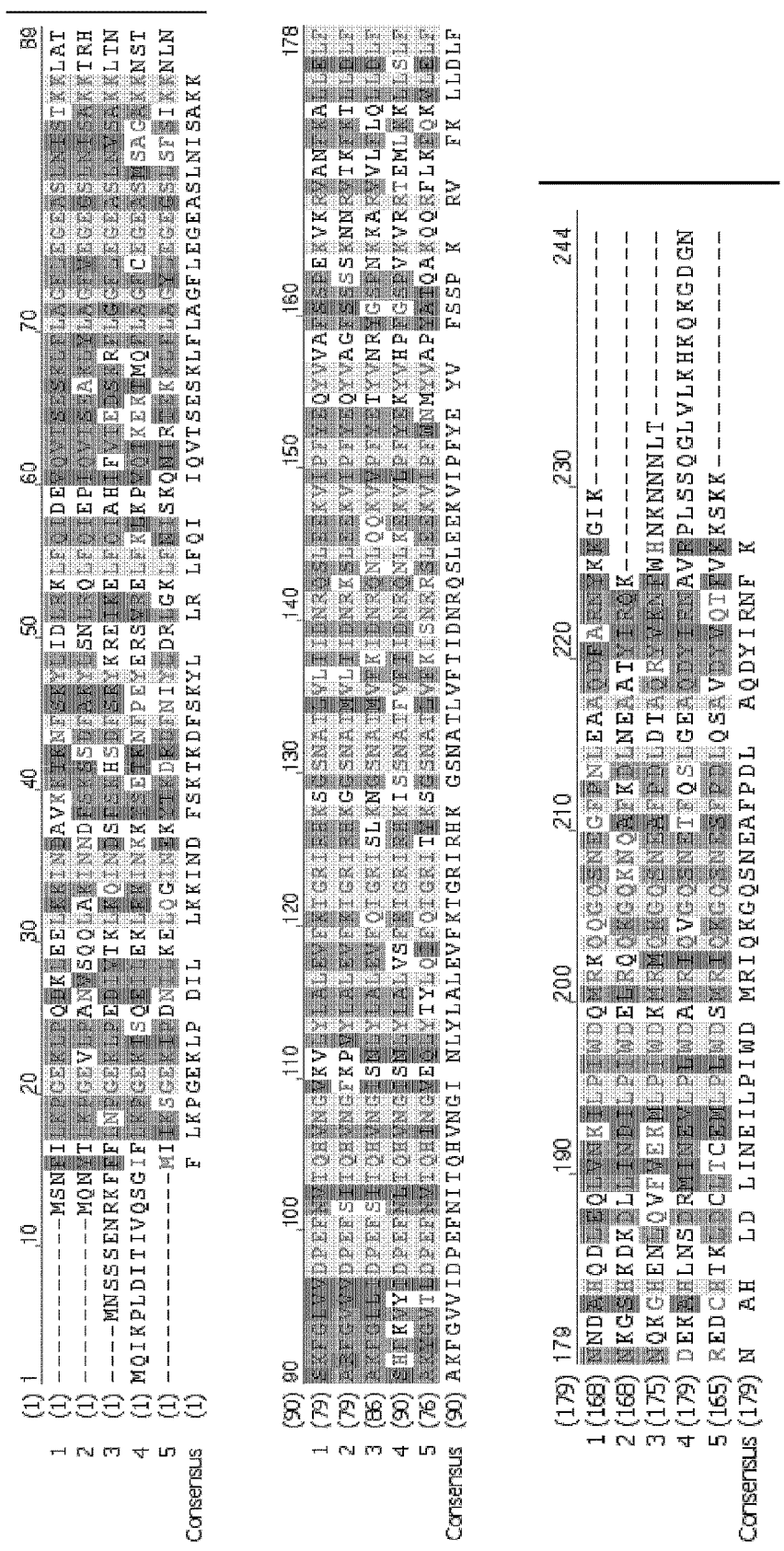
Figure 6: Sequence alignment of different I-CeuI homologs

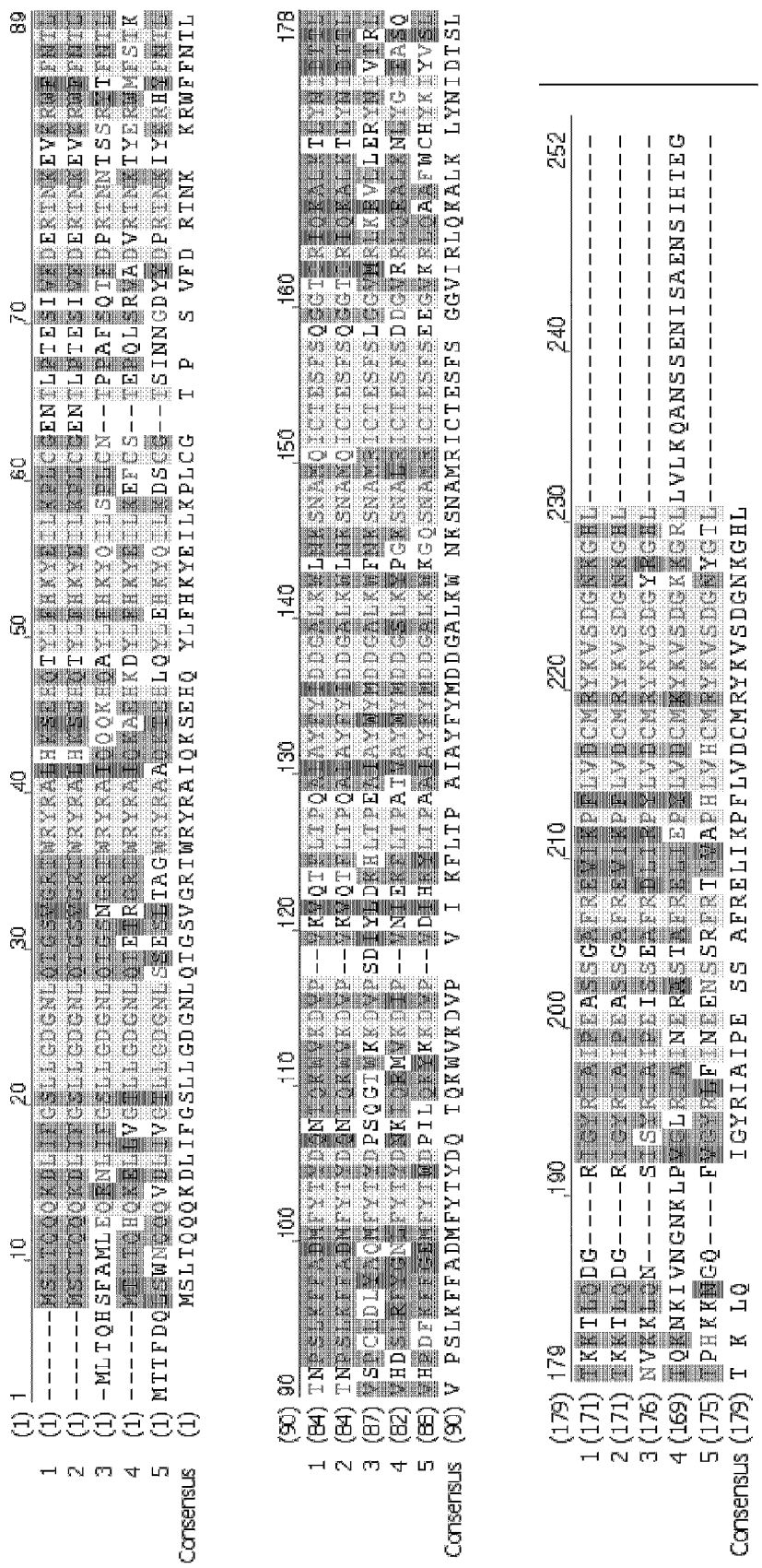
Figure 7: Sequence alignment of different I-ChuI homologs

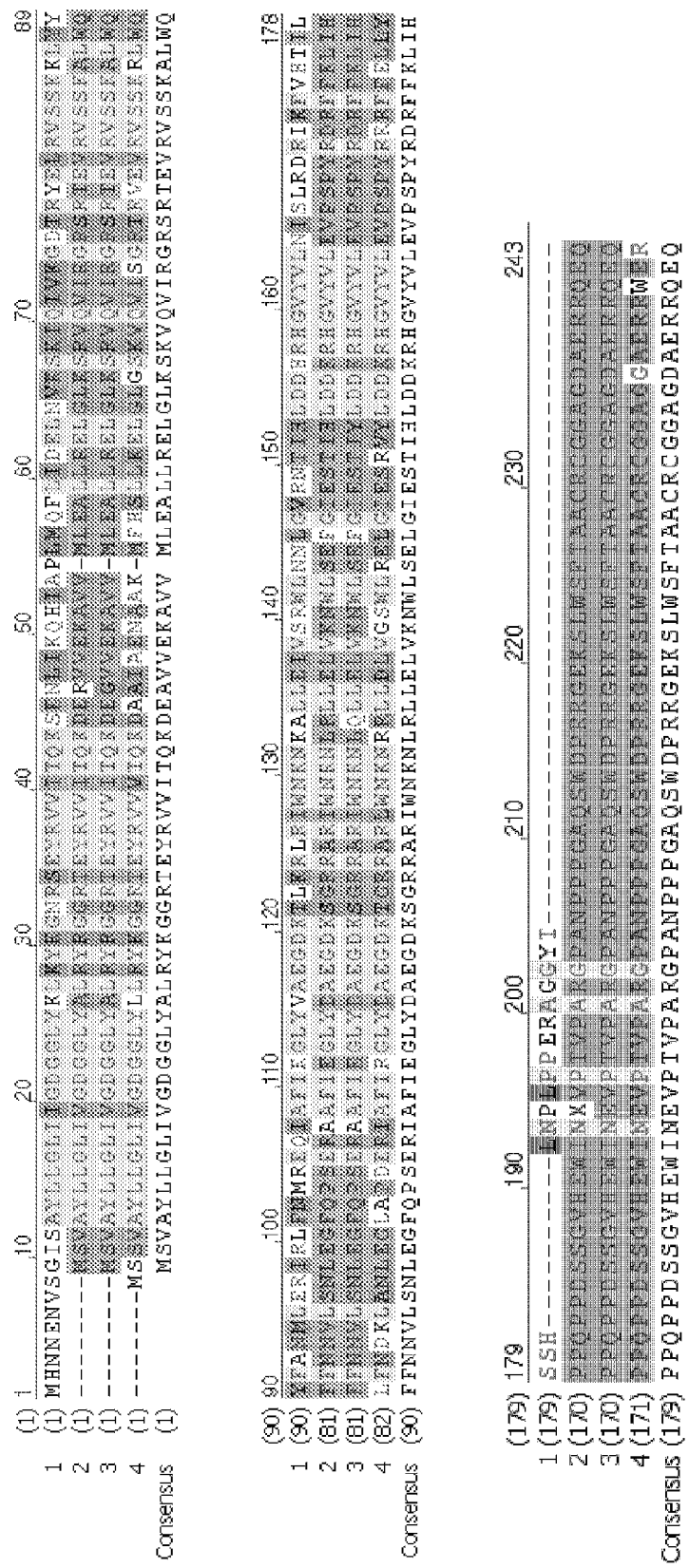
Figure 8: Sequence alignment of different I-DmoI homologs

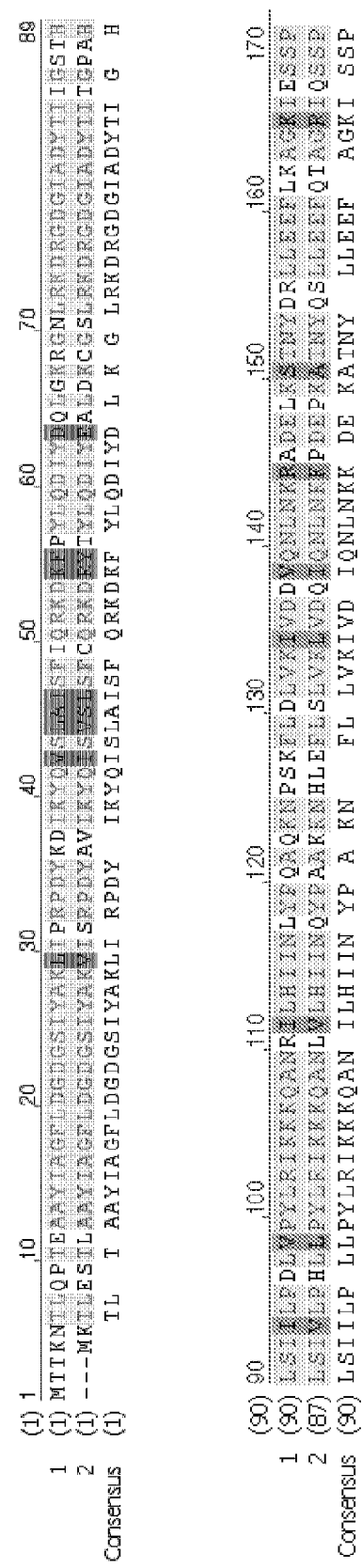
Figure 9: Sequence alignment of different I-MsoI homologs

Figure 10: Sequence Alignment of AlcR Homologs (AlcR 1 to AlcR 25)
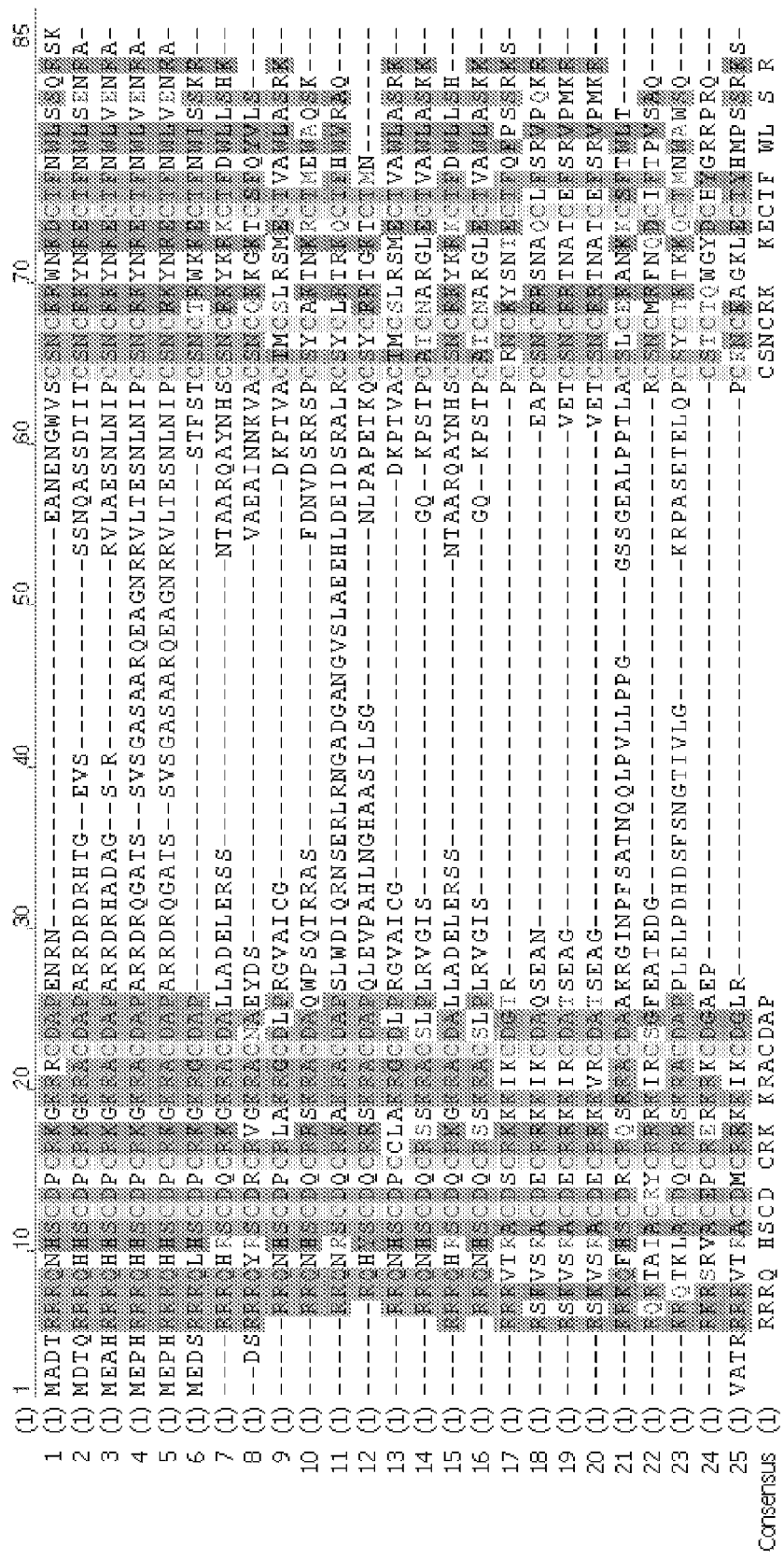

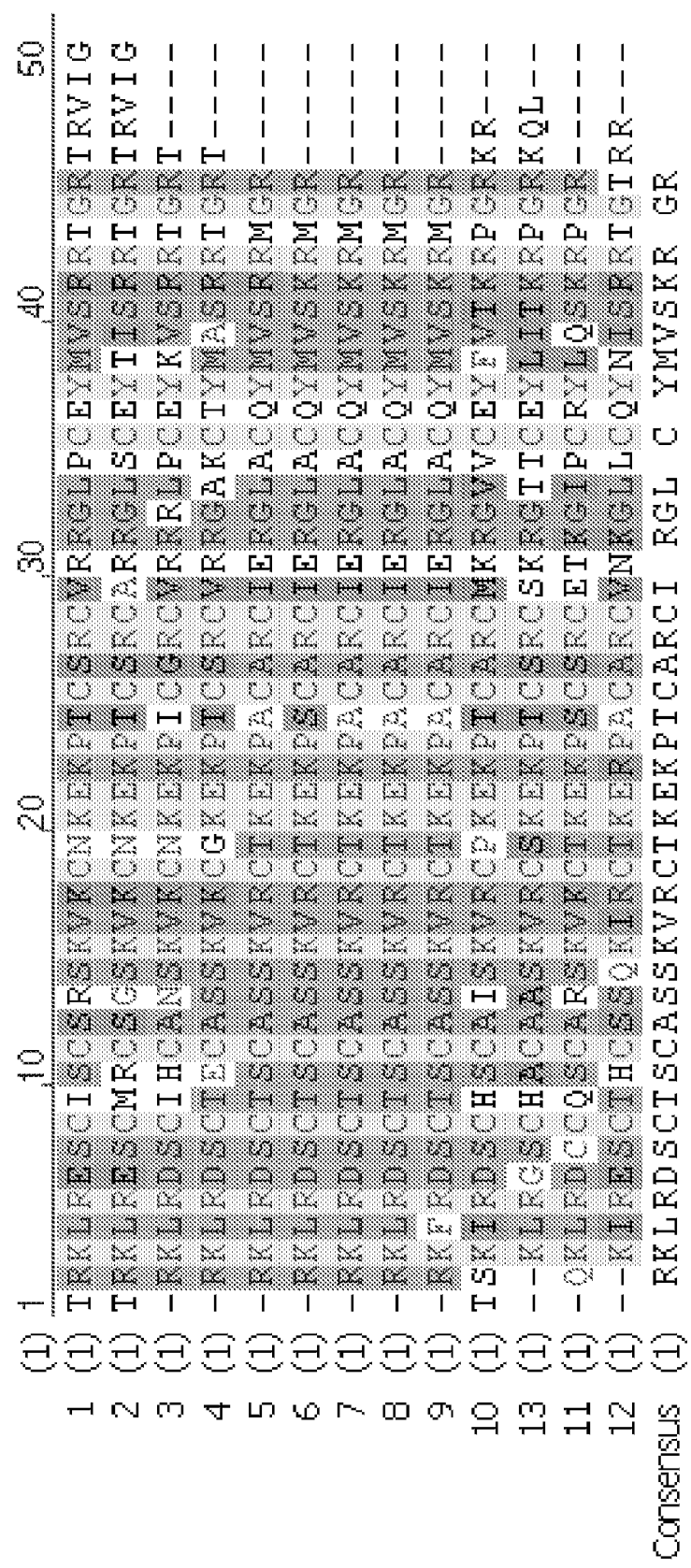
Figure 11: Sequence Alignment of AflR Homologs (AflR 1 to AflR 12)

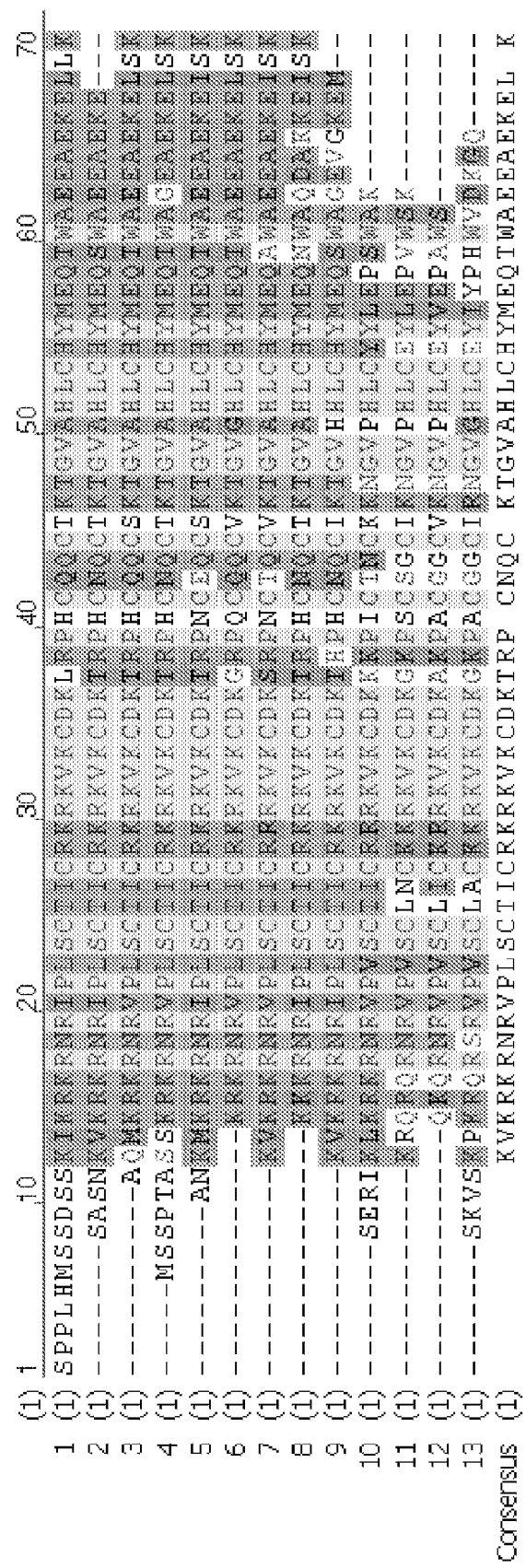
Figure 12: Sequence Alignment of Hap1 Homologs (Hap1 1 to Hap1 13)

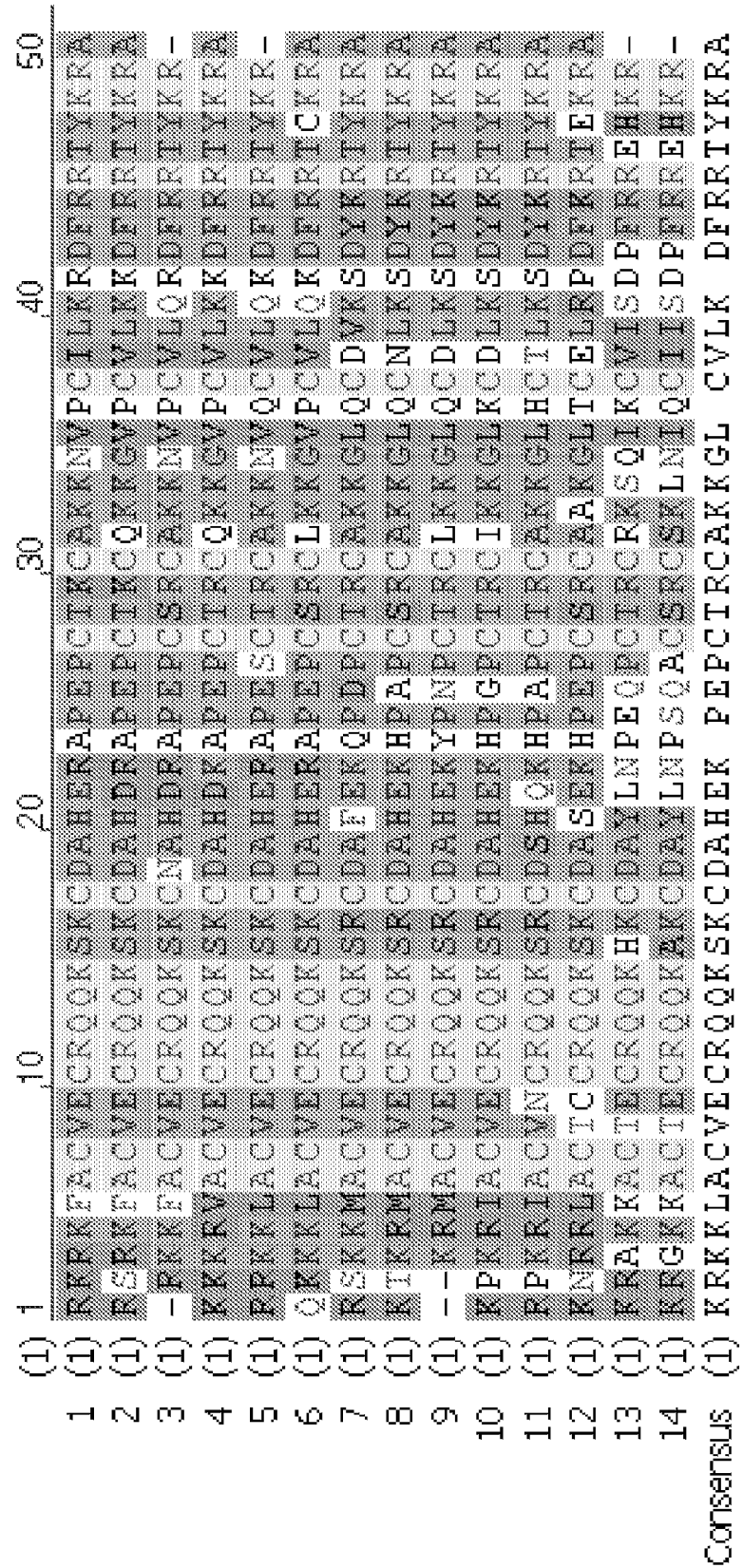
Figure 13: Sequence Alignment of Leu3 Homologs (Leu3 1 to Leu3 14)

US 10,316,304 B2

CHIMERIC ENDONUCLEASES AND USES THEREOF

RELATED APPLICATIONS

This application is a national stage application (under 35 U.S.C. § 371) of PCT/IB2010/055452, filed Nov. 26, 2010, which claims benefit of U.S. Provisional Application 61/264,715, filed Nov. 27, 2009, European application 09177375.4, filed Nov. 27, 2009, U.S. Provisional Application 61/365,809, filed Jul. 20, 2010, and European application 10170164.7, filed Jul. 20, 2010.

SUBMISSION OF SEQUENCE LISTING

The Sequence Listing associated with this application is filed in electronic format via EFS-Web and hereby incorporated by reference into the specification in its entirety. The name of the text file containing the Sequence Listing is Revised_Sequence_Listing_13987_00188_US. The size of the text file is 431 KB and the text file was created on Aug. 23, 2013.

FIELD OF THE INVENTION

The invention relates to chimeric endonucleases, comprising an endonuclease and a heterologous DNA binding domain comprising one or more $Zn_2C_6$ zinc fingers, as well as methods of targeted integration, targeted deletion or targeted mutation of polynucleotides using such chimeric endonucleases.

BACKGROUND OF THE INVENTION

Genome engineering is a common term to summarize different techniques to insert, delete, substitute or otherwise manipulate specific genetic sequences within a genome and has numerous therapeutic and biotechnological applications. More or less all genome engineering techniques use recombinases, integrases or endonucleases to create DNA double strand breaks at predetermined sites in order to promote homologous recombination.

In spite of the fact that numerous methods have been employed to create DNA double strand breaks, the development of effective means to create DNA double strand breaks at highly specific sites in a genome remains a major goal in gene therapy, agrotechnology, and synthetic biology.

One approach to achieve this goal is to use nucleases with specificity for a sequence that is sufficiently large to be present at only a single site within a genome. Nucleases recognizing such large DNA sequences of about 15 to 30 nucleotides are therefore called "meganucleases" or "homing endonucleases" and are frequently associated with parasitic DNA elements, such as group 1 self-splicing introns and inteins commonly found in the genomes of plants and fungi. Meganucleases are commonly grouped into four families: the LAGLIDADG family, the GIY-YIG family, the His-Cys box family and the HNH family. These families are characterized by structural motifs, which affect catalytic activity and the sequence of their DNA recognition sequences. Natural meganucleases from the LAGLIDADG family have been used to effectively promote site-specific genome modifications in insect and mammalian cell cultures, as well as in many organisms, such as plants, yeast or mice, but this approach has been limited to the modification of either homologous genes that conserve the DNA recognition sequence or to preengineered genomes into which a recognition sequence has been introduced. In order to avoid these limitations and to promote the systematic implementation of DNA double strand break stimulated gene modification new types of nucleases have been created.

One type of new nucleases consists of artificial combinations of unspecific nucleases to a highly specific DNA binding domain. The effectiveness of this strategy has been demonstrated in a variety of organisms using chimeric fusions between an engineered zinc finger DNA-binding domain and the non-specific nuclease domain of the FokI restriction enzyme (e.g. WO03/089452) a variation of this approach is to use an inactive variant of a meganuclease as DNA binding domain fused to an unspecific nuclease like FokI as disclosed in Lippow et al., "Creation of a type IIS restriction endonuclease with a long recognition sequence", Nucleic Acid Research (2009), Vol. 37, No. 9, pages 3061 to 3073.

An alternative approach is to genetically engineer natural meganucleases in order to customize their DNA binding regions to bind existing sites in a genome, thereby creating engineered meganucleases having new specificities (e.g WO07093918, WO2008/093249, WO09114321).

However, many meganucleases which have been engineered with respect to DNA cleavage specificity have decreased cleavage activity relative to the naturally occurring meganucleases from which they are derived (US2010/0071083). Most meganucleases do also act on sequences similar to their optimal binding site, which may lead to unintended or even detrimental off-target effects. Despite the fact, that several approaches have already been taken to avoid enhance the efficiency of meganuclease induced homologous recombination e.g. by fusing nucleases to the ligand binding domain of the rat Glucocorticoid Receptor in order to promote or even induce the transport of this modified nuclease to the cell nucleus and therefore its target sites by the addition of dexamethasone or similar compounds (WO02007/135022), there is still a need in the art to develop meganucleases having high induction rates of homologous recombination and/or a high specificity in regard to their binding site, thereby limiting the risk of off-target effects.

BRIEF SUMMARY OF THE INVENTION

The invention provides chimeric endonucleases comprising at least one LAGLIDADG endonuclease and at least one a heterologous DNA binding domain comprising one or more $Zn_2C_6$ zinc fingers. Preferably the chimeric endonuclease comprises at least one LAGLIDADG endonuclease comprising an amino acid sequence having at least 80% amino acid sequence identity to a polypeptide described by any one of SEQ ID NOs: 1, 2, 3, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 161 or 165. Preferably having at least 80% amino acid sequence identity to a polypeptide described by SEQ ID NO: 1, 2 or 3. In one preferred embodiment, the chimeric endonuclease comprises at least one LAGLIDADG endonuclease, which is an engineered or optimized endonuclease or an optimized version of an engineered endonuclease, preferably an optimized endonuclease or an optimized version of an engineered endonuclease. In a further embodiment, the chimeric endonuclease comprises a heterologous DNA binding domain comprising one or more $Zn_2C_6$ zinc fingers derived from a transcription factor. In an preferred embodiment, the chimeric endonuclease comprises a heterologous DNA binding domain comprising at least one polypeptide having at least 80% amino acid sequence identity to a polypeptide described by any one of SEQ ID NOs: 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120 or 121. The chimeric endonucleases described herein may or may not comprise a linker to connect at least one endonuclease with at least one heterologous DNA binding domain. Preferably the linker (synonymous "linker polypeptide") consists of at least 3 amino acids and wherein the at least one third of the amino acids in the amino acid sequence of this linker polypeptide are glycine or serine or alanine or a combination of glycine, serine and alanine. Preferably the chimeric endonucleases comprise at least one NLS-sequence and or a SecIII or SecIV secretion signal. One embodiment of the invention provides chimeric endonucleases, wherein the DNA binding activity of the heterologous DNA binding domain is inducible, preferably being inducible by expression of a second monomer of a dimeric or heterodimeric LAGLIDADG endonuclease. The invention provides further for isolated polynucleotides comprising a nucleotide sequence, which codes for a chimeric endonuclease of the invention. Preferably the isolated polynucleotide is codon optimized or has a low content RNA instability motives or has a low content of codon repeats, or has a low content of cryptic splice sites, or has a low content of alternative start codons, has a low content of restriction sites, or has a low content of RNA secondary structures or has any combination of those features. Another embodiment of the invention is an expression cassette comprising an isolated polynucleotide as described above in functional combination with a promoter and a terminator sequence.

Further embodiment of the invention are isolated polynucleotides comprising a chimeric recognition sequence having a length of about 15 to about 300 nucleotides and comprising a recognition sequence of a LAGLIDADG endonuclease and a recognition sequence of a heterologous DNA binding domain comprising one or more $Zn_2C_6$ zinc fingers. Preferably the recognition sequence of the heterologous DNA binding domain can be bound by at least one DNA binding domain comprising an amino acid sequence described by any one of SEQ ID NOs: 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121.

The invention does also provide for isolated polynucleotides comprising a chimeric recognition sequence, preferably the chimeric recognition sequence is comprised in en expression cassette, or close to the 5'- or 3'-end or close to both ends, wherein the expression cassette comprises a promoter, a terminator and a sequence capable to be expressed by the promoter. Preferably the sequence capable to be expressed codes for a marker gene.

The invention does further provide a chimeric recognition sequence comprising a DNA recognition sequence of I-SceI and a recognition sequence, which can be bound by at least one DNA binding domain comprising an amino acid sequence described by any one of SEQ ID NOs: 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, being directly connected or being connected by a sequence of 1 to 10 nucleotides. In one embodiment the chimeric recognition sequence comprises a DNA recognition sequence of I-SceI and a recognition sequence of AlcR, or AlcR (1-60) being directly connected or being connected by a sequence of 1 to 10 nucleotides. In one embodiment of the invention, the isolated polynucleotide comprises a chimeric recognition sequence, comprising a polynucleotide sequence as described by any one of SEQ ID NO: 13, 14, 15, 16, 43, 44, 45 or 46.

Other embodiments of the invention are vectors, host cells or non human organisms comprising a polynucleotide coding for a chimeric endonuclease, or an isolated polynucleotide coding for a chimeric endonuclease or an isolated polynucleotide comprising an chimeric recognition sequence, or an expression cassette comprising a polynucleotide coding for a chimeric endonuclease or an chimeric recognition sequence, and vectors, host cells or non human organisms comprising a combination of the chimeric endonucleases, isolated polynucleotides and expression cassettes described above. Preferably the non-human organism is a plant.

The invention provides methods of using the chimeric endonucleases and chimeric recognition sequences described herein to induce or facilitate homologous recombination or end joining events. Preferably in methods for targeted integration or excision of sequences. Preferably the sequences being excised are marker genes.

One embodiment of the invention is a method for providing a chimeric endonuclease, comprising the steps of: a) providing at least one endonuclease coding region, b) providing at least one heterologous DNA binding domain coding region, c) providing a polynucleotide having a potential DNA recognition sequence or potential DNA recognition sequences of the endonuclease or endonucleases of step a) and having a potential recognition sequence or having potential recognition sequences of the heterologous DNA binding domain or heterologous DNA binding domains of step b), d) creating a translational fusion of the coding regions of all endonucleases of step b) and all heterologous DNA binding domains of step c), e) expressing a chimeric endonuclease from the translational fusion created in step d), f) testing the chimeric endonuclease expressed in step e) for cleavage of the polynucleotide of step c).

The invention does further provide a method for homologous recombination of polynucleotides comprising the following steps: a) providing a cell competent for homologous recombination, b) providing a polynucleotide comprising a chimeric recognition site flanked by a sequence A and a sequence B, c) providing a polynucleotide comprising sequences A' and B', which are sufficiently long and homologous to sequence A and sequence B, to allow for homologous recombination in said cell and d) providing a chimeric endonuclease as described herein or an expression cassette as described herein, e) combining b), c) and d) in said cell and f) detecting recombined polynucleotides of b) and c), or selecting for or growing cells comprising recombined polynucleotides of b) and c). Preferably the method for homologous recombination of polynucleotides leads to a homologous recombination, wherein a polynucleotide sequence comprised in the competent cell of step a) is deleted from the genome of the growing cells of step f). A further method of the invention is a method for targeted mutation comprising the following steps: a) providing a cell comprising a polynucleotide comprising a chimeric recognition site of an chimeric endonuclease, b) providing an chimeric endonuclease being able to cleave the chimeric recognition site of step a), c) combining a) and b) in said cell and d) detecting mutated polynucleotides, or selecting for growing cells comprising mutated polynucleotides. In another preferred embodiment of the invention, the methods described above comprise a step, wherein the chimeric endonuclease and the chimeric recogntition site are combined in at least one cell via crossing of organisms, via transformation or via transport mediated via a Sec III or SecIV peptide fused to the optimized endonuclease.

BRIEF DESCRIPTION OF THE FIGURES

FIG. 2 does also comprise the polynucleotide sequence of the DNA recognition sequence of wildtype I-SceI, called wt target site, as well as the polynucleotide sequence of the chimeric recognition site of the chimeric endonucleases (I-SceI-AlcR(1-60), I-SceI#2-AlcR(1-60) and I-SceI#1-AlcR(1-60)). FIG. 2 provides further the amino acid sequence showing the c-terminus of SceI, comprising different mutations, the lysine (L) used as linker and the first six amino acids of the former N-terminus of AlcR (1-60) used to create the chimeric endonucleases. The different mutations on the former C-terminus of wt I-SceI change the wildtype amino acid sequence "TISSETFLK" (SEQ ID NO: 219) to "TIKSEETFLK" (SEQ ID NO: 202) in the chimeric endonuclease I-SceI#1-AlcR(1-60) and to "AIANQAFLK" (SEQ ID NO: 38) in the chimeric endonuclease I-SceI#2-AlcR(1-60). Sequences shown are: wt target site (SEQ ID NO: 186); #55 target site (SEQ ID NO: 187); I-SceI#1-AlcR(1-60) (SEQ ID NO: 188); and I-SceI#2-AlcR(1-60) (SEQ ID NO: 189).

FIG. 3 depicts a sequence alignment of different I-SceI homologs, wherein 1 is SEQ ID NO: 1, 2 is SEQ ID NO: 122, 3 is SEQ ID NO: 123, 4 is SEQ ID NO: 124, 5 is SEQ ID NO: 125. Consensus is SEQ ID NO: 190.

FIG. 4 depicts a sequence alignment of different I-CreI homologs, wherein 1 is SEQ ID NO: 126, 2 is SEQ ID NO: 127, 3 is SEQ ID NO: 128, 4 is SEQ ID NO: 129, 5 is SEQ ID NO: 130. Consensus is SEQ ID NO: 191.

FIGS. 5a to 5c depicts a sequence alignment of different PI-SceI homologs, wherein 1 is SEQ ID NO: 145, 2 is SEQ ID NO: 146, 3 is SEQ ID NO: 147, 4 is SEQ ID NO: 148, 5 is SEQ ID NO: 149. Consensus is SEQ ID NO: 192.

FIG. 6 depicts a sequence alignment of different I-CeuI homologs, wherein 1 is SEQ ID NO: 131, 2 is SEQ ID NO: 132, 3 is SEQ ID NO: 133, 4 is SEQ ID NO: 134, 5 is SEQ ID NO: 135. Consensus is SEQ ID NO: 193.

FIG. 7 depicts a sequence alignment of different I-ChuI homologs, wherein 1 is SEQ ID NO: 136, 2 is SEQ ID NO: 137, 3 is SEQ ID NO: 138, 4 is SEQ ID NO: 139, 5 is SEQ ID NO: 140. Consensus is SEQ ID NO: 194.

FIG. 8 depicts a sequence alignment of different I-DmoI homologs, wherein 1 is SEQ ID NO: 141, 2 is SEQ ID NO: 142, 3 is SEQ ID NO: 143, 4 is SEQ ID NO: 144. Consensus is SEQ ID NO: 195.

FIG. 9 depicts a sequence alignment of different I-MsoI homologs, wherein 1 is SEQ ID NO: 150 and 2 is SEQ ID NO: 151. Consensus is SEQ ID NO: 196.

FIG. 10 shows a sequence alignment of different $Zn_2C_6$ domains homologous to the DNA binding domain of A1cR (AlcR 1 to 60). The Consensus sequence shows amino acids being conserved in those homologs (A1cR 1 to 60 consensus sequence). Sequence No. 1, 2, 3, 4, 5, 6, 7, 8, 9, 10, 11, 12, 13, 14, 15, 16, 17, 18, 19, 20, 21, 22, 23, 24 and 25 refer to SEQ ID NO: 70, 71, 72 74, 75, 76, 77, 78, 79, 80, 81, 82, 83, 84, 85, 86, 87, 88, 89, 90, 91, 92, 93 and 94, respectively. Consensus sequences are SEQ ID NO: 197 and SEQ ID NO: 198.

FIG. 11 shows a sequence alignment of different $Zn_2C_6$ domains homologous to the DNA binding domain of AflR. The Consensus sequence shows amino acids being conserved in those homologs (AflR consensus sequence). Sequence No. 1, 2, 3, 4, 5, 6, 7, 8, 9, 10, 11 and 12 refer to SEQ ID NO: 57, 58, 59, 60, 61, 62, 63; 64, 65, 66, 67, 68 and 69, respectively. Consensus is SEQ ID NO: 199.

FIG. 12 shows a sequence alignment of different $Zn_2C_6$ domains homologous to the DNA binding domain of Hap 1. The Consensus sequence shows amino acids being conserved in those homologs (Hap1 consensus sequence). Sequence No. 1, 2, 3, 4, 5, 6, 7, 8, 9, 10, 11, 12 and 13 refer to SEQ ID NO: 95, 96, 97, 98, 99, 100, 101, 102, 103, 104, 105, 106 and 107, respectively. Consensus is SEQ ID NO: 200.

FIG. 13 shows a sequence alignment of different $Zn_2C_6$ domains homologous to the DNA binding domain of Leu3. The Consensus sequence shows amino acids being conserved in those homologs (Leu3 consensus sequence). Sequence No. 1, 2, 3, 4, 5, 6, 7, 8, 9, 10, 11, 12, 13 and 14 refer to SEQ ID NO: 108, 109, 110, 111, 112, 113, 114, 115, 116, 117, 118, 119, 120 and 121, respectively. Consensus is SEQ ID NO: 201.

DETAILED DESCRIPTION OF THE INVENTION

Figure 1:
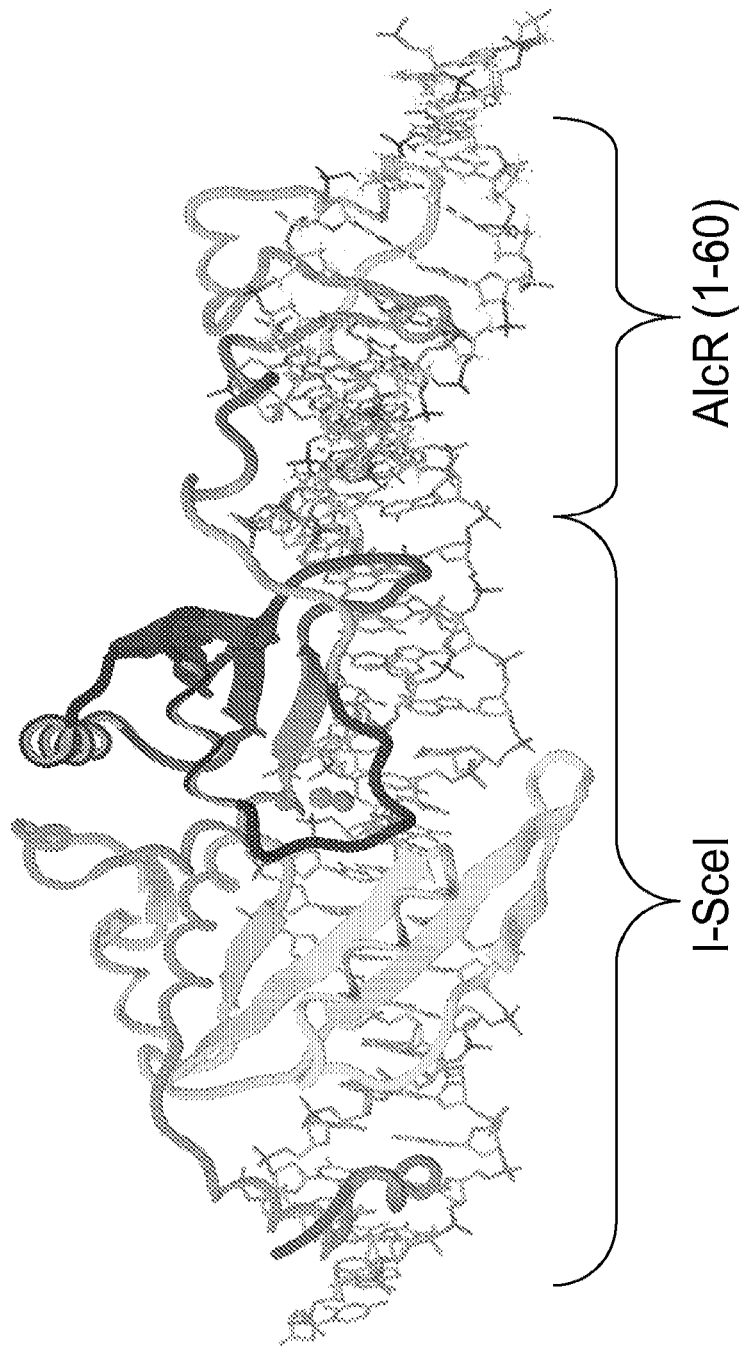
FIG. 1 depicts a model of a chimeric nuclease comprising I-SceI as N-terminal and amino acids 1 to 60 of AlcR as a C-terminal domain.

The invention provides chimeric LAGLIDADG endonucleases, comprising at least one LAGLIDADG endonuclease and at least one heterologous DNA binding domain comprising one or more $Zn_2C_6$ zinc fingers.

LAGLIDADG Endonucleases

LAGLIDADG endonucleases useful in the invention can be found in the genomes of algae, fungi, yeasts, protozoan, chloroplasts, mitochondria, bacteria and archaea. LAGLIDADG endonucleases comprise at least one conserved LAGLIDADG motif. The name of the LAGLIDADG motif is based on a characteristic amino acid sequence appearing in all LAGLIDADG endonucleases. The term LAGLIDADG is an acronym of this amino acid sequence according to the one-letter-code as described in the STANDARD ST.25 i.e. the standard adopted by the PCIPI Executive Coordination Committee for the presentation of nucleotide and amino acid sequence listings in patent applications.

However, the LAGLIDADG motif is not fully conserved in all LAGLIDADG endonucleases, (see for example Chevalier et al. (2001), Nucleic Acids Res. 29(18): 3757 to 3774, or Dalgaard et al. (1997), Nucleic Acids Res. 25(22): 4626 to 4638), so that some LAGLIDADG endonucleases comprise some one or several amino acid changes in their LAGLIDADG motif. LAGLIDADG endonucleases comprising only one LAGLIDADG motif act usually as homo- or heterodimers. LAGLIDADG endonucleases comprising two LAGLIDADG motifs act as monomers and comprise usually a pseudo-dimeric structure.

LAGLIDADG endonucleases can be isolated from polynucleotides of organisms mentioned for exemplary purposes in Table 1 to 6, or de novo synthesized by techniques known in the art, e.g. using sequence information available in public databases known to the person skilled in the art, for example Genbank (Benson (2010)), Nucleic Acids Res 38:D46-51 or Swissprot (Boeckmann (2003), Nucleic Acids Res 31:365-70)

A collection of LAGLIDADG endonucleases can be found in the PFAM-Database for protein families. The PFAM-Database accession number PF00961 describes the LAGLIDADG 1 protein family, which comprises about 800 protein sequences. PFAM-Database accession number PF03161 describes members of the LAGLIDADG 2 protein family, comprising about 150 protein sequences. An alternative collection of LAGLIDADG endonucleases can be found in the InterPro data base, e.g. InterPro accession number IPR004860.

The term LAGLIDADG endonucleases shall also encompass artificial homo- and heterodimeric LAGLIDADG endonucleases, which can be created by modifying the protein-protein interaction regions of the monomers in order to promote homo- or heterodimer formation. Examples of artificial heterodimeric LAGLIDADG endonuclease comprising the LAGLIDADG endonuclease I-Dmo I as one domain can be found for example in WO2009/074842 and WO2009/074873. In addition to that, the term LAGLIDADG endonucleases shall also encompass artificial single chain endonucleases, which can be created by making translational fusions of monomers of homo- or heterodimeric LAGLIDADG endonucleases.

In further embodiments the LAGLIDADG endonuclease comprised in the chimeric endonuclease can be a monomeric, homodimeric, artificial homo- or heterodimeric or artificial single chain LAGLIDADG endonuclease.

In one embodiment the LAGLIDAG endonuclease is a monomeric, homodimeric, heterodimeric, or artificial single chain LAGLIDADG endonuclease. Preferably the endonuclease is a monomeric or artificial single chain LAGLIDADG endonuclease.

Preferred LAGLIDADG endonucleases are: I-AniI, I-Sce I, I-Chu I, I-Dmo I, I-Cre I, I-Csm I, PI-Sce I, PI-Tli I, PI-Mtu I, I-Ceu I, I-Sce II, I-Sce III, HO, PI-Civ I, PI Ctr I, PI-Aae I, PI-Bsu I, PI-Dha I, PI-Dra I, PI-Mav I, PI-Mch I, PI-Mfu I, PI-Mfl I, PI-Mga I, PI-Mgo I, PI-Min I, PI-Mka I, PI-Mka I, PI-Mma I, PI-Msh I, PI-Msm I, PI-Mth I, PI-Mtu I, PI-Mxe I, PI-Npu I, PI-Pfu I, PI-Rma I, PI-Spb I, PI-Ssp I, PI-Fac I, PI-Mja I, PI-Pho I, PI-Tag I, PI-Thy I, PI-Tko I, and PI-Tsp I and homologs of any one of these having at least 49%, 51%, 58%, 60%, 70%, 80%, 85%, 90%, 92%, 93%, 94%, 95%, 96%, 97%, 98% or 99% sequence identity on amino acid level; more preferred are: I-Sce I, I-Chu I, I-Dmo I, I-Cre I, I-Csm I, PI-Pfu I, PI-Sce I, PI-Tli I, I-Mso I, PI-Mtu I, I-Ceu I, I-Sce II, I-Sce III, and HO and homologs of any one of these having at least 49%, 51%, 58%, 60%, 70%, 80%, 85%, 90%, 92%, 93%, 94%, 95%, 96%, 97%, 98% or 99% sequence identity on amino acid level; even more preferred are, I-Sce I, I-Chu I, I-Dmo I, I-Cre I, I-Csm I, PI-Sce I, PI-Pfu I, PI-Tli I, I-Mso I, PI-Mtu I and I-Ceu I and homologs of any one of these having at least 49%, 51%, 58%, 60%, 70%, 80%, 85%, 90%, 92%, 93%, 94%, 95%, 96%, 97%, 98% or 99% sequence identity on amino acid level;

still more preferred are I-Dmo I, I-Cre I, I-Sce I, I-Mso I and I-Chu I and homologs of any one of these having at least 49%, 51%, 58%, 60%, 70%, 80%, 85%, 90%, 92%, 93%, 94%, 95%, 96%, 97%, 98% or 99% sequence identity on amino acid level, most preferred is I-Sce I and homologs of I-Sce I having at least 49%, 51%, 58%, 60%, 70%, 80%, 85%, 90%, 92%, 93%, 94%, 95%, 96%, 97%, 98% or 99% sequence identity on amino acid level.

Preferred monomeric LAGLIDADG endonucleases are: I-AniI, I-SceI, I-Chu I, I-DmoI, I-Csm I, PI-Sce I, PI-Tli I, PI-Mtu I, I-Sce II, I-Sce III, HO, PI-Civ I, PI Ctr I, PI-Aae I, PI-Bsu I, PI-Dha I, PI-Dra I, PI-Mav I, PI-Mch I, PI-Mfu I, PI-Mfl I, PI-Mga I, PI-Mgo I, PI-Min I, PI-Mka I, PI-Mle I, PI-Mma I, PI-Msh I, PI-Msm I, PI-Mth I, PI-Mtu I, PI-Mxe I, PI-Npu I, PI-Pfu I, PI-Rma I, PI-Spb I, PI-Ssp I, PI-Fac I, PI-Mja I, PI-Pho I, PI-Tag I, PI-Thy I, PI-Tko I, and PI-Tsp I; and homologs of any one these having at least 49%, 51%, 58%, 60%, 70%, 80%, 85%, 90%, 92%, 93%, 94%, 95%, 96%, 97%, 98% or 99% sequence identity on amino acid level.

Preferably, I-Sce I, I-Chu I, I-Dmo I, I-Csm I, PI-Pfu I, PI-Sce I, PI-Tli I, PI-Mtu I, I-Sce II, I-Sce III, and HO; and homologs of any one these having at least 49%, 51%, 58%, 60%, 70%, 80%, 85%, 90%, 92%, 93%, 94%, 95%, 96%, 97%, 98% or 99% sequence identity on amino acid level.

More preferred monomeric LAGLIDADG endonucleases are: I-Sce I, I-Chu I, I-Dmo I, I-Csm I, PI-Sce I, PI-Tli I, and PI-Mtu I; and homologs of any one these having at least 49%, 51%, 58%, 60%, 70%, 80%, 85%, 90%, 92%, 93%, 94%, 95%, 96%, 97%, 98% or 99% sequence identity on amino acid level.

Still more preferred monomeric LAGLIDADG endonucleases are: I-Dmo I, I-Sce I, and I-Chu I; and homologs of any one these having at least 49%, 51%, 58%, 60%, 70%, 80%, 85%, 90%, 92%, 93%, 94%, 95%, 96%, 97%, 98% or 99% sequence identity on amino acid level.

Preferred LAGLIDADG endonucleases are the LAGLIDADG endonucleases mentioned in Tables 1 to 6 and homologs of these having at least 80%, 85%, 90%, 92%, 93%, 94%, 95%, 96%, 97%, 98% or 99% sequence identity on amino acid level.

One type of homolog LAGLIDADG endonucleases are artificial single chain LAGLIDADG endonucleases, which may comprise two sub-units of the same LAGLIDADG endonuclease, such as single-chain I-Cre, single-chain I-Ceu I or single-chain I-Ceu II as disclosed in WO03078619, or which may comprise two sub-units of different LAGLIDADG endonucleases. Artificial single chain LAGLIDADG endonucleases, which comprise two sub-units of different LAGLIDADG endonucleases are called hybrid meganucleases.

Preferred artificial single chain LAGLIDADG endonucleases are single-chain I-Cre I, single-chain I-CeuI or single-chain I-CeuII and hybrid meganucleases like: I-Sce/I-Chu I, I-Sce/PI-Pfu I, I-Chu/I-Sce I, I-Chu/PI-Pfu I, I-Sce/I-Dmo I, I Dmo I/I-Sce I, I-Dmo I/PI-Pfu I, I-Dmo I/I-Cre I, I-Cre I/I-Dmo I, I-Cre I/PI-Pfu I, I-Sce I/I-Csm I, I-Sce I/I-Cre I, I-Sce I/PI-Sce I, I-Sce I/PI-Tli I, I-Sce I/PI-Mtu I, I-Sce I/I-Ceu I, I-Cre I/I-Ceu I, I-Chu I/I-Cre I, I-Chu I/I-Dmo I, I-Chu I/I-Csm I, I-Chu I/PI-Sce I, I-Chu I/PI-Tli I, I-Chu I/PI-Mtu I, I-Cre I/I-Chu I, I-Cre I/I-Csm I, I-Cre I/PI-Sce I, I-Cre I/PI-Tli I, I-Cre I/PI-Mtu I, I-Cre I/I-Sce I, I-Dmo I/I-Chu I, I-Dmo I/I-Csm I, I Dmo I/PI-Sce I, I-Dmo I/PI-Tli I, I-Dmo I/PI-Mtu I, I-Csm I/I-Chu I, I-Csm I/PI-Pfu I, I-Csm I/I-Cre I, I-Csm I/I-Dmo I, I-Csm I/PI-Sce I, I-Csm I/PI-Tli I, I-Csm I/PI-Mtu I, I-Csm I/I-Sce I, PI-Sce I/I-Chu I, PI-Sce I/PI-Pfu I, PI-Sce I/I-Cre I, PI-Sce I/I-Dmo I, PI-Sce I/I-Csm I, PI-Sce I/PI-Tli I, PI-Sce I/PI-Mtu I, PI-Sce I/I-Sce I, PI-Tli I/I-Chu I, PI-Tli I/PI-Pfu I, PI-Tli I/I-Cre I, PI-Tli I/I-Dmo I, PI-Tli I/I-Csm I, PI-Tli I/PI Sce I, PI-Tli I/PI-Mtu I, PI-Tli I/I-Sce I, PI-Mtu I/I-Chu I, PI-Mtu I/PI-Pfu I, PI-Mtu I/I-Cre I, PI-Mtu I/I-Dmo I, PI-Mtu I/I-Csm I, PI-Mtu I/I-Sce I, PI-Mtu I/PI-Tli I, and PI-Mtu I/I-SceI disclosed in WO03078619, in WO09/074842, WO2009/059195 and in WO09/074873, as well as LIG3-4SC being disclosed in WO09/006297, or single chain I-Cre I V2 V3 being disclosed in Sylvestre Grizot et al., "Efficient targeting of a SCID gene by an engineered single-chain homing endonuclease", Nucleic Acids Research, 2009, Vol. 37, No. 16, pages 5405-5419. A particular preferred single chain LAGLIDADG endonuclease is single-chain I-Cre I.

Preferred dimeric LAGLIDADG endonucleases are: I-Cre I, I-Ceu I, I-Sce II, I-Mso I and I-Csm I and homologs of any one these having at least 49%, 51%, 58%, 60%, 70%, 80%, 85%, 90%, 92%, 93%, 94%, 95%, 96%, 97%, 98% or 99% sequence identity on amino acid level.

Preferred heterodimeric LAGLIDADG endonucleases are disclosed in WO 07/034262, WO 07/047859 and WO08093249.

Homologs of LAGLIDADG endonucleases can be cloned from other organisms or can be created by mutating LAGLIDADG endonucleases, e.g. by replacing, adding or deleting amino acids of the amino acid sequence of a given LAGLIDADG endonuclease, which preferably have no effect on its DNA-binding-affinity, its dimer formation affinity or which will change its DNA recognition sequence.

As used herein, the term "DNA-binding affinity" means the tendency of a meganuclease or LAGLIDADG endonuclease to non-covalently associate with a reference DNA molecule (e.g., a DNA recognition sequence or an arbitrary sequence). Binding affinity is measured by a dissociation constant, $K_D$ (e.g., the $K_D$ of I-CreI for the WT DNA recognition sequence is approximately 0.1 nM). As used herein, a meganuclease has "altered" binding affinity if the $K_D$ of the recombinant meganuclease for a reference DNA recognition sequence is increased or decreased by a statistically significant ($p<0.05$) amount relative to a reference meganuclease or or LAGLIDADG endonuclease.

As used herein with respect to meganuclease monomers or LAGLIDADG endonuclease monomers, the term "affinity for dimer formation" means the tendency of a monomer to non-covalently associate with a reference meganuclease monomer or LAGLIDADG endonuclease monomer. The affinity for dimer formation can be measured with the same monomer (i.e., homodimer formation) or with a different monomer (i.e., heterodimer formation) such as a reference wild-type meganuclease or a reference LAGLIDADG endonuclease. Binding affinity is measured by a dissociation constant, $K_D$. As used herein, a meganuclease has "altered" affinity for dimer formation, if the $K_D$ of the recombinant meganuclease monomer or the recombinant LAGLIDADG endonuclease monomer for a reference meganuclease monomer or for a reference LAGLIDADG endonuclease is increased or decreased by a statistically significant ($p<0.05$) amount relative to a reference meganuclease monomer or the reference LAGLIDADG endonuclease monomer.

As used herein, the term "enzymatic activity" refers to the rate at which a meganuclease e.g. a LAGLIDADG endonuclease cleaves a particular DNA recognition sequence. Such activity is a measurable enzymatic reaction, involving the hydrolysis of phospho-diester-bonds of double-stranded DNA. The activity of a meganuclease acting on a particular DNA substrate is affected by the affinity or avidity of the meganuclease for that particular DNA substrate which is, in turn, affected by both sequence-specific and non-sequence-specific interactions with the DNA.

For example, it is possible to add nuclear localization signals to the amino acid sequence of a LAGLIDADG endonuclease and/or change one or more amino acids and/or delete parts of its sequence, e.g. parts of the N-terminus or parts of its C-terminus.

For example, it is possible to create a homolog LAGLIDADG endonuclease of I-SceI, by mutating amino acids of its amino acid sequence.

Mutations which have little effect on the DNA binding affinity of I-SceI, or will change its DNA recognition sequence are for example, but not excluding others: A36G, L40M, L40V, I41S, I41N, L43A, H91A and I123L.

In one embodiment of the invention, the homologs of LAGLIDADG endonucleases are being selected from the groups of artificial single chain LAGLIDADG endonucleases, including or not including hybrid meganucleases, homologs which can be cloned from other organisms, engineered endonucleases or optimized nucleases.

In one embodiment, the LAGLIDADG endonuclease is selected from the group comprising: I-Sce I, I-Cre I, I-Mso I, I-Ceu I, I-Dmo I, I-Ani I, PI-Sce I, I-Pfu I or homologs of any one these having at least 49%, 51%, 58%, 60%, 70%, 80%, 85%, 90%, 92%, 93%, 94%, 95%, 96%, 97%, 98% or 99% sequence identity on amino acid level.

In another embodiment the LAGLIDADG endonuclease is selected from the group comprising: I-Sce I, I-Chu I, I-Cre I, I-Dmo I, I-Csm I, PI-Sce I, PI-Pfu I, PI-Tli I, PI-Mtu I, and I-Ceu I and homologs of any one these having at least 49%, 51%, 58%, 60%, 70%, 80%, 85%, 90%, 92%, 93%, 94%, 95%, 96%, 97%, 98% or 99% sequence identity on amino acid level.

TABLE 1

Exemplary homologs of I-SceI, which can be cloned from other organisms.

| Uni-Prot Accession Nr. | Organism | SEQ ID NO: | Amino Acid Sequence Identity to I-SceI |
|---|---|---|---|
| A7LCP1 | S. cerevisiae | 1 | 100 |
| Q36760 | S. cerevisiae | 122 | 98 |
| O63264 | Z. bisporus | 123 | 72 |
| Q34839 | K. thermotolerans | 124 | 71 |
| Q34807 | P. canadensis | 125 | 58 |

TABLE 2

Exemplary homologs of I-CreI, which can be cloned from other organisms.

| Uni-Prot Accession Nr. | Organism | SEQ ID NO: | Amino Acid Sequence Identity to I-CreI |
|---|---|---|---|
| P05725 | C. reinhardtii | 126 | 100 |
| Q8SMM1 | C. lunzensis | 127 | 56 |
| Q8SML7 | C. olivieri | 128 | 58 |
| Q1KVQ8 | S. obliquus | 129 | 49 |

TABLE 3

Exemplary homologs of PI-SceI, which can be cloned from other organisms.

| Uni-Prot Accession Nr. | Organism | SEQ ID NO: | Amino Acid Sequence Identity to PI-SceI |
|---|---|---|---|
| P17255 | S. cerevisiae | 145 | 100 |
| Q874G9 | S. cerevisiae | 146 | 99 |
| Q874F9 | S. pastorianus | 147 | 97 |

TABLE 3-continued

Exemplary homologs of PI-SceI, which can be cloned from other organisms.

| Uni-Prot Accession Nr. | Organism | SEQ ID NO: | Amino Acid Sequence Identity to PI-SceI |
|---|---|---|---|
| Q8J0H1 | S. cariocanus | 148 | 87 |
| Q8J0G4 | Z. bailii | 149 | 61 |

TABLE 4

Exemplary homologs of I-CeuI, which can be cloned from other organisms.

| Uni-Prot Accession Nr. | Organism | SEQ ID NO: | Amino Acid Sequence Identity to I-CeuI |
|---|---|---|---|
| P32761 | C. moewusii | 131 | 100% |
| Q8WKZ1 | C. echinozygotum | 132 | 63% |
| Q8WL12 | C. elongatum | 133 | 58% |
| Q8WL11 | A. stipitatus | 134 | 55% |
| Q8WKX7 | C. monadina | 135 | 51% |

TABLE 5

Exemplary homologs of I-ChuI, which can be cloned from other organisms are described in Table 1;

| Uni-Prot Accession Nr. | Organism | SEQ ID NO: | Amino Acid Sequence Identity to I-CeuI |
|---|---|---|---|
| Q53X18 | C. humicola | 136 | 100% |
| Q8WL03 | C. zebra | 137 | 67% |
| Q8WKX6 | C. monadina | 138 | 62% |
| Q8WL10 | A. stipitatus | 139 | 58% |
| Q8SMI6 | N. aquatica | 140 | 54% |

TABLE 6

Exemplary homologs of I-DmoI, which can be cloned from other organisms.

| Uni-Prot Accession Nr. | Organism | SEQ ID NO: | Amino Acid Sequence Identity to I-CeuI |
|---|---|---|---|
| P21505 | D. mobilis | 141 | 100% |
| Q6L6Z4 | Thermoproteus sp. | 142 | 51% |
| Q6L6Z5 | Thermoproteus sp. | 143 | 50% |
| A3MXB6 | P. calidifontis | 144 | 49% |

Homologs of endonucleases, which are cloned from other organisms might have a different enzymatic activity, DNA-binding-affinity, dimer formation affinity or changes in its DNA recognition sequence, when compared to the reference endonucleases, like I-SceI (SEQ ID NO: 1) for homologs described in Table 1, I-CreI (SEQ ID NO: 126) for homologs described in Table 2, PI-Sce I (SEQ ID NO: 145) for homologs described in Table 3, I-CeuI (SEQ ID NO: 131) for homologs described in Table 4, I-ChuI (SEQ ID NO: 136) for homologs described in Table 5, or I-DmoI (SEQ ID NO: 141) for homologs described in Table 6. The I-MsoI homolog described by SEQ ID NO: 151, might have a different enzymatic activity, DNA-binding-affinity, dimer formation affinity or changes in its DNA recognition sequence, when compared to the reference endonuclease of I-MsoI as described by SEQ ID NO: 150. Another preferred endonulcease is I-AniI (SEQ ID NO: 161), preferably comprising the activity enhancing mutations: F13Y and S111Y, or F13Y, S111Y and K222R, or F13Y, 155V, F91I, S92T and S111Y.

Accordingly, in one embodiment of the invention the chimeric endonuclease comprises at least one LAGLIDADG endonuclease comprising an amino acid sequence having at least 80%, 81%, 82%, 83%, 84%, 85%, 86%, 87%, 88%, 89%, 90%, 91%, 92%, 93%, 94%, 95%, 96%, 97%, 98% or 99% amino acid sequence identity to a polypeptide described by any one of SEQ ID NOs: 1, 2, 3, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 161 or 165.

In another embodiment of the invention the chimeric endonuclease comprises at least one LAGLIDADG endonuclease comprising an amino acid sequence having at least 80%, 81%, 82%, 83%, 84%, 85%, 86%, 87%, 88%, 89%, 90%, 91%, 92%, 93%, 94%, 95%, 96%, 97%, 98% or 99% amino acid sequence identity to a polypeptide described by any one of SEQ ID NOs: 126, 127, 128, 129, or 130.

In another embodiment of the invention the chimeric endonuclease comprises at least one LAGLIDADG endonuclease comprising an amino acid sequence having at least 80%, 81%, 82%, 83%, 84%, 85%, 86%, 87%, 88%, 89%, 90%, 91%, 92%, 93%, 94%, 95%, 96%, 97%, 98% or 99% amino acid sequence identity to a polypeptide described by any one of SEQ ID NOs: 131, 132, 133, 134 or 135.

In another embodiment of the invention the chimeric endonuclease comprises at least one LAGLIDADG endonuclease comprising an amino acid sequence having at least 80%, 81%, 82%, 83%, 84%, 85%, 86%, 87%, 88%, 89%, 90%, 91%, 92%, 93%, 94%, 95%, 96%, 97%, 98% or 99% amino acid sequence identity to a polypeptide described by any one of SEQ ID NOs: 136, 137, 138, 139 or 140.

In another embodiment of the invention the chimeric endonuclease comprises at least one LAGLIDADG endonuclease comprising an amino acid sequence having at least 80%, 81%, 82%, 83%, 84%, 85%, 86%, 87%, 88%, 89%, 90%, 91%, 92%, 93%, 94%, 95%, 96%, 97%, 98% or 99% amino acid sequence identity to a polypeptide described by any one of SEQ ID NOs: 141, 142, 143, or 144.

In another embodiment of the invention the chimeric endonuclease comprises at least one LAGLIDADG endonuclease comprising an amino acid sequence having at least 80%, 81%, 82%, 83%, 84%, 85%, 86%, 87%, 88%, 89%, 90%, 91%, 92%, 93%, 94%, 95%, 96%, 97%, 98% or 99% amino acid sequence identity to a polypeptide described by any one of SEQ ID NOs: 145, 146, 147, 148 or 149.

In another embodiment of the invention the chimeric endonuclease comprises at least one LAGLIDADG endonuclease comprising an amino acid sequence having at least 80%, 81%, 82%, 83%, 84%, 85%, 86%, 87%, 88%, 89%, 90%, 91%, 92%, 93%, 94%, 95%, 96%, 97%, 98% or 99% amino acid sequence identity to a polypeptide described by any one of SEQ ID NOs: 150 or 151.

In another embodiment of the invention the chimeric endonuclease comprises at least one LAGLIDADG endonuclease comprising an amino acid sequence having at least 80%, 81%, 82%, 83%, 84%, 85%, 86%, 87%, 88%, 89%, 90%, 91%, 92%, 93%, 94%, 95%, 96%, 97%, 98% or 99% amino acid sequence identity to a polypeptide described by any one of SEQ ID NOs: 161, preferably comprising the activity enhancing mutations: F13Y and S111Y, or F13Y, S111Y and K222R, or F13Y, 155V, F91I, S92T and S111Y.

In another embodiment of the invention the chimeric endonuclease comprises at least one LAGLIDADG endonuclease comprising an amino acid sequence having at least 80% amino acid sequence identity to a poly-peptide described by SEQ ID NO: 1, 2, 3 or 165.

Preferred are LAGLIDADG endonucleases for which exact protein crystal structures have been determined, like I-Dmo I, H-Dre I, I-Sce I, I-Cre I, and homologs of any one these having at least 49%, 51%, 58%, 60%, 70%, 80%, 85%, 90%, 92%, 93%, 94%, 95%, 96%, 97%, 98% or 99% sequence identity on amino acid level and which can easily be modeled on crystal structures of I-Dmo I, H-Dre I, I-Sce I, I-Cre I. One example, of an endonuclease, which can be modeled on the crystal structure of I-Cre I, is I-Mso I (Chevalier et al., Flexible DNA Target Site Recognition by Divergent Homing Endonuclease Isoschizomers I-CreI and I-MsoI, J. Mol. Biol. (2003) 329, pages 253-269).

Another way to create homologs of LAGLIDADG endonucleases is to mutate the amino acid sequence of a LAGLIDADG endonuclease in order to modify its DNA binding affinity, its dimer formation affinity or to change its DNA recognition sequence.

Homologs of LAGLIDADG endonucleases, which have been mutated in order to modify their DNA binding affinity, its dimer formation affinity or to change its DNA recognition sites are called engineered endonucleases.

One approach to create engineered endonucleases is to employ molecular evolution. Polynucleotides encoding a candidate endonuclease enzyme can, for example, be modulated with DNA shuffling protocols. DNA shuffling is a process of recursive recombination and mutation, performed by random fragmentation of a pool of related genes, followed by reassembly of the fragments by a polymerase chain reaction-like process. See, e.g., Stemmer (1994) Proc Natl Acad Sci USA 91:10747-10751; Stemmer (1994) Nature 370:389-391; and U.S. Pat. Nos. 5,605,793, 5,837,458, 5,830,721 and 5,811,238. Engineered endonucleases can also be created by using rational design, based on further knowledge of the crystal structure of a given endonuclease see for example Fajardo-Sanchez et al., "Computer design of obligate heterodimer meganucleases allows efficient cutting of custom DNA sequences", Nucleic Acids Research, 2008, Vol. 36, No. 7 2163-2173. The determination of protein structure as well as sequence alignments of homologs of LAGLIDADG endonucleases allows for rational choices concerning the amino acids, that can be changed to affect its enzymatic activity, its DNA-binding-affinity, its dimer formation affinity or to change its DNA recognition sequence.

Numerous examples of engineered endonucleases, as well as their respective DNA recognition sites are known in the art and are disclosed for example in: WO 2005/105989, WO 2007/034262, WO 2007/047859, WO 2007/093918, WO 2008/093249, WO 2008/102198, WO 2008/152524, WO 2009/001159, WO 2009/059195, WO 2009/076292, WO 2009/114321, or WO 2009/134714, WO 10/001189 all included herein by reference.

Engineered versions of I-SceI, I-CreI, I-MsoI and I-CeuI having an increased or decreased DNA-binding affinity are for example disclosed in WO07/047859 and WO09/076292. If not explicitly mentioned otherwise, all mutants will be named according to the amino acid numbers of the wildtype amino acid sequences of the respective endonuclease, e.g. the mutant L19 of I-SceI will have an amino acid exchange of leucine at position 19 of the wildtype I-SceI amino acid sequence, as described by SEQ ID NO: 1. The L19H mutant of I-SceI, will have a replacement of the amino acid leucine at position 19 of the wildtype I-SceI amino acid sequence with hystidine.

For example, the DNA-binding affinity of I-SceI can be increased by at least one modification corresponding to a substitution selected from the group consisting of:

(a) substitution of D201, L19, L80, L92, Y151, Y188, I191, Y199 or Y222 with H, N, Q, S, T, K or R; or (b) substitution of N15, N17, S81, H84, N94, N120, T156, N157, S159, N163, Q165, S166, N194 or S202 with K or R.

DNA-binding affinity of I-SceI can be decreased by at least one mutation corresponding to a substitution selected from the group consisting of:

(a) substitution of K20, K23, K63, K122, K148, K153, K190, K193, K195 or K223 with H, N, Q, S, T, D or E; or (b) substitution of L19, L80, L92, Y151, Y188, I191, Y199, Y222, N15, N17, S81, H84, N94, N120, T156, N157, S159, N163, Q165, S166, N194 or S202 with D or E.

Engineered versions of I-SceI, I-CreI, I-MsoI and I-CeuI having a changed DNA recognition sequence are disclosed for example in WO07/047859 and WO09/076292.

For example, an important DNA recognition site of I-SceI has the following sequence (described by SEQ ID NO: 12):

```
                                                              (SEQ ID NO: 203)
sense:          5'-T  T  A  C  C  C  T  G  T  T  A  T  C  C  C  T  A  G-3' base position:     1  2  3  4  5  6  7  8  9 10 11 12 13 14 15 16 17 18

(SEQ ID NO: 204)
antisense       3'-A  A  T  G  G  G  A  C  A  A  T  A  G  G  G  A  T  C-5'
```

The following mutations of I-SceI will change the preference for C at position 4 to A: K50

The following mutations of I-SceI will keep the preference for C at position 4: K50, CE57

The following mutations of I-SceI will change the preference for C at position 4 to G: E50, R57, K57.

The following mutations of I-SceI will change the preference for C at position 4 to T:K57, M57, Q50.

The following mutations of I-SceI will change the preference for C at position 5 to A: K48, Q102.

The following mutations of I-SceI will keep the preference for C at position 5: R48, K48, E102, E59

The following mutations of I-SceI will change the preference for C at position 5 to G: E48, K102, R102.

The following mutations of I-SceI will change the preference for C at position 5 to T: Q48, C102, L102, V102.

The following mutations of I-SceI will change the preference for C at position 6 to A: K59.

The following mutations of I-SceI will keep the preference for C at position 6: R59, K59.

The following mutations of I-SceI will change the preference for C at position 6 to G: K84, E59.

The following mutations of I-SceI will change the preference for C at position 6 to T: Q59, Y46.

The following mutations of I-SceI will change the preference for T at position 7 to A: C46, L46, V46.

The following mutations of I-SceI will change the preference for T at position 7 to C: R46, K46, E86.

The following mutations of I-SceI will change the preference for T at position 7 to G: K86, R86, E46.

The following mutations of I-SceI will keep the preference for T at position 7: K68, C86, L86, Q46*.

The following mutations of I-SceI will change the preference for G at position 8 to A: K61, S61, V61, A61, L61.

The following mutations of I-SceI will change the preference for G at position 8: E88, R61, H61.

The following mutations of I-SceI will keep the preference for G at position 8: E61, R88, K88.

The following mutations of I-SceI will change the preference for G at position 8 to T: K88, Q61, H61.

The following mutations of I-SceI will change the preference for T at position 9 to A: T98, C98, V98, L9B.

The following mutations of I-SceI will change the preference for T at position 9 to C: R98, K98.

The following mutations of I-SceI will change the preference for T at position 9 to G: E98, D98.

The following mutations of I-SceI will keep the preference for T at position 9: Q98.

The following mutations of I-SceI will change the preference for Tat position 10 to A: V96, C96, A96.

The following mutations of I-SceI will change the preference for T at position 10 to C: K96, R96.

The following mutations of I-SceI will change the preference for T at position 10 to G: D96, E96.

The following mutations of I-SceI will keep the preference for T at position 10: Q96.

The following mutations of I-SceI will keep the preference for A at position 11: C90, L90.

The following mutations of I-SceI will change the preference for A at position 11 to C: K90, R90.

The following mutations of I-SceI will change the preference for A at position 11 to G: E90.

The following mutations of I-SceI will change the preference for A at position 11 to T: Q90.

The following mutations of I-SceI will change the preference for T at position 12 to A: Q193.

The following mutations of I-SceI will change the preference for T at position 12 to C: E165, E193, D193.

The following mutations of I-SceI will change the preference for T at position 12 to G: K165, R165.

The following mutations of I-SceI will keep the preference for Tat position 12: C165, L165, C193, V193, A193, T193, S193.

The following mutations of I-SceI will change the preference for C at position 13 to A: C193, L193.

The following mutations of I-SceI will keep the preference for C at position 13: K193, R193, D192.

The following mutations of I-SceI will change the preference for C at position 13 to G: E193, D193, K163, R192.

The following mutations of I-SceI will change the preference for C at position 13 to T: Q193, C163, L163.

The following mutations of I-SceI will change the preference for C at position 14 to A: L192, C192.

The following mutations of I-SceI will keep the preference for C at position 14: E161, R192, K192.

The following mutations of I-SceI will change the preference for C at position 14 to G: K147, K161, R161, R197, D192, E192.

The following mutations of I-SceI will change the preference for C at position 14 to T: K161, Q192.

The following mutations of I-SceI will keep the preference for Cat position 15: E151.

The following mutations of I-SceI will change the preference for C at position 15 to G: K151.

The following mutations of I-SceI will change the preference for C at position 15 to T: C151, L151, K151.

The following mutations of I-SceI will keep the preference for A at position 17: N152, S152, C150, L150, V150, T150.

The following mutations of I-SceI will change the preference for A at position 17 to C: K152, K150.

The following mutations of I-SceI will change the preference for A at position 17 to G: N152, S152, D152, D150, E150.

The following mutations of I-SceI will change the preference for A at position 17 to T: Q152, Q150.

The following mutations of I-SceI will change the preference for G at position 18 to A: K155, C155.

The following mutations of I-SceI will change the preference for G at position 18: R155, K155.

The following mutations of I-SceI will keep the preference for G at position 18: E155.

The following mutations of I-SceI will change the preference for G at position 18 to T: H155, Y155.

Combinations of several mutations may enhance the effect. One example is the triple mutant W149G, D1500 and N152K, which will change the preference of I-SceI for A at position 17 to G.

In order to preserve the enzymatic activity of the LAGLIDADG endonucleases the following mutations should be avoided:

For I-Sce I: I38S, I38N, G39D, G39R, L40Q, L42R, D44E, D44G, D44H, D44S, A45E, A45D, Y46D, I47R, I47N, D144E, D145E, D145N and G146E.

for 1-CreI: Q47E, for 1-CeuI E66Q, for I-MsoI D22N, for PI-SceI mutations in D218, D229, D326 or T341.

Engineered endonuclease variants of I-AniI (SEQ ID NO: 161), having high enzymatic activity can be found in Takeuchi et al., Nucleic Acid Res. (2009), 73(3): 877 to 890. Preferred engineered endonuclease variants of I-AniI comprise the following mutations: F13Y and S111Y, or F13Y, S111Y and K222R, or F13Y, 155V, F91I, S92T and S111Y.

Mutations which alter the DNA-binding-affinity, the dimer formation affinity or change the DNA recognition sequence of a given endonuclease, e.g. a LAGLIDADG endonuclease, may be combined to create an engineered endonuclease, e.g. an engineered endonuclease based on I-SceI and having an altered DNA-binding-affinity and/or a changed DNA recognition sequence, when compared to I-SceI as described by SEQ ID NO: 1.

Optimized Nucleases:

Nucleases can be optimized for example by inserting mutations to change their DNA binding specificity, e.g to make their DNA recognition site more or less specific, or by adapting the polynucleotide sequence coding for the nuclease to the codon usage of the organism, in which the endonuclease is intended to be expressed, or by deleting alternative start codons, or by deleting cryptic polyadenylation signals or cryptic splice sites or cryptic miRNA targets from the polynucleotide sequence coding for the endonuclease.

Mutations and changes in order to create optimized nucleases may be combined with the mutations used to create engineered endonucleases, for example, a homologue of I-SceI may be an optimized nuclease as described herein, but may also comprise mutations used to alter its DNA-binding-affinity and/or change its DNA recognition sequence.

Further optimization of nucleases may enhance protein stability. Accordingly optimized nucleases do not comprise, or have a reduced number of:

a) PEST-Sequences, b) KEN-boxes c) A-boxes, d) D-boxes, or e) comprise an optimized N-terminal end for stability according to the N-end rule, f) comprise a glycin as the second N-terminal amino acid, or g) any combination of a), b), c) d), e) and f) when compared to the amino acid sequence of the non optimized nuclease.

PEST Sequences are defined as hydrophilic stretches of at least 12 amino acids length with required to contain at least one proline (P), one aspartate (D) or glutamate (E) and at least one serine (S) or threonine (T). Negatively charged amino acids are clustered within these motifs while positively charged amino acids, arginine (R), histidine (H) and lysine (K) are generally forbidden. PEST Sequences are for example described in Rechsteiner M, Rogers S W. "PEST sequences and regulation by proteolysis." Trends Biochem. Sci. 1996; 21(7), pages 267 to271. The amino acid consensus sequence of a KEN-box is: KENXXX(N/D) (SEQ ID NO: 205) The amino acid consensus sequence of a A-box is: AQRXLXXSXXXQRVL (SEQ ID NO: 206) The amino acid consensus sequence of a D-box is: RXXL (SEQ ID NO: 207)

A further way to stabilize nucleases against degradation is to optimize the amino acid sequence of the N-terminus of the respective endonuclease according to the N-end rule. Nucleases which are optimized for the expression in eucaryotes comprise either methionine, valine, glycine, threonine, serine, alanine or cysteine after the start methionine of their amino acid sequence. Nucleases which are optimized for the expression in procaryotes comprise either methionine, valine, glycine, threonine, serine, alanine, cysteine, glutamic acid, glutamine, aspartic acid, asparagine, isoleucine or histidine after the start methionine of their amino acid sequence.

Nucleases may further be optimized by deleting 50, 40, 30, 20, 10, 9, 8, 7, 6, 5, 4, 3, 2, or 1 amino acids of its amino acid sequence, without destroying its endonuclease activity. For example, in case parts of the amino acid sequence of a LAGLIDADG endonuclease is deleted, it is important to retain the LAGLIDADG endonuclease motif described above. It is preferred to delete PEST sequences or other destabilizing motifs like KEN-box, D-box and A-box. Those motifs can also be destroyed by introduction of single amino acid exchanges, e.g introduction of a positively charged amino acid (arginine, histidine and lysine) into the PEST sequence.

Another way to optimize nucleases is to add nuclear localization signals to the amino acid sequence of the nuclease. For example a nuclear localization signal as described by SEQ ID NO: 4.

Optimized nucleases may comprise a combination of the methods and features described above, e.g. they may comprise a nuclear localization signal, comprise a glycine as the second N-terminal amino acid, or a deletion at the C-terminus or a combination of these features. Examples of optimized nucleases having a combination of the methods and features described above are for example described by SEQ ID NOs: 2, 3 and 5.

In one embodiment the optimized nuclease is an optimized I-Sce-I, which does not comprise an amino acid sequence described by the sequence: HVCLLYDQWVLSPPH (SEQ ID NO: 208), LAYWFMDDGGK (SEQ ID NO: 209), KTIPNNLVENYLTPMSLAYWFMDDGGK (SEQ ID NO: 214 KPIIYIDSMSYLIFYNLIK (SEQ ID NO: 211), KLPNTISSETFLK (SEQ ID NO: 212) or TISSETFLK (SEQ ID NO: 219), or which does not comprise an amino acid sequence described by the sequence: HVCLLYDQWVLSPPH (SEQ ID NO: 208), LAYWFMDDGGK (SEQ ID NO: 209), KPIIYIDSMSYLIFYNLIK (SEQ ID NO: 211), KLPNTISSETFLK (SEQ ID NO: 212) or TISSETFLK (SEQ ID NO: 219), or which does not comprise an amino acid sequence described by the sequence: HVCLLYDQWVLSPPH (SEQ ID NO: 208), LAYWFMDDGGK (SEQ ID NO: 209), KLPNTISSETFLK (SEQ ID NO: 212) or TISSETFLK (SEQ ID NO: 219), or which does not comprise an amino acid sequence described by the sequence: LAYWFMDDGGK (SEQ ID NO: 209), KLPNTISSETFLK (SEQ ID NO: 212) or TISSETFLK (SEQ ID NO: 219), or which does not comprise an amino acid sequence described by the sequence: KLPNTISSETFLK (SEQ ID NO: 212) or TISSETFLK (SEQ ID NO: 219).

In one embodiment the optimized nuclease is I-SceI, or its homologs having at least 49%, 51%, 58%, 60%, 70%, 80%, 85%, 90%, 92%, 93%, 94%, 95%, 96%, 97%, 98% or 99% sequence identity on amino acid level in which the amino acid sequence TISSETFLK at the C-terminus of wildtype I-SceI or its homologs having at least 49%, 51%, 58%, 60%, 70%, 80%, 85%, 90%, 92%, 93%, 94%, 95%, 96%, 97%, 98% or 99% sequence identity on amino acid level and having an amino acid sequence TISSETFLK (SEQ ID NO: 219) at the C-terminus, is deleted or mutated.

The amino acid sequence TISSETFLK (SEQ ID NO: 219) may be deleted or mutated, by deleting or mutating at least 1, 2, 3, 4, 5, 6. 7, 8 or 9 amino acids of the C-terminus of wildtype I-SceI or its homologs having at least 49%, 51%, 58%, 60%, 70%, 80%, 85%, 90%, 92%, 93%, 94%, 95%, 96%, 97%, 98% or 99% sequence identity on amino acid level and having an amino acid sequence TISSETFLK (SEQ ID NO: 219) at the C-terminus.

TABLE 7

Different examples for deletions of the TISSETFLK (SEQ ID NO: 219) amino acid sequence in wildtype I-SceI

| Wildtype and optimized I-SceI | Amino Acid Sequence on C-terminus |
|---|---|
| I-SceI wildtype | TISSETFLK (SEQ ID NO: 219) |
| I-SceI-1 | TISSETFL (SEQ ID NO: 213) |
| I-SceI-2 | TISSETF (SEQ ID NO: 214) |
| I-SceI-3 | TISSET (SEQ ID NO: 215) |
| I-SceI-4 | TISSE (SEQ ID NO: 216) |
| I-SceI-5 | TISS (SEQ ID NO: 217) |
| I-SceI-6 | TIS |
| I-SceI-7 | TI |
| I-SceI-8 | T |
| I-SceI-9 | all 9 amino acids on C-terminus of wt I-SceI deleted |

Alternatively the amino acid sequence TISSETFLK (SEQ ID NO: 219) may be mutated, e.g. to the amino acid sequence: TIKSETFLK (SEQ ID NO: 37), or AIANQAFLK (SEQ ID NO: 38).

Equally preferred, is to mutate serine at position 229 of the amino acid sequence of wildtype I-SceI as disclosed in SEQ ID No. 1 (being amino acid 230 if referenced to SEQ ID No. 2) to Lys, Ala, Pro, Gly, Glu, Gln, Asp, Asn, Cys, Tyr or Thr. Thereby creating the I-SceI mutants S229K, S229A, S229P, S229G, S229E, S229Q, S229D, S229N, S229C, S229Y, or S229T (amino acids are numbered according to SEQ ID No. 1.

In another embodiment of the invention, the amino acid methionine at position 203 of the amino acid sequence of wildtype I-SceI as disclosed in SEQ ID No. 1 (being amino acid 204 if referenced to SEQ ID No. 2), is mutated to Lys, His or Arg. Thereby creating the I-SceI mutant M202K, M202H and M202R.

Preferred optimized versions of I-SceI are the deletions I-SceI-1, I-SceI-2, I-SceI-3, I-SceI-4, I-SceI-5, I-SceI-6, I-SceI-7, I-SceI-8, I-SceI-9 and the mutants S229K and S229H, S229R even more preferred are the deletions I-SceI-1, I-SceI-2, I-SceI-3, I-SceI-4, I-SceI-5, I-SceI-6 and the mutant S229K.

It is also possible to combine the deletions and mutations described above, e.g. by combining the deletion I-SceI-1 with the mutant S229K, thereby creating the amino acid sequence TIKSETFL (SEQ ID NO: 220) at the C-terminus.

It is also possible to combine the deletions and mutations described above, e.g. by combining the deletion I-SceI-1 with the mutant S229A, thereby creating the amino acid sequence TIASETFL SEQ ID NO: 221) at the C-terminus.

Further preferred optimized versions of I-SceI are the deletions I-SceI-1, I-SceI-2, I-SceI-3, I-SceI-4, I-SceI-5, I-SceI-6, I-SceI-7, I-SceI-8, I-SceI-9 or the mutants S229K and S229H, S229R, in combination with the mutation M203K, M203H, M203R. Even more preferred are the deletions I-SceI-1, I-SceI-2, I-SceI-3, I-SceI-4, I-SceI-5, I-SceI-6 or the mutant S229K in combination with the mutation M203K.

In another embodiment of the invention, the amino acids glutamine at position 75, glutamic acid at position 130, or tyrosine at position 199 of the amino acid sequence of wildtype I-SceI as disclosed in SEQ ID No. 1 (being amino acids 76, 131 and 120 if referenced to SEQ ID No. 2), are mutated to Lys, His or Arg. Thereby creating the I-SceI mutants Q75K, Q75H, Q75R, E130K, E130H, E130R, Y199K, Y199H and Y199R.

The deletions and mutations described above will also be applicable to homologs of I-SceI having at least 49%, 51%, 58%, 60%, 70%, 80%, 85%, 90%, 92%, 93%, 94%, 95%, 96%, 97%, 98% or 99% sequence identity on amino acid level and having an amino acid sequence TISSETFLK at the C-terminus.

Accordingly, in one embodiment of the invention, the optimized endonuclease, is an optimized version of I-SceI or one of its homologs having at least 49%, 51%, 58%, 60%, 70%, 80%, 85%, 90%, 92%, 93%, 94%, 95%, 96%, 97%, 98% or 99% sequence identity on amino acid level, and having one or more of the mutations or deletions selected from the group of: I-SceI-1, I-SceI-2, I-SceI-3, I-SceI-4, I-SceI-5, I-SceI-6, I-SceI-7, I-SceI-8, I-SceI-9, S229K, S229A, S229P, S229G, S229E, S229Q, S229D, S229N, S229C, S229Y, S229T, M203K, M203H, M203R, Q77K, Q77H, Q77R, E130K, E130H, E130R, Y199K, Y199H and Y199R, wherein the amino acid numbers are referenced to the amino acid sequence as described by SEQ ID NO: 1.

In a further embodiment of the invention, the optimized endonuclease, is an optimized version of I-SceI or one of its homologs having at least 49%, 51%, 58%, 60%, 70%, 80%, 85%, 90%, 92%, 93%, 94%, 95%, 96%, 97%, 98% or 99% sequence identity on amino acid level, and having one or more of the mutations or deletions selected from the group of: I-SceI-1, I-SceI-2, I-SceI-3, I-SceI-4, I-SceI-5, I-SceI-6, S229K and M203K, wherein the amino acid numbers are referenced to the amino acid sequence as described by SEQ ID NO: 1.

A particular preferred optimized endonuclease is a wild-type or engineered version of I-SceI, as described by SEQ ID NO: 1 or one of its homologs having at least 49%, 51%, 58%, 60%, 70%, 80%, 85%, 90%, 92%, 93%, 94%, 95%, 96%, 97%, 98% or 99% sequence identity on amino acid level and having one or more mutations selected from the groups of:

a) I-SceI-1, I-SceI-2, I-SceI-3, I-SceI-4, I-SceI-5, I-SceI-6, I-SceI-7, I-SceI-8 and I-SceI-9;

b) S229K, S229A, S229P, S229G, S229E, S229Q, S229D, S229N, S229C, S229Y, S229T, M203K, M203H, M203R, Q77K, Q77H, Q77R, E130K, E130H, E130R, Y199K, Y199H and Y199R;

c) a methionine, valine, glycine, threonine, serine, alanine, cysteine, glutamic acid, glutamine, aspartic acid, asparagine, isoleucine or histidine after the start methionine of their amino acid sequence; or d) a combination of one or more mutations selected from a) and b), a) and c), b) and c) or a) b) and c) above.

Heterologous DNA Binding Domains:

The chimeric endonuclease of the invention comprise at least one heterologous DNA binding domain comprising one or more $Zn_2C_6$ zinc fingers.

$Zn_2C_6$ zinc fingers form a unique group of DNA binding domains, which are more or less exclusively found in transcription factors of yeasts and fungi. They are characterized by a shared structure in which two Zinc ions are complexed by an amino acid motif described by the general formula:

(SEQ ID NO: 218)
-Cys-(X)$_2$-Cys-(X)$_6$-Cys-(X)$_{5-41}$-Cys-(X)$_2$-Cys-
(X)$_{6-8}$-Cys-, wherein Cys stands for Cysteine and X for any amino acid.

Mutational analysis of the 6 Cysteines, which are spaced by two, six, five to forty-one, two and six to eight other amino acids, has shown that all of them are necessary for complexation of the two Zinc ions, which in turn will facilitate correct folding of a cloverleaf-shaped structure. Basic residues usually predominate at the first, third, fourth, and sixth residues between the second and third cysteines. Nonconservative mutations in either of the third or the fourth of these residues frequently abolish the DNA binding capacity of this DNA binding domain. Amino acid residues between the second and third cysteines are usually basic, in particular at the first, third, fourth, and sixth position. Structural studies have shown that these basic residues frequently form contacts to the DNA. The loop region between the third and fourth Cysteine shows variability in length and sequence and is known as a variable subregion (see FIGS. 3 to 6). Mutations in the variable subregion generally show little effect, but some mutations reduce function.

In this variable subregion a proline residue is found in many cases one or two residues N-terminal to the fourth cysteine. This proline it thought to support a turn of the amino acid chain, which is necessary for correct folding, however the conserved proline is not absolutely required and can in many cases be replaced for example with leucine, glutamine, or arginine, in particular, if other prolines are present in the variable subregion.

Because of their structure, $Zn_2C_6$ zinc fingers can be easily distinguished from other zinc comprising DNA binding domains e.g. of the $C_2H_2$- or the CCHC-type, which are disclosed for example in WO07/014275, WO08/076290, WO08/076290 or WO03/062455.

$Zn_2C_6$ zinc fingers bind in the majority of cases to DNA binding sites having trinucleotides of guanine and cysteine in their core region, e.g CGG or CGA; however, other terminal trinucleotides are found in some binding sites, such as GGG or GGA, or even TCC, TCG, GCC or GCA.

Many transcription factors comprising $Zn_2C_6$ zinc fingers in or as their DNA binding domains have been described in the art, e.g. in WO 02/24865. Non limiting examples of $Zn_2C_6$ zinc finger comprising transcription factors are proteins described by SEQ ID NO: 166, 167, 168, 169, 170, 171, 172, 173, 174, 175, 176, 177, 177, 178, 179, 180, 181, 182, 183, 184 and 185.

Preferred heterologous DNA binding domains comprise transcription factors or their DNA binding domains comprising $Zn_2C_6$ zinc fingers domains, which form additional contacts via a N-terminal or C-terminal repeats of basic amino acids like argine or lysine (R or K in one letter code) and/or have the capacity to bind as monomers to DNA. Examples for those type of $Zn_2C_6$ zinc finger transcription factors are AflR, ArgR, Hap1 or Leu3.

In an preferred embodiment, the heterologous DNA binding domain of the chimeric LAGLIDADG endonuclease comprises AlcR as described by SEQ ID NO: 6 and homologs of AlcR having at least 50%, 60%, 70%, 80%, 85%, 90%, 92%, 93%, 94%, 95%, 96%, 97%, 98% or 99% of sequence identity on amino acid level.

In some embodiments of the invention it will be of advantage to use the full length sequence of the transcription factor comprising one or more $Zn_2C_6$ zinc finger or a large fragment thereof, e.g. in cases where the DNA binding activity of the transcription factor or its fragment is inducible. For Example, the DNA binding activity of AlcR is inducible by ethanol, acetaldehyde, threonine, ethylamine, propan-1-ol and butan-2-ol.

Accordingly, in one embodiment of the invention, at least one heterologous DNA binding domain of the chimeric LAGLIDADG endonuclease comprises a $Zn_2C_6$ zinc finger transcription factor, or a larger fragment thereof.

A larger fragment of $Zn_2C_6$ zinc finger transcription factor, means a fragment of at least 30%, 40%, 50%, 60%, 70%, 80%, 90%, 95%, 97% or 98% of the amino acid sequence of the wild-type $Zn_2C_6$ zinc finger transcription factor.

In one embodiment of the invention, at least one heterologous DNA binding domain of the chimeric LAGLIDADG endonuclease comprises a $Zn_2C_6$ zinc finger transcription factor having an inducible DNA binding activity.

In one embodiment of the invention, at least one heterologous DNA binding domain of the chimeric LAGLIDADG endonuclease comprises AlcR, AflR, Hap1, Leu3, or a homolog of any one of these having at least 50%, 60%, 70%, 80%, 85%, 90%, 92%, 93%, 94%, 95%, 96%, 97%, 98% or 99% of sequence identity on amino acid level.

In one embodiment of the invention, at least one heterologous DNA binding domain of the chimeric LAGLIDADG endonuclease comprises a larger fragment of AlcR, AflR, Hap1, Leu3, or a homolog of any one of these having at least 50%, 60%, 70%, 80%, 85%, 90%, 92%, 93%, 94%, 95%, 96%, 97%, 98% or 99% of sequence identity on amino acid level.

However, in other cases it will be preferable to use one or several small heterologous DNA binding domains. Accordingly in one embodiment of the invention, the heterologous DNA binding domain comprises more or less only the DNA binding domain of a $Zn_2C_6$ zinc finger comprising transcription factor i.e. a DNA binding domain fragment.

Accordingly, in an equally preferred embodiment, the heterologous DNA binding domain of the chimeric LAGLIDADG endonuclease comprises a DNA binding domain fragment of AlcR (AlcR 1 to 60) as described by SEQ ID NO: 70 and homologs of AlcR (1-60) having at least 50%, 60%, 70%, 80%, 85%, 90%, 92%, 93%, 94%, 95%, 96%, 97%, 98% or 99% of sequence identity on amino acid level.

Figure 3:
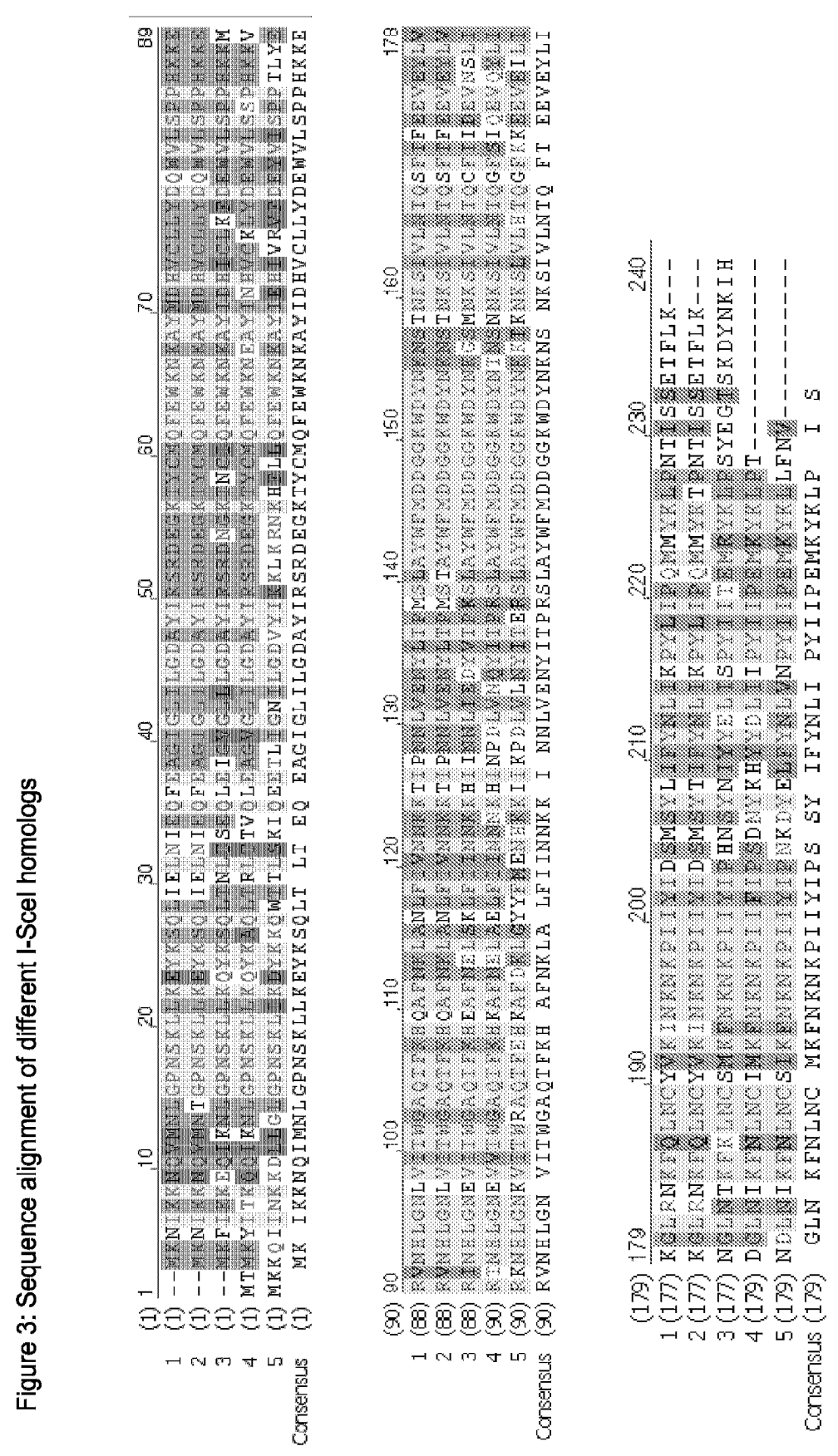

The DNA binding domain fragment of AlcR belongs to a group of homologs, which can be described by the consensus sequence shown in FIG. 3. Exemplary members of this group comprise an amino acid sequence as described by any one of SEQ ID NOs: 71, 72, 73, 74, 75, 76, 77, 78, 79, 80, 81, 82, 83, 84, 85, 86, 87, 88, 89, 90, 91, 92, 93 and 94.

Figure 5B:
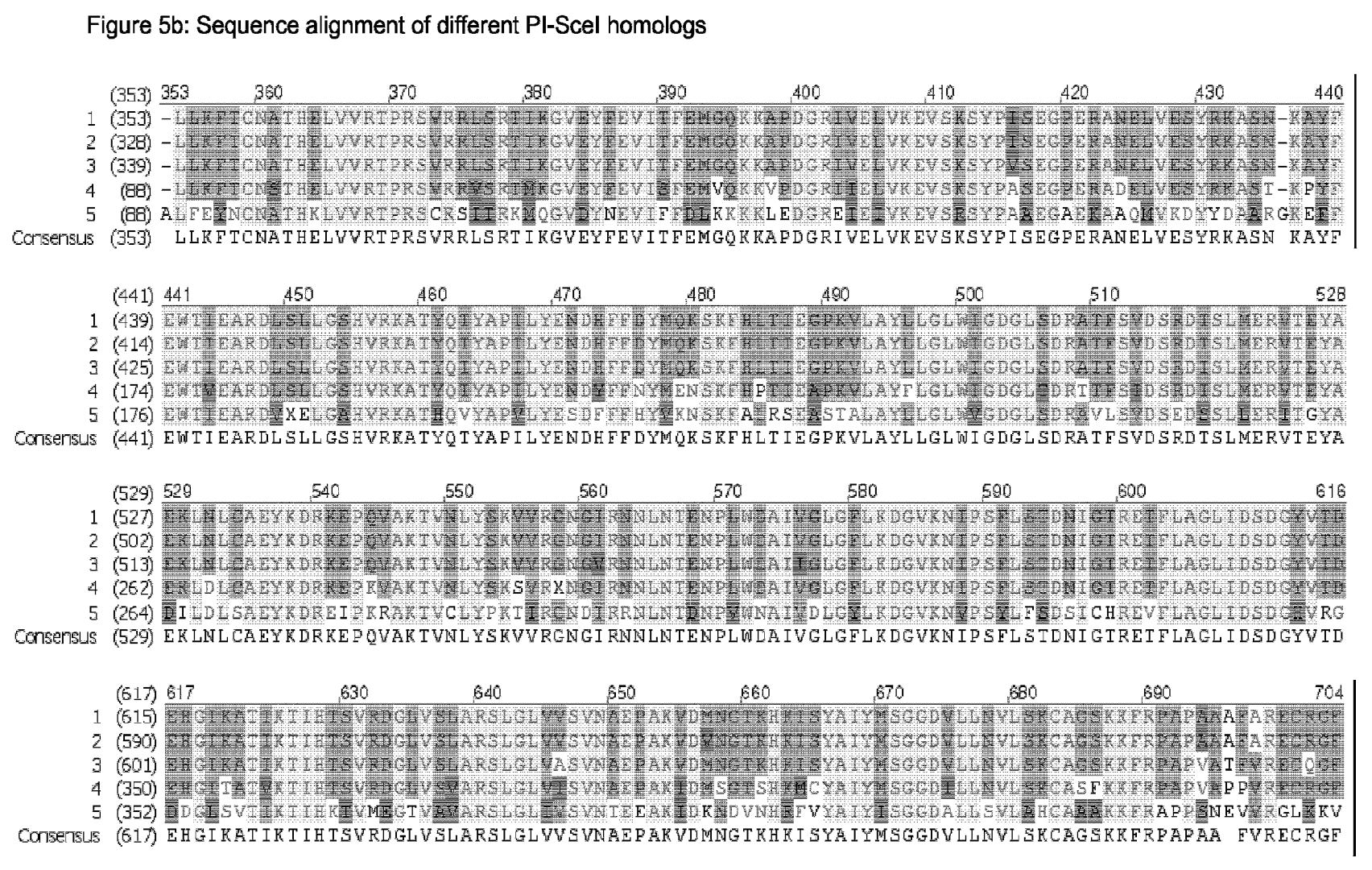

Further DNA binding domain fragments of $Zn_2C_6$ zinc finger comprising transcription factors, as well as their consensus sequences are described by FIGS. 4, 5 and 6.

Accordingly in another embodiment of the invention, the heterologous DNA binding domain of the chimeric LAGLIDADG endonuclease comprises an amino acid sequence selected from the group of sequences described by SEQ ID NO: 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120 and 121 or homologs of any one of these having at least 50%, 60%, 70%, 80%, 85%, 90%, 92%, 93%, 94%, 95%, 96%, 97%, 98% or 99% of sequence identity on amino acid level.

In an preferred embodiment, the chimeric endonuclease comprises a heterologous DNA binding domain comprising at least one polypeptide having at least 80%, 81%, 82%, 83%, 84%, 85%, 86%, 87%, 88%, 89%, 90%, 91%, 92%, 93%, 94%, 95%, 96%, 97%, 98%, 99% amino acid sequence identity to a polypeptide described by any one of SEQ ID NOs: 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120 or 121.

In another preferred embodiment, the chimeric endonuclease comprises a heterologous DNA binding domain comprising at least one polypeptide having at least 80%, 81%, 82%, 83%, 84%, 85%, 86%, 87%, 88%, 89%, 90%, 91%, 92%, 93%, 94%, 95%, 96%, 97%, 98%, 99% amino acid sequence identity to a polypeptide described by any one of SEQ ID NOs: 57, 58, 59, 60, 61, 62, 63, 64, 65, 66, 67, 68 or 69.

In another preferred embodiment, the chimeric endonuclease comprises a heterologous DNA binding domain comprising at least one polypeptide having at least 80%, 81%, 82%, 83%, 84%, 85%, 86%, 87%, 88%, 89%, 90%, 91%, 92%, 93%, 94%, 95%, 96%, 97%, 98%, 99% amino acid sequence identity to a polypeptide described by any one of SEQ ID NOs: 70, 71, 72, 73, 74, 75, 76, 77, 78, 79, 80, 81, 82, 83, 84, 85, 86, 87, 88, 89, 90, 91, 92, 93 or 94.

In another preferred embodiment, the chimeric endonuclease comprises a heterologous DNA binding domain comprising at least one polypeptide having at least 80%, 81%, 82%, 83%, 84%, 85%, 86%, 87%, 88%, 89%, 90%, 91%, 92%, 93%, 94%, 95%, 96%, 97%, 98%, 99% amino acid sequence identity to a polypeptide described by any one of SEQ ID NOs: 95, 96, 97, 98, 99, 100, 101, 102, 103, 104, 105, 106 or 107.

In another preferred embodiment, the chimeric endonuclease comprises a heterologous DNA binding domain comprising at least one polypeptide having at least 80%, 81%, 82%, 83%, 84%, 85%, 86%, 87%, 88%, 89%, 90%, 91%, 92%, 93%, 94%, 95%, 96%, 97%, 98%, 99% amino acid sequence identity to a polypeptide described by any one of SEQ ID NOs: 108, 109, 110, 111, 112, 113, 114, 115, 116, 117, 118, 119, 120 or 121.

In another preferred embodiment, the chimeric endonuclease comprises a heterologous DNA binding domain comprising at least one polypeptide having at least 80%, 81%, 82%, 83%, 84%, 85%, 86%, 87%, 88%, 89%, 90%, 91%, 92%, 93%, 94%, 95%, 96%, 97%, 98%, 99% amino acid sequence identity to a polypeptide described by any one of SEQ ID NOs: 57, 58, 59, 60, 61, 62, 63, 64, 65, 66, 67, 68, 69, 70, 71, 72, 73, 74 or 75.

In a further embodiment of the invention, the heterologous DNA-binding domain is selected from the group consisting of: AlcR, and homologs of any one these having at least 50%, 60%, 70%, 80%, 85%, 90%, 92%, at 93%, 94%, 95%, 96%, 97%, 98% or 99% of sequence identity on amino acid level, or the DNA binding domain fragment of AlcR, and homologs of any one these having at least 50%, 60%, 70%, 80%, 85%, 90%, 92%, at 93%, 94%, 95%, 96%, 97%, 98% or 99% of sequence identity on amino acid level.

A preferred DNA binding domain fragment are amino acids 1 to 60 of AlcR or its homologs having at least 50%, 60%, 70%, 80%, 85%, 90%, 92%, at 93%, 94%, 95%, 96%, 97%, 98% or 99% of sequence identity on amino acid level.

Preparation of Chimeric LAGLIDADG Endonucleases:

LAGLIDADG endonucleases and heterologous DNA binding domains can be combined in many alternative ways.

For example, it is possible, to combine more than one LAGLIDADG endonuclease with one or more heterologous DNA binding domains or to combine more than one heterologous DNA binding domain with one LAGLIDADG endonuclease. It is also possible to combine more than one LAGLIDADG endonuclease with more than one heterologous DNA binding domains.

The heterologous DNA-binding domain or the heterologous DNA-binding-domains can be fused at the N-terminal or at the C-terminal end of the LAGLIDADG endonuclease. It is also possible, to fuse one or more heterologous DNA binding domains at the N-terminal end and one or more heterologous DNA binding domains at the C-terminal end of the LAGLIDADG endonuclease. It is also possible to make alternating combinations of LAGLIDADG endonucleases and heterologous DNA binding domains.

In case the chimeric endonuclease comprises more than one LAGLIDADG endonuclease or more than one heterologous DNA binding domain, it is possible to use several copies of the same heterologous DNA binding domain or LAGLIDADG endonuclease or to use different heterologous DNA binding domains or LAGLIDADG endonucleases.

It is also possible to apply the methods and features described for optimized nucleases above, to the full sequence of chimeric endonucleases, e.g. by adding a nuclear localization signal to a chimeric LAGLIDADG endonuclease or by reducing the number of:
a) PEST-Sequences,
b) KEN-boxes
c) A-boxes,
d) D-boxes, or
e) comprise an optimized N-terminal end for stability according to the N-end rule,
f) comprise a glycin as the second N-terminal amino acid, or
g) any combination of a), b), c) d), e) and f). of the entire amino acid sequence of the chimeric endonuclease.

In one embodiment the chimeric LAGLIDADG endonucleases are combinations of:

I-SceI and AlcR, or I-SceI and AlcR (1 to 60), or I-CreI and AlcR, or I-CreI and AlcR (1 to 60), or I-MsoI and AlcR, or I-MsoI and AlcR (1 to 60), wherein AlcR, or AlcR (1 to 60) are fused N- or C-terminal to I-SceI, I-CreI or I-MsoI and wherein I-SceI, I-CreI, I-MsoI, AlcR, AlcR (1 to 60), include their homologs having at least 50%, 60%, 70%, 80%, 85%, 90%, 92%, at 93%, 94%, 95%, 96%, 97%, 98% or 99% of sequence identity on amino acid level.

A preferred embodiment is a N- or C-terminal fusion of AlcR or amino acids 1 to 60 of AlcR (AlcR 1 to 60) with I-SceI.

Even more preferred is a C-terminal fusion of AlcR or amino acids 1 to 60 of AlcR with I-SceI.

Preferred examples are C-terminal fusion of AlcR or amino acids 1 to 60 of AlcR with I-SceI comprising only one lysine as linker sequence, e.g as described by VC-SAH 48, 49, 50 and 51, having the amino acid sequence described by SEQ ID No: 7, 8, 8, and 10.

The chimeric endonucleases can be constructed in many ways and combinations. Examples are given by the following structure. N-terminus-LAGLIDADG endonuclease-$Zn_2C_6$ zinc finger-C-terminus, N-terminus-$Zn_2C_6$ zinc finger-LAGLIDADG endonuclease-C-terminus N-terminus-$Zn_2C_6$ zinc finger-LAGLIDADG endonuclease-$Zn_2C_6$ zinc finger-C-terminus, other combinations will be possible, wherein one chimeric endonuclease might comprise one or more $Zn_2C_6$ zinc finger at the N- or C-terminus.

In another embodiment of the invention the chimeric LAGLIDADG endonucleases have the following structure:
N-terminus-I-SceI-AlcR-C-terminus, or
N-terminus-I-SceI-AlcR (1 to 60)-C-terminus, or
N-terminus-I-CreI-AlcR-C-terminus, or
N-terminus-I-CreI-AlcR (1 to 60)-C-terminus, or
N-terminus-I-MsoI-AlcR-C-terminus, or
N-terminus-I-MsoI-AlcR (1 to 60)-C-terminus, or
N-terminus-AlcR-I-SceI-C-terminus, or
N-terminus-AlcR (1 to 60)-I-SceI-C-terminus, or
N-terminus-AlcR-I-CreI-C-terminus, or
N-terminus-AlcR (1 to 60)-I-CreI-C-terminus, or
N-terminus-AlcR-I-MsoI-C-terminus, or
N-terminus-AlcR (1 to 60)-I-MsoI-C-terminus, or The chimeric LAGLIDADG endonuclease is preferably expressed as a fusion protein with a nuclear localization sequence (NLS). This NLS sequence enables facilitated transport into the nucleus and increases the efficacy of the recombination system. A variety of NLS sequences are known to the skilled worker and described, inter alia, by Jicks G R and Raikhel N V (1995) Annu. Rev. Cell Biol. 11:155-188. Preferred for plant organisms is, for example, the NLS sequence of the SV40 large antigen. Examples are provided in WO 03/060133 included herein by reference. The NLS may be heterologous to the endonuclease and/or the DNA binding domain or may be naturally comprised within the endonuclease and/or DNA binding domain. Chimeric LAGLIDADG endonucleases having a nuclear localization signal are for example described by SEQ ID NOs: 8, 10, 50, 51, 52, 53.

In a preferred embodiment, the sequences encoding the chimeric LAGLIDADG endonucleases are modified by insertion of an intron sequence. This prevents expression of a functional enzyme in procaryotic host organisms and thereby facilitates cloning and transformations procedures (e.g., based on *E. coli* or *Agrobacterium*). In eukaryotic organisms, for example plant organisms, expression of a functional enzyme is realized, since plants are able to recognize and "splice" out introns. Preferably, introns are inserted in the homing endonucleases mentioned as preferred above (e.g., into I-SceI or I-CreI).

In another preferred embodiment, the amino acid sequences of the chimeric LAGLIDADG endonuclease can be modified by adding a Sec IV secretion signal to the N-, or C-Terminus of the chimeric LAGLIDADG endonuclease.

In a preferred embodiment the SecIV secretion signal is a SecIV secretion signal comprised in Vir proteins of *Agrobacterium*. Examples of such Sec IV secretion signals as well as methods how to apply these are disclosed in WO 01/89283, in Vergunst et al, Positive charge is an important feature of the C-terminal transport signal of the VirB/D4-translocated proteins of *Agrobacterium*, PNAS 2005, 102, 03, pages 832 to 837 included herein by reference. A Sec IV secretion signal might also be added, by adding fragments of a Vir protein or even a complete Vir protein, for example a complete VirE2 protein to a endonuclease or chimeric endonuclease, in a similar way as described in the description of WO01/38504 included herein by reference, which describes a RecA/VirE2 fusion protein.

In another preferred embodiment the amino acid sequences of the chimeric LAGLIDADG endonuclease can be modified by adding a Sec III secretion signal to the N-, or C-Terminus of the chimeric LAGLIDADG endonuclease. Suitable Sec III secretion signals are for example disclosed in WO 00/02996, included herein by reference.

In case a Sec III secretion signal is added, it can be of advantage, to express this chimeric LAGLIDADG endonuclease in a cell, which does also comprise a recombinant construct encoding parts of, or a complete functional type III secretion system, in order to overexpress or complement parts or the complete functional type III secretion system in such cell. Recombinant constructs encoding parts or a complete functional type III secretion system are for example disclosed in WO 00/02996 and WO05/085417 included herein by reference.

If a SecIV secretion signal is added to the chimeric LAGLIDADG endonuclease and the chimeric LAGLIDADG endonuclease is intended to be expressed for example in *Agrobacterium rhizogenes* or in *Agrobacterium tumefaciens*, it is of advantage to adapt the DNA sequence coding for the chimeric LAGLIDADG endonuclease to the codon usage of the expressing organism. Preferably the chimeric LAGLIDADG endonuclease does not have or has only few DNA recognition sequences in the genome of the expressing organism. It is of even greater advantage, if the selected chimeric LAGLIDADG endonuclease does not have a DNA recognition sequence or less preferred DNA recognition sequence in the *Agrobacterium* genome. In case the chimeric LAGLIDADG endonuclease is intended to be expressed in a prokaryotic organism the nuclease or chimeric nuclease encoding sequence must not have an intron.

In one embodiment the LAGLIDADG endonuclease and the heterologous DNA binding domain are connected via a linker polypeptide (linker).

Preferably the linker polypeptide consists of 1 to 30 amino acids, more preferred 1 to 20 and even more preferred 1 to 10 amino acids.

For example, the linker polypeptide can be composed of a plurality of residues selected from the group consisting of glycine, serine, threonine, cysteine, asparagine, glutamine, and proline. Preferably the linker polypeptide is designed to lack secondary structures under physiological conditions and is preferably hydrophilic. Charged or non polar residues may be included, but they may interact to form secondary structures or may reduce solubility and are therefore less preferred.

In some embodiments the linker polypeptide consists essentially of a plurality of residues selected from glycine and serine. Examples of such linkers have the amino acid sequence (in one letter code): GS, or GGS, or GSGS (SEQ ID NO: 222), or GSGSGS (SEQ ID NO: 223), or GGSGG (SEQ ID NO: 224), or GGSGGSGG (SEQ ID NO: 225), or GSGSGGSG (SEQ ID NO: 226).

In case the linker consists of at least 3 amino acids, it is preferred that the amino acid sequence of the linker polypeptide comprises at least one third Glycines or Alanines or Glycines and Alanines.

In one preferred embodiment, the linker sequence has the amino acid sequence GSGS (SEQ ID NO: 222) or GSGSGS (SEQ ID NO: 223).

Preferably the polypeptide linker is rationally designed using bioinformatic tools, capable of modeling both the LAGLIDADG endonuclease and the respective DNA recognition site, as well as the heterologous DNA-binding domain and the respective DNA binding site. Suitable bioinformatic tools are for example described in Desjarlais & Berg, (1994), PNAS, 90, 2256 to 2260 and in Desjarlais & Berg (1994), PNAS, 91, 11099 to 11103.

DNA Recognition Sequences of Chimeric Endonucleases (Chimeric Recognition Sequences):

The chimeric endonucleases bind to DNA sequences being combinations of the DNA recognition sequence of the endonuclease and the recognition sequence of the heterologous DNA binding domain. In case the chimeric endonuclease comprises more than one endonuclease or more than one heterologous DNA binding domain the DNA the chimeric endonuclease will bind to DNA sequences being a combination of the DNA recognition sequence of the endonucleases used and the DNA binding sequences of the heterologous DNA binding domains used. It is obvious, that the sequence of the DNA, which is bound by the chimeric endonuclease will reflect the order, in which the endonuclease and the heterologous DNA binding domains are combined.

Endonucleases known in the art cut a huge variety of different polynucleotide sequences. The terms DNA recognition sequence and DNA recognition site are used synonymously and refer to a polynucleotide of a particular sequence which can be bound and cut by a given endonuclease. A polynucleotide of a given sequence may therefore be a DNA recognition sequence or DNA recognition site for one endonuclease, but may or may not be a DNA recognition sequence or DNA recognition site for another endonuclease.

Examples of polynucleotide sequences which can be bound and cut by endonucleases, i.e. which represent a DNA recognition sequence or DNA recognition site for this endonuclease, are described in Table 8: "A" indicates the cleavage site of the sequence specific DNA-endonuclease within a DNA recognition sequence, the letter N represents any nucleotide, and can be replaced by A, T, G or C).

TABLE 8

| Endo-nuclease | Organism of origin | DNA recognition sequence |
|---|---|---|
| I-CreI | Chlamydomonas reinhardtii | 5'-CAAAACGTCGTGAGACAGTTTC-3' (SEQ ID NO: 157) |
| I-CeuI | Chlamydomonas eugametos | 5'-ATAACGGTCCTAAGGTAGCGAA-3' (SEQ ID NO: 158) |
| I-DmoI | Desulfurococcus mobilis | 5'-ATGCCTTGCCGGGTAAGTTCCGGCGCGCAT-3' (SEQ ID NO: 159) |
| I-MsoI | Monomastix spec. | 5'-CAGAACGTCGTGAGACAGTTCC-3' (SEQ ID NO: 162) |
| PI-SceI | S. cerevisiae | 5'-ATCTATGTCGGGTGCGGAGAAAGAGGTAAT-3' (SEQ ID NO: 163) |
| I-AniI | Emericella nidulans (former Aspergillus nidulans) | 5'-GCGCGCTGAGGAGGTTTCTCTGTAAAGCGCA-3' (SEQ ID NO: 160) |

Endonucleases do not have stringently-defined DNA recognition sequences, so that single base changes do not abolish cleavage but may reduce its efficiency to variable extents. A DNA recognition sequence listed herein for a given endonuclease represents only one site that is known to be recognized and cleaved.

Examples for deviations of a DNA recognition site are for example disclosed in Chevelier et al. (2003), J. Mol. Biol. 329, 253 to 269, in Marcaida et al. (2008), PNAS, 105 (44), 16888 to 16893 and in the Supporting Information to Marcaida et al. 10.1073/pnas.0804795105, in Doyon et al. (2006), J. AM. CHEM. SOC. 128, 2477 to 2484, in Argast et al, (1998), J. Mol. Biol. 280, 345 to 353, in Spiegel et al. (2006), Structure, 14, 869 to 880, in Posey et al. (2004), Nucl. Acids Res. 32 (13), 3947 to 3956, or in Chen et al. (2009), Protein Engineering, Design & Selection, 22 (4), 249 to 256.

It is therefore possible to identify a naturally occurring endonuclease having a predetermined polynucleotide sequence as a DNA recognition sequence.

Methods to identify naturally occurring endonucleases, their genes and their DNA recognition sequences are disclosed for example in WO 2009/101625.

The cleavage specificity or respectively its degeneration of its DNA recognition sequence can be tested by testing its activity on different substrates. Suitable in vivo techniques are for example disclosed in WO009074873.

Alternatively, in vitro tests can be used, for example by employing labeled polynucleotides spotted on arrays, wherein different spots comprise essentially only polynucleotides of a particular sequence, which differs from the polynucleotides of different spots and which may or may not be DNA recognition sequences of the endonuclease to be tested for its activity. A similar technique is disclosed for example in US 2009/0197775.

However, it is possible to mutate the amino acid sequence of a given LAGLIDADG endonuclease, to bind and cut new polynucleotides, i.e. creating an engineered endonuclease having a changed DNA recognition site.

Numerous examples DNA recognition sites of engineered endonucleases are known in the art and are disclosed for example in WO 2005/105989, WO 2007/034262, WO 2007/047859, WO 2007/093918, WO 2008/093249, WO 2008/102198, WO 2008/152524, WO 2009/001159, WO 2009/059195, WO 2009/076292, WO 2009/114321, or WO 2009/134714 WO 10/001189, and WO 10/009147.

Therefore it is also possible to create an engineered endonuclease which will have a DNA recognition sequence identical to a particular predetermined polynucleotide sequence.

Preferably the DNA recognition sequence of the endonuclease and the operator sequence are separated by 1, 2, 3, 4, 5, 6, 7, 8, 9, 10 or more base pairs. Preferably they are separated by 1 to 10, 1 to 8, 1 to 6, 1 to 4, 1 to 3, or 2 base pairs.

The amount of base pairs used to separate the DNA recognition sequence of the nuclease and the recognition sequence of the heterologous DNA binding domain depends on the distance of the DNA binding regions of the nuclease and the DNA binding region of the heterologous DNA binding domain in the chimeric endonuclease. A larger distance between the DNA binding regions of the nuclease and the DNA binding region of the heterologous DNA binding domain will be reflected by a higher amount of base pairs separating the DNA recognition sequence of the nuclease and the recognition sequence of the heterologous DNA binding domain. The optimal amount of separating base pairs can be determined by using computer models or by testing the binding and cutting efficiency of a given chimeric endonuclease on several polynucleotides comprising a varying amount of base pairs between the DNA recognition sequence of the nuclease and the recognition sequence of the heterologous DNA binding domain.

Examples for DNA recognition sequences of chimeric endonucleases (chimeric recognition site or target site of the respective chimeric endonuclease) are:

A chimeric endonuclease having the structure: I-SceI-AlcR or I-SceI AlcR (1 to 60), preferably having an amino acid sequence described by SEQ ID NO: 7, 8, 9, 10, 50, 51, 52 and 53.

(SEQ ID NO: 13)
I-SceI AlcR          cgtgcggatctagggataacagggtaat
or
I-SceI AlcR (1 to 60) target site 1

```
                                                            (SEQ ID NO: 14)
I-SceI AlcR                         cgtgcggatcctagggataacagggtaat
or
I-SceI AlcR (1 to 60) target site 2

(SEQ ID NO: 15)
I-SceI AlcR                         cgtgcggatcgctagggataacagggtaat
or
I-SceI AlcR (1 to 60) target site 3

(SEQ ID NO: 16)
I-SceI AlcR                         cgtgcggatccgctagggataacagggtaat
or
I-SceI AlcR (1 to 60) target site 4
```

A chimeric endonuclease having the structure: AlcR (1 to 60)-I-SceI, preferably having an amino acid sequence described by SEQ ID NO: 54, 55 and 56

```
                                                            (SEQ ID NO: 43)
AlcR (1-60) I-SceI   cgtgcggatcattaccctgttatcccta
or
AlcR-I-SceI target
site 1
                                                            (SEQ ID NO: 44)
AlcR (1-60) I-SceI   cgtgcggatcnattaccctgttatcccta
or
AlcR-I-SceI target
site 2
                                                            (SEQ ID NO: 45)
AlcR (1-60) I-SceI   cgtgcggatcnnattaccctgttatcccta
or
AlcR-I-SceI target
site 3
                                                            (SEQ ID NO: 46)
AlcR (1-60) I-SceI   cgtgcggatcnnnattaccctgttatcccta
or
AlcR-I-SceI target
site 4
```

Examples of recognition sequences of heterologous DNA binding domains are:

```
    AlcR and AlcR (1-60)    5'-WGCGG-3'

(SEQ ID NO: 164)
    AflR                    5'-TCGNNNNNCGA-3'

Hap1                    5'-CGGNNNTA-3'

Leu3                    5'-RGCCG-3'
``` wherein A stands for adenine, G for guanine, C for cytosine, T for thymine, W for adenine or thymine, R for guanine or adenine and N for adenine or guanine or cytosine or thymine.

$Zn_2C_6$ zinc finger domains homologous to the $Zn_2C_6$ zinc finger domains of AlcR, AflR, Hap1, Leu3 comprising transcription factors and fragments thereof comprising the $Zn_2C_6$ zinc fingers will bind to the same or very similar binding sites, like AlcR (1-60) binds to the same or similar recogntition sequences as AlcR.

Polynucleotides:

The invention does also comprise isolated polynucleotides coding for the chimeric endonucleases described above.

Examples of such isolated polynucleotides are isolated polynucleotides coding for amino acid sequences described by SEQ ID NO: 2, 3, 5, 7, 8, 9, 10, 50, 51, 52, 53, 54, 55, and 56 or amino acid sequences having at least 70%, 80%, 90% 91%, 92%, 93%, 94%, 95%, 96%, 97%, 98% or 99% amino acid sequence similarity, preferably having at least 70%, 80%, 90% 91%, 92%, 93%, 94%, 95%, 96%, 97%, 98% or 99% amino acid sequence identity to any one of the amino acid sequences described by SEQ ID NO: 2, 3, 5, 7, 8, 9, 10, 50, 51, 52, 53, 54, 55 and 56.

Preferably the isolated polynucleotide has a optimized codon usage for expression in a particular host organism, or has a low content of RNA instability motifs, or has a low content of codon repeats, or has a low contend of cryptic splice sites, or has a low contend of cryptic polyA sites, or has a low contend of cryptic miRNA targets, or has a low content of alternative start codons, or has a low content of restriction sites, or has a low content of RNA secondary structures or has any combination of these features.

The codon usage of the isolated polypeptide may be optimized e.g. for the expression in plants, preferably in a plant selected from the group comprising: rice, corn, wheat, rape seed, sugar cane, sunflower, sugar beet, tobacco.

Preferably the isolated polynucleotide is combined with a promoter sequence and a terminator sequence suitable to form a functional expression cassette for expression of the chimeric endonuclease in a particular host organism.

Suitable promoters are for example constitutive, heat- or pathogen-inducible, or seed, pollen, flower or fruit specific promoters.

The person skilled in the art knows numerous promoters having those features.

For example several constitutive promoters in plants are known. Most of them are derived from viral or bacterial sources such as the nopaline synthase (nos) promoter (Shaw et al. (1984) Nucleic Acids Res. 12 (20): 7831-7846), the mannopine synthase (mas) promoter (Co-mai et al. (1990) Plant Mol Biol 15(3):373-381), or the octopine synthase (ocs) pro-moter (Leisner and Gelvin (1988) Proc Natl Acad Sci USA 85 (5):2553-2557) from *Agrobacterium tumefaciens* or the CaMV35S promote from the Cauliflower Mosaic Vi-rus (U.S. Pat. No. 5,352,605). The latter was most frequently used in constitutive expression of transgenes in plants (Odell et al. (1985) Nature 313:810-812; Battraw and Hall (1990) Plant Mol Biol 15:527-538; Benfey et al. (1990) EMBO J 9(69):1677-1684; U.S. Pat. No. 5,612,472). However, the CaMV 35S promoter demonstrates variability not only in dif-ferent plant species but also in different plant tissues (Atanassova et al. (1998) Plant Mol Biol 37:275-85; Battraw and Hall (1990) Plant Mol Biol 15:527-538; Holtorf et al. (1995) Plant Mol Biol 29:637-646; Jefferson et al. (1987) EMBO J 6:3901-3907). An additional disadvantage is an interference of the transcription regulating activity of the 35S promoter with wild-type CaMV virus (Al-Kaff et al. (2000) Nature Biotechnology 18:995-99). Another viral promoter for constitutive expression is the Sugarcane bacilliform badnavirus (ScBV) promoter (Schenk et al. (1999) Plant Mol Biol 39 (6):1221-1230).

Several plant constitutive promoters are described such as the ubiquitin promoter from *Arabidopsis thaliana* (Callis et al. (1990) J Biol Chem 265:12486-12493; Holtorf S et al. (1995) Plant Mol Biol 29:637-747), which—however—is reported to be unable to regulate expression of selection markers (WO03102198), or two maize ubiquitin promoter (Ubi-1 and Ubi-2; U.S. Pat. Nos. 5,510,474; 6,020,190; 6,054,574), which beside a constitutive expression profile demonstrate a heat-shock induction (Christensen et al. (1992) Plant. Mol. Biol. 18(4):675-689). A comparison of specificity and expression level of the CaMV 35S, the barley thionine promoter, and the *Arabidopsis* ubiquitin promoter based on stably transformed *Arabidopsis* plants demonstrates a high expression rate for the CaMV 35S promoter, while the thionine promoter was inactive in most lines and the ubi1 promoter from *Arabisopsis* resulted only in moderate expression activity (Holtorf et al. (1995) Plant Mol Biol 29 (4):637-6469).

Chimeric Recognition Sequences:

The invention does also comprise isolated polynucleotides comprising a chimeric recognition sequence, having a length of about 15 to about 300, or of about 20 to about 200 or of about 25 to about 100 nucleotides, comprising a recognition sequence of an endonuclease and a recognition sequence of a heterologous DNA binding domain.

Preferably isolated polynucleotides comprise a DNA recognition sequence of a homing endonuclease, preferably of a LAGLIDADG endonuclease.

In one embodiment the isolated polynucleotide comprises a DNA recognition sequence of I-SceI.

Preferably the recognition sequence of a heterologous DNA binding domain comprised in the isolated polynucleotide is a recognition sequence of a transcription factor.

More preferably the recognition sequence is the recognition sequence of the transcription factors scTet, scArc or AlcR.

In one embodiment the isolated polynucleotide comprises a DNA recognition sequence of I-SceI and a linker sequence of 0 to 10 polynucleotides and a recognition sequence of scTet, scArc or AlcR.

In one embodiment the isolated polynucleotide comprise a sequence of a DNA recognition site or a chimeric recognition site selected from the group comprising: SEQ ID NO: 13, 14, 15, 16, 26, 27, 28, 29, 33, 34, 35, 36, 43, 44, 45 and 46.

The isolated polynucleotides may comprise a combination of a chimeric recognition site and a polynucleotide sequence coding for a chimeric nuclease.

Vectors:

The polynucleotides described above may be comprised in a DNA vector suitable for transformation, transfection, cloning or overexpression.

In one example, the polynucleotides described above are comprised in a vector for transformation of non-human organisms or cells, preferably the non-human organisms are plants or plant cells.

The vectors of the invention usually comprise further functional elements, which may include but shall not be limited to:

i) Origins of replication which ensure replication of the expression cassettes or vectors according to the invention in, for example, *E. coli*. Examples which may be mentioned are ORI (origin of DNA replication), the pBR322 on or the P15A on (Sam-brook et al.: Molecular Cloning. A Laboratory Manual, 2nd ed. Cold Spring Harbor Laboratory Press, Cold Spring Harbor, N.Y., 1989)

ii) Multiple cloning sites (MCS) to enable and facilitate the insertion of one or more nucleic acid sequences.

iii) Sequences which make possible homologous recombination or insertion into the genome of a host organism.

iv) Elements, for example border sequences, which make possible the *Agrobacterium*-mediated transfer in plant cells for the transfer and integration into the plant genome, such as, for example, the right or left border of the T-DNA or the vir region.

The Marker Sequence

The term "marker sequence" is to be understood in the broad sense to include all nucleotide sequences (and/or polypeptide sequences translated therefrom) which facilitate detection, identification, or selection of transformed cells, tissues or organism (e.g., plants). The terms "sequence allowing selection of a transformed plant material", "selection marker" or "selection marker gene" or "selection marker protein" or "marker" have essentially the same meaning.

Markers may include (but are not limited to) selectable marker and screenable marker. A selectable marker confers to the cell or organism a phenotype resulting in a growth or viability difference. The selectable marker may interact with a selection agent (such as a herbicide or antibiotic or pro-drug) to bring about this phenotype. A screenable marker confers to the cell or organism a readily detectable phenotype, preferably a visibly detectable phenotype such a color or staining. The screenable marker may interact with a screening agent (such as a dye) to bring about this phenotype.

Selectable marker (or selectable marker sequences) comprise but are not limited to a) negative selection marker, which confers resistance against one or more toxic (in case of plants phytotoxic) agents such as an antibiotica, herbicides or other biocides, b) counter selection marker, which confer a sensitivity against certain chemical compounds (e.g., by converting a non-toxic compound into a toxic compound), and c) positive selection marker, which confer a growth advantage (e.g., by expression of key elements of the cytokinin or hormone biosynthesis leading to the production of a plant hormone e.g., auxins, gibberllins, cytokinins, abscisic acid and ethylene; Ebi-numa H et al. (2000) Proc Natl Acad Sci USA 94:2117-2121).

When using negative selection markers, only cells or plants are selected which comprise said negative selection marker. When using counter selection marker, only cells or plants are selected which lack said counter-selection marker. Counter-selection marker may be employed to verify successful excision of a sequence (comprising said counter-selection marker) from a genome. Screenable marker sequences include but are not limited to reporter genes (e.g. luciferase, glucuronidase, chloramphenicol acetyl transferase (CAT, etc.). Preferred marker sequences include but shall not be limited to:

i) Negative Selection Marker

As a rule, negative selection markers are useful for selecting cells which have success-fully undergone transformation. The negative selection marker, which has been introduced with the DNA construct of the invention, may confer resistance to a biocide or phytotoxic agent (for example a herbicide such as phosphinothricin, glyphosate or bromoxynil), a metabolism inhibitor such as 2-deoxyglucose-6-phosphate (WO 98/45456) or an antibiotic such as, for example, tetracyclin, ampicillin, kanamycin, G 418, neomycin, bleomycin or hygromycin to the cells which have successfully under-gone transformation. The negative selection marker permits the selection of the trans-formed cells from untransformed cells (McCormick et al. (1986) Plant Cell Reports 5:81-84). Negative selection marker in a vector of the invention may be employed to confer resistance in more than one organism. For example a vector of the invention may comprise a selection marker for amplification in bacteria (such as E. coli or Agrobacterium) and plants. Examples of selectable markers for E. coli include: genes specifying resistance to antibiotics, i.e., ampicillin, tetracycline, kanamycin, erythromycin, or genes conferring other types of selectable enzymatic activities such as galactosidase, or the lactose operon. Suitable selectable markers for use in mammalian cells include, for example, the dihydrofolate reductase gene (DHFR), the thymidine kinase gene (TK), or prokaryotic genes conferring drug resistance, gpt (xanthine-guanine phosphoribosyltransferase, which can be selected for with mycophenolic acid; neo (neomycin phosphotransferase), which can be selected for with G418, hygromycin, or puromycin; and DHFR (dihydrofolate reductase), which can be selected for with methotrexate (Mulligan & Berg (1981) Proc Natl Acad Sci USA 78:2072; Southern & Berg (1982) J Mol Appl Genet 1: 327). Selection markers for plant cells often confer resistance to a biocide or an antibiotic, such as, for example, kanamycin, G 418, bleomycin, hygromycin, or chloramphenicol, or herbicide resistance, such as resistance to chlorsulfuron or Basta.

Especially preferred negative selection markers are those which confer resistance to herbicides.

Examples of negative selection markers are:

DNA sequences which encode phosphinothricin acetyltransferases (PAT), which acetylates the free amino group of the glutamine synthase inhibitor phosphinothricin (PPT) and thus brings about detoxification of PPT (de Block et al. (1987) EMBO J 6:2513-2518) (also referred to as Bialophos-resistance gene bar; EP 242236), 5-enolpyruvylshikimate-3-phosphate synthase genes (EPSP synthase genes), which confer resistance to Glyphosate-(N-(phosphonomethyl)glycine), the gox gene, which encodes the Glyphosate-degrading enzyme Glyphosate oxi-doreductase, the deh gene (encoding a dehalogenase which inactivates Dalapon-), acetolactate synthases which confer resistance to sulfonylurea and imidazolinone, bxn genes which encode Bromoxynil-degrading nitrilase enzymes, the kanamycin, or G418, resistance gene (NPTII). The NPTII gene encodes a neomycin phosphotransferase which reduces the inhibitory effect of kanamycin, neomycin, G418 and paromomycin owing to a phosphorylation reaction (Beck et al (1982) Gene 19: 327), the DOGR1 gene. The DOGR1 gene has been isolated from the yeast Saccharomy-ces cerevisiae (EP 0 807 836). It encodes a 2-deoxyglucose-6-phosphate phosphatase which confers resistance to 2-DOG (Randez-Gil et al. (1995) Yeast 11:1233-1240).

the hyg gene, which codes for the enzyme hygromycin phosphotransferase and confers resistance to the antibiotic hygromycin (Gritz and Davies (1983) Gene 25: 179);

especially preferred are negative selection markers that confer resistance against the toxic effects imposed by D-amino acids like e.g., D-alanine and D-serine (WO 03/060133; Erikson 2004). Especially preferred as negative selection marker in this contest are the daol gene (EC: 1.4. 3.3: GenBank Acc.-No.: U60066) from the yeast Rhodotorula gracilis (Rhodosporidium toruloides) and the E. coli gene dsdA (D-serine dehydratase (D-serine deaminase) (EC: 4.3. 1.18; GenBank Acc.-No.: J01603).

ii) Positive Selection Marker

Positive selection marker comprise but are not limited to growth stimulating selection marker genes like isopentenyltransferase from Agrobacterium tumefaciens (strain:PO22; Genbank Acc.-No.: AB025109) may—as a key enzyme of the cytokinin biosynthesis—facilitate regeneration of transformed plants (e.g., by selection on cyto-kinin-free medium). Corresponding selection methods are described (Ebinuma H et al. (2000) Proc Natl Acad Sci USA 94:2117-2121; Ebinuma H et al. (2000) Selection of Marker-free transgenic plants using the oncogenes (ipt, rol A, B, C) of Agrobacterium as selectable markers, In Molecular Biology of Woody Plants. Kluwer Academic Publishers). Additional positive selection markers, which confer a growth advantage to a transformed plant in comparison with a non-transformed one, are described e.g., in EP-A 0 601 092. Growth stimulation selection markers may include (but shall not be limited to) beta-Glucuronidase (in combination with e.g., a cytokinin glucuronide), mannose-6-phosphate isomerase (in combination with mannose), UDP-galactose-4-epimerase (in combination with e.g., galactose), wherein mannose-6-phosphate isomerase in combination with mannose is especially preferred.

iii) Counter Selection Markers

Counter-selection marker enable the selection of organisms with successfully deleted sequences (Koprek T et al. (1999) Plant J 19(6):719-726). TK thymidine kinase (TK) and diphtheria toxin A fragment (DT-A), codA gene encoding a cytosine deaminase (Gleve A P et al. (1999) Plant Mol Biol 40(2):223-35; Pereat R I et al. (1993) Plant Mol Biol 23(4):793-799; Stougaard J (1993) Plant J 3:755-761), the cytochrome P450 gene (Koprek et al. (1999) Plant J 16:719-726), genes encoding a haloalkane dehalogenase (Naested H (1999) Plant J 18:571-576), the iaaH gene (Sundaresan V et al. (1995) Genes & Development 9:1797-1810), the tms2 gene (Fedoroff N V & Smith D L (1993) Plant J 3:273-289), and D-amino acid oxidases causing toxic effects by conversion of D-amino acids (WO 03/060133).

In a preferred embodiment the excision cassette includes at least one of said counter-selection markers to distinguish plant cells or plants with successfully excised sequences from plant which still contain these. In a more preferred embodiment the excision cassette of the invention comprises a dual-function marker i.e. a marker with can be employed as both a negative and a counter selection marker depending on the substrate employed in the selection scheme. An example for a dual-function marker is the daol gene (EC: 1.4. 3.3: GenBank Acc.-No.: U60066) from the yeast Rhodotorula gracilis, which can be employed as negative selection marker with D-amino acids such as D-alanine and D-serine, and as counter-selection marker with D-amino acids such as D-isoleucine and D-valine (see European Patent Appl. No.: 04006358.8)

iv) Screenable Marker (Reporter Genes)

Screenable marker (such as reporter genes) encode readily quantifiable or detectable proteins and which, via intrinsic color or enzyme activity, ensure the assessment of the transformation efficacy or of the location or timing of expression. Especially preferred are genes encoding reporter proteins (see also Schenborn E, Groskreutz D. (1999) Mol Biotechnol 13(1):29-44) such as "green fluorescence protein" (GFP) (Chuff W L et al. (1996) Curr Biol 6:325-330; Lef-fel S M et al. (1997) Biotechniques 23(5):912-8; Sheen et al. (1995) Plant J 8(5):777-784; Haseloff et al. (1997) Proc Natl Acad Sci USA 94(6):2122-2127; Reichel et al. (1996) Proc Natl Acad Sci USA 93(12):5888-5893; Tian et al. (1997) Plant Cell Rep 16:267-271; WO 97/41228).

Chloramphenicol transferase, luciferase (Millar et al. (1992) Plant Mol Biol Rep 10:324-414; Ow et al. (1986) Science 234:856-859) permits selection by detection of bioluminescence, beta-galactosidase, encodes an enzyme for which a variety of chromogenic substrates are available, beta-glucuronidase (GUS) (Jefferson et al. (1987) EMBO J 6:3901-3907) or the uidA gene, which encodes an enzyme for a variety of chromogenic substrates, R locus gene product: protein which regulates the production of anthocyanin pig-ments (red coloration) in plant tissue and thus makes possible the direct analysis of the promoter activity without the addition of additional adjuvants or chromogenic substrates (Dellaporta et al. (1988) In: Chromosome Structure and Function: Impact of New Concepts, 18th Stadler Genetics Symposium, 11:263-282), beta-lactamase (Sutcliffe (1978) Proc Natl Acad Sci USA 75:3737-3741), enzyme for a variety of chromogenic substrates (for example PADAC, a chromogenic cephalosporin), xyIE gene product (Zukowsky et al. (1983) Proc Natl Acad Sci USA 80:1101-1105), catechol dioxygenase capable of converting chromogenic catechols, alpha-amylase (Ikuta et al. (1990) Bio/technol. 8:241-242), tyrosinase (Katz et al. (1983) J Gene Microbiol 129:2703-2714), enzyme which oxi-dizes tyrosine to give DOPA and dopaquinone which subsequently form melanine, which is readily detectable, aequorin (Prasher et al. (1985) Biochem Biophys Res Commun 126(3):1259-1268), can be used in the calcium-sensitive bioluminescence detection.

Target Organisms

Any organism suitable for transformation or delivery of chimeric endonuclease can be used as target organism. This includes prokaryotes, eukaryotes, and archaea, in particular non-human organisms, plants, fungi or yeasts, but also human or animal cells.

In one embodiment the target organism is a plant.

The term "plant" includes whole plants, shoot vegetative organs/structures (e.g. leaves, stems and tubers), roots, flowers and floral organs/structures (e.g. bracts, sepals, petals, stamens, carpels, anthers and ovules), seeds (including embryo, endosperm, and seed coat) and fruits (the mature ovary), plant tissues (e. g. vascular tissue, ground tissue, and the like) and cells (e.g. guard cells, egg cells, trichomes and the like), and progeny of same. The class of plants that can be used in the method of the invention is generally as broad as the class of higher and lower plants amenable to transformation techniques, including angiosperms (monocotyledonous and dicotyledonous plants), gymnosperms, ferns, and multicellular algae. It includes plants of a variety of ploidy levels, including aneuploid, polyploid, diploid, haploid and hemizygous.

Included within the scope of the invention are all genera and species of higher and lower plants of the plant kingdom. Included are furthermore the mature plants, seed, shoots and seedlings, and parts, propagation material (for example seeds and fruit) and cultures, for example cell cultures, derived therefrom.

Preferred are plants and plant materials of the following plant families: Amaranthaceae, Brassicaceae, Carophyllaceae, Chenopodiaceae, Compositae, Cucurbitaceae, Labiatae, Leguminosae, Papilionoideae, Liliaceae, Linaceae, Malvaceae, Rosaceae, Saxi-fragaceae, Scrophulariaceae, Solanaceae, Tetragoniaceae.

Annual, perennial, monocotyledonous and dicotyledonous plants are preferred host organisms for the generation of transgenic plants. The use of the recombination system, or method according to the invention is furthermore advantageous in all ornamental plants, useful or ornamental trees, flowers, cut flowers, shrubs or turf. Said plant may include—but shall not be limited to—bryophytes such as, for example, Hepaticae (hepaticas) and Musci (mosses); pteridophytes such as ferns, horsetail and club-mosses; gymnosperms such as conifers, cycads, ginkgo and Gnetaeae; algae such as Chlorophyceae, Phaeophpyceae, Rhodophyceae, Myxophyceae, Xanthophyceae, Bacillariophyceae (diatoms) and Euglenophyceae.

Plants for the purposes of the invention may comprise the families of the Rosaceae such as rose, Ericaceae such as rhododendrons and azaleas, Euphorbiaceae such as poinsettias and croton, Caryophyllaceae such as pinks, Solanaceae such as petunias, Gesneriaceae such as African violet, Balsaminaceae such as touch-me-not, Orchida-ceae such as orchids, lridaceae such as gladioli, iris, freesia and crocus, Compositae such as marigold, Geraniaceae such as geraniums, Liliaceae such as drachaena, Moraceae such as ficus, Araceae such as philodendron and many others.

The transgenic plants according to the invention are furthermore selected in particular from among dicotyledonous crop plants such as, for example, from the families of the Leguminosae such as pea, alfalfa and soybean; Solanaceae such as tobacco and many others; the family of the Umbelliferae, particularly the genus *Daucus* (very particularly the species *carota* (carrot)) and *Apium* (very particularly the species *graveolens* dulce (celery)) and many others; the family of the Solanaceae, particularly the genus *Lycopersicon*, very particularly the species *esculentum* (tomato) and the genus *Solanum*, very particularly the species *tuberosum* (potato) and *melongena* (au-bergine) and many others; and the genus *Capsicum*, very particularly the species *an-num* (pepper) and many others; the family of the Leguminosae, particularly the genus *Glycine*, very particularly the species *max* (soybean) and many others; and the family of the Cruciferae, particularly the genus *Brassica*, very particularly the species *napus* (oilseed rape), *campestris* (beet), *oleracea* cv Tastie (cabbage), *oleracea* cv Snowball Y (cauliflower) and *oleracea* cv Emperor (broccoli); and the genus *Arabidopsis*, very particularly the species *thaliana* and many others; the family of the Compositae, par-ticularly the genus *Lactuca*, very particularly the species *sativa* (lettuce) and many others.

The transgenic plants according to the invention are selected in particular among monocotyledonous crop plants, such as, for example, cereals such as wheat, barley, sorghum and millet, rye, triticale, maize, rice or oats, and sugar cane.

Especially preferred are *Arabidopsis thaliana, Nicotiana tabacum*, oilseed rape, soybean, corn (maize), wheat, linseed, potato and tagetes.

Plant organisms are furthermore, for the purposes of the invention, other organisms which are capable of photosynthetic activity, such as, for example, algae or cyanobacteria, and also mosses. Preferred algae are green algae, such as, for example, algae of the genus *Haematococcus, Phaedactylum tricornatum, Volvox* or *Dunaliella*.

Genetically modified plants according to the invention which can be consumed by humans or animals can also be used as food or feedstuffs, for example directly or following processing known in the art.

Construction of Polynucleotide Constructs

Typically, polynucleotide constructs (e.g., for an expression cassette) to be introduced into non-human organism or cells, e.g. plants or plant cells are prepared using transgene expression techniques. Recombinant expression techniques involve the construction of recombinant nucleic acids and the expression of genes in transfected cells. Molecular cloning techniques to achieve these ends are known in the art. A wide variety of cloning and in vitro amplification methods suitable for the construction of recombinant nucleic acids are well-known to persons of skill in the art. Examples of these techniques and instructions sufficient to direct persons of skill in the art through many cloning exercises are found in Berger and Kimmel, Guide to Molecular Cloning Techniques, Methods in Enzymology, Vol. 152, Academic Press, hic., San Diego, Calif. (Berger); Current Protocols in Molecular Biology, F. M. Ausubel et al., eds., Current Protocols, a joint venture between Greene Publish-ing Associates, Inc. and John Wiley & Sons, Inc., (1998 Supplement), T. Maniatis, E. F. Fritsch and J. Sambrook, Molecular Cloning: A Laboratory Manual, Cold Spring Harbor Laboratory, Cold Spring Harbor, N.Y. (1989), in T. J. Silhavy, M. L. Berman and L. W. Enquist, Experiments with Gene Fusions, Cold Spring Harbor Laboratory, Cold Spring Harbor, N.Y. (1984). Preferably, the DNA constructs employed in the invention are generated by joining the abovementioned essential constituents of the DNA construct together in the abovementioned sequence using the recombination and cloning techniques with which the skilled worker is familiar.

The construction of polynucleotide constructs generally requires the use of vectors able to replicate in bacteria. A plethora of kits are commercially available for the purification of plasmids from bacteria. The isolated and purified plasmids can then be further manipulated to produce other plasmids, used to transfect cells or incorporated into *Agrobacterium tumefaciens* or *Agrobacterium rhizogenes* to infect and transform plants. Where *Agrobacterium* is the means of transformation, shuttle vectors are constructed.

Methods for Introducing Constructs into Target Cells

A DNA construct employed in the invention may advantageously be introduced into cells using vectors into which said DNA construct is inserted. Examples of vectors may be plasmids, cosmids, phages, viruses, retroviruses or agrobacteria. In an advantageous embodiment, the expression cassette is introduced by means of plasmid vectors. Preferred vectors are those which enable the stable integration of the expression cassette into the host genome.

A DNA construct can be introduced into the target plant cells and/or organisms by any of the several means known to those of skill in the art, a procedure which is termed transformation (see also Keown et al. (1990) Meth Enzymol 185:527-537). For instance, the DNA constructs can be introduced into cells, either in culture or in the organs of a plant by a variety of conventional techniques. For example, the DNA constructs can be introduced directly to plant cells using ballistic methods, such as DNA particle bombardment, or the DNA construct can be introduced using techniques such as electroporation and microinjection of cells. Particle-mediated transformation techniques (also known as "biolistics") are described in, e.g., Klein et al. (1987) Nature 327:70-73; Vasil V et al. (1993) BiolTechnol 11:1553-1558; and Becker D et al. (1994) Plant J 5:299-307. These methods involve penetration of cells by small particles with the nucleic acid either within the matrix of small beads or particles, or on the surface. The biolistic PDS-1000 Gene Gun (Biorad, Hercules, Calif.) uses helium pressure to accelerate DNA-coated gold or tungsten microcarriers toward target cells. The process is applicable to a wide range of tissues and cells from organisms, including plants. Other transformation methods are also known to those of skill in the art.

Microinjection techniques are known in the art and are well described in the scientific and patent literature. Also, the cell can be permeabilized chemically, for example using polyethylene glycol, so that the DNA can enter the cell by diffusion. The DNA can also be introduced by protoplast fusion with other DNA-containing units such as minicells, cells, lysosomes or liposomes. The introduction of DNA constructs using polyethylene glycol (PEG) precipitation is described in Paszkowski et al. (1984) EMBO J 3:2717. Liposome-based gene delivery is e.g., described in WO 93/24640; Mannino and Gould-Fogerite (1988) BioTechniques 6(7):682-691; U.S. Pat. No. 5,279,833; WO 91/06309; and Feigner et al. (1987) Proc Natl Acad Sci USA 84:7413-7414).

Another suitable method of introducing DNA is electroporation, where the cells are permeabilized reversibly by an electrical pulse. Electroporation techniques are described in Fromm et al. (1985) Proc Natl Acad Sci USA 82:5824. PEG-mediated transformation and electroporation of plant protoplasts are also discussed in Lazzeri P (1995) Methods Mol Biol 49:95-106. Preferred general methods which may be mentioned are the calcium-phosphate-mediated transfection, the DEAE-dextran-mediated transfection, the cationic lipid-mediated transfection, electroporation, transduction and infection. Such methods are known to the skilled worker and described, for example, in Davis et al., Basic Methods In Molecular Biology (1986). For a review of gene transfer methods for plant and cell cultures, see, Fisk et al. (1993) Scientia Horticulturae 55:5-36 and Potrykus (1990) CIBA Found Symp 154:198.

Methods are known for introduction and expression of heterologous genes in both monocot and dicot plants. See, e.g., U.S. Pat. Nos. 5,633,446, 5,317,096, 5,689,052, 5,159, 135, and 5,679,558; Weising et al. (1988) Ann. Rev. Genet. 22: 421-477. Transformation of monocots in particular can use various techniques including electroporation (e.g., Shimamoto et al. (1992) Nature 338:274-276; biolistics (e.g., EP-A1 270,356); and *Agrobacterium* (e.g., Bytebier et al. (1987) Proc Natl Acad Sci USA 84:5345-5349).

In plants, methods for transforming and regenerating plants from plant tissues or plant cells with which the skilled worker is familiar are exploited for transient or stable transformation. Suitable methods are especially protoplast transformation by means of poly-ethylene-glycol-induced DNA uptake, biolistic methods such as the gene gun ("particle bombardment" method), electroporation, the incubation of dry embryos in DNA-containing solution, sonication and microinjection, and the transformation of intact cells or tissues by micro- or macroinjection into tissues or embryos, tissue electroporation, or vacuum infiltration of seeds. In the case of injection or electroporation of DNA into plant cells, the plasmid used does not need to meet any particular requirement. Simple plasmids such as those of the pUC series may be used. If intact plants are to be regenerated from the transformed cells, the presence of an additional selectable marker gene on the plasmid is useful.

In addition to these "direct" transformation techniques, transformation can also be carried out by bacterial infection by means of *Agrobacterium tumefaciens* or *Agrobacterium rhizogenes*. These strains contain a plasmid (Ti or Ri plasmid). Part of this plasmid, termed T-DNA (transferred DNA), is transferred to the plant following *Agrobacterium* infection and integrated into the genome of the plant cell.

For *Agrobacterium*-mediated transformation of plants, a DNA construct of the invention may be combined with suitable T-DNA flanking regions and introduced into a conventional *Agrobacterium tumefaciens* host vector. The virulence functions of the *A. tumefaciens* host will direct the insertion of a transgene and adjacent marker gene(s) (if present) into the plant cell DNA when the cell is infected by the bacteria. *Agrobacterium tumefaciens*-mediated transformation techniques are well described in the scientific literature. See, for example, Horsch et al. (1984) Science 233: 496-498, Fraley et al. (1983) Proc Natl Acad Sci USA 80:4803-4807, Hooykaas (1989) Plant Mol Biol 13:327-336, Horsch R B (1986) Proc Natl Acad Sci USA 83(8): 2571-2575), Bevans et al. (1983) Nature 304:184-187, Bechtold et al. (1993) Comptes Rendus De L'Academie Des Sciences Serie III-Sciences De La Vie-Life Sciences 316: 1194-1199, Valvekens et al. (1988) Proc Natl Acad Sci USA 85:5536-5540.

A DNA construct of the invention is preferably integrated into specific plasmids, either into a shuttle, or intermediate, vector or into a binary vector). If, for example, a Ti or Ri plasmid is to be used for the transformation, at least the right border, but in most cases the right and the left border, of the Ti or Ri plasmid T-DNA is linked with the expression cassette to be introduced as a flanking region. Binary vectors are preferably used. Bi-nary vectors are capable of replication both in *E. coli* and in *Agrobacterium*. As a rule, they contain a selection marker gene and a linker or polylinker flanked by the right or left T-DNA flanking sequence. They can be transformed directly into *Agrobacterium* (Holsters et al. (1978) Mol Gen Genet 163:181-187). The selection marker gene permits the selection of transformed agrobacteria and is, for example, the nptll gene, which imparts resistance to kanamycin. The *Agrobacterium*, which acts as host organism in this case, should already contain a plasmid with the vir region. The latter is required for transferring the T-DNA to the plant cell. An *Agrobacterium* thus transformed can be used for transforming plant cells.

Many strains of *Agrobacterium tumefaciens* are capable of transferring genetic material—for example a DNA constructs according to the invention—, such as, for example, the strains EHA101(pEHA101) (Hood E E et al. (1996) J Bacteriol 168(3):1291-1301), EHA105(pEHA105) (Hood et al. 1993, Transgenic Research 2, 208-218), LBA4404 (pAL4404) (Hoekema et al. (1983) Nature 303:179-181), C58C1(pMP90) (Koncz and Schell (1986) Mol Gen Genet 204,383-396) and C58C1(pGV2260) (De-blaere et al. (1985) Nucl Acids Res. 13, 4777-4788).

The agrobacterial strain employed for the transformation comprises, in addition to its disarmed Ti plasmid, a binary plasmid with the T-DNA to be transferred, which, as a rule, comprises a gene for the selection of the transformed cells and the gene to be transferred. Both genes must be equipped with transcriptional and translational initiation and termination signals. The binary plasmid can be transferred into the agrobacterial strain for example by electroporation or other transformation methods (Mozo & Hooykaas (1991) Plant Mol Biol 16:917-918). Coculture of the plant explants with the agrobacterial strain is usually performed for two to three days.

A variety of vectors could, or can, be used. In principle, one differentiates between those vectors which can be employed for the *Agrobacterium*-mediated transformation or agroinfection, i.e. which comprise a DNA construct of the invention within a T-DNA, which indeed permits stable integration of the T-DNA into the plant genome. Moreover, border-sequence-free vectors may be employed, which can be transformed into the plant cells for example by particle bombardment, where they can lead both to transient and to stable expression.

The use of T-DNA for the transformation of plant cells has been studied and described intensively (EP-A1 120 516; Hoekema, In: The Binary Plant Vector System, Offsetdrukkerij Kanters B. V., Alblasserdam, Chapter V; Fraley et al. (1985) Crit Rev Plant Sci 4:1-45 and An et al. (1985) EMBO J 4:277-287). Various binary vectors are known, some of which are commercially available such as, for example, pBIN19 (Clontech Laboratories, Inc. USA).

To transfer the DNA to the plant cell, plant explants are cocultured with *Agrobacterium tumefaciens* or *Agrobacterium rhizogenes*. Starting from infected plant material (for example leaf, root or stalk sections, but also protoplasts or suspensions of plant cells), intact plants can be regenerated using a suitable medium which may contain, for example, antibiotics or biocides for selecting transformed cells. The plants obtained can then be screened for the presence of the DNA introduced, in this case a DNA construct according to the invention. As soon as the DNA has integrated into the host genome, the genotype in question is, as a rule, stable and the insertion in question is also found in the subsequent generations. As a rule, the expression cassette integrated contains a selection marker which confers a resistance to a biocide (for example a herbicide) or an antibiotic such as kanamycin, G 418, bleomycin, hygromycin or phosphinotricin and the like to the transformed plant. The selection marker permits the selection of transformed cells (McCormick et al., Plant Cell Reports 5 (1986), 81-84). The plants obtained can be cultured and hybridized in the customary fashion. Two or more generations should be grown in order to ensure that the genomic integration is stable and hereditary.

The abovementioned methods are described, for example, in B. Jenes et al., Techniques for Gene Transfer, in: Transgenic Plants, Vol. 1, Engineering and Utilization, edited by SD Kung and R Wu, Academic Press (1993), 128-143 and in Potrykus (1991) Annu Rev Plant Physiol Plant Molec Biol 42:205-225). The construct to be expressed is preferably cloned into a vector which is suitable for the transformation of *Agrobacterium tumefaciens*, for example pBin19 (Bevan et al. (1984) Nucl Acids Res 12:8711).

The DNA construct of the invention can be used to confer desired traits on essentially any plant. One of skill will recognize that after DNA construct is stably incorporated in transgenic plants and confirmed to be operable, it can be introduced into other plants by sexual crossing. Any of a number of standard breeding techniques can be used, depending upon the species to be crossed.

The nucleases or chimeric endonuclease may alternatively be expressed transiently. The chimeric endonuclease may be transiently expressed as a DNA or RNA delivered into the target cell and/or may be delivered as a protein. Delivery as a protein may be achieved with the help of cell penetrating peptides or by fusion with SEciV signal peptides fused to the nucleases or chimeric endonucleases, which mediate the secretion from a delivery organism into a cell of a target organism e.g. from *Agrobacterium rhizogenes* or *Agrobacterium tumefaciens* to a plant cell.

Regeneration of Transgenic Plants

Transformed cells, i.e. those which comprise the DNA integrated into the DNA of the host cell, can be selected from untransformed cells if a selectable marker is part of the DNA introduced. A marker can be, for example, any gene which is capable of conferring a resistance to antibiotics or herbicides (for examples see above). Transformed cells which express such a marker gene are capable of surviving in the presence of concentrations of a suitable antibiotic or herbicide which kill an untransformed wild type. As soon as a transformed plant cell has been generated, an intact plant can be obtained using methods known to the skilled worker. For example, callus cultures are used as starting material. The formation of shoot and root can be induced in this as yet undifferentiated cell biomass in the known fashion. The shoots obtained can be planted and cultured.

Transformed plant cells, derived by any of the above transformation techniques, can be cultured to regenerate a whole plant which possesses the transformed genotype and thus the desired phenotype. Such regeneration techniques rely on manipulation of certain phytohormones in a tissue culture growth medium, typically relying on a biocide and/or herbicide marker that has been introduced together with the desired nucleotide sequences. Plant regeneration from cultured protoplasts is described in Evans et al., Protoplasts Isolation and Culture, Handbook of Plant Cell Culture, pp. 124176, Macmillian Publishing Company, New York (1983); and in Binding, Regeneration of Plants, Plant Protoplasts, pp. 21-73, CRC Press, Boca Raton, (1985). Regeneration can also be obtained from plant callus, explants, somatic embryos (Dandekar et al. (1989) J Tissue Cult Meth 12:145; McGranahan et al. (1990) Plant Cell Rep 8:512), organs, or parts thereof. Such regeneration techniques are described generally in Klee et al. (1987) Ann Rev Plant Physiol 38:467-486.

Combination with Other Recombination Enhancing Techniques

In a further preferred embodiment, the efficacy of the recombination system is increased by combination with systems which promote homologous recombination. Such systems are described and encompass, for example, the expression of proteins such as RecA or the treatment with PARP inhibitors. It has been demonstrated that the intrachromosomal homologous recombination in tobacco plants can be increased by using PARP inhibitors (Puchta H et al. (1995) Plant J. 7:203-210). Using these inhibitors, the homologous recombination rate in the recombination cassette after induction of the sequence-specific DNA double-strand break, and thus the efficacy of the deletion of the transgene sequences, can be increased further. Various PARP inhibitors may be employed for this purpose. Preferably encompassed are inhibitors such as 3-aminobenzamide, 8-hydroxy-2-methylquinazolin-4-one (NU1025), 1,1,1b-dihydro-(2H)benzopyrano(4,3,2-de)isoquinolin-3-one (GPI 6150), 5-aminoisoquino-linone, 3,4-dihydro-5-(4-(1-piperidinyl)butoxy)-1(2H)-isoquinolinone, or the compounds described in WO 00/26192, WO 00/29384, WO 00/32579, WO 00/64878, WO 00/68206, WO 00/67734, WO 01/23386 and WO 01/23390.

In addition, it was possible to increase the frequency of various homologous recombination reactions in plants by expressing the E. coli RecA gene (Reiss B et al. (1996) Proc Natl Acad Sci USA 93(7):3094-3098). Also, the presence of the protein shifts the ratio between homologous and illegitimate DSB repair in favor of homologous repair (Reiss B et al. (2000) Proc Natl Acad Sci USA 97(7):3358-3363). Reference may also be made to the methods described in WO 97/08331 for increasing the homologous recombination in plants. A further increase in the efficacy of the recombination system might be achieved by the simultaneous expression of the RecA gene or other genes which increase the homologous recombination efficacy (Shalev G et al. (1999) Proc Natl Acad Sci USA 96(13):7398-402). The above-stated systems for promoting homologous recombination can also be advantageously employed in cases where the recombination construct is to be introduced in a site-directed fashion into the genome of a eukaryotic organism by means of homologous recombination.

Methods of Providing Chimeric LAGLIDADG Endonucleases:

The current invention provides a method of providing a chimeric LAGLIDADG endonuclease as described above.

The method comprises the steps of:

a. providing at least one LAGLIDADG endonuclease coding region
b. providing at least one heterologous DNA binding domain coding region,
c. providing a polynucleotide having a potential DNA recognition sequence or potential DNA recognition sequences of the LAGLIDADG endonuclease or LAGLIDADG endonucleases of step a) and having a potential recognition sequence or having potential recognition sequences of the heterologous DNA binding domain or heterologous DNA binding domains of step b),
d. creating a translational fusion of all LAGLIDADG endonuclease coding regions of step b) and all heterologous DNA binding domains of step c),
e. expressing a chimeric LAGLIDADG endonuclease from the translational fusion created in step d),
f. testing the chimeric LAGLIDADG endonuclease expressed in step e) for cleavage of the polynucleotide of step c).

Depending on the intended purpose, the method steps a), b), c) and d) can be used in varying order. For example, the method can be used to provide a particular combination of at least one LAGLIDADG endonuclease and at least one heterologous DNA binding domain and providing thereafter a polynucleotide comprising potential DNA recognition sites and potential recognition sites reflecting the order in which the at least one LAGLIDADG nuclease and the at least one heterologous DNA binding site were arranged in the translational fusion, and testing the chimeric LAGLIDADG endonuclease for cleaving activity on a polynucleotide having potential DNA recognition sites and potential recognition sites for the LAGLIDADG nucleases and heterologous DNA binding domains comprised by the chimeric LAGLIDADG endonuclease and selecting at least one polynucleotide that is cut by the chimeric LAGLIDADG endonuclease.

The method can also be used to design a chimeric LAGLIDADG endonuclease for cleaving activity on a pre-selected polynucleotide, by first providing a polynucleotide having a specific sequence, thereafter selecting at least one LAGLIDADG endonuclease and at least one heterologous DNA binding domain having non-overlapping potential DNA recognition sites and potential recognition sites in the nucleotide sequence of the polynucleotide, creating a translational fusion of the at least one LAGLIDADG endonuclease and the at least one heterologous DNA binding domain, expressing the chimeric LAGLIDADG endonuclease encoded by said translational fusion and testing the chimeric LAGLIDADG endonuclease of cleavage activity on the preselected polynucleotide sequence, and selecting a chimeric LAGLIDADG endonuclease having such cleavage activity.

This method can be used to design a chimeric LAGLIDADG endonuclease having an enhanced cleavage activity on a specific polynucleotide, for example, if a polynucleotide comprises a DNA recognition site of a nuclease it will be possible to identify a potential recognition site of a heterologous DNA binding domain, which can be used to create a chimeric LAGLIDADG endonuclease comprising the nuclease and the heterologous DNA binding domain.

Alternatively, this method can also be used to create a chimeric LAGLIDADG endonuclease having cleavage activity on a specific polynucleotide comprising a recognition site of a heterologous DNA binding domain. For example, in case the specific polynucleotide is known to be bound by a heterologous DNA binding domain, it is possible to identify a LAGLIDADG endonuclease having a potential DNA recognition site close to but not overlapping with the recognition site of the identified heterologous DNA binding domain. By creating a translational fusion and expressing the chimeric LAGLIDADG endonuclease comprising the identified LAGLIDADG endonuclease and the heterologous DNA binding domain, it will be possible to test the chimeric LAGLIDADG endonuclease for cleavage activity on said preselected polynucleotide.

Suitable endonucleases and heterologous DNA binding domains can be identified by searching databases comprising DNA recognition sites of LAGLIDADG endonucleases and recognition sites of DNA binding proteins like $Zn_2C_6$ transcription factors.

Further, it is possible to mutate the amino acid sequence of LAGLIDADG endonucleases, like I-SceI, I-CreI, I-DmoI or I-MsoI to create new binding and DNA cleavage activity. By creating chimeric LAGLIDADG endonucleases comprising endonucleases like I-SceI, I-CreI, I-DmoI or I-MsoI and heterologous DNA binding domains it is possible to create chimeric LAGLIDADG endonucleases which will bind and cleave such preselected polypeptides.

Methods for homologous recombination and targeted mutation using chimeric LAGLIDADG endonucleases.

The current invention provides a method for homologous recombination of polynucleotides comprising:
a. providing a cell competent for homologous recombination,
b. providing a polynucleotide comprising a recombinant polynucleotide flanked by a sequence A and a sequence B,
c. providing a polynucleotide comprising sequences A' and B', which are sufficiently long and homologous to sequence A and sequence B, to allow for homologous recombination in said cell and
d. providing a chimeric LAGLIDADG endonuclease or an expression cassette coding for a chimeric LAGLIDADG endonuclease,
e. combining b), c) and d) in said cell and
f. detecting recombined polynucleotides of b) and c), or selecting for or growing cells comprising recombined polynucleotides of b) and c).

In one embodiment of the invention, the polynucleotide provided in step b) comprises at least one chimeric recognition site, preferably a chimeric recognition site selected from the group of sequences described by SEQ ID NO: 13, 14, 15, 16, 26, 27, 28, 29, 43, 44, 45 or 46.

In one embodiment of the invention, the polynucleotide provided in step c) comprises at least one chimeric recognition site, preferably selected from the group of sequences described by SEQ ID NO: SEQ ID NO: 13, 14, 15, 16, 26, 27, 28, 29, 43, 44, 45 or 46.

In one embodiment of the invention, the polynucleotide provided in step b) and the polynucleotide provided in step c) comprise at least one chimeric recognition site, preferably selected from the group of sequences described by SEQ ID NO: 13, 14, 15, 16, 26, 27, 28, 29, 43, 44, 45 or 46.

In one embodiment of the invention, step e) leads to deletion of a polynucleotide comprised in the polynucleotide provided in step c).

In one embodiment of the invention the deleted polynucleotide comprised in the polynucleotide provided in step c) codes for a marker gene or parts of a marker gene.

In one embodiment of the invention, the polynucleotide provided in step b) comprises at least one expression cassette.

In one embodiment of the invention, the polynucleotide provided in step b) comprises at least one expression cassette leading to expression of a selection marker gene or a reporter gene.

In one embodiment of the invention, the polynucleotide provided in step b) comprises at least one expression cassette leading to expression of a selection marker gene or a reporter gene and comprises at least one DNA recognition site or at least one chimeric recognition site.

A further embodiment of the invention provides a method for targeted mutation of polynucleotides comprising:
a. providing a cell comprising a polynucleotide comprising a chimeric recognition site, preferably selected from the group of sequences described by SEQ ID NO: 13, 14, 15, 16, 26, 27, 28, 29, 43, 44, 45 or 46.
b. providing a chimeric endonuclease, e.g. an chimeric endonuclease comprising an endonuclease having a sequence selected from the group of sequences described by SEQ ID NO: 2, 3, 5, 7, 8, 9, 10, 50, 51, 52, 53, 54, 55, and 56 and being able to cleave the chimeric recognition site of step a),
c. combining a) and b) in said cell and
d. detecting mutated polynucleotides, or selecting for growing cells comprising mutated polynucleotides.

The invention provides in another embodiment a method for homologous recombination as described above or a method for targeted mutation of polynucleotides as described above, comprising:
combining the chimeric endonuclease and the chimeric recognition site via crossing of organisms, via transformation of cells or via a SecIV peptide fused to the chimeric endonuclease and contacting the cell comprising the chimeric recognition site with an organism expressing the chimeric endonuclease and expressing a SecIV transport complex able to recognize the SecIV peptide fused to the chimeric endonuclease.

EXAMPLES

General Methods:

The chemical synthesis of oligonucleotides can be effected for example in the known manner using the phosphoamidite method (Voet, Voet, 2nd edition, Wiley Press New York, pages 896-897). The cloning steps carried out for the purposes of the present invention, such as, for example, restriction cleavages, agarose gel electrophoresis, purification of DNA fragments, the transfer of nucleic acids to nitrocellulose and nylon membranes, the linkage of DNA fragments, the transformation of *E. coli* cells, bacterial cultures, the propagation of phages and the sequence analysis of recombinant DNA are carried out as described by Sambrook et al. (1989) Cold Spring Harbor Laboratory Press; ISBN 0-87969-309-6. Recombinant DNA molecules were sequenced using an ALF Express laser fluorescence DNA sequencer (Pharmacia, Upsala [sic], Sweden) following the method of Sanger (Sanger et al., Proc. Natl. Acad. Sci. USA 74 (1977), 5463-5467).

Example 1: Constructs Harboring Sequence Specific DNA-endonuclease Expression Cassettes for Expression in *E. coli*

Example 1a: Basic Construct

In this example we present the general outline of a vector, named "Construct" suitable for transformation in *E. coli*. This general outline of the vector comprises an ampicillin resistance gene for selection, a replication origin for *E. coli* and the gene araC, which encodes an Arabinose inducible transcription regulator. A sequence stretch of "NNNNNNNNNN" in sequences of the sequence protocol is meant to be a placeholder for genes encoding the different versions of the sequence specific DNA-endonuclease. The different genes can be expressed from the Arabinose inducible pBAD promoter (Guzman et al., J Bacterial 177: 4121-4130(1995)), the sequences of the genes encoding the different nuclease versions are given in the following examples.

The control construct, in which the placeholder is replaced by the sequence of I-SceI (SEQ ID NO: 18), was called VC-SAH40-4.

Example 1b: I-SceI-AlcR Fusion Constructs

In Gene 73 (2), 385-396 (1988) Felenbok et al. described the AlcR Protein as a transcriptional activator in *A. nidulans*. The AlcR encoding sequence was fused to the C terminus of the I-SceI sequence, with a single lysine as linker. The linker was designed in a way that the resulting fusion protein recognizes a cognate binding site, which represents a combination of the binding sites of I-SceI and AlcR. AlcR function can be regulated by the addition of ethanol. This could provide the potential to regulate the activity or DNA binding affinity of the fusion protein in the same manner. The resulting plasmid was called VC-SAH51-40. The sequence of the construct is identical to the sequence of construct I, whereas the sequence "NNNNNNNNNN" was replaced by the sequence described by SEQ ID NO: 19.

A similar construct was generated, which in addition to the latter contains a NLS sequence. The resulting plasmid was called VC-SAH50-37. The sequence of the construct is identical to the sequence of construct I, whereas the sequence "NNNNNNNNNN" was replaced by the sequence described by SEQ ID NO: 20.

The first 60 amino acids of AlcR are represent the DNA binding domain of the protein, so another construct was generated, where only those first 60 amino acids are fused to the C terminus of I-SceI to create an I-SceI-AlcR (1-60) fusion. The resulting plasmid was called VC-SAH49-1. The sequence of the construct is identical to the sequence of construct I, whereas the sequence "NNNNNNNNNN" was replaced by the sequence described by SEQ ID NO: 21.

A similar construct was generated, which in addition to the latter contains a NLS sequence. The resulting plasmid was called VC-SAH48-8. The sequence of the construct is identical to the sequence of construct I, whereas the sequence "NNNNNNNNNN" was replaced by the sequence described by SEQ ID NO: 22.

Example 2: Constructs Harboring Nuclease Recognition Sequences/target Sites to Monitor I-SceI Activity in *E. coli*

Example 2a: Basic Construct

In this example we present the general outline of a vector, named "Construct II" suitable for transformation in *E. coli*. This general outline of the vector comprises a Kanamycin resistance gene for selection, a replication origin for *E. coli*, which is compatible with the on of Construct I. SEQ ID NO: 23 shows a sequence stretch of "NNNNNNNNNN". This is meant to be a placeholder for different recognition/target sites for the diverse versions and protein fusions of the sequence specific DNA-endonucleases. The control construct, in which the placeholder is replaced by a sequence stretch encompassing the native target sequence of I-SceI (SEQ ID NO: 24), was called VC-SAH6-1. A control plasmid without a target site was called VC-SAH7-1 (SEQ ID NO 25)

The different combined target sites are given in the following examples.

Example 2b: Target Sites Combined of I-SceI Recognition Sequence and AlcR Binding Sequence In Structure 9, 827-36 (2001) Cahuzac et al. described the DNA binding domain of AlcR in complex with its cognate recognition sequence. Based on this information, combined target sites were generated, that consist of the target site of the nuclease I-SceI and AlcR. Different combined target sites with varying distances of the single sites were generated. The goal was to identify the one that is best recognized by the cognate I-SceI fusion protein. The resulting plasmids were called VC-SAH56-1, VC-SAH57-2, VC-SAH58-2, VC-SAH59-1. The sequence of the constructs is identical to the sequence of Construct II, whereas the sequence "NNNNNNNNNN" was replaced by the sequences described by SEQ ID NO: 26, NO: 27, NO: 28, NO: 29 respectively.

Example 3: Cotransformation of DNA Endonuclease Encoding Constructs and Constructs Harboring Nuclease Recognition Sequences Two plasmids with different selection markers and identical concentrations were transformed in chemical competent *E. coli* Top10 cells, according to the manufacturer description. The cells were plated on LB with the respective antibiotics for selection, and grown over night at 37° C. With this method constructs harboring sequence specific DNA-endonuclease expression cassettes and cognate constructs harboring nuclease recognition sequences/target sites were combined in the same transformant to allow monitoring of the nuclease activity.

Example 4: Demonstration of the Endonuclease Activity in *E. coli*

Cotransformants which carry the combination of two plasmids, one encoding a nuclease or a nuclease-fusion (Construct I) and the other one harboring a compatible target site (Construct II) were grown over night in LB with Ampicillin and Kanamycin. The cultures were diluted 1:100 and grown until they reached $OD_{600}=0.5$. The expression of the fusion protein from Construct I was induced by addition of Arabinose for 3 to 4 hours. The pBAD promoter is described to be dose dependent (Guzman 1995), therefore the culture was divided in different aliquots and protein expression was induced with Arabinose concentrations varying from 0.2% to 0.0002%. 5 µl of each aliquot were plated on LB solid media, supplemented with Ampicillin and Kanamycin. The plates were incubated over night at 37° C. and cell growth was analyzed semi quantitatively. Active nuclease fusions did cut the constructs, which harbor the target site. This led to the loss of Construct II or Construct III, which confer Kanamycin resistance. Therefore, activity of the fusion protein was observed due to the lost ability of the cotransformants to grow on Kanamycin containing medium.

Results:

The result are simplified and summarized in Table 9. ++ and + represent very strong and strong growth, which indicates no or little activity of the expressed nuclease towards the respective target site.—and—represent reduced or no growth, which indicates high or very high activity of the nuclease towards the respective target site.

TABLE 9

I-SceI-AlcR fusions: E. coli growth assay indicates endonuclease activity (enzymatic acitivity) against the respective target sites.

|  | VC-SAH40-4 | VC-SAH48-8 | VC-SAH49-1 | VC-SAH50-37 | VC-SAH51-40 |
|---|---|---|---|---|---|
| VC-SAH7-1 | ++ | ++ | ++ | ++ | ++ |
| VC-SAH6-1 | -- | + | x | + | + |
| VC-SAH56-1 |  | + | + | + | - |
| VC-SAH57-2 | - | - | - | - | - |
| VC-SAH58-2 |  | na | na | - | -- |
| VC-SAH59-1 | -- | -- | -- | -- | -- |

Example 5: Transformation of *Arabidopsis thaliana*

*A. thaliana* plants were grown in soil until they flowered. *Agrobacterium tumefaciens* (strain C58C1 [pMP90]) transformed with the construct of interest was grown in 500 mL in liquid YEB medium (5 g/L Beef extract, 1 g/L Yeast Extract (Duchefa), 5 g/L Peptone (Duchefa), 5 g/L sucrose (Duchefa), 0.49 g/L $MgSO_4$ (Merck)) until the culture reached an $OD_{600}$ 0.8-1.0. The bacterial cells were harvested by centrifugation (15 minutes, 5,000 rpm) and resuspended in 500 mL infiltration solution (5% sucrose, 0.05% SILWET L-77 [distributed by Lehle seeds, Cat. No. VIS-02]). Flowering plants were dipped for 10-20 seconds into the *Agrobacterium* solution. Afterwards the plants were kept in the dark for one day and then in the greenhouse until seeds could be harvested. Transgenic seeds were selected by plating surface sterilized seeds on growth medium A (4.4 g/L MS salts [Sigma-Aldrich], 0.5 g/L MES [Duchefa]; 8 g/L Plant Agar [Duchefa]) supplemented with 50 mg/L kanamycin for plants carrying the nptII resistance marker gene, and 10 mg/L Phosphinotricin for plants carrying the pat gene, respectively. Surviving plants were transferred to soil and grown in the greenhouse.

Example 6: Constructs Harbouring Sequence Specific DNA-endonuclease Expression Cassettes for *A. thaliana*

Example 6a: Basic Construct

In this example we present the general outline of a binary vector, named "Construct IV" suitable for plant transformation. This general outline of the binary vector comprises a T-DNA with a p-Mas1del100::cBAR::t-Ocs1 cassette, which enables selection on Phosphinotricin, when integrated into the plant genome. SEQ ID NO: 31 shows a sequence stretch of "NNNNNNNNNN". This is meant to be a placeholder for genes encoding the different versions of the sequence specific DNA-endonuclease. The sequence of the latter is given in the following examples.

Example 6b: I-SceI—AlcR Fusion Constructs

The sequence stretch of "NNNNNNNNNN" of "Construct IV" was separately replaced by genes encoding three different versions of I-SceI-AlcR fusions, described in Example 1b. The resulting plasmids were called VC-SAH91-1 (NLS-I-SceI-AlcR(1-60)), VC-SAH92-1 (1-SceI-AlcR(1-60)), VC-SAH103-3 (NLS-I-SceI-AlcR) and VC-SAH104-22 (1-SceI-AlcR).

Example 7: Constructs Harboring Nuclease Recognition Sequences/target Sites to Monitor Nuclease Activity in *A. thaliana*

Example 7a: Basic Construct

In this example we present the general outline of a binary vector, named "Construct V", suitable for transformation in *A. thaliana*. This general outline of the vector comprises a T-DNA with a nos-promoter::nptII::nos-terminator cassette, which confers kanamycin resistance when integrated into the plant genome.

The T-DNA also comprises a partial uidA (GUS) gene (called "GU") and another partial uidA gene (called "US"). Between GU and US a stretch of "NNNNNNNNNN" is shown in SEQ ID NO: 32. This is meant to be a placeholder for different recognition/target sites for the diverse versions and protein fusions of the sequence specific DNA-endonucleases. The sequences of the different target sites are given in the following examples.

If the recognition sequence is cut by the respective nuclease, the partially overlapping and non-functional halves of the GUS gene (GU and US) will be restored as a result of intrachromosomal homologous recombination (ICHR). This can be monitored by histochemical GUS staining Jefferson et al. (1987) EMBO J 6:3901-3907).

Example 7b: Target Sites Combined of Nuclease Recognition Sequence and AlcR Binding Sequence Combined target sites were generated, that consist of the target site of the nuclease I-SceI and AlcR. Different combined target sites with varying distances of the single sites were generated. The goal was to identify the one that is best recognized by the cognate I-SceI fusion protein. The resulting plasmids were/are called VC-SAH52-21, VC-SAH 111, VC-SAH 112, VC-SAH55-22. The sequence of the constructs is identical to the sequence of construct V, whereas the sequence "NNNNNNNNNN" was replaced by the sequences described by SEQ ID NO: 33, NO: 34, NO: 35, NO: 36 respectively.

Example 8: Transformation of Sequence-Specific DNA Endonuclease Encoding Constructs into *A. thaliana*

Plasmids VC-SAH87-4, VC-SAH91-1, VC-SAH92-1, VC-SAH103-3, VC-SAH105, VC-SAH140, VC-SAH139-

20, VC-SAH89-10, VC-SAH90 were/are transformed into *A. thaliana* according to the protocol described in Example 5. Selected transgenic lines (T1 generation) were/are grown in the greenhouse and some flowers were/are used for crossings (see below).

Example 9: Transformation of Constructs Harboring Combined Target Sites to Monitor Recombination into *A. thaliana*

Plasmids VC-SAH52-21, VC-SAH111, VC-SAH112, VC-SAH55-22, VC-SAH113, VC-SAH114, VC-SAH115, VC-SAH16-4, VC-SAH17-8, VC-SAH18-7 and VC-SAH19-15 were/are transformed into *A. thaliana* according to the protocol described in Example 5. Selected transgenic lines (T1 generation) were/are grown in the greenhouse and some flowers were used for crossings (see Example 10).

Example 10: Monitoring Activity of the Nuclease Fusions in *A. thaliana*

Transgenic lines of *Arabidopsis* harboring a T-DNA encoding a sequence-specific DNA endonuclease were/are crossed with lines of *Arabidopsis* harboring the T-DNA carrying a GU-US reporter construct with a corresponding combined target site. As a result of I-SceI activity on the target site a functional GUS gene will be restored by homologous intrachromosomal recombination (ICHR). This can be monitored by histochemical GUS staining (Jefferson et al. (1987) EMBO J 6:3901-3907)

To visualize I-SceI activity of the AlcR fusions, transgenic lines of *Arabidopsis* harboring the T-DNA of the nuclease encoding constructs VC-SAH91-1 and VC-SAH87-4 were crossed with lines of *Arabidopsis* harboring the T-DNA of constructs VC-SAH52-21, VC-SAH55-22 and VC-SCB734-4, harboring the target sites. To visualize the activity of additional AlcR fusions, transgenic lines of *Arabidopsis* harboring the T-DNA of the nuclease encoding constructs VC-SAH91-1, VC-SAH92-1 and VC-SAH103-3 were crossed with lines of *Arabidopsis* harboring the T-DNA of constructs VC-SCB743-4, VC-SAH52-21 and VC-SAH55-22, harboring the target sites.

F1 seeds of the crosses were harvested. The seeds were surface sterilized and grown on medium A supplemented with the respective antibiotics and/or herbicides. Leafs were/are harvested and used for histochemical GUS staining. The percentage of plants showing blue staining is an indicator of the frequency of ICHR and therefore for I-SceI activity.

Activity of the different fusion proteins is determined by comparison of the number ICHR events of these crossings. An increase in specificity of the I-SceI fusions with respect to the native nuclease can be observed by comparing these results with control crosses. For these all transgenic lines of *Arabidopsis* harboring the T-DNA of constructs encoding the different fusions of I-SceI were crossed with lines of *Arabidopsis* harboring the T-DNA of the construct carrying the native I-SceI target site (VC-SAH743-4).

The next generation of these plants is analyzed for fully blue seedlings.

Results:
Three independent lines harbouring the T-DNA of the nuclease encoding construct VC-SAH91-1 (NLS-I-SceI-AlcR(1-60)) were crossed with tree independent lines harbouring the T-DNA of the nuclease encoding construct VC-SAH743-4 (native I-SceI site) and with tree independent lines harbouring the T-DNA of the nuclease encoding construct VC-SAH55-22 (target site I-SceI-AlcR).

Leafs were harvested and used for histochemical GUS staining. The combination of NLS-I-SceI-AlcR(1-60), alternatively called I-SceI-AlcR(1-60), with the combined target site (SAH55-22 also called #55) resulted in 49% blue plants, whereas the crossing to the native I-SceI site resulted only in 3% blue plants.

In contrast, the native version of the nuclease I-SceI, alternatively called wt I-SceI, showed only very little recombinant activity (0% for the native (wt) target site and 8% for the native target site comprised in the combined target site SAH55-22).

Figure 2:
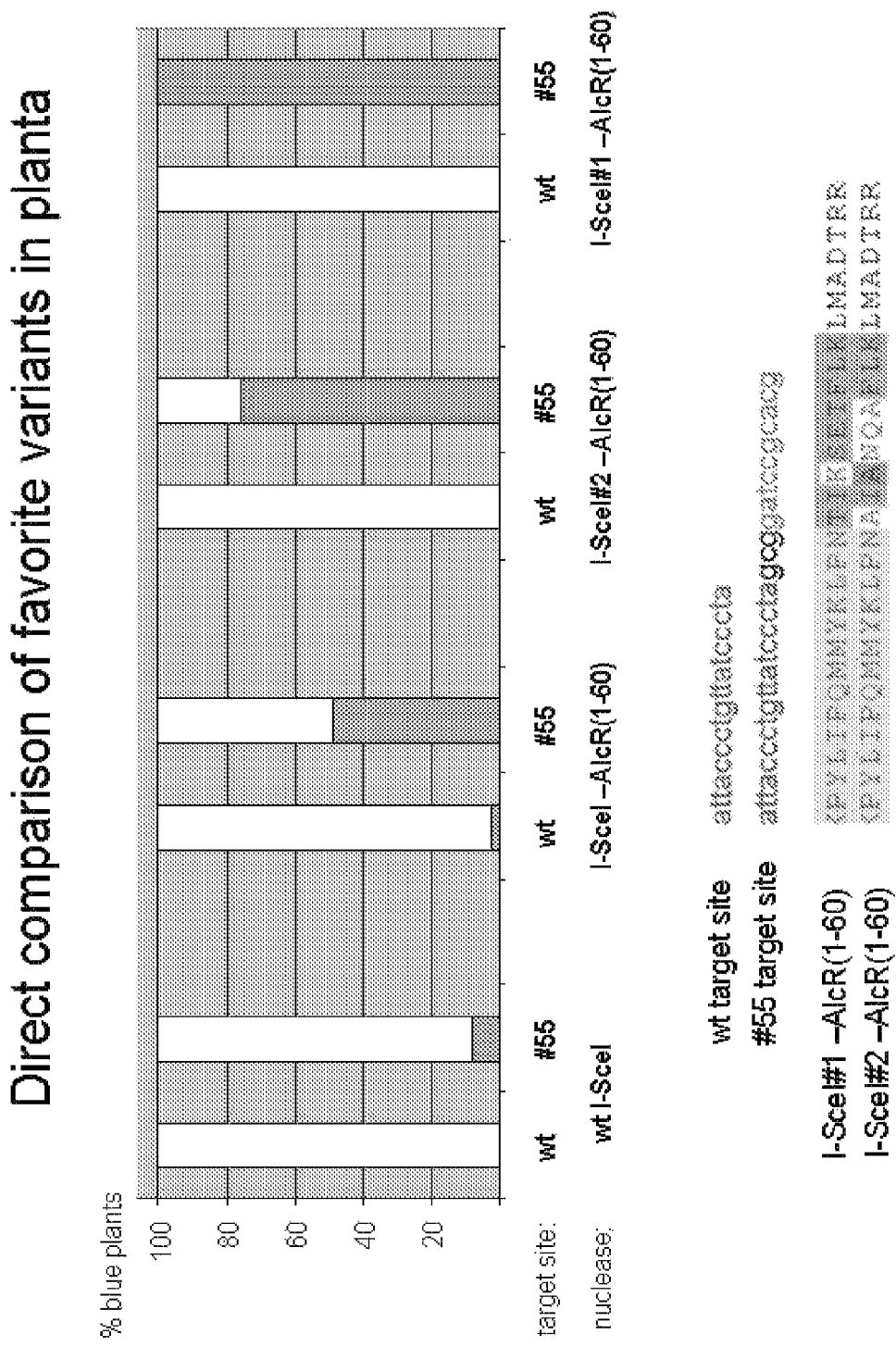
FIG. 2 is a graphical representation of the experimental results of Examples 10 and 20d as described herein. Thereby providing a comparison of the capability of wildtype I-SceI and three different variants of chimeric endonucleases to induce homologous recombination in plants. The frequency of induced homologous recombination is represented by, the percentage of plants showing GUS-activity after homologous recombination (% blue plants).

See FIG. 2

Example 20: Stabilized Versions of I-SceI Fused to AlcR

Example 20 a): Constructs Harboring Sequence Specific DNA-endonuclease Expression Cassettes, Encoding the C Terminal Shortened Version of I-SceI Fused to AlcR for Expression in *E. coli*

To generate I-SceI variants with an increased specificity and stability, fusion proteins were generated between AlcR and versions of I-SceI, where the proposed C-terminal PEST sequence (amino acids 228-236) is altered. Two different alterations of the C terminus were chosen, in the first one (C term mod #1) the C terminus was replaced by the SEQ ID NO: 37, in the second one (C term mod #2) the C terminus was replaced by the SEQ ID NO: 38.

The resulting plasmids are based on the construct described in Example 1a), where the placeholder was replaced by genes encoding the different I-SceI fusions. In the plasmid named VC-SAH128-3, NNNNNN was replaced by NLS-I-SceI C term mod #1 AlcR (1-60) (SEQ ID NO:39). In the plasmid named VC-SAH129-1, NNNNNN was replaced by NLS-I-SceI C term mod #2 AlcR (1-60) (SEQ ID NO:40).

Also plasmids with full length versions of AlcR are generated. These are named VC-SAH130-30, where NNNNNN was replaced by NLS-I-SceI C term mod #1 AlcR (SEQ ID NO:41) and VC-SAH131-6, where NNNNNN was replaced by NLS-I-SceI C term mod #2 AlcR (SEQ ID NO:42).

Similar constructs were generated, which encode a fusion of AlcR(1-60) to the N terminus of I-SceI, which has a deletion of the C terminal PEST sequence (amino acids 228-236).

Tree variants were generated: VC-SAH186-5 a direct fusion, VC-SAH185-1 a version with one amino acid linker and VC-SAH187-10 a version with a linker of 3 amino acids (SEQ ID NO: 47, 48 and 49).

To tests these N terminal fusions of AlcR to I-SceI, additional target sites had to be created. The resulting target vectors were the following:

```
VC-SAH181-1
                              (SEQ ID NO: 43)
(CGTGCGGATCATTACCCTGTTATCCCTA)

VC-SAH182-2
                              (SEQ ID NO: 44)
(CGTGCGGATCNATTACCCTGTTATCCCTA)
```

-continued

VC-SAH183-3
(SEQ ID NO: 45)
(CGTGCGGATCNNATTACCCTGTTATCCCTA)

VC-SAH184-2
(SEQ ID NO: 46)
(CGTGCGGATCNNNATTACCCTGTTATCCCTA)

Example 20 b): Demonstration of the Endonuclease Activity in *E. coli*

The nuclease versions with a C terminal fusion of AlcR, encoded by plasmids described in example 20a, were cotransformed in *E. coli* with vectors VC-SAH56-1, VC-SAH57-2, VC-SAH58-2, VC-SAH59-1, encoding the combined target sites. The activity and specificity of these versions of I-SceI was analyzed as described in Example 3 and 4.

Results:

In *E. coli*, the C terminal I-SceI-AlcR Fusions described in Example 20a) behaved comparable to VC-SAH48 to VC-SAH51, which are shown in Example 4, table 1. VC-SAH128-3, VC-SAH129-1, VC-SAH130-30, SAH131-6 did all cut the combined target site encoded by VC-SAH59-1 with highest efficiency. Whereas the activity on the native I-SceI target site was much lower than by the native nuclease.

Example 20c): Constructs Harboring Sequence Specific DNA-endonuclease Expression Cassettes, Encoding the C Terminal Shortened Version of I-SceI Fused to AlcR for Expression in *A. thaliana*

The versions of I-SceI-AlcR fusions described in Example 20a were cloned into Construct IV. In the plasmid named VC-SAH126-1, the placeholder was replaced by NLS-I-SceI C term mod #1 AlcR (1-60) (SEQ ID N0:39). In the plasmid named VC-SAH127-1, NNNNNN was replaced by NLS-I-SceI C term mod #2 AlcR (1-60) (SEQ ID N0:40). Also plasmids with full length versions of AlcR were generated. These are named VC-SAH 137-1, where NNNNNN was replaced by NLS-I-SceI C term mod #1 AlcR (SEQ ID N0:41) and VC-SAH138-2, where NNNNNN was replaced by NLS-I-SceI C term mod #2 AlcR (SEQ ID NO:42).

Example 20 d): Demonstration of the Endonuclease Activity in *A. thaliana*

Plasmids SAH126-1 and VC-SAH127-1 were transformed in *A. thaliana* as described in Example 5). Plants were crossed with lines carrying the T-DNA with a reporter construct encompassing cognate target sites, as described in Example 7b). Similarly, VC-SAH137-1 and VC-SAH138-2 were transformed in *A. thaliana*. Plants were crossed with lines carrying the T-DNA with a reporter construct encompassing cognate target sites, as described in Example 7b).

Activity and specificity of these versions of the nuclease is analyzed as described in Example 10. Transgenic lines of *Arabidopsis* harboring a T-DNA encoding a sequence-specific DNA endonuclease are crossed with lines of *Arabidopsis* harboring the T-DNA carrying a GU-US reporter construct with a corresponding combined target site. As a result of I-SceI activity on the target site a functional GUS gene will be restored by homologous intrachromosomal recombination (ICHR). This can be monitored by histochemical GUS staining Jefferson et al. (1987) EMBO J 6:3901-3907).

To visualize I-SceI activity of the AlcR fusions, transgenic lines of *Arabidopsis* harboring the T-DNA of the nuclease encoding constructs SAH126-1 and VC-SAH127-1 were crossed with lines of *Arabidopsis* harboring the T-DNA of constructs VC-SAH55-22 and VC-SCB734-4, harboring the target sites.

F1 seeds of the crosses were harvested. The seeds were surface sterilized and grown on medium A supplemented with the respective antibiotics and/or herbicides. Leafs were harvested and used for histochemical GUS staining. The percentage of plants showing blue staining is an indicator of the frequency of ICHR and therefore for I-SceI activity.

Activity of the different fusion proteins is determined by comparison of the number ICHR events of these crossings. An increase in specificity of the I-SceI fusions with respect to the native nuclease was observed by comparing these results with control crosses. All transgenic lines of *Arabidopsis* harboring the T-DNA of constructs encoding the different fusions of I-SceI tested so far, were also crossed with lines of *Arabidopsis* harboring the T-DNA of the construct carrying the native I-SceI target site (VC-SAH743-4).

The next generation of these plants was analyzed for fully blue seedlings.

Results:

Three independent lines harbouring the T-DNA of the nuclease encoding construct SAH126-1 (NLS-I-SceI C term mod #1 AlcR (1-60)) and three independent lines harbouring the T-DNA of the nuclease encoding construct SAH127-1 (NLS-I-SceI C term mod #2 AlcR (1-60)) were crossed with tree independent lines harbouring the T-DNA of the nuclease encoding construct VC-SAH743-4 (native I-SceI site) and with tree independent lines harbouring the T-DNA of the nuclease encoding construct VC-SAH55-22 (target site I-SceI-AlcR).

Leafs were harvested and used for histochemical GUS staining. The combination of NLS-I-SceI C term mod #1-AlcR(1-60), alternatively called I-SceI#1-AlcR(1-60)), with the combined target site (SAH55-22 alternatively called #55) resulted in 100% blue plants, whereas the crossing to the native I-SceI gave 0% blue plants.

The combination of NLS-I-SceI C term mod #2-AlcR(1-60)), alternatively called I-SceI#2-AlcR(1-60)), with the combined target site (SAH55-22) resulted in 76% blue plants, whereas the crossing to the native I-SceI gave 0% blue plants.

See FIG. 2

The invention claimed is:

1. A chimeric endonuclease comprising:
   a) at least one LAGLIDADG endonuclease having DNA double strand break inducing activity and having at least 80% sequence identity to the amino acid sequence of SEQ ID NO: 1, 2, 3, 122, 123, 124, 125 or 165, wherein said at least one LAGLIDADG endonuclease has a DNA recognition sequence; and
   b) at least one heterologous DNA binding domain comprising one or more $Zn_2C_6$ zinc fingers, wherein the heterologous DNA binding domain has a DNA recognition sequence;
   wherein the chimeric endonuclease binds to and has specificity for a chimeric DNA recognition sequence that is a combination of the DNA recognition sequence of the endonuclease and the DNA recognition sequence of the heterologous DNA binding domain, and
   wherein the chimeric endonuclease has lower or no activity on the DNA recognition sequence of the LAGLIDADG endonuclease as compared to the activity on the chimeric DNA recognition sequence.

2. The chimeric endonuclease of claim 1, wherein the at least one LAGLIDADG endonuclease comprises an amino acid sequence having at least 90% sequence identity to the amino acid sequence of SEQ ID NO: 1, 2, 3, 122, 123, 124, 125 or 165.

3. The chimeric endonuclease of claim 1, wherein the heterologous DNA binding domain is obtained from a transcription factor.

4. The chimeric endonuclease of claim 1, wherein the heterologous DNA binding domain comprises a polypeptide having at least 80% sequence identity to the amino acid sequence of SEQ ID NO: 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120 or 121.

5. The chimeric endonuclease of claim 1, wherein the heterologous DNA binding domain is connected to the LAGLIDADG endonuclease via a linker polypeptide.

6. The chimeric endonuclease of claim 5, wherein the linker polypeptide comprises at least 3 amino acids, and wherein at least one third of said amino acids are glycine, serine, alanine, or a combination of glycine, serine, and alanine.

7. The chimeric endonuclease of claim 1, comprising at least one NLS-sequence.

8. The chimeric endonuclease of claim 1, wherein the DNA binding activity of the heterologous DNA binding domain is inducible.

9. The chimeric endonuclease of claim 1, wherein the at least one LAGLIDADG endonuclease comprises the amino acid sequence of SEQ ID NO: 1, 2, 3, 122, 123, 124, 125 or 165.

10. The chimeric endonuclease of claim 1, wherein the heterologous DNA binding domain comprises the amino acid sequence of SEQ ID NO: 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120 or 121.

11. A method for targeted mutation of a polynucleotide comprising:
   a. providing a cell comprising a polynucleotide comprising a chimeric recognition site;
   b. providing the chimeric endonuclease of claim 1, wherein the chimeric endonuclease is able to cleave said chimeric recognition site;
   c. combining said polynucleotide and said chimeric endonuclease in said cell; and
   d. detecting a mutated polynucleotide, or selecting for growing cells comprising a mutated polynucleotide.

12. The method of claim 11, wherein the chimeric endonuclease and the chimeric recognition site are combined in at least one cell via crossing of organisms, transformation, or transport mediated via a SecIII or SecIV peptide fused to the chimeric endonuclease.

\* \* \* \* \*

SEQUENCE LISTING

<160> NUMBER OF SEQ ID NOS: 226

<210> SEQ ID NO 1
<211> LENGTH: 235
<212> TYPE: PRT

<213> ORGANISM: Saccharomyces cerevisiae

<400> SEQUENCE: 1

Met Lys Asn Ile Lys Lys Asn Gln Val Met Asn Leu Gly Pro Asn Ser
1               5                   10                  15

Lys Leu Leu Lys Glu Tyr Lys Ser Gln Leu Ile Glu Leu Asn Ile Glu
            20                  25                  30

Gln Phe Glu Ala Gly Ile Gly Leu Ile Leu Gly Asp Ala Tyr Ile Arg
        35                  40                  45

Ser Arg Asp Glu Gly Lys Thr Tyr Cys Met Gln Phe Glu Trp Lys Asn
    50                  55                  60

Lys Ala Tyr Met Asp His Val Cys Leu Leu Tyr Asp Gln Trp Val Leu
65                  70                  75                  80

Ser Pro Pro His Lys Lys Glu Arg Val Asn His Leu Gly Asn Leu Val
                85                  90                  95

Ile Thr Trp Gly Ala Gln Thr Phe Lys His Gln Ala Phe Asn Lys Leu
            100                 105                 110

Ala Asn Leu Phe Ile Val Asn Asn Lys Lys Thr Ile Pro Asn Asn Leu
        115                 120                 125

Val Glu Asn Tyr Leu Thr Pro Met Ser Leu Ala Tyr Trp Phe Met Asp
    130                 135                 140

Asp Gly Gly Lys Trp Asp Tyr Asn Lys Asn Ser Thr Asn Lys Ser Ile
145                 150                 155                 160

Val Leu Asn Thr Gln Ser Phe Thr Phe Glu Glu Val Glu Tyr Leu Val
                165                 170                 175

Lys Gly Leu Arg Asn Lys Phe Gln Leu Asn Cys Tyr Val Lys Ile Asn
            180                 185                 190

Lys Asn Lys Pro Ile Ile Tyr Ile Asp Ser Met Ser Tyr Leu Ile Phe
        195                 200                 205

Tyr Asn Leu Ile Lys Pro Tyr Leu Ile Pro Gln Met Met Tyr Lys Leu
    210                 215                 220

Pro Asn Thr Ile Ser Ser Glu Thr Phe Leu Lys
225                 230                 235

<210> SEQ ID NO 2
<211> LENGTH: 236
<212> TYPE: PRT
<213> ORGANISM: Artificial Sequence
<220> FEATURE:
<223> OTHER INFORMATION: derived from I-SceI sequence

<400> SEQUENCE: 2

Met Gly Lys Asn Ile Lys Lys Asn Gln Val Met Asn Leu Gly Pro Asn
1               5                   10                  15

Ser Lys Leu Leu Lys Glu Tyr Lys Ser Gln Leu Ile Glu Leu Asn Ile
            20                  25                  30

Glu Gln Phe Glu Ala Gly Ile Gly Leu Ile Leu Gly Asp Ala Tyr Ile
        35                  40                  45

Arg Ser Arg Asp Glu Gly Lys Thr Tyr Cys Met Gln Phe Glu Trp Lys
    50                  55                  60

Asn Lys Ala Tyr Met Asp His Val Cys Leu Leu Tyr Asp Gln Trp Val
65                  70                  75                  80

Leu Ser Pro Pro His Lys Lys Glu Arg Val Asn His Leu Gly Asn Leu
                85                  90                  95

Val Ile Thr Trp Gly Ala Gln Thr Phe Lys His Gln Ala Phe Asn Lys
            100                 105                 110

```
Leu Ala Asn Leu Phe Ile Val Asn Asn Lys Lys Thr Ile Pro Asn Asn
        115                 120                 125

Leu Val Glu Asn Tyr Leu Thr Pro Met Ser Leu Ala Tyr Trp Phe Met
    130                 135                 140

Asp Asp Gly Gly Lys Trp Asp Tyr Asn Lys Asn Ser Thr Asn Lys Ser
145                 150                 155                 160

Ile Val Leu Asn Thr Gln Ser Phe Thr Phe Glu Glu Val Glu Tyr Leu
                165                 170                 175

Val Lys Gly Leu Arg Asn Lys Phe Gln Leu Asn Cys Tyr Val Lys Ile
            180                 185                 190

Asn Lys Asn Lys Pro Ile Ile Tyr Ile Asp Ser Met Ser Tyr Leu Ile
        195                 200                 205

Phe Tyr Asn Leu Ile Lys Pro Tyr Leu Ile Pro Gln Met Met Tyr Lys
    210                 215                 220

Leu Pro Asn Thr Ile Ser Ser Glu Thr Phe Leu Lys
225                 230                 235

<210> SEQ ID NO 3
<211> LENGTH: 227
<212> TYPE: PRT
<213> ORGANISM: Artificial Sequence
<220> FEATURE:
<223> OTHER INFORMATION: derived from I-SceI sequence

<400> SEQUENCE: 3

Met Gly Lys Asn Ile Lys Lys Asn Gln Val Met Asn Leu Gly Pro Asn
1               5                   10                  15

Ser Lys Leu Leu Lys Glu Tyr Lys Ser Gln Leu Ile Glu Leu Asn Ile
                20                  25                  30

Glu Gln Phe Glu Ala Gly Ile Gly Leu Ile Leu Gly Asp Ala Tyr Ile
            35                  40                  45

Arg Ser Arg Asp Glu Gly Lys Thr Tyr Cys Met Gln Phe Glu Trp Lys
50                  55                  60

Asn Lys Ala Tyr Met Asp His Val Cys Leu Leu Tyr Asp Gln Trp Val
65                  70                  75                  80

Leu Ser Pro Pro His Lys Lys Glu Arg Val Asn His Leu Gly Asn Leu
                85                  90                  95

Val Ile Thr Trp Gly Ala Gln Thr Phe Lys His Gln Ala Phe Asn Lys
            100                 105                 110

Leu Ala Asn Leu Phe Ile Val Asn Asn Lys Lys Thr Ile Pro Asn Asn
        115                 120                 125

Leu Val Glu Asn Tyr Leu Thr Pro Met Ser Leu Ala Tyr Trp Phe Met
    130                 135                 140

Asp Asp Gly Gly Lys Trp Asp Tyr Asn Lys Asn Ser Thr Asn Lys Ser
145                 150                 155                 160

Ile Val Leu Asn Thr Gln Ser Phe Thr Phe Glu Glu Val Glu Tyr Leu
                165                 170                 175

Val Lys Gly Leu Arg Asn Lys Phe Gln Leu Asn Cys Tyr Val Lys Ile
            180                 185                 190

Asn Lys Asn Lys Pro Ile Ile Tyr Ile Asp Ser Met Ser Tyr Leu Ile
        195                 200                 205

Phe Tyr Asn Leu Ile Lys Pro Tyr Leu Ile Pro Gln Met Met Tyr Lys
    210                 215                 220

Leu Pro Asn
225
```

<210> SEQ ID NO 4
<211> LENGTH: 7
<212> TYPE: PRT
<213> ORGANISM: SV40

<400> SEQUENCE: 4

Pro Lys Lys Lys Arg Lys Val
1               5

<210> SEQ ID NO 5
<211> LENGTH: 234
<212> TYPE: PRT
<213> ORGANISM: Artificial Sequence
<220> FEATURE:
<223> OTHER INFORMATION: derived from I-SceI sequence ; S. cerevisiae

<400> SEQUENCE: 5

Met Gly Pro Lys Lys Lys Arg Lys Val Lys Asn Ile Lys Lys Asn Gln
1               5                   10                  15

Val Met Asn Leu Gly Pro Asn Ser Lys Leu Leu Lys Glu Tyr Lys Ser
            20                  25                  30

Gln Leu Ile Glu Leu Asn Ile Glu Gln Phe Glu Ala Gly Ile Gly Leu
        35                  40                  45

Ile Leu Gly Asp Ala Tyr Ile Arg Ser Arg Asp Glu Gly Lys Thr Tyr
    50                  55                  60

Cys Met Gln Phe Glu Trp Lys Asn Lys Ala Tyr Met Asp His Val Cys
65                  70                  75                  80

Leu Leu Tyr Asp Gln Trp Val Leu Ser Pro Pro His Lys Lys Glu Arg
                85                  90                  95

Val Asn His Leu Gly Asn Leu Val Ile Thr Trp Gly Ala Gln Thr Phe
            100                 105                 110

Lys His Gln Ala Phe Asn Lys Leu Ala Asn Leu Phe Ile Val Asn Asn
        115                 120                 125

Lys Lys Thr Ile Pro Asn Asn Leu Val Glu Asn Tyr Leu Thr Pro Met
    130                 135                 140

Ser Leu Ala Tyr Trp Phe Met Asp Asp Gly Gly Lys Trp Asp Tyr Asn
145                 150                 155                 160

Lys Asn Ser Thr Asn Lys Ser Ile Val Leu Asn Thr Gln Ser Phe Thr
                165                 170                 175

Phe Glu Glu Val Glu Tyr Leu Val Lys Gly Leu Arg Asn Lys Phe Gln
            180                 185                 190

Leu Asn Cys Tyr Val Lys Ile Asn Lys Asn Lys Pro Ile Ile Tyr Ile
        195                 200                 205

Asp Ser Met Ser Tyr Leu Ile Phe Tyr Asn Leu Ile Lys Pro Tyr Leu
    210                 215                 220

Ile Pro Gln Met Met Tyr Lys Leu Pro Asn
225                 230

<210> SEQ ID NO 6
<211> LENGTH: 821
<212> TYPE: PRT
<213> ORGANISM: Aspergillus nidulans

<400> SEQUENCE: 6

Met Ala Asp Thr Arg Arg Arg Gln Asn His Ser Cys Asp Pro Cys Arg
1               5                   10                  15

Lys Gly Lys Arg Arg Cys Asp Ala Pro Glu Asn Arg Asn Glu Ala Asn

```
                   20                  25                  30
Glu Asn Gly Trp Val Ser Cys Ser Asn Cys Lys Arg Trp Asn Lys Asp
            35                  40                  45
Cys Thr Phe Asn Trp Leu Ser Ser Gln Arg Ser Lys Ala Lys Gly Ala
        50                  55                  60
Ala Pro Arg Ala Arg Thr Lys Lys Ala Arg Thr Ala Thr Thr Thr Ser
65                  70                  75                  80
Glu Pro Ser Thr Ser Ala Ala Thr Ile Pro Thr Pro Glu Ser Asp Asn
                85                  90                  95
His Asp Ala Pro Pro Val Ile Asn Ser His Asp Ala Leu Pro Ser Trp
            100                 105                 110
Thr Gln Gly Leu Leu Ser His Pro Gly Asp Leu Phe Asp Phe Ser His
        115                 120                 125
Ser Ala Ile Pro Ala Asn Ala Glu Asp Ala Ala Asn Val Gln Ser Asp
        130                 135                 140
Ala Pro Phe Pro Trp Asp Leu Ala Ile Pro Gly Asp Phe Ser Met Gly
145                 150                 155                 160
Gln Gln Leu Glu Lys Pro Leu Ser Pro Leu Ser Phe Gln Ala Val Leu
                165                 170                 175
Leu Pro Pro His Ser Pro Asn Thr Asp Asp Leu Ile Arg Glu Leu Glu
            180                 185                 190
Glu Gln Thr Thr Asp Pro Asp Ser Val Thr Asp Thr Asn Ser Val Gln
        195                 200                 205
Gln Val Ala Gln Asp Gly Ser Leu Trp Ser Asp Arg Gln Ser Pro Leu
        210                 215                 220
Leu Pro Glu Asn Ser Leu Cys Met Ala Ser Asp Ser Thr Ala Arg Arg
225                 230                 235                 240
Tyr Ala Arg Ser Thr Met Thr Lys Asn Leu Met Arg Ile Tyr His Asp
                245                 250                 255
Ser Met Glu Asn Ala Leu Ser Cys Trp Leu Thr Glu His Asn Cys Pro
            260                 265                 270
Tyr Ser Asp Gln Ile Ser Tyr Leu Pro Pro Lys Gln Arg Ala Glu Trp
        275                 280                 285
Gly Pro Asn Trp Ser Asn Arg Met Cys Ile Arg Val Cys Arg Leu Asp
        290                 295                 300
Arg Val Ser Thr Ser Leu Arg Gly Arg Ala Leu Ser Ala Glu Glu Asp
305                 310                 315                 320
Lys Ala Ala Ala Arg Ala Leu His Leu Ala Ile Val Ala Phe Ala Ser
                325                 330                 335
Gln Trp Thr Gln His Ala Gln Arg Gly Ala Gly Leu Asn Val Pro Ala
            340                 345                 350
Asp Ile Ala Ala Asp Glu Arg Ser Ile Arg Arg Asn Ala Trp Asn Glu
        355                 360                 365
Ala Arg His Ala Leu Gln His Thr Thr Gly Ile Pro Ser Phe Arg Val
        370                 375                 380
Ile Phe Ala Asn Ile Ile Phe Ser Leu Thr Gln Ser Val Leu Asp Asp
385                 390                 395                 400
Asp Glu Gln His Gly Met Gly Ala Arg Leu Asp Lys Leu Leu Glu Asn
                405                 410                 415
Asp Gly Ala Pro Val Phe Leu Glu Thr Ala Asn Arg Gln Leu Tyr Thr
            420                 425                 430
Phe Arg His Lys Phe Ala Arg Met Gln Arg Arg Gly Lys Ala Phe Asn
        435                 440                 445
```

Arg Leu Pro Gly Gly Ser Val Ala Ser Thr Phe Ala Gly Ile Phe Glu
    450                 455                 460

Thr Pro Thr Pro Ser Ser Glu Ser Pro Gln Leu Asp Pro Val Val Ala
465                 470                 475                 480

Ser Glu Glu His Arg Ser Thr Leu Ser Leu Met Phe Trp Leu Gly Ile
            485                 490                 495

Met Phe Asp Thr Leu Ser Ala Ala Met Tyr Gln Arg Pro Leu Val Val
            500                 505                 510

Ser Asp Glu Asp Ser Gln Ile Ser Ser Ala Ser Pro Pro Arg Arg Gly
        515                 520                 525

Ala Glu Thr Pro Ile Asn Leu Asp Cys Trp Glu Pro Arg Gln Val
530                 535                 540

Pro Ser Asn Gln Glu Lys Ser Asp Val Trp Gly Asp Leu Phe Leu Arg
545                 550                 555                 560

Thr Ser Asp Ser Leu Pro Asp His Glu Ser His Thr Gln Ile Ser Gln
                565                 570                 575

Pro Ala Ala Arg Trp Pro Cys Thr Tyr Glu Gln Ala Ala Ala Ala Leu
                580                 585                 590

Ser Ser Ala Thr Pro Val Lys Val Leu Leu Tyr Arg Arg Val Thr Gln
            595                 600                 605

Leu Gln Thr Leu Leu Tyr Arg Gly Ala Ser Pro Ala Arg Leu Glu Ala
    610                 615                 620

Ala Ile Gln Arg Thr Leu Tyr Val Tyr Asn His Trp Thr Ala Lys Tyr
625                 630                 635                 640

Gln Pro Phe Met Gln Asp Cys Val Ala Asn His Glu Leu Leu Pro Ser
                645                 650                 655

Arg Ile Gln Ser Trp Tyr Val Ile Leu Asp Gly His Trp His Leu Ala
            660                 665                 670

Ala Met Leu Leu Ala Asp Val Leu Glu Ser Ile Asp Arg Asp Ser Tyr
        675                 680                 685

Ser Asp Ile Asn His Ile Asp Leu Val Thr Lys Leu Arg Leu Asp Asn
690                 695                 700

Ala Leu Ala Val Ser Ala Leu Ala Arg Ser Ser Leu Arg Gly Gln Glu
705                 710                 715                 720

Leu Asp Pro Gly Lys Ala Ser Pro Met Tyr Arg His Phe His Asp Ser
                725                 730                 735

Leu Thr Glu Val Ala Phe Leu Val Glu Pro Trp Thr Val Val Leu Ile
            740                 745                 750

His Ser Phe Ala Lys Ala Ala Tyr Ile Leu Leu Asp Cys Leu Asp Leu
        755                 760                 765

Asp Gly Gln Gly Asn Ala Leu Ala Gly Tyr Leu Gln Leu Arg Gln Asn
770                 775                 780

Cys Asn Tyr Cys Ile Arg Ala Leu Gln Phe Leu Gly Arg Lys Ser Asp
785                 790                 795                 800

Met Ala Ala Leu Val Ala Lys Asp Leu Glu Arg Gly Leu Asn Gly Lys
                805                 810                 815

Val Asp Ser Phe Leu
            820

<210> SEQ ID NO 7
<211> LENGTH: 1058
<212> TYPE: PRT
<213> ORGANISM: Artificial Sequence
<220> FEATURE:

<223> OTHER INFORMATION: chimeric protein

<400> SEQUENCE: 7

```
Met Gly Lys Asn Ile Lys Lys Asn Gln Val Met Asn Leu Gly Pro Asn
1               5                   10                  15

Ser Lys Leu Leu Lys Glu Tyr Lys Ser Gln Leu Ile Glu Leu Asn Ile
            20                  25                  30

Glu Gln Phe Glu Ala Gly Ile Gly Leu Ile Leu Gly Asp Ala Tyr Ile
        35                  40                  45

Arg Ser Arg Asp Glu Gly Lys Thr Tyr Cys Met Gln Phe Glu Trp Lys
    50                  55                  60

Asn Lys Ala Tyr Met Asp His Val Cys Leu Leu Tyr Gln Trp Val
65                  70                  75                  80

Leu Ser Pro Pro His Lys Lys Glu Arg Val Asn His Leu Gly Asn Leu
                85                  90                  95

Val Ile Thr Trp Gly Ala Gln Thr Phe Lys His Gln Ala Phe Asn Lys
            100                 105                 110

Leu Ala Asn Leu Phe Ile Val Asn Asn Lys Lys Thr Ile Pro Asn Asn
        115                 120                 125

Leu Val Glu Asn Tyr Leu Thr Pro Met Ser Leu Ala Tyr Trp Phe Met
    130                 135                 140

Asp Asp Gly Gly Lys Trp Asp Tyr Asn Lys Asn Ser Thr Asn Lys Ser
145                 150                 155                 160

Ile Val Leu Asn Thr Gln Ser Phe Thr Phe Glu Val Glu Tyr Leu
                165                 170                 175

Val Lys Gly Leu Arg Asn Lys Phe Gln Leu Asn Cys Tyr Val Lys Ile
            180                 185                 190

Asn Lys Asn Lys Pro Ile Ile Tyr Ile Asp Ser Met Ser Tyr Leu Ile
        195                 200                 205

Phe Tyr Asn Leu Ile Lys Pro Tyr Leu Ile Pro Gln Met Met Tyr Lys
    210                 215                 220

Leu Pro Asn Thr Ile Ser Ser Glu Thr Phe Leu Lys Leu Met Ala Asp
225                 230                 235                 240

Thr Arg Arg Arg Gln Asn His Ser Cys Asp Pro Cys Arg Lys Gly Lys
                245                 250                 255

Arg Arg Cys Asp Ala Pro Glu Asn Arg Asn Glu Ala Asn Glu Asn Gly
            260                 265                 270

Trp Val Ser Cys Ser Asn Cys Lys Arg Trp Asn Lys Asp Cys Thr Phe
        275                 280                 285

Asn Trp Leu Ser Ser Gln Arg Ser Lys Ala Lys Gly Ala Ala Pro Arg
    290                 295                 300

Ala Arg Thr Lys Lys Ala Arg Thr Ala Thr Thr Ser Glu Pro Ser
305                 310                 315                 320

Thr Ser Ala Ala Thr Ile Pro Thr Pro Glu Ser Asp Asn His Asp Ala
                325                 330                 335

Pro Pro Val Ile Asn Ser His Asp Ala Leu Pro Ser Trp Thr Gln Gly
            340                 345                 350

Leu Leu Ser His Pro Gly Asp Leu Phe Asp Phe Ser His Ser Ala Ile
        355                 360                 365

Pro Ala Asn Ala Glu Asp Ala Ala Asn Val Gln Ser Asp Ala Pro Phe
    370                 375                 380

Pro Trp Asp Leu Ala Ile Pro Gly Asp Phe Ser Met Gly Gln Gln Leu
385                 390                 395                 400
```

```
Glu Lys Pro Leu Ser Pro Leu Ser Phe Gln Ala Val Leu Leu Pro Pro
                405                 410                 415

His Ser Pro Asn Thr Asp Asp Leu Ile Arg Glu Leu Glu Glu Gln Thr
            420                 425                 430

Thr Asp Pro Asp Ser Val Thr Asp Thr Asn Ser Val Gln Gln Val Ala
        435                 440                 445

Gln Asp Gly Ser Leu Trp Ser Asp Arg Gln Ser Pro Leu Leu Pro Glu
    450                 455                 460

Asn Ser Leu Cys Met Ala Ser Asp Ser Thr Ala Arg Arg Tyr Ala Arg
465                 470                 475                 480

Ser Thr Met Thr Lys Asn Leu Met Arg Ile Tyr His Asp Ser Met Glu
                485                 490                 495

Asn Ala Leu Ser Cys Trp Leu Thr Glu His Asn Cys Pro Tyr Ser Asp
            500                 505                 510

Gln Ile Ser Tyr Leu Pro Pro Lys Gln Arg Ala Glu Trp Gly Pro Asn
        515                 520                 525

Trp Ser Asn Arg Met Cys Ile Arg Val Cys Arg Leu Asp Arg Val Ser
    530                 535                 540

Thr Ser Leu Arg Gly Arg Ala Leu Ser Ala Glu Asp Lys Ala Ala
545                 550                 555                 560

Ala Arg Ala Leu His Leu Ala Ile Val Ala Phe Ala Ser Gln Trp Thr
                565                 570                 575

Gln His Ala Gln Arg Gly Ala Gly Leu Asn Val Pro Ala Asp Ile Ala
            580                 585                 590

Ala Asp Glu Arg Ser Ile Arg Arg Asn Ala Trp Asn Glu Ala Arg His
        595                 600                 605

Ala Leu Gln His Thr Thr Gly Ile Pro Ser Phe Arg Val Ile Phe Ala
    610                 615                 620

Asn Ile Ile Phe Ser Leu Thr Gln Ser Val Leu Asp Asp Glu Gln
625                 630                 635                 640

His Gly Met Gly Ala Arg Leu Asp Lys Leu Leu Glu Asn Asp Gly Ala
                645                 650                 655

Pro Val Phe Leu Glu Thr Ala Asn Arg Gln Leu Tyr Thr Phe Arg His
            660                 665                 670

Lys Phe Ala Arg Met Gln Arg Arg Gly Lys Ala Phe Asn Arg Leu Pro
        675                 680                 685

Gly Gly Ser Val Ala Ser Thr Phe Ala Gly Ile Phe Glu Thr Pro Thr
    690                 695                 700

Pro Ser Ser Glu Ser Pro Gln Leu Asp Pro Val Val Ala Ser Glu Glu
705                 710                 715                 720

His Arg Ser Thr Leu Ser Leu Met Phe Trp Leu Gly Ile Met Phe Asp
                725                 730                 735

Thr Leu Ser Ala Ala Met Tyr Gln Arg Pro Leu Val Val Ser Asp Glu
            740                 745                 750

Asp Ser Gln Ile Ser Ser Ala Ser Pro Arg Arg Gly Ala Glu Thr
        755                 760                 765

Pro Ile Asn Leu Asp Cys Trp Glu Pro Pro Arg Gln Val Pro Ser Asn
    770                 775                 780

Gln Glu Lys Ser Asp Val Trp Gly Asp Leu Phe Leu Arg Thr Ser Asp
785                 790                 795                 800

Ser Leu Pro Asp His Glu Ser His Thr Gln Ile Ser Gln Pro Ala Ala
                805                 810                 815

Arg Trp Pro Cys Thr Tyr Glu Gln Ala Ala Ala Ala Leu Ser Ser Ala
```

```
                    820                 825                 830
Thr Pro Val Lys Val Leu Leu Tyr Arg Arg Val Thr Gln Leu Gln Thr
            835                 840                 845
Leu Leu Tyr Arg Gly Ala Ser Pro Ala Arg Leu Glu Ala Ala Ile Gln
        850                 855                 860
Arg Thr Leu Tyr Val Tyr Asn His Trp Thr Ala Lys Tyr Gln Pro Phe
865                 870                 875                 880
Met Gln Asp Cys Val Ala Asn His Glu Leu Leu Pro Ser Arg Ile Gln
                885                 890                 895
Ser Trp Tyr Val Ile Leu Asp Gly His Trp His Leu Ala Ala Met Leu
            900                 905                 910
Leu Ala Asp Val Leu Glu Ser Ile Asp Arg Asp Ser Tyr Ser Asp Ile
        915                 920                 925
Asn His Ile Asp Leu Val Thr Lys Leu Arg Leu Asp Asn Ala Leu Ala
    930                 935                 940
Val Ser Ala Leu Ala Arg Ser Ser Leu Arg Gly Gln Glu Leu Asp Pro
945                 950                 955                 960
Gly Lys Ala Ser Pro Met Tyr Arg His Phe His Asp Ser Leu Thr Glu
                965                 970                 975
Val Ala Phe Leu Val Glu Pro Trp Thr Val Val Leu Ile His Ser Phe
            980                 985                 990
Ala Lys Ala Ala Tyr Ile Leu Leu Asp Cys Leu Asp Leu Asp Gly Gln
        995                1000                1005
Gly Asn Ala Leu Ala Gly Tyr Leu Gln Leu Arg Gln Asn Cys Asn
    1010                1015                1020
Tyr Cys Ile Arg Ala Leu Gln Phe Leu Gly Arg Lys Ser Asp Met
    1025                1030                1035
Ala Ala Leu Val Ala Lys Asp Leu Glu Arg Gly Leu Asn Gly Lys
    1040                1045                1050
Val Asp Ser Phe Leu
    1055

<210> SEQ ID NO 8
<211> LENGTH: 1065
<212> TYPE: PRT
<213> ORGANISM: Artificial Sequence
<220> FEATURE:
<223> OTHER INFORMATION: chimeric protein

<400> SEQUENCE: 8

Met Gly Pro Lys Lys Arg Lys Val Lys Asn Ile Lys Lys Asn Gln
1               5                   10                  15
Val Met Asn Leu Gly Pro Asn Ser Lys Leu Leu Lys Glu Tyr Lys Ser
            20                  25                  30
Gln Leu Ile Glu Leu Asn Ile Glu Gln Phe Glu Ala Gly Ile Gly Leu
        35                  40                  45
Ile Leu Gly Asp Ala Tyr Ile Arg Ser Arg Asp Glu Gly Lys Thr Tyr
    50                  55                  60
Cys Met Gln Phe Glu Trp Lys Asn Lys Ala Tyr Met Asp His Val Cys
65                  70                  75                  80
Leu Leu Tyr Asp Gln Trp Val Leu Ser Pro Pro His Lys Lys Glu Arg
                85                  90                  95
Val Asn His Leu Gly Asn Leu Val Ile Thr Trp Gly Ala Gln Thr Phe
            100                 105                 110
Lys His Gln Ala Phe Asn Lys Leu Ala Asn Leu Phe Ile Val Asn Asn
```

```
              115                 120                 125
Lys Lys Thr Ile Pro Asn Asn Leu Val Glu Asn Tyr Leu Thr Pro Met
130                 135                 140

Ser Leu Ala Tyr Trp Phe Met Asp Asp Gly Gly Lys Trp Asp Tyr Asn
145                 150                 155                 160

Lys Asn Ser Thr Asn Lys Ser Ile Val Leu Asn Thr Gln Ser Phe Thr
                165                 170                 175

Phe Glu Glu Val Glu Tyr Leu Val Lys Gly Leu Arg Asn Lys Phe Gln
                180                 185                 190

Leu Asn Cys Tyr Val Lys Ile Asn Lys Asn Lys Pro Ile Ile Tyr Ile
                195                 200                 205

Asp Ser Met Ser Tyr Leu Ile Phe Tyr Asn Leu Ile Lys Pro Tyr Leu
210                 215                 220

Ile Pro Gln Met Met Tyr Lys Leu Pro Asn Thr Ile Ser Ser Glu Thr
225                 230                 235                 240

Phe Leu Lys Leu Met Ala Asp Thr Arg Arg Arg Gln Asn His Ser Cys
                245                 250                 255

Asp Pro Cys Arg Lys Gly Lys Arg Arg Cys Asp Ala Pro Glu Asn Arg
                260                 265                 270

Asn Glu Ala Asn Glu Asn Gly Trp Val Ser Cys Ser Asn Cys Lys Arg
                275                 280                 285

Trp Asn Lys Asp Cys Thr Phe Asn Trp Leu Ser Ser Gln Arg Ser Lys
290                 295                 300

Ala Lys Gly Ala Ala Pro Arg Ala Arg Thr Lys Lys Ala Arg Thr Ala
305                 310                 315                 320

Thr Thr Thr Ser Glu Pro Ser Thr Ser Ala Ala Thr Ile Pro Thr Pro
                325                 330                 335

Glu Ser Asp Asn His Asp Ala Pro Pro Val Ile Asn Ser His Asp Ala
                340                 345                 350

Leu Pro Ser Trp Thr Gln Gly Leu Leu Ser His Pro Gly Asp Leu Phe
                355                 360                 365

Asp Phe Ser His Ser Ala Ile Pro Ala Asn Ala Glu Asp Ala Ala Asn
                370                 375                 380

Val Gln Ser Asp Ala Pro Phe Pro Trp Asp Leu Ala Ile Pro Gly Asp
385                 390                 395                 400

Phe Ser Met Gly Gln Gln Leu Glu Lys Pro Leu Ser Pro Leu Ser Phe
                405                 410                 415

Gln Ala Val Leu Leu Pro Pro His Ser Pro Asn Thr Asp Asp Leu Ile
                420                 425                 430

Arg Glu Leu Glu Glu Gln Thr Thr Asp Pro Asp Ser Val Thr Asp Thr
                435                 440                 445

Asn Ser Val Gln Gln Val Ala Gln Asp Gly Ser Leu Trp Ser Asp Arg
                450                 455                 460

Gln Ser Pro Leu Leu Pro Glu Asn Ser Leu Cys Met Ala Ser Asp Ser
465                 470                 475                 480

Thr Ala Arg Arg Tyr Ala Arg Ser Thr Met Thr Lys Asn Leu Met Arg
                485                 490                 495

Ile Tyr His Asp Ser Met Glu Asn Ala Leu Ser Cys Trp Leu Thr Glu
                500                 505                 510

His Asn Cys Pro Tyr Ser Asp Gln Ile Ser Tyr Leu Pro Pro Lys Gln
                515                 520                 525

Arg Ala Glu Trp Gly Pro Asn Trp Ser Asn Arg Met Cys Ile Arg Val
530                 535                 540
```

-continued

Cys Arg Leu Asp Arg Val Ser Thr Ser Leu Arg Gly Arg Ala Leu Ser
545                 550                 555                 560

Ala Glu Glu Asp Lys Ala Ala Arg Ala Leu His Leu Ala Ile Val
            565                 570                 575

Ala Phe Ala Ser Gln Trp Thr Gln His Ala Gln Arg Gly Ala Gly Leu
                580                 585                 590

Asn Val Pro Ala Asp Ile Ala Ala Asp Glu Arg Ser Ile Arg Arg Asn
            595                 600                 605

Ala Trp Asn Glu Ala Arg His Ala Leu Gln His Thr Thr Gly Ile Pro
            610                 615                 620

Ser Phe Arg Val Ile Phe Ala Asn Ile Ile Phe Ser Leu Thr Gln Ser
625                 630                 635                 640

Val Leu Asp Asp Asp Glu Gln His Gly Met Gly Ala Arg Leu Asp Lys
                645                 650                 655

Leu Leu Glu Asn Asp Gly Ala Pro Val Phe Leu Glu Thr Ala Asn Arg
            660                 665                 670

Gln Leu Tyr Thr Phe Arg His Lys Phe Ala Arg Met Gln Arg Arg Gly
            675                 680                 685

Lys Ala Phe Asn Arg Leu Pro Gly Gly Ser Val Ala Ser Thr Phe Ala
690                 695                 700

Gly Ile Phe Glu Thr Pro Thr Pro Ser Ser Glu Ser Pro Gln Leu Asp
705                 710                 715                 720

Pro Val Val Ala Ser Glu Glu His Arg Ser Thr Leu Ser Leu Met Phe
                725                 730                 735

Trp Leu Gly Ile Met Phe Asp Thr Leu Ser Ala Ala Met Tyr Gln Arg
                740                 745                 750

Pro Leu Val Val Ser Asp Glu Asp Ser Gln Ile Ser Ser Ala Ser Pro
            755                 760                 765

Pro Arg Arg Gly Ala Glu Thr Pro Ile Asn Leu Asp Cys Trp Glu Pro
770                 775                 780

Pro Arg Gln Val Pro Ser Asn Gln Glu Lys Ser Asp Val Trp Gly Asp
785                 790                 795                 800

Leu Phe Leu Arg Thr Ser Asp Ser Leu Pro Asp His Glu Ser His Thr
                805                 810                 815

Gln Ile Ser Gln Pro Ala Ala Arg Trp Pro Cys Thr Tyr Glu Gln Ala
            820                 825                 830

Ala Ala Ala Leu Ser Ser Ala Thr Pro Val Lys Val Leu Leu Tyr Arg
            835                 840                 845

Arg Val Thr Gln Leu Gln Thr Leu Leu Tyr Arg Gly Ala Ser Pro Ala
850                 855                 860

Arg Leu Glu Ala Ala Ile Gln Arg Thr Leu Tyr Val Tyr Asn His Trp
865                 870                 875                 880

Thr Ala Lys Tyr Gln Pro Phe Met Gln Asp Cys Val Ala Asn His Glu
                885                 890                 895

Leu Leu Pro Ser Arg Ile Gln Ser Trp Tyr Val Ile Leu Asp Gly His
            900                 905                 910

Trp His Leu Ala Ala Met Leu Leu Ala Asp Val Leu Glu Ser Ile Asp
            915                 920                 925

Arg Asp Ser Tyr Ser Asp Ile Asn His Ile Asp Leu Val Thr Lys Leu
930                 935                 940

Arg Leu Asp Asn Ala Leu Ala Val Ser Ala Leu Ala Arg Ser Ser Leu
945                 950                 955                 960

-continued

```
Arg Gly Gln Glu Leu Asp Pro Gly Lys Ala Ser Pro Met Tyr Arg His
            965                 970                 975

Phe His Asp Ser Leu Thr Glu Val Ala Phe Leu Val Glu Pro Trp Thr
            980                 985                 990

Val Val Leu Ile His Ser Phe Ala Lys Ala Ala Tyr Ile Leu Leu Asp
            995                 1000                1005

Cys Leu Asp Leu Asp Gly Gln Gly Asn Ala Leu Ala Gly Tyr Leu
        1010                1015                1020

Gln Leu Arg Gln Asn Cys Asn Tyr Cys Ile Arg Ala Leu Gln Phe
        1025                1030                1035

Leu Gly Arg Lys Ser Asp Met Ala Ala Leu Val Ala Lys Asp Leu
        1040                1045                1050

Glu Arg Gly Leu Asn Gly Lys Val Asp Ser Phe Leu
        1055                1060                1065

<210> SEQ ID NO 9
<211> LENGTH: 297
<212> TYPE: PRT
<213> ORGANISM: Artificial Sequence
<220> FEATURE:
<223> OTHER INFORMATION: chimeric protein

<400> SEQUENCE: 9

Met Gly Lys Asn Ile Lys Lys Asn Gln Val Met Asn Leu Gly Pro Asn
1               5                   10                  15

Ser Lys Leu Leu Lys Glu Tyr Lys Ser Gln Leu Ile Glu Leu Asn Ile
            20                  25                  30

Glu Gln Phe Glu Ala Gly Ile Gly Leu Ile Leu Gly Asp Ala Tyr Ile
        35                  40                  45

Arg Ser Arg Asp Glu Gly Lys Thr Tyr Cys Met Gln Phe Glu Trp Lys
    50                  55                  60

Asn Lys Ala Tyr Met Asp His Val Cys Leu Leu Tyr Asp Gln Trp Val
65                  70                  75                  80

Leu Ser Pro Pro His Lys Lys Glu Arg Val Asn His Leu Gly Asn Leu
                85                  90                  95

Val Ile Thr Trp Gly Ala Gln Thr Phe Lys His Gln Ala Phe Asn Lys
            100                 105                 110

Leu Ala Asn Leu Phe Ile Val Asn Asn Lys Lys Thr Ile Pro Asn Asn
        115                 120                 125

Leu Val Glu Asn Tyr Leu Thr Pro Met Ser Leu Ala Tyr Trp Phe Met
    130                 135                 140

Asp Asp Gly Gly Lys Trp Asp Tyr Asn Lys Asn Ser Thr Asn Lys Ser
145                 150                 155                 160

Ile Val Leu Asn Thr Gln Ser Phe Thr Phe Glu Glu Val Glu Tyr Leu
                165                 170                 175

Val Lys Gly Leu Arg Asn Lys Phe Gln Leu Asn Cys Tyr Val Lys Ile
            180                 185                 190

Asn Lys Asn Lys Pro Ile Ile Tyr Ile Asp Ser Met Ser Tyr Leu Ile
        195                 200                 205

Phe Tyr Asn Leu Ile Lys Pro Tyr Leu Ile Pro Gln Met Met Tyr Lys
    210                 215                 220

Leu Pro Asn Thr Ile Ser Ser Glu Thr Phe Leu Lys Leu Met Ala Asp
225                 230                 235                 240

Thr Arg Arg Arg Gln Asn His Ser Cys Asp Pro Cys Arg Lys Gly Lys
                245                 250                 255
```

```
Arg Arg Cys Asp Ala Pro Glu Asn Arg Asn Glu Ala Asn Glu Asn Gly
            260                 265                 270

Trp Val Ser Cys Ser Asn Cys Lys Arg Trp Asn Lys Asp Cys Thr Phe
        275                 280                 285

Asn Trp Leu Ser Ser Gln Arg Ser Lys
        290                 295

<210> SEQ ID NO 10
<211> LENGTH: 304
<212> TYPE: PRT
<213> ORGANISM: Artificial Sequence
<220> FEATURE:
<223> OTHER INFORMATION: chimeric protein

<400> SEQUENCE: 10

Met Gly Pro Lys Lys Arg Lys Val Lys Asn Ile Lys Lys Asn Gln
1               5                   10                  15

Val Met Asn Leu Gly Pro Asn Ser Lys Leu Leu Lys Glu Tyr Lys Ser
            20                  25                  30

Gln Leu Ile Glu Leu Asn Ile Glu Gln Phe Glu Ala Gly Ile Gly Leu
        35                  40                  45

Ile Leu Gly Asp Ala Tyr Ile Arg Ser Arg Asp Glu Gly Lys Thr Tyr
50                  55                  60

Cys Met Gln Phe Glu Trp Lys Asn Lys Ala Tyr Met Asp His Val Cys
65                  70                  75                  80

Leu Leu Tyr Asp Gln Trp Val Leu Ser Pro Pro His Lys Lys Glu Arg
                85                  90                  95

Val Asn His Leu Gly Asn Leu Val Ile Thr Trp Gly Ala Gln Thr Phe
            100                 105                 110

Lys His Gln Ala Phe Asn Lys Leu Ala Asn Leu Phe Ile Val Asn Asn
        115                 120                 125

Lys Lys Thr Ile Pro Asn Asn Leu Val Glu Asn Tyr Leu Thr Pro Met
130                 135                 140

Ser Leu Ala Tyr Trp Phe Met Asp Asp Gly Gly Lys Trp Asp Tyr Asn
145                 150                 155                 160

Lys Asn Ser Thr Asn Lys Ser Ile Val Leu Asn Thr Gln Ser Phe Thr
                165                 170                 175

Phe Glu Glu Val Glu Tyr Leu Val Lys Gly Leu Arg Asn Lys Phe Gln
            180                 185                 190

Leu Asn Cys Tyr Val Lys Ile Asn Lys Asn Lys Pro Ile Ile Tyr Ile
        195                 200                 205

Asp Ser Met Ser Tyr Leu Ile Phe Tyr Asn Leu Ile Lys Pro Tyr Leu
210                 215                 220

Ile Pro Gln Met Met Tyr Lys Leu Pro Asn Thr Ile Ser Ser Glu Thr
225                 230                 235                 240

Phe Leu Lys Leu Met Ala Asp Thr Arg Arg Gln Asn His Ser Cys
                245                 250                 255

Asp Pro Cys Arg Lys Gly Lys Arg Arg Cys Asp Ala Pro Glu Asn Arg
            260                 265                 270

Asn Glu Ala Asn Glu Asn Gly Trp Val Ser Cys Ser Asn Cys Lys Arg
        275                 280                 285

Trp Asn Lys Asp Cys Thr Phe Asn Trp Leu Ser Ser Gln Arg Ser Lys
290                 295                 300

<210> SEQ ID NO 11
<211> LENGTH: 30
```

-continued

```
<212> TYPE: PRT
<213> ORGANISM: Artificial Sequence
<220> FEATURE:
<223> OTHER INFORMATION: linker peptide

<400> SEQUENCE: 11

Ile Gly Ala Arg Ser Gly Gly Gly Ser Gly Gly Gly Thr Gly Gly Gly
1               5                   10                  15

Ser Gly Gly Gly Ala Pro Lys Lys Lys Arg Lys Val Leu Glu
                20                  25                  30

<210> SEQ ID NO 12
<211> LENGTH: 18
<212> TYPE: DNA
<213> ORGANISM: Artificial Sequence
<220> FEATURE:
<223> OTHER INFORMATION: chimeric recognition site

<400> SEQUENCE: 12
tagggataac agggtaat                                                     18

<210> SEQ ID NO 13
<211> LENGTH: 28
<212> TYPE: DNA
<213> ORGANISM: Artificial Sequence
<220> FEATURE:
<223> OTHER INFORMATION: chimeric recognition site

<400> SEQUENCE: 13
cgtgcggatc tagggataac agggtaat                                          28

<210> SEQ ID NO 14
<211> LENGTH: 29
<212> TYPE: DNA
<213> ORGANISM: Artificial Sequence
<220> FEATURE:
<223> OTHER INFORMATION: chimeric recognition site

<400> SEQUENCE: 14
cgtgcggatc ctagggataa cagggtaat                                         29

<210> SEQ ID NO 15
<211> LENGTH: 30
<212> TYPE: DNA
<213> ORGANISM: Artificial Sequence
<220> FEATURE:
<223> OTHER INFORMATION: chimeric recognition site

<400> SEQUENCE: 15
cgtgcggatc gctagggata acagggtaat                                        30

<210> SEQ ID NO 16
<211> LENGTH: 31
<212> TYPE: DNA
<213> ORGANISM: Artificial Sequence
<220> FEATURE:
<223> OTHER INFORMATION: chimeric recognition site

<400> SEQUENCE: 16
cgtgcggatc cgctagggat aacagggtaa t                                      31

<210> SEQ ID NO 17
<211> LENGTH: 4065
<212> TYPE: DNA
<213> ORGANISM: Artificial Sequence
<220> FEATURE:
```

<223> OTHER INFORMATION: plasmid
<220> FEATURE:
<221> NAME/KEY: misc_feature
<222> LOCATION: (3)..(12)
<223> OTHER INFORMATION: n is a, c, g, or t

<400> SEQUENCE: 17

| | | | | | |
|---|---|---|---|---|---|
| ccnnnnnnnn | nngaattcga | agcttgggcc | cgaacaaaaa | ctcatctcag | aagaggatct | 60 |
| gaatagcgcc | gtcgaccatc | atcatcatca | tcattgagtt | taaacggtct | ccagcttggc | 120 |
| tgttttggcg | gatgagagaa | gattttcagc | ctgatacaga | ttaaatcaga | acgcagaagc | 180 |
| ggtctgataa | aacagaattt | gcctggcggc | agtagcgcgg | tggtcccacc | tgaccccatg | 240 |
| ccgaactcag | aagtgaaacg | ccgtagcgcc | gatggtagtg | tggggtctcc | ccatgcgaga | 300 |
| gtagggaact | gccaggcatc | aaataaaacg | aaaggctcag | tcgaaagact | gggcctttcg | 360 |
| ttttatctgt | tgtttgtcgg | tgaacgctct | cctgagtagg | acaaatccgc | cgggagcgga | 420 |
| tttgaacgtt | gcgaagcaac | ggcccggagg | gtggcgggca | ggacgcccgc | cataaactgc | 480 |
| caggcatcaa | attaagcaga | aggccatcct | gacggatggc | cttttgcgt | ttctacaaac | 540 |
| tcttttgttt | attttctaa | atacattcaa | atatgtatcc | gctcatgaga | caataaccct | 600 |
| gataaatgct | tcaataatat | tgaaaaagga | agagtatgag | tattcaacat | ttccgtgtcg | 660 |
| cccttattcc | cttttttgcg | gcattttgcc | ttcctgtttt | tgctcaccca | gaaacgctgg | 720 |
| tgaaagtaaa | agatgctgaa | gatcagttgg | gtgcacgagt | gggttacatc | gaactggatc | 780 |
| tcaacagcgg | taagatcctt | gagagttttc | gccccgaaga | acgttttcca | atgatgagca | 840 |
| cttttaaagt | tctgctatgt | ggcgcggtat | tatcccgtgt | tgacgccggg | caagagcaac | 900 |
| tcggtcgccg | catacactat | tctcagaatg | acttggttga | gtactcacca | gtcacagaaa | 960 |
| agcatcttac | ggatggcatg | acagtaagag | aattatgcag | tgctgccata | accatgagtg | 1020 |
| ataacactgc | ggccaactta | cttctgacaa | cgatcggagg | accgaaggag | ctaaccgctt | 1080 |
| ttttgcacaa | catgggggat | catgtaactc | gccttgatcg | ttgggaaccg | gagctgaatg | 1140 |
| aagccatacc | aaacgacgag | cgtgacacca | cgatgcctgt | agcaatggca | acaacgttgc | 1200 |
| gcaaactatt | aactggcgaa | ctacttactc | tagcttcccg | gcaacaatta | atagactgga | 1260 |
| tggaggcgga | taaagttgca | ggaccacttc | tgcgctcggc | ccttccggct | ggctggttta | 1320 |
| ttgctgataa | atctggagcc | ggtgagcgtg | ggtctcgcgg | tatcattgca | gcactggggc | 1380 |
| cagatggtaa | gccctcccgt | atcgtagtta | tctacacgac | ggggagtcag | gcaactatgg | 1440 |
| atgaacgaaa | tagacagatc | gctgagatag | gtgcctcact | gattaagcat | tggtaactgt | 1500 |
| cagaccaagt | ttactcatat | atactttaga | ttgatttaaa | acttcatttt | taatttaaaa | 1560 |
| ggatctaggt | gaagatcctt | tttgataatc | tcatgaccaa | aatcccttaa | cgtgagtttt | 1620 |
| cgttccactg | agcgtcagac | cccgtagaaa | agatcaaagg | atcttcttga | gatcctttt | 1680 |
| ttctgcgcgt | aatctgctgc | ttgcaaacaa | aaaaaccacc | gctaccagcg | gtggtttgtt | 1740 |
| tgccggatca | agagctacca | actctttttc | cgaaggtaac | tggcttcagc | agagcgcaga | 1800 |
| taccaaatac | tgtccttcta | gtgtagccgt | agttaggcca | ccacttcaag | aactctgtag | 1860 |
| caccgcctac | atacctcgct | ctgctaatcc | tgttaccagt | ggctgctgcc | agtggcgata | 1920 |
| agtcgtgtct | taccgggttg | gactcaagac | gatagttacc | ggataaggcg | cagcggtcgg | 1980 |
| gctgaacggg | gggttcgtgc | acacagccca | gcttggagcg | aacgacctac | accgaactga | 2040 |
| gatacctaca | gcgtgagcta | tgagaaagcg | ccacgcttcc | cgaagggaga | aaggcggaca | 2100 |
| ggtatccggt | aagcggcagg | gtcggaacag | gagagcgcac | gagggagctt | ccagggggaa | 2160 |

```
acgcctggta tctttatagt cctgtcgggt ttcgccacct ctgacttgag cgtcgatttt    2220
tgtgatgctc gtcagggggg cggagcctat ggaaaaacgc cagcaacgcg ccttttttac    2280
ggttcctggc cttttgctgg cctttttgctc acatgttctt tcctgcgtta tcccctgatt   2340
ctgtggataa ccgtattacc gcctttgagt gagctgatac cgctcgccgc agccgaacga    2400
ccgagcgcag cgagtcagtg agcgaggaag cggaagagcg cctgatgcgg tattttctcc    2460
ttacgcatct gtgcggtatt tcacaccgca tatggtgcac tctcagtaca atctgctctg    2520
atgccgcata gttaagccag tatacactcc gctatcgcta cgtgactggg tcatggctgc    2580
gccccgacac ccgccaacac ccgctgacgc gccctgacgg gcttgtctgc tcccggcatc    2640
cgcttacaga caagctgtga ccgtctccgg gagctgcatg tgtcagaggt tttcaccgtc    2700
atcaccgaaa cgcgcgaggc agcagatcaa ttcgcgcgcg aaggcgaagc ggcatgcata    2760
atgtgcctgt caaatggacg aagcagggat tctgcaaacc ctatgctact ccgtcaagcc    2820
gtcaattgtc tgattcgtta ccaattatga caacttgacg gctacatcat tcactttttc    2880
ttcacaaccg gcacggaact cgctcgggct ggccccggtg cattttttaa atacccgcga    2940
gaaatagagt tgatcgtcaa accaacatt gcgaccgacg gtggcgatag gcatcccgggt   3000 ggtgctcaaa agcagcttcg cctggctgat acgttggtcc tcgcgccagc ttaagacgct    3060
aatccctaac tgctggcgga aaagatgtga cagacgcgac ggcgacaagc aaacatgctg    3120
tgcgacgctg gcgatatcaa aattgctgtc tgccaggtga tcgctgatgt actgacaagc    3180
ctcgcgtacc cgattatcca tcggtggatg gagcgactcg ttaatcgctt ccatgcgccg    3240
cagtaacaat tgctcaagca gatttatcgc cagcagctcc gaatagcgcc cttccccttg    3300
cccggcgtta atgatttgcc caaacaggtc gctgaaatgc ggctggtgcg cttcatccgg    3360
gcgaaagaac cccgtattgg caaatattga cggccagtta agccattcat gccagtaggc    3420
gcgcggacga agtaaaccc actggtgata ccattcgcga gcctccggat gacgaccgta    3480
gtgatgaatc tctcctggcg ggaacagcaa atatcaccc ggtcggcaaa caaattctcg    3540
tccctgattt ttcaccaccc cctgaccgcg aatggtgaga ttgagaatat aacctttcat    3600
tcccagcggt cggtcgataa aaaaatcgag ataaccgttg gcctcaatcg gcgttaaacc    3660
cgccaccaga tgggcattaa acgagtatcc cggcagcagg ggatcatttt gcgcttcagc    3720 catactttc atactcccgc cattcagaga agaaccaat tgtccatatt gcatcagaca    3780
ttgccgtcac tgcgtctttt actggctctt ctcgctaacc aaaccggtaa ccccgcttat    3840
taaaagcatt ctgtaacaaa gcgggaccaa agccatgaca aaaacgcgta acaaaagtgt    3900
ctataatcac ggcagaaaag tccacattga ttatttgcac ggcgtcacac tttgctatgc    3960
catagcattt ttatccataa gattagcgga tcctacctga cgctttttat cgcaactctc    4020
tactgtttct ccatacccgt tttttgggct aacaggagga attaa                   4065
```

<210> SEQ ID NO 18
<211> LENGTH: 711
<212> TYPE: DNA
<213> ORGANISM: Artificial Sequence
<220> FEATURE:
<223> OTHER INFORMATION: Insert of VC-SAH40-4

<400> SEQUENCE: 18

```
atgggtaaga acattaagaa gaaccaggtg atgaacctgg ccctaactc taagctgctt      60 aaggaataca agtctcagct gattgagctg aacattgagc agttcgaggc tggcataggc    120
```

| | |
|---|---|
| ctgattctgg gcgatgctta cattaggtct agggatgagg gcaagaccta ctgcatgcag | 180 |
| ttcgagtgga agaacaaggc ttacatggat cacgtgtgcc tgctgtacga tcagtgggtg | 240 |
| ctgtctcctc ctcacaagaa ggagagggtg aaccacttgg gaaacctggt gattacctgg | 300 |
| ggcgctcaaa ccttcaagca ccaggctttc aacaagctgg ctaacctgtt cattgtgaac | 360 |
| aacaagaaga ccattcctaa caacctggtg agaactacc tgaccccctat gtctctggct | 420 |
| tactggttca tggatgatgg cggcaagtgg gattacaaca agaactctac caacaagtct | 480 |
| attgtgctga cacccagtc tttcaccttc gaggaggtgg aatacctggt gaagggcctg | 540 |
| aggaacaagt tccagctgaa ctgctacgtg aagattaaca agaacaagcc tattatttac | 600 |
| attgattcta tgtcttacct gattttctac aacctgatta agccttacct gattcctcag | 660 |
| atgatgtaca agctgcctaa caccatctct tctgagacct tcctgaagtg a | 711 |

<210> SEQ ID NO 19
<211> LENGTH: 3177
<212> TYPE: DNA
<213> ORGANISM: Artificial Sequence
<220> FEATURE:
<223> OTHER INFORMATION: Insert of VC-SAH51-40

<400> SEQUENCE: 19

| | |
|---|---|
| atgggtaaga acattaagaa gaaccaggtg atgaacctgg gccctaactc taagctgctt | 60 |
| aaggaataca gtctcagct gattgagctg aacattgagc agttcgaggc tggcataggc | 120 |
| ctgattctgg gcgatgctta cattaggtct agggatgagg gcaagaccta ctgcatgcag | 180 |
| ttcgagtgga agaacaaggc ttacatggat cacgtgtgcc tgctgtacga tcagtgggtg | 240 |
| ctgtctcctc ctcacaagaa ggagagggtg aaccacttgg gaaacctggt gattacctgg | 300 |
| ggcgctcaaa ccttcaagca ccaggctttc aacaagctgg ctaacctgtt cattgtgaac | 360 |
| aacaagaaga ccattcctaa caacctggtg agaactacc tgaccccctat gtctctggct | 420 |
| tactggttca tggatgatgg cggcaagtgg gattacaaca agaactctac caacaagtct | 480 |
| attgtgctga cacccagtc tttcaccttc gaggaggtgg aatacctggt gaagggcctg | 540 |
| aggaacaagt tccagctgaa ctgctacgtg aagattaaca agaacaagcc tattatttac | 600 |
| attgattcta tgtcttacct gattttctac aacctgatta agccttacct gattcctcag | 660 |
| atgatgtaca agctgcctaa caccatctct tctgagacct tcctgaagct tatggctgat | 720 |
| acaagaagaa ggcagaacca ctcttgcgat ccttgtagaa agggaaaaag aagatgtgac | 780 |
| gctcctgaga acagaaatga ggctaacgag aacggatggg tgtcatgttc taactgcaag | 840 |
| agatggaaca aggattgcac tttcaactgg ctctcatctc agagatcaaa ggctaagggt | 900 |
| gctgctccta gagctagaac taagaaggct agaactgcta ctactacttc tgagccttct | 960 |
| acttctgctg ctactatccc tactcctgag tctgataacc atgatgctcc tccagtgatc | 1020 |
| aactctcatg atgctctccc atcttggact caggggacttc tttctcatcc tggtgatctc | 1080 |
| ttcgatttct ctcactctgc tatccctgct aatgctgagg atgctgctaa cgttcaatct | 1140 |
| gatgctcctt tcccttggga tcttgctatt cctggtgatt tctctatggg acagcagctt | 1200 |
| gagaaacctc tttctcctct ctcttttccag gctgttcttc tccctcctca ctctcctaac | 1260 |
| actgatgatc tcatcagaga gcttgaggaa cagactactg atcctgattc tgtgactgat | 1320 |
| acaaactctg ttcagcaggt tgcacaggat ggatctttgt ggagtgatag acagtctcct | 1380 |
| cttctccctg agaactctct ctgtatggct tctgattcta ctgctagaag atacgctaga | 1440 |
| tcaactatga ctaagaacct catgagaatc taccacgatt ctatggaaaa cgctctctct | 1500 |

```
tgttggctta ctgagcacaa ctgcccttac tctgatcaaa tctcttacct ccctcctaag    1560
cagcgtgctg aatggggacc taactggtct aacagaatgt gcatcagagt gtgcagactc    1620
gatagagtgt ctacttctct cagaggtaga gctttgtctg ctgaagagga taaggctgct    1680
gctagagcac ttcatctcgc tatcgtggct tttgcttctc aatggactca gcatgctcaa    1740
agaggtgctg gacttaacgt tcctgctgat atcgctgctg atgagagatc aatcagaaga    1800
aacgcttgga acgaggctag acatgctctc aacacacta ctggaatccc atctttcaga     1860
gtgatcttcg ctaacatcat cttctcactc actcagtctg tgctcgatga tgatgagcaa    1920
catggaatgg gagctagact tgataagctc cttgagaacg atggtgctcc tgttttctt     1980 gagactgcta acagacagct ctacactttc agacacaagt tcgctagaat gcaaagaaga    2040
ggaaaggctt tcaacagact ccctggtgga tctgttgctt ctactttcgc tggaatcttc    2100
gagactccta ctccttcttc tgagtctcct cagctcgatc ctgttgttgc ttctgaggaa    2160
cacagatcaa cactctcact catgttctgg ctcggaatca tgttcgatac actctcagct    2220
gctatgtacc aaagacctct cgttgtgtct gatgaggatt ctcaaatctc ttctgcttct    2280
cctcctagaa gaggtgctga gacacctatc aaccttgatt gctgggaacc tcctagacaa    2340
gttccttcta accaggaaaa gtctgatgtt tggggtgatc ttttcctcag aacttctgat    2400
tctctccctg atcacgagtc tcacactcaa atctctcagc tgctgctag atggccttgt     2460 acttacgaac aagctgctgc tgctcttttct tctgctactc ctgttaaggt gctcctctac    2520
agaagagtta ctcagcttca gactcttctc tacagaggag cttctcctgc tagacttgag    2580
gctgctatcc agagaactct ctacgtttac aaccactgga ctgctaagta ccagcctttc    2640
atgcaagatt gcgtggctaa ccatgagctt ctcccttcta gaatccagtc ttggtacgtg    2700
atccttgatg gacattggca tcttgctgct atgcttctcg ctgatgtgct tgagtctatc    2760
gatagagatt cttactctga tatcaaccac atcgatctcg tgactaagct cagactcgat    2820
aacgctcttg ctgtttctgc tctcgctaga tcatctctca gaggacagga acttgatcct    2880
ggaaaggctt ctcctatgta cagacacttc cacgattctc tcactgaagt tgctttcctt    2940
gtggagcctt ggactgttgt tctcatccac tcattcgcta aggctgctta catccttctt    3000
gattgcctcg atcttgatgg acagggaaat gctcttgctg atacctcca gcttagacag     3060 aactgcaact actgcatcag agcacttcag ttcctcggaa gaaagtctga tatggctgct    3120
ctcgttgcta aggatcttga gagggactt aacggaaaag tggattcttt cctctga         3177
```

<210> SEQ ID NO 20
<211> LENGTH: 3198
<212> TYPE: DNA
<213> ORGANISM: Artificial Sequence
<220> FEATURE:
<223> OTHER INFORMATION: Insert of VC-SAH50-37

<400> SEQUENCE: 20

```
atgggtccta agaagaagag aaaggttaag aacattaaga gaaccaggt gatgaacctg       60 ggccctaact ctaagctgct taaggaatac aagtctcagc tgattgagct gaacattgag     120
cagttcgagg ctggcatagg cctgattctg ggcgatgctt acattaggtc tagggatgag    180
ggcaagacct actgcatgca gttcgagtgg aagaacaagg cttacatgga tcacgtgtgc    240
ctgctgtacg atcagtgggt gctgtctcct cctcacaaga aggagagggt gaaccacttg    300
ggaaacctgg tgattacctg gggcgctcaa accttcaagc caccaggcttt caacaagctg    360
```

```
gctaacctgt tcattgtgaa caacaagaag accattccta caacctggt ggagaactac    420 ctgacccta tgtctctggc ttactggttc atggatgatg gcggcaagtg ggattacaac    480
aagaactcta ccaacaagtc tattgtgctg aacacccagt ctttcacctt cgaggaggtg    540
gaatacctgg tgaagggcct gaggaacaag ttccagctga actgctacgt gaagattaac    600
aagaacaagc ctattattta cattgattct atgtcttacc tgattttcta caacctgatt    660
aagccttacc tgattcctca gatgatgtac aagctgccta caccatctc ttctgagacc    720 ttcctgaagc ttatggctga tacaagaaga aggcagaacc actcttgcga tccttgtaga    780
aagggaaaaa gaagatgtga cgctcctgag aacagaaatg aggctaacga aacggatgg    840 gtgtcatgtt ctaactgcaa gagatggaac aaggattgca ctttcaactg gctctcatct    900
cagagatcaa aggctaaggg tgctgctcct agagctagaa ctaagaaggc tagaactgct    960
actactactt ctgagccttc tacttctgct gctactatcc ctactcctga gtctgataac   1020
catgatgctc ctccagtgat caactctcat gatgctctcc catcttggac tcagggactt   1080
ctttctcatc ctggtgatct cttcgatttc tctcactctg ctatccctgc taatgctgag   1140
gatgctgcta cgttcaatc tgatgctcct ttcccttggg atcttgctat tcctggtgat   1200
ttctctatgg gacagcagct tgagaaacct cttttctcct ctctctttcca ggctgttctt   1260 ctccctcctc actctcctaa cactgatgat ctcatcagag agcttgagga acagactact   1320
gatcctgatt ctgtgactga tacaaactct gttcagcagg ttgcacagga tggatctttg   1380
tggagtgata gacagtctcc tcttctcct gagaactctc tctgtatggc ttctgattct   1440
actgctagaa gatacgctag atcaactatg actaagaacc tcatgagaat ctaccacgat   1500
tctatggaaa acgctctctc ttgttggctt actgagcaca actgcccta ctctgatcaa   1560 atctcttacc tccctcctaa gcagcgtgct gaatggggac ctaactggtc taacagaatg   1620
tgcatcagag tgtgcagact cgatagagtg tctacttctc tcagaggtag agctttgtct   1680
gctgaagagg ataaggctgc tgctagagca cttcatctcg ctatcgtggc tttgcttct   1740 caatggactc agcatgctca aagaggtgct ggacttaacg ttcctgctga tatcgctgct   1800
gatgagagat caatcagaag aaacgcttgg aacgaggcta acatgctct ccaacacact   1860 actggaatcc catcttcag agtgatctt gctaacatca tcttctcact cactcagtct   1920
gtgctcgatg atgatgagca acatggaatg ggagctagac ttgataagct ccttgagaac   1980
gatggtgctc ctgttttct tgagactgct aacagacagc tctacacttt cagacacaag   2040
ttcgctagaa tgcaaagaag aggaaaggct ttcaacagac tccctggtgg atctgttgct   2100
tctactttcg ctggaatctt cgagactcct actccttctt ctgagtctcc tcagctcgat   2160
cctgttgttg cttctgagga acacagatca acactctcac tcatgttctg gctcggaatc   2220
atgttcgata cactctcagc tgctatgtac caaagacctc tcgttgtgtc tgatgaggat   2280
tctcaaatct cttctgcttc tcctcctaga gaggtgctg agacacctat caaccttgat   2340
tgctgggaac tccctagaca agttccttct aaccaggaaa agtctgatgt ttggggtgat   2400
cttttcctca gaacttctga ttctctcct gatcacgagt ctcacactca aatctctcag   2460
cctgctgcta gatggccttg tacttacgaa caagctgctg ctgctctttc ttctgctact   2520
cctgttaagg tgctcctcta cagaagagtt actcagcttc agactcttct ctacagagga   2580
gcttctcctg ctagacttga ggctgctatc cagagaactc tctacgttta caaccactgg   2640
actgctaagt accagccttt catgcaagat tgcgtggcta accatgagct ctcccttcct   2700
agaatccagt cttggtacgt gatccttgat ggacattggc atcttgctgc tatgcttctc   2760
```

```
gctgatgtgc ttgagtctat cgatagagat tcttactctg atatcaacca catcgatctc    2820
gtgactaagc tcagactcga taacgctctt gctgtttctg ctctcgctag atcatctctc    2880
agaggacagg aacttgatcc tggaaaggct tctcctatgt acagacactt ccacgattct    2940
ctcactgaag ttgctttcct tgtggagcct tggactgttg ttctcatcca ctcattcgct    3000
aaggctgctt acatccttct tgattgcctc gatcttgatg gacagggaaa tgctcttgct    3060
ggataccttc agcttagaca gaactgcaac tactgcatca gagcacttca gttcctcgga    3120
agaaagtctg atatggctgc tctcgttgct aaggatcttg agagaggact aacggaaaa     3180 gtggattctt tcctctga                                                  3198

<210> SEQ ID NO 21
<211> LENGTH: 894
<212> TYPE: DNA
<213> ORGANISM: Artificial Sequence
<220> FEATURE:
<223> OTHER INFORMATION: Insert of VC-SAH49-1

<400> SEQUENCE: 21
atgggtaaga acattaagaa gaaccaggtg atgaacctgg gccctaactc taagctgctt      60
aaggaataca agtctcagct gattgagctg aacattgagc agttcgaggc tggcataggc     120
ctgattctgg gcgatgctta cattaggtct agggatgagg caagaccta ctgcatgcag      180 ttcgagtgga agaacaaggc ttacatggat cacgtgtgcc tgctgtacga tcagtgggtg     240
ctgtctcctc ctcacaagaa ggagagggtg aaccacttgg gaaacctggt gattacctgg     300
ggcgctcaaa ccttcaagca ccaggctttc aacaagctgg ctaacctgtt cattgtgaac     360
aacaagaaga ccattcctaa caacctggtg gagaactacc tgaccccctat gtctctggct    420 tactggttca tggatgatgg cggcaagtgg gattacaaca gaactctac caacaagtct     480 attgtgctga acacccagtc tttcaccttc gaggaggtgg aatacctggt gaagggcctg    540
aggaacaagt tccagctgaa ctgctacgtg aagattaaca gaacaagcc tattatttac    600 attgattcta tgtcttacct gattttctac aacctgatta gccttacct gattcctcag    660 atgatgtaca agctgcctaa caccatctct tctgagacct tcctgaagct tatggctgat    720
acaagaagaa ggcagaacca ctcttgcgat ccttgtagaa agggaaaaag aagatgtgac   780
gctcctgaga acagaaatga ggctaacgag aacggatggg tgtcatgttc taactgcaag    840
agatggaaca aggattgcac tttcaactgg ctctcatctc agagatcaaa gtga          894

<210> SEQ ID NO 22
<211> LENGTH: 915
<212> TYPE: DNA
<213> ORGANISM: Artificial Sequence
<220> FEATURE:
<223> OTHER INFORMATION: Insert of VC-SAH48-8

<400> SEQUENCE: 22
atgggtccta agaagaagag aaaggttaag aacattaaga gaaccaggt gatgaacctg       60 ggccctaact ctaagctgct taaggaatac aagtctcagc tgattgagct gaacattgag     120
cagttcgagg ctggcatagg cctgattctg ggcgatgctt acattaggtc tagggatgag     180
ggcaagacct actgcatgca gttcgagtgg aagaacaagg cttacatgga tcacgtgtgc    240
ctgctgtacg atcagtgggt gctgtctcct cctcacaaga aggagagggt gaaccacttg    300
ggaaacctgg tgattacctg gggcgctcaa accttcaagc accaggcttt caacaagctg    360
```

| | |
|---|---|
| gctaacctgt tcattgtgaa caacaagaag accattccta caacctggt ggagaactac | 420 |
| ctgacccta tgtctctggc ttactggttc atggatgatg cggcaagtg ggattacaac | 480 |
| aagaactcta ccaacaagtc tattgtgctg aacacccagt ctttcacctt cgaggaggtg | 540 |
| gaatacctgg tgaagggcct gaggaacaag ttccagctga actgctacgt gaagattaac | 600 |
| aagaacaagc ctattattta cattgattct atgtcttacc tgattttcta caacctgatt | 660 |
| aagccttacc tgattcctca gatgatgtac aagctgccta acaccatctc ttctgagacc | 720 |
| ttcctgaagc ttatggctga tacaagaaga aggcagaacc actcttgcga tccttgtaga | 780 |
| aagggaaaaa aagatgtga cgctcctgag aacagaaatg aggctaacga aacggatgg | 840 |
| gtgtcatgtt ctaactgcaa agatggaac aaggattgca ctttcaactg gctctcatct | 900 |
| cagagatcaa agtga | 915 |

<210> SEQ ID NO 23
<211> LENGTH: 4905
<212> TYPE: DNA
<213> ORGANISM: Artificial Sequence
<220> FEATURE:
<223> OTHER INFORMATION: Construct II
<220> FEATURE:
<221> NAME/KEY: misc_feature
<222> LOCATION: (1218)..(1227)
<223> OTHER INFORMATION: n is a, c, g, or t

<400> SEQUENCE: 23

| | |
|---|---|
| agcgctggca gtccttgcca ttgccgggat cggggcagta acgggatggg cgatcagccc | 60 |
| gagcgcgacg cccggaagca ttgacgtgcc gcaggtgctg gcatcgacat tcagcgacca | 120 |
| ggtgccgggc agtgagggcg gcggcctggg tggcggcctg cccttcactt cggccgtcgg | 180 |
| ggcattcacg gacttcatgg cggggccggc aatttttacc ttgggcattc ttggcatagt | 240 |
| ggtcgcgggt gccgtgctcg tgttcggggg tgcgataaac ccagcgaacc atttgaggtg | 300 |
| ataggtaaga ttataccgag gtatgaaaac gagaattgga cctttacaga attactctat | 360 |
| gaagcgccat atttaaaaag ctaccaagac gaagaggatg aagaggatga ggaggcagat | 420 |
| tgccttgaat atattgacaa tactgataag ataatatatc ttttatatag aagatatcgc | 480 |
| cgtatgtaag gatttcaggg ggcaaggcat aggcagcgcg cttatcaata tatctataga | 540 |
| atgggcaaag cataaaaact tgcatggact aatgcttgaa acccaggaca ataaccttat | 600 |
| agcttgtaaa ttctatcata attgggtaat gactccaact tattgatagt gttttatgtt | 660 |
| cagataatgc ccgatgactt tgtcatgcag ctccaccgat tttgagaacg acagcgactt | 720 |
| ccgtcccagc cgtgccaggt gctgcctcag attcaggtta tgccgctcaa ttcgctgcgt | 780 |
| atatcgcttg ctgattacgt gcagcttttcc cttcaggcgg gattcataca gcggccagcc | 840 |
| atccgtcatc catatcacca cgtcaaaggg tgacagcagg ctcataagac gccccagcgt | 900 |
| cgccatagtg cgttcaccga atacgtgcgc aacaaccgtc ttccggagac tgtcatacgc | 960 |
| gtaaaacagc cagcgctggc gcgatttagc cccgacatag ccccactgtt cgtccatttc | 1020 |
| cgcgcagacg atgacgtcac tgcccggctg tatgcgcgag gttaccgact gcggcctgag | 1080 |
| ttttttaagt gacgtaaaat cgtgttgagg ccaacgccca taatgcgggc tgttgcccgg | 1140 |
| catccaacgc cattcatggc catatcaatg attttctggt gcgtaccggg ttgagaagcg | 1200 |
| gtgtaagtga actgcagnnn nnnnnnnaag cttgactctc ttaagggagc gtcgagtacg | 1260 |
| cgcccgggga gcccaagggc acgccctggc acccgaagct ctagtatcaa atttggcaca | 1320 |
| aaaagcaaaa ttaaaatact gataattgcc aacacaatta acatctcaat caaggtaaat | 1380 |

```
gcttttttgct ttttttgcca aagctatctt ccgtgatcag agctccagct tttgttccct    1440
ttagtgaggg ttaattgcgc gcttggcgta atcatggtca tagctgtttc ctgtgtgaaa    1500
ttgttatccg ctcacaattc cacacaacat acgagccgga agcataaagt gtaaagcctg    1560
gggtgcctaa tgagtgagct aactcacatt aattgcgttg cgctcactgc ccgctttcca    1620
gtcgggaaac ctgtcgtgcc agctgataga cacagaagcc actggagcac ctcaaaaaca    1680
ccatcataca ctaaatcagt aagttggcag catcacccat aattgtggtt tcaaaatcgg    1740
ctccgtcgat actatgttat acgccaactt tgaaaacaac tttgaaaaag ctgttttctg    1800
gtatttaagg ttttagaatg caaggaacag tgaattggag ttcgtcttgt tataattagc    1860
ttcttggggt atctttaaat actgtagaaa agaggaagga aataataaat ggctaaaatg    1920
agaatatcac cggaattgaa aaactgatc gaaaaatacc gctgcgtaaa agatacggaa    1980
ggaatgtctc ctgctaaggt atataagctg gtgggagaaa atgaaaacct atatttaaaa    2040
atgacggaca gccggtataa agggaccacc tatgatgtgg aacgggaaaa ggacatgatg    2100
ctatggctgg aaggaaagct gcctgttcca aaggtcctgc actttgaacg gcatgatggc    2160
tggagcaatc tgctcatgag tgaggccgat ggcgtccttt gctcggaaga gtatgaagat    2220
gaacaaagcc ctgaaaagat tatcgagctg tatgcggagt gcatcaggct ctttcactcc    2280
atcgacatat cggattgtcc ctatacgaat agcttagaca gccgcttagc cgaattggat    2340
tacttactga ataacgatct ggccgatgtg gattgcgaaa actgggaaga agacactcca    2400
tttaaagatc cgcgcgagct gtatgatttt ttaaagacgg aaaagcccga gaggaacttt    2460
gtcttttccc acggcgacct gggagacagc aacatctttg tgaaagatgg caaagtaagt    2520
ggctttattg atcttgggag aagcggcagg cggacaagt ggtatgacat tgccttctgc    2580
gtccggtcga tcagggagga tatcggggaa gaacagtatg tcgagctatt ttttgactta    2640
ctggggatca agcctgattg ggagaaaata aatatttata ttttactgga tgaattgttt    2700
tagtacctag atgtggcgca acgatgccgg cgacaagcag gagcgcaccg acttcttccg    2760
catcaagtgt tttggctctc aggccgaggc ccacggcaag tatttgggca aggggtcgct    2820
ggtattcgtg cagggcaaga ttcggaatac caagtacgag aaggacggcc agacggtcta    2880
cgggaccgac ttcattgccg ataaggtgga ttatctggac accaaggcac caggcgggtc    2940
aaatcaggaa taagggcaca ttgccccggc gtgagtcggg gcaatcccgc aaggagggtg    3000
aatgaatcgg acgtttgacc ggaaggcata caggcaagaa ctgatcgacg cggggttttc    3060
cgccgaggat gccgaaacca tcgcaagcgc caccgtcatg cgtgcgcccc gcgaaacctt    3120
ccagtccgtc ggctcgatgg tccagcaagc tacgccaag atcgagcgcg acagcgtgca    3180
actggctccc cctgccctgc ccgcgccatc ggccgccgtg gagcgttcgc gtcgtctcga    3240
acaggaggcg gcaggtttgg cgaagtcgat gaccatcgac acgcgaggaa ctatgacgac    3300
caagaagcga aaaccgccg gcgaggacct ggcaaaacag gtcagcgagg ccaagcaggc    3360
cgcgttgctg aaacacacga agcagcagat caaggaaatg cagcttttcct tgttcgatat    3420
tgcgccgtgg ccggacacga tgcgagcgat gccaaacgac acggcccgct ctgccctgtt    3480
caccacgcgc aacaagaaaa tcccgcgcga ggcgctgcaa acaaggtca tttttccacgt    3540
caacaaggac gtgaagatca cctacaccgg cgtcgagctg cgggccgacg atgacgaact    3600
ggtgtggcag caggtgttgg agtacgcgaa gcgcaccct atcggcgagc cgatcacctt    3660
cacgttctac gagctttgcc aggacctggg ctggtcgatc aatggccggt attacacgaa    3720
```

```
ggccgaggaa tgcctgtcgc gcctacaggc gacggcgatg ggcttcacgt ccgaccgcgt      3780
tgggcacctg gaatcggtgt cgctgctgca ccgcttccgc gtcctggacc gtggcaagaa      3840
aacgtcccgt tgccaggtcc tgatcgacga ggaaatcgtc gtgctgtttg ctggcgacca      3900
ctacacgaaa ttcatatggg agaagtaccg caagctgtcg ccgacggccc gacggatgtt      3960
cgactatttc agctcgcacc gggagccgta cccgctcaag ctggaaacct tccgcctcat      4020
gtgcggatcg gattccaccc gcgtgaagaa gtggcgcgag caggtcggcg aagcctgcga      4080
agagttgcga ggcagcggcc tggtggaaca cgcctgggtc aatgatgacc tggtgcattg      4140
caaacgctag ggccttgtgg ggtcagttcc ggctgggggt tcagcagcca gcgctttact      4200
ctagtgacgc tcaccgggct ggttgccctc gccgctgggc tggcggccgt ctatggccct      4260
gcaaacgcgc cagaaacgcc gtcgaagccg tgtgcgagac accgcggccg ccggcgttgt      4320
ggatacctcg cggaaaactt ggccctcact gacagatgag gggcggacgt tgacacttga      4380
ggggccgact cacccggcgc ggcgttgaca gatgaggggc aggctcgatt tcggccggcg      4440
acgtggagct ggccagcctc gcaaatcggc gaaaacgcct gattttacgc gagtttccca      4500
cagatgatgt ggacaagcct ggggataagt gccctgcggt attgacactt gaggggcgcg      4560
actactgaca gatgaggggc gcgatccttg acacttgagg ggcagagtgc tgacagatga      4620
ggggcgcacc tattgacatt tgaggggctg tccacaggca gaaatccag catttgcaag      4680 ggtttccgcc cgtttttcgg ccaccgctaa cctgtctttt aacctgcttt taaaccaata      4740
tttataaacc ttgttttaa ccagggctgc gccctgtgcg cgtgaccgcg cacgccgaag      4800
gggggtgccc cccttctcg aaccctcccg gcccgctaac gcgggcctcc catcccccca      4860
ggggctgcgc ccctcggccg cgaacggcct caccccaaaa atggc                     4905
```

<210> SEQ ID NO 24
<211> LENGTH: 260
<212> TYPE: DNA
<213> ORGANISM: Artificial Sequence
<220> FEATURE:
<223> OTHER INFORMATION: Insert of VC-SAH6-1

<400> SEQUENCE: 24

```
ttgccatgtt ttacggcagt gagagcagag atagcgctga tgtccggcgg tgcttttgcc       60
gttacgcacc accccgtcag tagctgaaca ggagggacag ctggcgaaag ggggatgtgc      120
tgcaaggcga ttaagttggg taacgccagg gttttcccag tcacgacgtt gtaaaacgac      180
ggccagtgag cgcgcgtaat acgactcact atagggcgaa ttgggtactc gagtacgcta      240
gggataacag ggtaatatag                                                 260
```

<210> SEQ ID NO 25
<211> LENGTH: 4580
<212> TYPE: DNA
<213> ORGANISM: Artificial Sequence
<220> FEATURE:
<223> OTHER INFORMATION: VC-SAH7-1

<400> SEQUENCE: 25

```
ctagtgacgc tcaccgggct ggttgccctc gccgctgggc tggcggccgt ctatggccct       60
gcaaacgcgc cagaaacgcc gtcgaagccg tgtgcgagac accgcggccg ccggcgttgt      120
ggatacctcg cggaaaactt ggccctcact gacagatgag gggcggacgt tgacacttga      180
ggggccgact cacccggcgc ggcgttgaca gatgaggggc aggctcgatt tcggccggcg      240
acgtggagct ggccagcctc gcaaatcggc gaaaacgcct gattttacgc gagtttccca      300
```

```
cagatgatgt ggacaagcct ggggataagt gccctgcggt attgacactt gaggggcgcg    360
actactgaca gatgaggggc gcgatccttg acacttgagg ggcagagtgc tgacagatga    420
ggggcgcacc tattgacatt tgaggggctg tccacaggca gaaatccag catttgcaag     480 ggtttccgcc cgttttcgg ccaccgctaa cctgtctttt aacctgcttt taaaccaata    540
tttataaacc ttgttttaa ccagggctgc gccctgtgcg cgtgaccgcg cacgccgaag    600
gggggtgccc cccttctcg aaccctcccg gcccgctaac gcgggcctcc catccccca    660 ggggctgcgc ccctcggccg cgaacggcct cacccaaaa atggcagcgc tggcagtcct    720
tgccattgcc gggatcgggg cagtaacggg atgggcgatc agcccgagcg cgacgcccgg    780
aagcattgac gtgccgcagg tgctggcatc gacattcagc gaccaggtgc cgggcagtga    840
gggcggcggc ctgggtggcg gcctgcccct cacttcggcc gtcggggcat tcacggactt    900
catggcgggg ccggcaattt ttaccttggg cattcttggc atagtggtcg cgggtgccgt    960
gctcgtgttc gggggtgcga taaacccagc gaaccatttg aggtgatagg taagattata   1020
ccgaggtatg aaaacgagaa ttggaccttt acagaattac tctatgaagc gccatattta   1080
aaaagctacc aagacgaaga ggatgaagag gatgaggagg cagattgcct tgaatatatt   1140
gacaatactg ataagataat atatctttta tatagaagat atcgccgtat gtaaggattt   1200 caggggggcaa ggcataggca gcgcgcttat caatatatct atagaatggg caaagcataa   1260
aaacttgcat ggactaatgc ttgaaaccca ggacaataac cttatagctt gtaaattcta   1320
tcataattgg gtaatgactc caacttattg atagtgtttt atgttcagat aatgcccgat   1380
gactttgtca tgcagctcca ccgattttga gaacgacagc gacttccgtc ccagccgtgc   1440
caggtgctgc ctcagattca ggttatgccg ctcaattcgc tgcgtatatc gcttgctgat   1500
tacgtgcagc tttcccttca ggcgggattc atacagcggc cagccatccg tcatccatat   1560
caccacgtca aagggtgaca gcaggctcat aagacgcccc agcgtcgcca tagtgcgttc   1620
accgaatacg tgcgcaacaa ccgtcttccg gagactgtca tacgcgtaaa acagccagcg   1680
ctggcgcgat ttagccccga catagcccca ctgttcgtcc atttccgcgc agacgatgac   1740
gtcactgccc ggctgtatgc gcgaggttac cgactgcggc ctgagttttt taagtgacgt   1800
aaaatcgtgt tgaggccaac gcccataatg cgggctgttg cccggcatcc aacgccattc   1860
atggccatat caatgatttt ctggtgcgta ccggggttgag aagcggtgta agtgaactgc   1920
agttgccatg ttttacggca gtgagagcag agatagcgct gatgtccggc ggtgcttttg   1980
ccgttacgca ccaccccgtc agtagctgaa caggagggac agctgataga cacagaagcc   2040
actggagcac ctcaaaaaca ccatcataca ctaaatcagt aagttggcag catcacccat   2100
aattgtggtt tcaaaatcgg ctccgtcgat actatgttat acgccaactt tgaaaacaac   2160
tttgaaaaag ctgttttctg gtatttaagg ttttagaatg caaggaacag tgaattggag   2220
ttcgtcttgt tataattagc ttcttgggt atctttaaat actgtagaaa agaggaagga   2280
aataataaat ggctaaaatg agaatatcac cggaattgaa aaaactgatc gaaaaatacc   2340
gctgcgtaaa agatacggaa ggaatgtctc ctgctaaggt atataagctg gtgggagaaa   2400
atgaaaacct atatttaaaa atgacggaca gccggtataa agggaccacc tatgatgtgg   2460
aacgggaaaa ggacatgatg ctatggctgg aaggaaagct gcctgttcca aggtcctgc    2520 actttgaacg gcatgatggc tggagcaatc tgctcatgag tgaggccgat ggcgtccttt   2580
gctcggaaga gtatgaagat gaacaaagcc ctgaaaagat tatcgagctg tatgcggagt   2640
```

-continued gcatcaggct ctttcactcc atcgacatat cggattgtcc ctatacgaat agcttagaca 2700
gccgcttagc cgaattggat tacttactga ataacgatct ggccgatgtg gattgcgaaa 2760
actgggaaga agacactcca tttaaagatc cgcgcgagct gtatgatttt ttaaagacgg 2820
aaaagcccga agaggaactt gtcttttccc acggcgacct gggagacagc aacatctttg 2880
tgaaagatgg caaagtaagt ggctttattg atcttgggag aagcggcagg gcggacaagt 2940
ggtatgacat tgccttctgc gtccggtcga tcagggagga tatcggggaa gaacagtatg 3000
tcgagctatt ttttgactta ctggggatca agcctgattg ggagaaaata aaatattata 3060
ttttactgga tgaattgttt tagtacctag atgtggcgca acgatgccgg cgacaagcag 3120
gagcgcaccg acttcttccg catcaagtgt tttggctctc aggccgaggc ccacggcaag 3180
tatttgggca aggggtcgct ggtattcgtg cagggcaaga ttcggaatac caagtacgag 3240
aaggacggcc agacggtcta cgggaccgac ttcattgccg ataaggtgga ttatctggac 3300
accaaggcac caggcgggtc aaatcaggaa taagggcaca ttgccccggc gtgagtcggg 3360
gcaatcccgc aaggagggtg aatgaatcgg acgtttgacc ggaaggcata caggcaagaa 3420
ctgatcgacg cggggttttc cgccgaggat gccgaaacca tcgcaagccg caccgtcatg 3480
cgtgcgcccc gcgaaacctt ccagtccgtc ggctcgatgg tccagcaagc tacggccaag 3540
atcgagcgcg acagcgtgca actggctccc cctgccctgc ccgcgccatc ggccgccgtg 3600
gagcgttcgc gtcgtctcga acaggaggcg gcaggtttgg cgaagtcgat gaccatcgac 3660
acgcgaggaa ctatgacgac caagaagcga aaaaccgccg gcgaggacct ggcaaaacag 3720
gtcagcgagg ccaagcaggc cgcgttgctg aaacacacga agcagcagat caaggaaatg 3780
cagctttcct tgttcgatat tgcgccgtgg ccggacacga tgcgagcgat gccaaacgac 3840
acggcccgct ctgccctgtt caccacgcgc aacaagaaaa tcccgcgcga ggcgctgcaa 3900
aacaaggtca ttttccacgt caacaaggac gtgaagatca cctacaccgg cgtcgagctg 3960
cgggccgacg atgacgaact ggtgtggcag caggtgttgg agtacgcgaa gcgcacccct 4020
atcggcgagc cgatcacctt cacgttctac gagctttgcc aggacctggg ctggtcgatc 4080
aatggccggt attacacgaa ggccgaggaa tgcctgtcgc gcctacaggc gacggcgatg 4140
ggcttcacgt ccgaccgcgt tgggcacctg gaatcggtgt cgctgctgca ccgcttccgc 4200
gtcctggacc gtggcaagaa aacgtcccgt tgccaggtcc tgatcgacga ggaaatcgtc 4260
gtgctgtttg ctggcgacca ctacacgaaa ttcatatggg agaagtaccg caagctgtcg 4320
ccgacggccc gacggatgtt cgactatttc agctcgcacc gggagccgta cccgctcaag 4380
ctggaaacct tccgcctcat gtgcggatcg gattccaccc gcgtgaagaa gtggcgcgag 4440
caggtcggcg aagcctgcga agagttgcga ggcagcggcc tggtggaaca cgcctgggtc 4500
aatgatgacc tggtgcattg caaacgctag ggccttgtgg ggtcagttcc ggctgggggt 4560
tcagcagcca gcgctttact 4580

<210> SEQ ID NO 26
<211> LENGTH: 32
<212> TYPE: DNA
<213> ORGANISM: Artificial Sequence
<220> FEATURE:
<223> OTHER INFORMATION: Insert of VX-SAH56-1

<400> SEQUENCE: 26
cgtgcggatc tagggataac agggtaatat ag 32

```
<210> SEQ ID NO 27
<211> LENGTH: 33
<212> TYPE: DNA
<213> ORGANISM: Artificial Sequence
<220> FEATURE:
<223> OTHER INFORMATION: Insert of VX-SAH57-2

<400> SEQUENCE: 27
cgtgcggatc ctagggataa cagggtaata tag                                 33

<210> SEQ ID NO 28
<211> LENGTH: 34
<212> TYPE: DNA
<213> ORGANISM: Artificial Sequence
<220> FEATURE:
<223> OTHER INFORMATION: Insert of VX-SAH58-2

<400> SEQUENCE: 28
cgtgcggatc gctagggata acagggtaat atag                                34

<210> SEQ ID NO 29
<211> LENGTH: 35
<212> TYPE: DNA
<213> ORGANISM: Artificial Sequence
<220> FEATURE:
<223> OTHER INFORMATION: Insert of VX-SAH59-1

<400> SEQUENCE: 29
cgtgcggatc cgctagggat aacagggtaa tatag                               35

<210> SEQ ID NO 30
<211> LENGTH: 5221
<212> TYPE: DNA
<213> ORGANISM: Artificial Sequence
<220> FEATURE:
<223> OTHER INFORMATION: Construct III
<220> FEATURE:
<221> NAME/KEY: misc_feature
<222> LOCATION: (1557)..(1566)
<223> OTHER INFORMATION: n is a, c, g, or t

<400> SEQUENCE: 30
agcgctggca gtccttgcca ttgccgggat cggggcagta acgggatggg cgatcagccc     60
gagcgcgacg cccggaagca ttgacgtgcc gcaggtgctg gcatcgacat tcagcgacca    120
ggtgccgggc agtgagggcg gcggcctggg tggcggcctg cccttcactt cggccgtcgg    180
ggcattcacg gacttcatgg cggggccggc aattttttacc ttgggcattc ttggcatagt    240
ggtcgcgggt gccgtgctcg tgttcggggt gcgataaaac ccagcgaacc atttgaggtg    300
ataggtaaga ttataccgag gtatgaaaac gagaattgga cctttacaga attactctat    360
gaagcgccat atttaaaaag ctaccaagac gaagaggatg aagaggatga ggaggcagat    420
tgccttgaat atattgacaa tactgataag ataatatatc ttttatatag aagatatcgc    480
cgtatgtaag gatttcaggg ggcaaggcat aggcagcgcg cttatcaata tatctataga    540
atgggcaaag cataaaaaact tgcatggact aatgcttgaa acccaggaca ataaccttat    600
agcttgtaaa ttctatcata attgggtaat gactccaact tattgatagt gttttatgtt    660
cagataatgc ccgatgactt tgtcatgcag ctccaccgat tttgagaacg acagcgactt    720
ccgtcccagc cgtgccaggt gctgcctcag attcaggtta tgccgctcaa ttcgctgcgt    780
atatcgcttg ctgattacgt gcagctttcc cttcaggcgg gattcataca gcggccagcc    840
atccgtcatc catatcacca cgtcaaaggg tgacagcagg ctcataagac gccccagcgt    900
```

```
cgccatagtg cgttcaccga atacgtgcgc aacaaccgtc ttccggagac tgtcatacgc    960
gtggttacag tcttgcgcga catgcgtcac cacggtgata tcgtccaccc aggtgttcgg   1020
cgtggtgtag agcattacgc tgcgatggat tccggcatag ttaaagaaat catggaagta   1080
agactgcttt ttcttgccgt tttcgtcggt aatcaccatt cccggcggga tagtctgcca   1140
gttcagttcg ttgttcacac aaacggtgat acgtacactt ttcccggcaa taacatacgg   1200
cgtgacatcg gcttcaaatg gcgtatagcc gccctgatgc tccatcactt cctgattatt   1260
gacccacact ttgccgtaat gagtgaccgc atcgaaacgc agcacgatac gctggcctgc   1320
ccaacctttc ggtataaaga cttcgcgctg ataccagacg ttgcccgcat aattacgaat   1380
atctgcatcg gcgaactgat cgttaaaact gcctggcaca gcaattgccc ggctttcttg   1440
taacgcgctt tcccaccaac gctgatcaat tccacagttt tcgcggtcca gactgaatgc   1500
ccacaggccg tcgagttttt tgatttcacg ggttgggggtt tctacaggac tctagannnn   1560
nnnnnngcgg ccgctggcac cacctgccag tcaacagacg cgtaaaacag ccagcgctgg   1620
cgcgatttag ccccgacata gccccactgt tcgtccattt ccgcgcagac gatgacgtca   1680
ctgcccggct gtatgcgcga ggttaccgac tgcggcctga gttttttaag tgacgtaaaa   1740
tcgtgttgag gccaacgccc ataatgcggg ctgttgcccg gcatccaacg ccattcatgg   1800
ccatatcaat gattttctgg tgcgtaccgg gttgagaagc ggtgtaagtg aactgcagtt   1860
gccatgtttt acggcagtga gagcagagat agcgctgatg tccggcggtg cttttgccgt   1920
tacgcaccac cccgtcagta gctgaacagg agggacagct gatagacaca gaagccactg   1980
gagcacctca aaacaccat catacactaa atcagtaagt tggcagcatc acccataatt   2040
gtggtttcaa aatcggctcc gtcgatacta tgttatacgc caactttgaa aacaactttg   2100
aaaaagctgt tttctggtat ttaaggtttt agaatgcaag gaacagtgaa ttggagttcg   2160
tcttgttata attagcttct tggggtatct ttaaatactg tagaaaagag gaaggaaata   2220
ataaatggct aaaatgagaa tatcaccgga attgaaaaaa ctgatcgaaa ataccgctg    2280
cgtaaaagat acggaaggaa tgtctcctgc taaggtatat aagctggtgg gagaaaatga   2340
aaacctatat ttaaaaatga cggacagccg gtataaaggg accacctatg atgtggaacg   2400
ggaaaaggac atgatgctat ggctggaagg aaagctgcct gttccaaagg tcctgcactt   2460
tgaacggcat gatggctgga gcaatctgct catgagtgag gccgatgcg tcctttgctc   2520
ggaagagtat gaagatgaac aaagccctga aaagattatc gagctgtatg cggagtgcat   2580
caggctcttt cactccatcg acatatcgga ttgtccctat acgaatagct tagacagccg   2640
cttagccgaa ttggattact tactgaataa cgatctggcc gatgtggatt gcgaaaactg   2700
ggaagaagac actccattta agatccgcg cgagctgtat gattttttaa agacggaaaa   2760
gcccgaagag gaacttgtct tttcccacgg cgacctggga gacagcaaca tctttgtgaa   2820
agatggcaaa gtaagtggct ttattgatct tgggagaagc ggcagggcgg acaagtggta   2880
tgacattgcc ttctgcgtcc ggtcgatcag ggaggatatc ggggaagaac agtatgtcga   2940
gctattttt gacttactgg ggatcaagcc tgattgggag aaaataaaat attatatttt   3000
actggatgaa ttgttttagt acctagatgt ggcgcaacga tgccggcgac aagcaggagc   3060
gcaccgactt cttccgcatc aagtgttttg gctctcaggc cgaggccac ggcaagtatt   3120
tgggcaaggg gtcgctggta ttcgtgcagg gcaagattcg gaataccaag tacgagaagg   3180
acggccagac ggtctacggg accgacttca ttgccgataa ggtggattat ctggacacca   3240
aggcaccagg cgggtcaaat caggaataag ggcacattgc cccggcgtga gtcggggcaa   3300
```

```
tcccgcaagg agggtgaatg aatcggacgt ttgaccggaa ggcatacagg caagaactga   3360
tcgacgcggg gttttccgcc gaggatgccg aaaccatcgc aagccgcacc gtcatgcgtg   3420
cgccccgcga aaccttccag tccgtcggct cgatggtcca gcaagctacg gccaagatcg   3480
agcgcgacag cgtgcaactg gctcccctg ccctgcccgc gccatcggcc gccgtggagc    3540
gttcgcgtcg tctcgaacag gaggcggcag gtttggcgaa gtcgatgacc atcgacacgc   3600
gaggaactat gacgaccaag aagcgaaaaa ccgccggcga ggacctggca aaacaggtca   3660
gcgaggccaa gcaggccgcg ttgctgaaac acacgaagca gcagatcaag gaaatgcagc   3720
tttccttgtt cgatattgcg ccgtggccgg acacgatgcg agcgatgcca acgacacgg    3780 cccgctctgc cctgttcacc acgcgcaaca agaaaatccc gcgcgaggcg ctgcaaaaca   3840
aggtcatttt ccacgtcaac aaggacgtga agatcaccta caccggcgtc gagctgcggg   3900
ccgacgatga cgaactggtg tggcagcagg tgttggagta cgcgaagcgc acccctatcg   3960
gcgagccgat caccttcacg ttctacgagc tttgccagga cctgggctgg tcgatcaatg   4020
gccggtatta cacgaaggcc gaggaatgcc tgtcgcgcct acaggcgacg gcgatgggct   4080
tcacgtccga ccgcgttggg cacctggaat cggtgtcgct gctgcaccgc ttccgcgtcc   4140
tggaccgtgg caagaaaacg tcccgttgcc aggtcctgat cgacgaggaa atcgtcgtgc   4200
tgtttgctgg cgaccactac acgaaattca tatgggagaa gtaccgcaag ctgtcgccga   4260
cggcccgacg gatgttcgac tatttcagct cgcaccggga gccgtacccg ctcaagctgg   4320
aaaccttccg cctcatgtgc ggatcggatt ccacccgcgt gaagaagtgg cgcgagcagg   4380
tcggcgaagc ctgcgaagag ttgcgaggca gcggcctggt ggaacacgcc tgggtcaatg   4440
atgacctggt gcattgcaaa cgctagggcc ttgtggggtc agttccggct gggggttcag   4500
cagccagcgc tttactctag tgacgctcac cgggctggtt gccctcgccg ctgggctggc   4560
ggccgtctat ggccctgcaa acgcgccaga aacgccgtcg aagccgtgtg cgagacaccg   4620
cggccgccgg cgttgtggat acctcgcgga aaacttggcc ctcactgaca gatgaggggc   4680
ggacgttgac acttgagggg ccgactcacc cggcgcggcg ttgacagatg aggggcaggc   4740
tcgatttcgg ccggcgacgt ggagctggcc agcctcgcaa atcggcgaaa acgcctgatt   4800
ttacgcgagt ttcccacaga tgatgtggac aagcctgggg ataagtgccc tgcggtattg   4860
acacttgagg ggcgcgacta ctgacagatg aggggcgcga tccttgacac ttgaggggca   4920
gagtgctgac agatgagggg cgcacctatt gacatttgag gggctgtcca caggcagaaa   4980
atccagcatt tgcaagggtt tccgcccgtt tttcggccac cgctaacctg tcttttaacc   5040
tgctttaaaa ccaatattta taaaccttgt ttttaaccag gctgcgccc  tgtgcgcgtg    5100 accgcgcacg ccgaaggggg gtgccccccc ttctcgaacc ctcccggccc gctaacgcgg   5160
gcctcccatc cccccagggg ctgcgcccct cggccgcgaa cggcctcacc ccaaaaatgg   5220
c                                                                   5221

<210> SEQ ID NO 31
<211> LENGTH: 8885
<212> TYPE: DNA
<213> ORGANISM: Artificial Sequence
<220> FEATURE:
<223> OTHER INFORMATION: Construct IV
<220> FEATURE:
<221> NAME/KEY: misc_feature
<222> LOCATION: (3)..(12)
<223> OTHER INFORMATION: n is a, c, g, or t
```

```
<400> SEQUENCE: 31
ccnnnnnnnn nnttaattaa cgaagagcaa gagctcgaat tcccccgatc gttcaaacat      60
ttggcaataa agtttcttaa gattgaatcc tgttgccggt cttgcgatga ttatcatata     120
atttctgttg aattacgtta agcatgtaat aattaacatg taatgcatga cgttatttat     180
gagatgggtt tttatgatta gagtcccgca attatacatt taatacgcga tagaaaacaa     240
aatatagcgc gcaaactagg ataaattatc gcgcgcggtg tcatctatgt tactagatcg     300
ggaattggca tgcaagcttg gcactggccg tcgttttaca acgtcgtgac tgggaaaacc     360
ctggcgttac ccaacttaat cgccttgcag cacatccccc tttcgccagc tggcgtaata     420
gcgaagaggc ccgcaccgat cgcccttccc aacagttgcg cagcctgaat ggcgaatgct     480
agagcagctt gagcttggat cagattgtcg tttcccgcct tcagtttaaa ctatcagtgt     540
ttgacaggat atattggcgg gtaaacctaa gagaaagag cgtttattag aataatcgga     600
tatttaaaag ggcgtgaaaa ggtttatccg ttcgtccatt tgtatgtgca tgccaaccac     660
agggttcccc tcgggatcaa agtactttga tccaacccct ccgctgctat agtgcagtcg     720
gcttctgacg ttcagtgcag ccgtcttctg aaaacgacat gtcgcacaag tcctaagtta     780
cgcgacaggc tgccgccctg ccctttttcct ggcgttttct tgtcgcgtgt tttagtcgca     840
taaagtagaa tacttgcgac tagaaccgga gacattacgc catgaacaag agcgccgccg     900
ctggcctgct gggctatgcc gcgtcagca ccgacgacca ggacttgacc aaccaacggg     960
ccgaactgca cgcggccggc tgcaccaagc tgttttccga agatcaccc ggcaccaggc    1020 gcgaccgccc ggagctggcc aggatgcttg accacctacg ccctggcgac gttgtgacag    1080
tgaccaggct agaccgcctg gcccgcagca cccgcgacct actggacatt gccgagcgca    1140 tccaggagc cggcgcgggc ctgcgtagcc tggcagagcc gtgggccgac accaccacgc    1200
cggccggccg catggtgttg accgtgttcg ccggcattgc cgagttcgag cgttccctaa    1260
tcatcgaccg cacccggagc gggcgcgagg ccgccaaggc ccgaggcgtg aagtttggcc    1320
cccgccctac cctcaccccg gcacagatcg cgcacgcccg cgagctgatc gaccaggaag    1380
gccgcaccgt gaaagaggcg gctgcactgc ttggcgtgca tcgctcgacc ctgtaccgcg    1440
cacttgagcg cagcgaggaa gtgacgccca ccgaggccag gcggcgcggt gccttccgtg    1500
aggacgcatt gaccgaggcc gacgccctgg cggccgccga gaatgaacgc caagaggaac    1560
aagcatgaaa ccgcaccagg acggccagga cgaaccgttt ttcattaccg aagagatcga    1620
ggcggagatg atcgcggccg ggtacgtgtt cgagccgccc gcgcacgtct caaccgtgcg    1680
gctgcatgaa atcctggccg gtttgtctga tgccaagctg gcggcctggc cggccagctt    1740
ggccgctgaa gaaaccgagc gccgccgtct aaaaaggtga tgtgtatttg agtaaaacag    1800
cttgcgtcat gcggtcgctg cgtatatgat gcgatgagta aataaacaaa tacgcaaggg    1860
gaacgcatga aggttatcgc tgtacttaac cagaaaggcg gtcaggcaa gacgaccatc    1920 gcaacccatc tagcccgcgc cctgcaactc gccggggccg atgttctgtt agtcgattcc    1980
gatccccagg gcagtgcccg cgattgggcg ccgtgcggg aagatcaacc gctaaccgtt    2040
gtcggcatcg accgcccgac gattgaccgc gacgtgaagg ccatcggccg gcgcgacttc    2100
gtagtgatcg acggagcgcc ccaggcggcg gacttggctg tgtccgcgat caaggcagcc    2160
gacttcgtgc tgattccggt gcagccaagc ccttacgaca tatggccac cgccgacctg    2220 gtggagctgt ttaagcagcg cattgaggtc acgatggaa ggctacaagc ggcctttgtc    2280
gtgtcgcggg cgatcaaagg cacgcgcatc ggcggtgagg ttgccgaggc gctggccggg    2340
```

```
tacgagctgc ccattcttga gtcccgtatc acgcagcgcg tgagctaccc aggcactgcc    2400
gccgccggca caaccgttct tgaatcagaa cccgagggcg acgctgcccg cgaggtccag    2460
gcgctggccg ctgaaattaa atcaaaactc atttgagtta atgaggtaaa gagaaaatga    2520
gcaaaagcac aaacacgcta agtgccggcc gtccgagcgc acgcagcagc aaggctgcaa    2580
cgttggccag cctggcagac acgccagcca tgaagcgggt caactttcag ttgccggcgg    2640
aggatcacac caagctgaag atgtacgcgg tacgccaagg caagaccatt accgagctgc    2700
tatctgaata catcgcgcag ctaccagagt aaatgagcaa atgaataaat gagtagatga    2760
attttagcgg ctaaaggagg cggcatggaa aatcaagaac aaccaggcac cgacgccgtg    2820
gaatgcccca tgtgtggagg aacgggcggt tggccaggcg taagcggctg ggttgcctgc    2880
cggccctgca atggcactgg aaccccaag cccgaggaat cggcgtgagc ggtcgcaaac    2940
catccggccc ggtacaaatc ggcgcggcgc tgggtgatga cctggtggag aagttgaagg    3000
ccgcgcaggc cgcccagcgg caacgcatcg aggcagaagc acgccccggt gaatcgtggc    3060
aagcggccgc tgatcgaatc cgcaaagaat cccggcaacc gccggcagcc ggtgcgccgt    3120
cgattaggaa gccgcccaag ggcgacgagc aaccagattt tttcgttccg atgctctatg    3180
acgtgggcac ccgcgatagt cgcagcatca tggacgtggc cgttttccgt ctgtcgaagc    3240
gtgaccgacg agctggcgag gtgatccgct acgagcttcc agacgggcac gtagaggttt    3300
ccgcagggcc ggccggcatg ccagtgtgt gggattacga cctggtactg atggcggttt    3360
cccatctaac cgaatccatg aaccgatacc gggaagggaa gggagacaag cccggccgcg    3420
tgttccgtcc acacgttgcg gacgtactca agttctgccg gcgagccgat ggcggaaagc    3480
agaaagacga cctggtagaa acctgcattc ggttaaacac cacgcacgtt gccatgcagc    3540
gtacgaagaa ggccaagaac ggccgcctgg tgacggtatc cgagggtgaa gccttgatta    3600
gccgctacaa gatcgtaaag agcgaaaccg ggcggccgga gtacatcgag atcgagctag    3660
ctgattggat gtaccgcgag atcacagaag gcaagaaccc ggacgtgctg acggttcacc    3720
ccgattactt tttgatcgat cccggcatcg gccgttttct ctaccgcctg cacgccgcg    3780
ccgcaggcaa ggcagaagcc agatggttgt tcaagacgat ctacgaacgc agtggcagcg    3840
ccggagagtt caagaagttc tgtttcaccg tgcgcaagct gatcgggtca atgacctgc    3900
cggagtacga tttgaaggag gaggcggggc aggctggccc gatcctagtc atgcgctacc    3960
gcaacctgat cgagggcgaa gcatccgccg gttcctaatg tacggagcag atgctagggc    4020
aaattgccct agcaggggaa aaaggtcgaa aaggtctctt tcctgtggat agcacgtaca    4080
ttgggaaccc aaagccgtac attgggaacc ggaacccgta cattgggaac ccaaagccgt    4140
acattgggaa ccggtcacac atgtaagtga ctgatataaa agagaaaaaa ggcgattttt    4200
ccgcctaaaa ctctttaaaa cttattaaaa ctcttaaaac ccgcctggcc tgtgcataac    4260
tgtctggcca gcgcacagcc gaagagctgc aaaaagcgcc tacccttcgg tcgctgcgct    4320
ccctacgccc cgccgcttcg cgtcggccta tcgcggccgc tggccgctca aaaatggctg    4380
gcctacggcc aggcaatcta ccagggcgcg acaagccgc cgtcgcca ctcgaccgcc    4440
ggcgcccaca tcaaggcacc ctgcctcgcg cgtttcggtg atgacggtga aaacctctga    4500
cacatgcagc tcccggagac ggtcacagct tgtctgtaag cggatgccgg gagcagacaa    4560
gcccgtcagg gcgcgtcagc gggtgttggc gggtgtcggg gcgcagccat gacccagtca    4620
cgtagcgata gcggagtgta tactggctta actatgcggc atcagagcag attgtactga    4680
```

```
gagtgcacca tatgcggtgt gaaataccgc acagatgcgt aaggagaaaa taccgcatca    4740
ggcgctcttc cgcttcctcg ctcactgact cgctgcgctc ggtcgttcgg ctgcggcgag    4800
cggtatcagc tcactcaaag gcggtaatac ggttatccac agaatcaggg gataacgcag    4860
gaaagaacat gtgagcaaaa ggccagcaaa aggccaggaa ccgtaaaaag gccgcgttgc    4920
tggcgttttt ccataggctc cgcccccctg acgagcatca caaaaatcga cgctcaagtc    4980
agaggtggcg aaacccgaca ggactataaa gataccaggc gtttccccct ggaagctccc    5040
tcgtgcgctc tcctgttccg accctgccgc ttaccggata cctgtccgcc tttctccctt    5100
cgggaagcgt ggcgctttct catagctcac gctgtaggta tctcagttcg gtgtaggtcg    5160
ttcgctccaa gctgggctgt gtgcacgaac cccccgttca gcccgaccgc tgcgccttat    5220
ccggtaacta tcgtcttgag tccaacccgg taagacacga cttatcgcca ctggcagcag    5280
ccactggtaa caggattagc agagcgaggt atgtaggcgg tgctacagag ttcttgaagt    5340
ggtggcctaa ctacggctac actagaagga cagtatttgg tatctgcgct ctgctgaagc    5400
cagttacctt cggaaaaaga gttggtagct cttgatccgg caaacaaacc accgctggta    5460
gcggtggttt ttttgtttgc aagcagcaga ttacgcgcag aaaaaaagga tctcaagaag    5520
atcctttgat cttttctacg gggtctgacg ctcagtggaa cgaaaactca cgttaaggga    5580
ttttggtcat gcattctagg tactaaaaca attcatccag taaaatataa tattttattt    5640
tctcccaatc aggcttgatc cccagtaagt caaaaaatag ctcgacatac tgttcttccc    5700
cgatatcctc cctgatcgac cggacgcaga aggcaatgtc ataccacttg tccgccctgc    5760
cgcttctccc aagatcaata aagccactta ctttgccatc tttcacaaag atgttgctgt    5820
ctcccaggtc gccgtgggaa aagacaagtt cctcttcggg cttttccgtc tttaaaaaat    5880
catacagctc gcgcggatct ttaaatggag tgtcttcttc ccagttttcg caatccacat    5940
cggccagatc gttattcagt aagtaatcca attcggctaa gcggctgtct aagctattcg    6000
tatagggaca atccgatatg tcgatggagt gaaagagcct gatgcactcc gcatacagct    6060
cgataatctt ttcagggctt tgttcatctt catactcttc cgagcaaagg acgccatcgg    6120
cctcactcat gagcagattg ctccagccat catgccgttc aaagtgcagg accttttggaa    6180 caggcagctt tccttccagc catagcatca tgtccttttc ccgttccaca tcataggtgg    6240
tccctttata ccggctgtcc gtcattttta aatataggtt ttcatttct cccaccagct    6300 tatataccct agcaggagac attccttccg tatcttttac gcagcggtat ttttcgatca    6360
gttttttcaa ttccggtgat attctcattt tagccattta ttatttcctt cctcttttct    6420
acagtattta aagataccc aagaagctaa ttataacaag acgaactcca attcactgtt    6480
ccttgcattc taaaacctta aataccagaa aacagctttt tcaaagttgt tttcaaagtt    6540
ggcgtataac atagtatcga cggagccgat tttgaaaccg cggtgatcac aggcagcaac    6600
gctctgtcat cgttacaatc aacatgctac cctccgcgag atcatccgtg tttcaaaccc    6660
ggcagcttag ttgccgttct tccgaatagc atccgtaaca tgagcaaagt ctgccgcctt    6720
acaacggctc tcccgctgac gccgtcccgg actgatgggc tgcctgtatc gagtggtgat    6780
tttgtgccga gctgccggtc ggggagctgt tggctggctg gtggcaggat atattgtggt    6840
gtaaacaaat tgacgcttag acaacttaat aacacattgc ggacgttttt aatgtactga    6900
attaacgccg aattaagctt ggacaatcag taaattgaac ggagaatatt attcataaaa    6960
atacgatagt aacgggtgat atattcatta gaatgaaccg aaaccggcgg taaggatctg    7020
agctacacat gctcaggttt tttacaacgt gcacaacaga attgaaagca aatatcatgc    7080
```

```
gatcataggc gtctcgcata tctcattaaa gcagggcatg ccggtcgagt caaatctcgg    7140
tgacgggcag gaccggacgg ggcggtaccg gcaggctgaa gtccagctgc cagaaaccca    7200
cgtcatgcca gttcccgtgc ttgaagccgg ccgcccgcag catgccgcgg ggggcatatc    7260
cgagcgcctc gtgcatgcgc acgctcgggt cgttgggcag cccgatgaca gcgaccacgc    7320
tcttgaagcc ctgtgcctcc agggacttca gcaggtgggt gtagagcgtg gagcccagtc    7380
ccgtccgctg gtggcggggg gagacgtaca cggtcgactc ggccgtccag tcgtaggcgt    7440
tgcgtgcctt ccaggggccc gcgtaggcga tgccggcgac ctcgccgtcc acctcggcga    7500
cgagccaggg atagcgctcc cgcagacgga cgaggtcgtc cgtccactcc tgcggttcct    7560
gcggctcggt acggaagttg accgtgcttg tctcgatgta gtggttgacg atggtgcaga    7620
ccgccggcat gtccgcctcg gtggcacggc ggatgtcggc cgggcgtcgt tctgggctca    7680
tggtagactc gacggatcca cgtgtggaag atatgaattt ttttgagaaa ctagataaga    7740
ttaatgaata tcggtgtttt ggttttttct tgtggccgtc tttgtttata ttgagatttt    7800
tcaaatcagt gcgcaagacg tgacgtaagt atccgagtca gttttattt ttctactaat     7860 ttggtcgaag ctttgggcgg atcctctaga attcgaatcc aaaaattacg gatatgaata    7920
taggcatatc cgtatccgaa ttatccgttt gacagctagc aacgattgta caattgcttc    7980
tttaaaaaag gaagaaagaa agaaagaaaa gaatcaacat cagcgttaac aaacggcccc    8040
gttacggccc aaacggtcat atagagtaac ggcgttaagc gttgaaagac tcctatcgaa    8100
atacgtaacc gcaaacgtgt catagtcaga tcccctcttc cttcaccgcc tcaaacacaa    8160
aaataatctt ctacagccta tatatacaac ccccccttct atctctcctt tctcacaatt    8220
catcatcttt ctttctctac ccccaatttt aagaaatcct ctcttctcct cttcattttc    8280
aaggtaaatc tctctctctc tctctctctc tgttattcct tgttttaatt aggtatgtat    8340
tattgctagt ttgttaatct gcttatctta tgtatgcctt atgtgaatat ctttatcttg    8400
ttcatctcat ccgtttagaa gctataaatt tgttgatttg actgtgtatc tacacgtggt    8460 tatgttttata tctaatcaga tatgaatttc ttcatattgt tgcgtttgtg tgtaccaatc    8520
cgaaatcgtt gatttttttc atttaatcgt gtagctaatt gtacgtatac atatggatct    8580
acgtatcaat tgttcatctg tttgtgtttg tatgtataca gatctgaaaa catcacttct    8640
ctcatctgat tgtgttgtta catacataga tatagatctg ttatatcatt ttttttatta    8700
attgtgtata tatatatgtg catagatctg gattacatga ttgtgattat ttacatgatt    8760
ttgttattta cgtatgtata tatgtagatc tggacttttt ggagttgttg acttgattgt    8820
atttgtgtgt gtatatgtgt gttctgatct tgatatgtta tgtatgtgca gcccgggttg    8880
ctctt                                                                8885

<210> SEQ ID NO 32
<211> LENGTH: 10934
<212> TYPE: DNA
<213> ORGANISM: Artificial Sequence
<220> FEATURE:
<223> OTHER INFORMATION: Construct V
<220> FEATURE:
<221> NAME/KEY: misc_feature
<222> LOCATION: (612)..(621)
<223> OTHER INFORMATION: n is a, c, g, or t

<400> SEQUENCE: 32
gtagaaaccc caacccgtga aatcaaaaaa ctcgacggcc tgtgggcatt cagtctggat       60
```

```
cgcgaaaact gtggaattga tcagcgttgg tgggaaagcg cgttacaaga aagccgggca    120
attgctgtgc caggcagttt taacgatcag ttcgccgatg cagatattcg taattatgcg    180
ggcaacgtct ggtatcagcg cgaagtcttt ataccgaaag gttgggcagg ccagcgtatc    240
gtgctgcgtt tcgatgcggt cactcattac ggcaaagtgt gggtcaataa tcaggaagtg    300
atggagcatc agggcggcta tacgccattt gaagccgatg tcacgccgta tgttattgcc    360
gggaaaagtg tacgtatcac cgtttgtgtg aacaacgaac tgaactggca gactatcccg    420
ccgggaatgg tgattaccga cgaaaacggc aagaaaaagc agtcttactt ccatgatttc    480
tttaactatg ccggaatcca tcgcagcgta atgctctaca ccacgccgaa cacctgggtg    540
gacgatatca ccgtggtgac gcatgtcgcg caagactgta accacgcgtc tgttgactgg    600
caggtggtgc cnnnnnnnnn nctagagtcc tgtagaaacc ccaacccgtg aaatcaaaaa    660
actcgacggc ctgtgggcat tcagtctgga ccgcgaaaac tgtggaattg atcagcgttg    720
gtgggaaagc gcgttacaag aaagccgggc aattgctgtg ccaggcagtt ttaacgatca    780
gttcgccgat gcagatattc gtaattatgc gggcaacgtc tggtatcagc gcgaagtctt    840
tataccgaaa ggttgggcag ccagcgtat cgtgctgcgt ttcgatgcgg tcactcatta    900
cggcaaagtg tgggtcaata atcaggaagt gatggagcat cagggcggct atacgccatt    960
tgaagccgat gtcacgccgt atgttattgc cgggaaaagt gtacgtatca ccgtttgtgt   1020
gaacaacgaa ctgaactggc agactatccc gccgggaatg gtgattaccg acgaaaacgg   1080
caagaaaaag cagtcttact tccatgattt ctttaactat gccggaatcc atcgcagcgt   1140
aatgctctac accacgccga acacctgggt ggacgatatc accgtggtga cgcatgtcgc   1200
gcaagactgt aaccacgcgt ctgttgactg gcaggtggtg ccaatggtga tgtcagcgt   1260 tgaactgcgt gatgcggatc aacaggtggt tgcaactgga caaggcacta gcgggacttt   1320
gcaagtggtg aatccgcacc tctggcaacc gggtgaaggt tatctctatg aactgtgcgt   1380
cacagccaaa agccagacag agtgtgatat ctacccgctt cgcgtcggca tccggtcagt   1440
ggcagtgaag ggcgaacagt tcctgattaa ccacaaaccg ttctacttta ctggctttgg   1500
tcgtcatgaa gatgcggact gcgtggcaa aggattcgat aacgtgctga tggtgcacga   1560
ccacgcatta atggactgga ttggggccaa ctcctaccgt acctcgcatt cccttacgc   1620 tgaagagatg ctcgactggg cagatgaaca tggcatcgtg gtgattgatg aaactgctgc   1680
tgtcggcttt aacctctctt taggcattgg tttcgaagcg ggcaacaagc cgaaagaact   1740
gtacagcgaa gaggcagtca acggggaaac tcagcaagcg cacttacagg cgattaaaga   1800
gctgatagcg cgtgacaaaa accacccaag cgtggtgatg tggagtattg ccaacgaacc   1860
ggatacccgt ccgcaaggtg cacgggaata tttcgcgcca ctgcggaag caacgcgtaa   1920 actcgacccg acgcgtccga tcacctgcgt caatgtaatg ttctgcgacg ctcacaccga   1980
taccatcagc gatctctttg atgtgctgtg cctgaaccgt tattacggat ggtatgtcca   2040
aagcggcgat ttggaagcgg cagagaaggt actggaaaaa gaacttctgg cctggcagga   2100
gaaactgcat cagccgatta tcatcaccga atacggcgtg gatacgttag ccgggctgca   2160
ctcaatgtac accgacatgt ggagtgaaga gtatcagtgt gcatggctgg atatgtatca   2220
ccgcgtcttt gatcgcgtca gcgccgtcgt cggtgaacag gtatggaatt cgccgatttt   2280
tgcgacctcg caaggcatat tgcgcgttgg cggtaacaag aaaggatct tcactcgcga   2340 ccgcaaaccg aagtcggcgg ctttctgctg caaaaacgc tggactggca tgaacttcgg   2400
tgaaaaaccg cagcagggag gcaaacaatg aatcaacaac tctcctggcg caccatcgtc   2460
```

```
ggctacagcc tcgggaattg ctaccgagct cgaatttccc cgatcgttca aacatttggc    2520
aataaagttt cttaagattg aatcctgttg ccggacttgc gatgattatc atataatttc    2580
tgttgaatta cgttaagcat gtaataatta acatgtaatg catgacgtta tttatgagat    2640
gggtttttat gattagagtc ccgcaattat acatttaata cgcgatagaa aacaaaatat    2700
agcgcgcaaa ctaggataaa ttatcgcgcg cggtgtcatc tatgttacta gatcggaata    2760
agcttggcgt aatcatggtc atagctgttt cctactagat ctgattgtcg tttcccgcct    2820
tcagtttaaa ctatcagtgt ttgacaggat atattggcgg gtaaacctaa gagaaaagag    2880
cgtttattag aataatcgga tatttaaaag ggcgtgaaaa ggtttatccg ttcgtccatt    2940
tgtatgtcca tggaacgcag tggcggtttt catggcttgt tatgactgtt tttttggggt    3000
acagtctatg cctcgggcat ccaagcagca agcgcgttac gccgtgggtc gatgtttgat    3060
gttatggagc agcaacgatg ttacgcagca gggcagtcgc cctaaaacaa agttaaacat    3120
catgggggaa gcggtgatcg ccgaagtatc gactcaacta tcagaggtag ttggcgtcat    3180
cgagcgccat ctcgaaccga cgttgctggc cgtacatttg tacggctccg cagtggatgg    3240
cggcctgaag ccacacagtg atattgattt gctggttacg gtgaccgtaa ggcttgatga    3300
aacaacgcgg cgagctttga tcaacgacct tttggaaact tcggcttccc ctggagagag    3360
cgagattctc cgcgctgtag aagtcaccat tgttgtgcac gacgacatca ttccgtggcg    3420
ttatccagct aagcgcgaac tgcaatttgg agaatggcag cgcaatgaca ttcttgcagg    3480
tatcttcgag ccagccacga tcgacattga tctggctatc ttgctgacaa agcaagaga    3540 acatagcgtt gccttggtag gtccagcggc ggaggaactc tttgatccgg ttcctgaaca    3600
ggatctattt gaggcgctaa atgaaaacct taacgctatg gaactcgccg ccgactgggc    3660
tggcgatgag cgaaatgtag tgcttacgtt gtcccgcatt tggtacagcg cagtaaccgg    3720
caaaatcgcg ccgaaggatg tcgctgccga ctgggcaatg gagcgcctgc cggcccagta    3780
tcagcccgtc atacttgaag ctagacaggc ttatcttgga caagaagaag atcgcttggc    3840
ctcgcgcgca gatcagttgg aagaatttgt ccactacgtg aaaggcgaga tcaccaaggt    3900
agtcggcaaa taatgtctag ctagaaattc gttcaagccg acgccgcttc gcggcgcggc    3960
ttaactcaag cgttagatgc actaagcaca taattgctca cagccaaact atcaggtcaa    4020
gtctgctttt attattttta agcgtgcata ataagcccta cacaaattgg gagatatatc    4080
atgcatgacc aaaatccctt aacgtgagtt ttcgttccac tgagcgtcag accccgtaga    4140
aaagatcaaa ggatcttctt gagatccttt tttttctgcg cgtaatctgct gcttgcaaac    4200 aaaaaaacca ccgctaccag cggtggtttg tttgccggat caagagctac caactctttt    4260
tccgaaggta actggcttca gcagagcgca gataccaaat actgtccttc tagtgtagcc    4320
gtagttaggc caccacttca agaactctgt agcaccgcct acatacctcg ctctgctaat    4380
cctgttacca gtggctgctg ccagtggcga taagtcgtgt cttaccgggt tggactcaag    4440
acgatagtta ccggataagg cgcagcggtc gggctgaacg gggggttcgt gcacacagcc    4500
cagcttggag cgaacgacct acaccgaact gagatacta cagcgtgagc tatgagaaag    4560
cgccacgctt cccgaaggga gaaaggcgga caggtatccg gtaagcggca gggtcggaac    4620
aggagagcgc acgagggagc ttccaggggg aaacgcctgg tatctttata gtcctgtcgg    4680
gtttcgccac ctctgacttg agcgtcgatt tttgtgatgc tcgtcagggg gcggagccta    4740
atggaaaaac gccagcaacg cggccttttt acggttcctg gccttttgct ggccttttgc    4800
```

```
tcacatgttc tttcctgcgt tatccccctga ttctgtggat aaccgtatta ccgcctttga    4860
gtgagctgat accgctcgcc gcagccgaac gaccgagcgc agcgagtcag tgagcgagga    4920
agcggaagag cgcctgatgc ggtattttct ccttacgcat ctgtgcggta tttcacaccg    4980
catatggtgc actctcagta caatctgctc tgatgccgca tagttaagcc agtatacact    5040
ccgctatcgc tacgtgactg ggtcatggct gcgccccgac acccgccaac acccgctgac    5100
gcgccctgac gggcttgtct gctcccggca tccgcttaca caagctgt gaccgtctcc    5160
gggagctgca tgtgtcagag gttttcaccg tcatcaccga aacgcgcgag gcagggtgcc    5220
ttgatgtggg cgccggcggt cgagtggcga cggcgcggct tgtccgcgcc ctggtagatt    5280
gcctggccgt aggccagcca ttttttgagcg gccagcggcc gcgataggcc gacgcgaagc    5340
ggcggggcgt agggagcgca gcgaccgaag ggtaggcgct ttttgcagct cttcggctgt    5400
gcgctggcca gacagttatg cacaggccag gcgggtttta agagttttaa taagttttaa    5460
agagttttag gcgaaaaaat cgccttttt ctctttata tcagtcactt acatgtgtga    5520
ccggttccca atgtacggct ttgggttccc aatgtacggg ttccggttcc caatgtacgg    5580
ctttgggttc ccaatgtacg tgctatccac aggaaagaga ccttttcgac ctttttcccc    5640
tgctagggca atttgcccta gcatctgctc cgtacattag gaaccggcgg atgcttcgcc    5700
ctcgatcagg ttgcggtagc gcatgactag gatcgggcca gcctgccccg cctcctcctt    5760
caaatcgtac tccggcaggt catttgaccc gatcagcttg cgcacggtga acagaactt     5820
cttgaactct ccggcgctgc cactgcgttc gtagatcgtc ttgaacaacc atctggcttc    5880
tgccttgcct gcggcgcggc gtgccaggcg gtagagaaaa cggccgatgc cgggatcgat    5940
caaaaagtaa tcggggtgaa ccgtcagcac gtccgggttc ttgccttctg tgatctcgcg    6000
gtacatccaa tcagctagct cgatctcgat gtactccggc cgcccggttt cgctctttac    6060
gatcttgtag cggctaatca aggcttcacc ctcggatacc gtcaccaggc ggccgttctt    6120
ggccttcttc gtacgctgca tggcaacgtg cgtggtgttt aaccgaatgc aggtttctac    6180
caggtcgtct ttctgctttc cgccatcggc tcgccggcag aacttgagta cgtccgcaac    6240
gtgtggacgg aacacgcggc cgggcttgtc tccttccct tccggtatc ggttcatgga    6300
ttcggttaga tgggaaaccg ccatcagtac caggtcgtaa tcccacacac tggccatgcc    6360
ggccggccct gcggaaaacct ctacgtgccc gtctggaagc tcgtagcgga tcacctcgcc    6420
agctcgtcgg tcacgcttcg acagacggaa aacggccacg tccatgatgc tgcgactatc    6480
gcgggtgccc acgtcataga gcatcggaac gaaaaatct ggttgctcgt cgcccttggg    6540
cggcttccta atcgacggcg caccggctgc cggcggttgc cgggattctt tgcggattcg    6600
atcagcggcc gcttgccacg attcaccggg gcgtgcttct gcctcgatgc gttgccgctg    6660
ggcggcctgc gcggccttca acttctccac caggtcatca cccagcgccg cgccgatttg    6720
taccgggccg gatggtttgc gaccgctcac gccgattcct cgggcttggg ggttccagtg    6780
ccattgcagg gccggcagac aacccagccg cttacgcctg ccaaccgcc cgttcctcca    6840
cacatggggc attccacggc gtcggtgcct ggttgttctt gattttccat gccgcctcct    6900
ttagccgcta aaattcatct actcatttat tcatttgctc atttactctg gtagctgcgc    6960
gatgtattca gatagcagct cggtaatggt cttgccttgg cgtaccgcgt acatcttcag    7020
cttggtgtga tcctccgccg gcaactgaaa gttgacccgc ttcatggctg gcgtgtctgc    7080
caggctggcc aacgttgcag ccttgctgct gcgtgcgctc ggacggccgg cacttagcgt    7140
gtttgtgctt ttgctcattt tctctttacc tcattaactc aaatgagttt tgatttaatt    7200
```

```
tcagcggcca gcgcctggac ctcgcgggca gcgtcgccct cgggttctga ttcaagaacg    7260
gttgtgccgg cggcggcagt gcctgggtag ctcacgcgct gcgtgatacg ggactcaaga    7320
atgggcagct cgtacccggc cagcgcctcg gcaacctcac cgccgatgcg cgtgcctttg    7380
atcgcccgcg acacgacaaa ggccgcttgt agccttccat ccgtgacctc aatgcgctgc    7440
ttaaccagct ccaccaggtc ggcggtggcc catatgtcgt aagggcttgg ctgcaccgga    7500
atcagcacga agtcggctgc cttgatcgcg gacacagcca agtccgccgc ctggggcgct    7560
ccgtcgatca ctacgaagtc gcgccggccg atggccttca cgtcgcggtc aatcgtcggg    7620
cggtcgatgc cgacaacggt tagcggttga tcttcccgca cggccgccca atcgcgggca    7680
ctgccctggg gatcggaatc gactaacaga acatcggccc cggcgagttg cagggcgcgg    7740
gctagatggg ttgcgatggt cgtcttgcct gacccgcctt tctggttaag tacagcgata    7800
accttcatgc gttcccctttg cgtatttgtt tatttactca tcgcatcata tacgcagcga    7860
ccgcatgacg caagctgttt tactcaaata cacatcacct ttttagacgg cggcgctcgg    7920
tttcttcagc ggccaagctg gccggccagg ccgccagctt ggcatcagac aaaccggcca    7980
ggatttcatg cagccgcacg gttgagacgt gcgcgggcgg ctcgaacacg tacccggccg    8040
cgatcatctc cgcctcgatc tcttcggtaa tgaaaaacgg ttcgtcctgg ccgtcctggt    8100
gcggtttcat gcttgttcct cttggcgttc attctcggcg gccgcagggg cgtcggcctc    8160
ggtcaatgcg tcctcacgga aggcaccgcg ccgcctggcc tcggtgggcg tcacttcctc    8220
gctgcgctca agtgcgcggt acagggtcga gcgatgcacg ccaagcagtg cagccgcctc    8280
tttcacggtg cggccttcct ggtcgatcag ctcgcgggcg tgcgcgatct gtgccggggt    8340
gagggtaggg cggggggccaa acttcacgcc tcgggccttg gcggcctcgc gcccgctccg    8400
ggtgcggtcg atgattaggg aacgctcgaa ctcggcaatg ccggcgaaca cggtcaacac    8460
catgcggccg gccggcgtgg tggtaacgcg tggtgatttt gtgccgagct gccggtcggg    8520
gagctgttgg ctggctggtg gcaggatata ttgtggtgta aacaaattga cgcttagaca    8580
acttaataac acattgcgga cgtctttaat gtactgaatt aacatccgtt tgatacttgt    8640
ctaaaattgg ctgatttcga gtgcatctat gcataaaaac aatctaatga caattattac    8700
caagcaggat cctgtcaaac actgatagtt taaactgaag gcgggaaacg acaatctgat    8760
catgagcgga gaattaaggg agtcacgtta tgaccccgc cgatgacgcg ggacaagccg    8820
ttttacgttt ggaactgaca gaaccgcaac gttgaaggag ccactcagcc gcgggtttct    8880
ggagtttaat gagctaagca catacgtcag aaaccattat tgcgcgttca aaagtcgcct    8940
aaggtcacta tcagctagca aatatttctt gtcaaaaatg ctccactgac gttccataaa    9000
ttcccctcgg tatccaatta gagtctcata ttcactctca atccaaataa tctgcaccgg    9060
atctggatcg tttcgcatga ttgaacaaga tggattgcac gcaggttctc cggccgcttg    9120
ggtggagagg ctattcggct atgactgggc acaacagaca atcggctgct ctgatgccgc    9180
cgtgttccgg ctgtcagcgc agggggcgccc ggttcttttt gtcaagaccg acctgtccgg    9240
tgccctgaat gaactgcagg acgaggcagc gcggctatcg tggctggcca cgacgggcgt    9300
tccttgcgca gctgtgctcg acgttgtcac tgaagcggga agggactggc tgctattggg    9360
cgaagtgccg gggcaggatc tcctgtcatc tcaccttgct cctgccgaga aagtatccat    9420
catggctgat gcaatgcggc ggctgcatac gcttgatccg gctacctgcc cattcgacca    9480
ccaagcgaaa catcgcatcg agcgagcacg tactcggatg gaagccggtc ttgtcgatca    9540
```

```
ggatgatctg acgaagagc atcaggggct cgcgccagcc gaactgttcg ccaggctcaa    9600
ggcgcgcatg cccgacggcg aggatctcgt cgtgacccat ggcgatgcct gcttgccgaa    9660
tatcatggtg aaaatggcc gcttttctgg attcatcgac tgtggccggc tgggtgtggc     9720
ggaccgctat caggacatag cgttggctac ccgtgatatt gctgaagagc ttggcggcga    9780
atgggctgac cgcttcctcg tgctttacgg tatcgccgct cccgattcgc agcgcatcgc    9840
cttctatcgc cttcttgacg agttcttctg agcgggaccc aagctctaga tcttgctgcg    9900
ttcggatatt ttcgtggagt tcccgccaca gacccggatg atccccgatc gttcaaacat    9960
ttggcaataa agtttcttaa gattgaatcc tgttgccggt cttgcgatga ttatcatata   10020
atttctgttg aattacgtta agcatgtaat aattaacatg taatgcatga cgttatttat   10080
gagatgggtt tttatgatta gagtcccgca attatacatt taatacgcga tagaaaacaa   10140
aatatagcgc gcaaactagg ataaattatc gcgcgcggtg tcatctatgt tactagatcg   10200
ggcctcctgt caagctctga gtcgttgtaa aacgacggcc agtgaattga gctcggtacc   10260
gagtcaaaga ttcaaataga ggacctaaca gaactcgccg taaagactgg cgaacagttc   10320
atacagagtc tcttacgact caatgacaag aagaaaatct tcgtcaacat ggtggagcac   10380
gacacgcttg tctactccaa aaatatcaaa gatacagtct cagaagacca aagggcaatt   10440 gagactttc aacaagggt aatatccgga aacctcctcg gattccattg cccagctatc   10500
tgtcacttta ttgtgaagat agtggaaaag gaaggtggct cctacaaatg ccatcattgc   10560
gataaaggaa aggccatcgt tgaagatgcc tctgccgaca gtggtcccaa agatggaccc   10620
ccacccacga ggagcatcgt ggaaaaagaa gacgttccaa ccacgtcttc aaagcaagtg   10680
gattgatgtg atatctccac tgacgtaagg gatgacgcac aatcccacta tccttcgcaa   10740
gacccttcct ctatataagg aagttcattt catttggaga ggacagggta cgtacctaga   10800
atacaaagaa gaggaagaag aaacctctac agaagaaagt gatggatccc cgggatcatc   10860
tacttctgaa gactcagact cagactaagc aggtgacgaa cgtcaccaat cccaattcga   10920
tctacatccg tcct                                                      10934

<210> SEQ ID NO 33
<211> LENGTH: 200
<212> TYPE: DNA
<213> ORGANISM: Artificial Sequence
<220> FEATURE:
<223> OTHER INFORMATION: I-SceI AlrcR target site insert in VC-SAH52-21

<400> SEQUENCE: 33
acggccgcct agggatccga caggttacgg ggcggcgacc tcgcgggttt tcgctattta     60
tgaaaatttt ccggtttaag gcgtttccgt tcttcttcgt cataacttaa tgttttttatt   120 taaaatacccc tctgaaaaga aggaaacga caggtgcatt accctgttat ccctagatcc    180
gcacgttatc cctatctaga                                                 200

<210> SEQ ID NO 34
<211> LENGTH: 197
<212> TYPE: DNA
<213> ORGANISM: Artificial Sequence
<220> FEATURE:
<223> OTHER INFORMATION: I-SceI AlrcR target site insert in VC-SAH111

<400> SEQUENCE: 34
agcggccgcc tagggatccg acaggttacg gggcggcgac ctcgcgggtt ttcgctattt     60
atgaaaattt tccggtttaa ggcgtttccg ttcttcttcg tcataactta atgtttttat   120
```

```
ttaaaatacc ctctgaaaag aaaggaaacg acaggtgcat taccctgtta tccctaggat    180
ccgcacgtta tccctat                                                   197

<210> SEQ ID NO 35
<211> LENGTH: 198
<212> TYPE: DNA
<213> ORGANISM: Artificial Sequence
<220> FEATURE:
<223> OTHER INFORMATION: I-SceI AlrcR target site insert in VC-SAH112

<400> SEQUENCE: 35
agcggccgcc tagggatccg acaggttacg gggcggcgac ctcgcgggtt ttcgctattt    60
atgaaaattt tccggtttaa ggcgtttccg ttcttcttcg tcataactta atgtttttat   120
ttaaaatacc ctctgaaaag aaaggaaacg acaggtgcat taccctgtta tccctagcga   180
tccgcacgtt atccctat                                                 198

<210> SEQ ID NO 36
<211> LENGTH: 221
<212> TYPE: DNA
<213> ORGANISM: Artificial Sequence
<220> FEATURE:
<223> OTHER INFORMATION: I-SceI AlrcR target site insert in VC-SAH55-22

<400> SEQUENCE: 36
agcggccgcc tagggatccg acaggttacg gggcggcgac ctcgcgggtt ttcgctattt    60
atgaaaattt tccggtttaa ggcgtttccg ttcttcttcg tcataactta atgtttttat   120
ttaaaatacc ctctgaaaag aaaggaaacg acaggtgcat taccctgtta tccctagcgg   180
atccgcacgt tatccctagc ggatccgcac gttatcccta t                       221

<210> SEQ ID NO 37
<211> LENGTH: 9
<212> TYPE: PRT
<213> ORGANISM: Artificial Sequence
<220> FEATURE:
<223> OTHER INFORMATION: C term mod No1

<400> SEQUENCE: 37

Thr Ile Lys Ser Glu Thr Phe Leu Lys
1               5

<210> SEQ ID NO 38
<211> LENGTH: 9
<212> TYPE: PRT
<213> ORGANISM: Artificial Sequence
<220> FEATURE:
<223> OTHER INFORMATION: C-term mod No2

<400> SEQUENCE: 38

Ala Ile Ala Asn Gln Ala Phe Leu Lys
1               5

<210> SEQ ID NO 39
<211> LENGTH: 915
<212> TYPE: DNA
<213> ORGANISM: Artificial Sequence
<220> FEATURE:
<223> OTHER INFORMATION: insert of VC-SAH128-3

<400> SEQUENCE: 39
atgggtccta agaagaagag aaaggttaag aacattaaga agaaccaggt gatgaacctg    60
```

```
ggccctaact ctaagctgct taaggaatac aagtctcagc tgattgagct gaacattgag      120
cagttcgagg ctggcatagg cctgattctg ggcgatgctt acattaggtc tagggatgag      180
ggcaagacct actgcatgca gttcgagtgg aagaacaagg cttacatgga tcacgtgtgc      240
ctgctgtacg atcagtgggt gctgtctcct cctcacaaga aggagagggt gaaccacttg      300
ggaaacctgg tgattacctg gggcgctcaa accttcaagc accaggcttt caacaagctg      360
gctaacctgt tcattgtgaa caacaagaag accattccta caacctggt ggagaactac       420 ctgaccccta tgtctctggc ttactggttc atggatgatg gcggcaagtg ggattacaac      480
aagaactcta ccaacaagtc tattgtgctg aacacccagt ctttcacctt cgaggaggtg      540
gaatacctgg tgaagggcct gaggaacaag ttccagctga actgctacgt gaagattaac      600
aagaacaagc ctattattta cattgattct atgtcttacc tgattttcta caacctgatt      660
aagccttacc tgattcctca gatgatgtac aagctgccta caccatcaa gtctgagacc       720 ttcctgaagc ttatggctga tacaagaaga aggcagaacc actcttgcga tccttgtaga      780
aagggaaaaa gaagatgtga cgctcctgag aacagaaatg aggctaacga aacggatgg       840 gtgtcatgtt ctaactgcaa gagatggaac aaggattgca ctttcaactg gctctcatct      900
cagagatcaa agtga                                                       915

<210> SEQ ID NO 40
<211> LENGTH: 915
<212> TYPE: DNA
<213> ORGANISM: Artificial Sequence
<220> FEATURE:
<223> OTHER INFORMATION: insert of VX-SAH129-1

<400> SEQUENCE: 40
atgggtccta agaagaagag aaaggttaag aacattaaga agaaccaggt gatgaacctg       60
ggccctaact ctaagctgct taaggaatac aagtctcagc tgattgagct gaacattgag      120
cagttcgagg ctggcatagg cctgattctg ggcgatgctt acattaggtc tagggatgag      180
ggcaagacct actgcatgca gttcgagtgg aagaacaagg cttacatgga tcacgtgtgc      240
ctgctgtacg atcagtgggt gctgtctcct cctcacaaga aggagagggt gaaccacttg      300
ggaaacctgg tgattacctg gggcgctcaa accttcaagc accaggcttt caacaagctg      360
gctaacctgt tcattgtgaa caacaagaag accattccta caacctggt ggagaactac       420 ctgaccccta tgtctctggc ttactggttc atggatgatg gcggcaagtg ggattacaac      480
aagaactcta ccaacaagtc tattgtgctg aacacccagt ctttcacctt cgaggaggtg      540
gaatacctgg tgaagggcct gaggaacaag ttccagctga actgctacgt gaagattaac      600
aagaacaagc ctattattta cattgattct atgtcttacc tgattttcta caacctgatt      660
aagccttacc tgattcctca gatgatgtac aagctgccta acgccatcgc aaccaggcc       720 ttcctgaagc ttatggctga tacaagaaga aggcagaacc actcttgcga tccttgtaga      780
aagggaaaaa gaagatgtga cgctcctgag aacagaaatg aggctaacga aacggatgg       840 gtgtcatgtt ctaactgcaa gagatggaac aaggattgca ctttcaactg gctctcatct      900
cagagatcaa agtga                                                       915

<210> SEQ ID NO 41
<211> LENGTH: 3198
<212> TYPE: DNA
<213> ORGANISM: Artificial Sequence
<220> FEATURE:
<223> OTHER INFORMATION: Insert of VC-SAH130-30  NLS - I-SceI C term mod
```

1 AlcR

<400> SEQUENCE: 41

```
atgggtccta agaagaagag aaaggttaag aacattaaga agaaccaggt gatgaacctg      60
ggccctaact ctaagctgct taaggaatac aagtctcagc tgattgagct gaacattgag     120
cagttcgagg ctggcatagg cctgattctg ggcgatgctt acattaggtc tagggatgag     180
ggcaagacct actgcatgca gttcgagtgg aagaacaagg cttacatgga tcacgtgtgc     240
ctgctgtacg atcagtgggt gctgtctcct cctcacaaga aggagagggt gaaccacttg     300
ggaaacctgg tgattacctg gggcgctcaa accttcaagc accaggcttt caacaagctg     360
gctaacctgt tcattgtgaa caacaagaag accattccta caacctggt ggagaactac      420
ctgaccccta tgtctctggc ttactggttc atggatgatg gcggcaagtg ggattacaac     480
aagaactcta ccaacaagtc tattgtgctg aacacccagt ctttcacctt cgaggaggtg     540
gaatacctgg tgaagggcct gaggaacaag ttccagctga actgctacgt gaagattaac     600
aagaacaagc ctattattta cattgattct atgtcttacc tgattttcta caacctgatt     660
aagccttacc tgattcctca gatgatgtac aagctgccta acaccatcaa gtctgagacc     720
ttcctgaagc ttatggctga tacaagaaga aggcagaacc actcttgcga tccttgtaga     780
aagggaaaaa gaagatgtga cgctcctgag aacagaaatg aggctaacga gaacggatgg     840
gtgtcatgtt ctaactgcaa gagatggaac aaggattgca ctttcaactg ctctcatct      900
cagagatcaa aggctaaggg tgctgctcct agagctagaa ctaagaaggc tagaactgct     960
actactactt ctgagccttc tacttctgct gctactatcc ctactcctga gtctgataac    1020
catgatgctc ctccagtgat caactctcat gatgctctcc catcttggac tcagggactt    1080
cttttctcatc ctggtgatct cttcgatttc tctcactctg ctatccctgc taatgctgag    1140
gatgctgcta acgttcaatc tgatgctcct ttcccttggg atcttgctat tcctggtgat    1200
ttctctatgg gacagcagct tgagaaacct cttttctcctc tctctttcca ggctgttctt    1260
ctccctcctc actctcctaa cactgatgat ctcatcagag agcttgagga acagactact    1320
gatcctgatt ctgtgactga tacaaactct gttcagcagg ttgcacagga tggatctttg    1380
tggagtgata gacagtctcc tcttctccct gagaactctc tctgtatggc ttctgattct    1440
actgctagaa gatacgctag atcaactatg actaagaacc tcatgagaat ctaccacgat    1500
tctatggaaa acgctctctc ttgttggctt actgagcaca actgcccta ctctgatcaa     1560
atctcttacc tccctcctaa gcagcgtgct gaatggggac taactggtc taacagaatg     1620
tgcatcagag tgtgcagact cgatagagtg tctacttctc tcagaggtag agctttgtct    1680
gctgaagagg ataaggctgc tgctagagca cttcatctcg ctatcgtggc ttttgcttct    1740
caatggactc agcatgctca agaggtgct ggacttaacg ttcctgctga tatcgctgct     1800
gatgagagat caatcagaag aaacgcttgg aacgaggcta acatgctctc caacacact     1860
actggaatcc catctttcag agtgatcttc gctaacatca tcttctcact cactcagtct    1920
gtgctcgatg atgatgagca acatggaatg ggagctagac ttgataagct ccttgagaac    1980
gatggtgctc ctgttttttct tgagactgct aacagacagc tctacacttt cagacacaag    2040
ttcgctagaa tgcaaagaag aggaaaggct ttcaacagac tccctggtgg atctgttgct    2100
tctactttcg ctggaatctt cgagactcct actccttctt ctgagtctcc tcagctcgat    2160
cctgttgttg cttctgagga acacagatca acactctcac tcatgttctg gctcggaatc    2220
atgttcgata cactctcagc tgctatgtac caaagacctc tcgttgtgtc tgatgaggat    2280
```

```
tctcaaatct cttctgcttc tcctcctaga agaggtgctg agacacctat caaccttgat   2340
tgctgggaac ctcctagaca agttccttct aaccaggaaa agtctgatgt ttggggtgat   2400
cttttcctca gaacttctga ttctctccct gatcacgagt ctcacactca aatctctcag   2460
cctgctgcta gatggccttg tacttacgaa caagctgctg ctgctctttc ttctgctact   2520
cctgttaagg tgctcctcta cagaagagtt actcagcttc agactcttct ctacagagga   2580
gcttctcctg ctagacttga ggctgctatc cagagaactc tctacgttta caaccactgg   2640
actgctaagt accagccttt catgcaagat tgcgtggcta accatgagct tctcccttct   2700
agaatccagt cttggtacgt gatccttgat ggacattggc atcttgctgc tatgcttctc   2760
gctgatgtgc ttgagtctat cgatagagat tcttactctg atatcaacca catcgatctc   2820
gtgactaagc tcagactcga taacgctctt gctgtttctg ctctcgctag atcatctctc   2880
agaggacagg aacttgatcc tggaaaggct tctcctatgt acagacactt ccacgattct   2940
ctcactgaag ttgctttcct tgtggagcct tggactgttg ttctcatcca ctcattcgct   3000
aaggctgctt acatccttct tgattgcctc gatcttgatg gacagggaaa tgctcttgct   3060
ggataccttc agcttagaca gaactgcaac tactgcatca gagcacttca gttcctcgga   3120
agaaagtctg atatggctgc tctcgttgct aaggatcttg agagaggact taacggaaaa   3180
gtggattctt tcctctga                                                 3198
```

<210> SEQ ID NO 42
<211> LENGTH: 3198
<212> TYPE: DNA
<213> ORGANISM: Artificial Sequence
<220> FEATURE:
<223> OTHER INFORMATION: insert of VX-SAH 131-6 NLS - I-SceI C term mod #2 AlcR

<400> SEQUENCE: 42

```
atgggtccta agaagaagag aaaggttaag aacattaaga agaaccaggt gatgaacctg     60
ggccctaact ctaagctgct taaggaatac aagtctcagc tgattgagct gaacattgag    120
cagttcgagg ctggcatagg cctgattctg ggcgatgctt acattaggtc tagggatgag    180
ggcaagacct actgcatgca gttcgagtgg aagaacaagg cttacatgga tcacgtgtgc    240
ctgctgtacg atcagtgggt gctgtctcct cctcacaaga aggagagggt gaaccacttg    300
ggaaacctgg tgattacctg ggcgctcaa accttcaagc accaggcttt caacaagctg     360
gctaacctgt tcattgtgaa caacaagaag accattccta acaacctggt ggagaactac    420
ctgacccta tgtctctggc ttactggttc atggatgatg gcggcaagtg ggattacaac     480
aagaactcta ccaacaagtc tattgtgctg aacacccagt ctttcacctt cgaggaggtg    540
gaatacctgg tgaagggcct gaggaacaag ttccagctga actgctacgt gaagattaac    600
aagaacaagc ctattattta cattgattct atgtcttacc tgattttcta caacctgatt    660
aagccttacc tgattcctca gatgatgtac aagctgccta acgccatcgc caaccaggcc    720
ttcctgaagc ttatggctga tacaagaaga aggcagaacc actcttgcga tccttgtaga    780
aagggaaaaa gaagatgtga cgctcctgag aacagaaatg aggctaacga gaacggatgg    840
gtgtcatgtt ctaactgcaa gagatggaac aaggattgca ctttcaactg gctctcatct    900
cagagatcaa aggctaaggg tgctgctcct agagctagaa ctaagaaggc tagaactgct    960
actactactt ctgagccttc tacttctgct gctactatcc ctactcctga gtctgataac   1020
catgatgctc ctccagtgat caactctcat gatgctctcc catcttggac tcagggactt   1080
```

```
ctttctcatc ctggtgatct cttcgatttc tctcactctg ctatccctgc taatgctgag    1140
gatgctgcta acgttcaatc tgatgctcct ttcccttggg atcttgctat tcctggtgat    1200
ttctctatgg gacagcagct tgagaaacct ctttctcctc tctctttcca ggctgttctt    1260
ctccctcctc actctcctaa cactgatgat ctcatcagag agcttgagga acagactact    1320
gatcctgatt ctgtgactga tacaaactct gttcagcagg ttgcacagga tggatctttg    1380
tggagtgata gacagtctcc tcttctccct gagaactctc tctgtatggc ttctgattct    1440
actgctagaa gatacgctag atcaactatg actaagaacc tcatgagaat ctaccacgat    1500
tctatggaaa acgctctctc ttgttggctt actgagcaca actgcccctta ctctgatcaa    1560 atctcttacc tccctcctaa gcagcgtgct gaatggggac ctaactggtc taacagaatg    1620
tgcatcagag tgtgcagact cgatagagtg tctacttctc tcagaggtag agctttgtct    1680
gctgaagagg ataaggctgc tgctagagca cttcatctcg ctatcgtggc ttttgcttct    1740
caatggactc agcatgctca aagaggtgct ggacttaacg ttcctgctga tatcgctgct    1800
gatgagagat caatcagaag aaacgcttgg aacgaggcta gacatgctct ccaacacact    1860
actggaatcc catctttcag agtgatcttc gctaacatca tcttctcact cactcagtct    1920
gtgctcgatg atgatgagca acatggaatg ggagctagac ttgataagct ccttgagaac    1980
gatggtgctc ctgtttttct tgagactgct aacagacagc tctacacttt cagacacaag    2040
ttcgctagaa tgcaaagaag aggaaaggct ttcaacagac tccctggtgg atctgttgct    2100
tctactttcg ctggaatctt cgagactcct actccttctt ctgagtctcc tcagctcgat    2160
cctgttgttg cttctgagga acacagatca acactctcac tcatgttctg gctcggaatc    2220
atgttcgata cactctcagc tgctatgtac caaagacctc tcgttgtgtc tgatgaggat    2280
tctcaaatct cttctgcttc tcctcctaga agaggtgctg agacacctat caaccttgat    2340
tgctgggaac tcctagaca agttccttct aaccaggaaa agtctgatgt ttggggtgat    2400
cttttcctca gaacttctga ttctctccct gatcacgagt ctcacactca aatctctcag    2460
cctgctgcta gatggccttg tacttacgaa caagctgctg ctgctctttc ttctgctact    2520
cctgttaagg tgctcctcta cagaagagtt actcagcttc agactcttct ctacagagga    2580
gcttctcctg ctagacttga ggctgctatc cagagaactc tctacgttta caaccactgg    2640
actgctaagt accagccttt catgcaagat tgcgtggcta accatgagct tctcccttct    2700
agaatccagt cttggtacgt gatccttgat ggacattggc atcttgctgc tatgcttctc    2760
gctgatgtgc ttgagtctat cgatagagat tcttactctg atatcaacca catcgatctc    2820
gtgactaagc tcagactcga taacgctctt gctgtttctg ctctcgctag atcatctctc    2880
agaggacagg aacttgatcc tggaaaggct ctcctatgt acagacactt ccacgattct    2940
ctcactgaag ttgctttcct tgtggagcct tggactgttg ttctcatcca ctcattcgct    3000
aaggctgctt acatccttct tgattgcctc gatcttgatg gacagggaaa tgctcttgct    3060 ggatacctttc agcttagaca gaactgcaac tactgcatca gagcacttca gttcctcgga    3120
agaaagtctg atatggctgc tctcgttgct aaggatcttg agagaggact aacggaaaaa    3180
gtggattctt tcctctga                                                 3198
```

<210> SEQ ID NO 43
<211> LENGTH: 28
<212> TYPE: DNA
<213> ORGANISM: Artificial Sequence
<220> FEATURE:

```
<223> OTHER INFORMATION: insert of VC-SAH181-1, AlcR (1-60) I-SceI
      target site fusion

<400> SEQUENCE: 43
cgtgcggatc attaccctgt tatcccta                                          28

<210> SEQ ID NO 44
<211> LENGTH: 29
<212> TYPE: DNA
<213> ORGANISM: Artificial Sequence
<220> FEATURE:
<223> OTHER INFORMATION: insert of VC-SAH182-2, AlcR (1-60) I-SceI
      target site fusion
<220> FEATURE:
<221> NAME/KEY: misc_feature
<222> LOCATION: (11)..(11)
<223> OTHER INFORMATION: n is a, c, g, or t

<400> SEQUENCE: 44
cgtgcggatc nattaccctg ttatcccta                                         29

<210> SEQ ID NO 45
<211> LENGTH: 30
<212> TYPE: DNA
<213> ORGANISM: Artificial Sequence
<220> FEATURE:
<223> OTHER INFORMATION: insert of VC-SAH183-3, AlcR (1-60) I-SceI
      target site fusion
<220> FEATURE:
<221> NAME/KEY: misc_feature
<222> LOCATION: (11)..(12)
<223> OTHER INFORMATION: n is a, c, g, or t

<400> SEQUENCE: 45
cgtgcggatc nnattaccct gttatcccta                                        30

<210> SEQ ID NO 46
<211> LENGTH: 31
<212> TYPE: DNA
<213> ORGANISM: Artificial Sequence
<220> FEATURE:
<223> OTHER INFORMATION: insert of VC-SAH184-2, AlcR (1-60) I-SceI
      target site fusion
<220> FEATURE:
<221> NAME/KEY: misc_feature
<222> LOCATION: (11)..(13)
<223> OTHER INFORMATION: n is a, c, g, or t

<400> SEQUENCE: 46
cgtgcggatc nnnattaccc tgttatccct a                                      31

<210> SEQ ID NO 47
<211> LENGTH: 861
<212> TYPE: DNA
<213> ORGANISM: Artificial Sequence
<220> FEATURE:
<223> OTHER INFORMATION: AlcR(1-60) I-SceI -C-term del

<400> SEQUENCE: 47
atggctgata caagaagaag gcagaaccac tcttgcgatc cttgtagaaa gggaaaaaga       60
agatgtgacg ctcctgagaa cagaaatgag gctaacgaga acggatgggt gtcatgttct     120
aactgcaaga gatggaacaa ggattgcact ttcaactggc tctcatctca acgttctaaa     180
ggtaagaaca ttaagaagaa ccaggtgatg aacctgggcc ctaactctaa gctgcttaag     240
gaatacaagt ctcagctgat tgagctgaac attgagcagt cgaggctgg catagcctg       300 attctgggcg atgcttacat taggtctagg gatgagggca agacctactg catgcagttc     360
```

```
gagtggaaga acaaggctta catggatcac gtgtgcctgc tgtacgatca gtgggtgctg      420
tctcctcctc acaagaagga gagggtgaac cacttgggaa acctggtgat tacctggggc      480
gctcaaacct tcaagcacca ggctttcaac aagctggcta acctgttcat tgtgaacaac      540
aagaagacca ttcctaacaa cctggtggag aactacctga ccccctatgtc tctggcttac      600 tggttcatgg atgatggcgg caagtgggat tacaacaaga actctaccaa caagtctatt      660
gtgctgaaca cccagtcttt caccttcgag gaggtggaat acctggtgaa gggcctgagg      720
aacaagttcc agctgaactg ctacgtgaag attaacaaga acaagcctat tatttacatt      780
gattctatgt cttacctgat tttctacaac ctgattaagc ttacctgat tcctcagatg      840 atgtacaagc tgcctaactg a                                                861

<210> SEQ ID NO 48
<211> LENGTH: 879
<212> TYPE: DNA
<213> ORGANISM: Artificial Sequence
<220> FEATURE:
<223> OTHER INFORMATION: AlcR(1-60) I-SceI -C-term del with one amino
      acid linker

<400> SEQUENCE: 48
atggctgata caagaagaag gcagaaccac tcttgcgatc cttgtagaaa gggaaaaaga      60
agatgtgacg ctcctgagaa cagaaatgag gctaacgaga acggatgggt gtcatgttct      120
aactgcaaga gatggaacaa ggattgcact ttcaactggc tctcatctca acgttctaaa      180
ggctctggat ccggtagcgg taagaacatt aagaagaacc aggtgatgaa cctgggccct      240
aactctaagc tgcttaagga atacaagtct cagctgattg agctgaacat tgagcagttc      300
gaggctggca taggcctgat tctgggcgat gcttacatta ggtctaggga tgagggcaag      360
acctactgca tgcagttcga gtggaagaac aaggcttaca tggatcacgt gtgcctgctg      420
tacgatcagt gggtgctgtc tcctcctcac aagaaggaga gggtgaacca cttgggaaac      480
ctggtgatta cctggggcgc tcaaaccttc aagcaccagg ctttcaacaa gctggctaac      540
ctgttcattg tgaacaacaa gaagaccatt cctaacaacc tggtgagaa ctacctgacc      600 cctatgtctc tggcttactg gttcatggat gatggcggca agtgggatta caacaagaac      660
tctaccaaca gtctattgt gctgaacacc cagtctttca ccttcgagga ggtggaatac      720
ctggtgaagg gcctgaggaa caagttccag ctgaactgct acgtgaagat taacaagaac      780
aagcctatta tttacattga ttctatgtct tacctgattt tctacaacct gattaagcct      840
tacctgattc tcagatgat gtacaagctg cctaactga                             879

<210> SEQ ID NO 49
<211> LENGTH: 873
<212> TYPE: DNA
<213> ORGANISM: Artificial Sequence
<220> FEATURE:
<223> OTHER INFORMATION: AlcR(1-60) I-SceI -C-term del with three amino
      acid linker

<400> SEQUENCE: 49
atggctgata caagaagaag gcagaaccac tcttgcgatc cttgtagaaa gggaaaaaga      60
agatgtgacg ctcctgagaa cagaaatgag gctaacgaga acggatgggt gtcatgttct      120
aactgcaaga gatggaacaa ggattgcact ttcaactggc tctcatctca acgttctaaa      180
ggctctggat ccggtaagaa cattaagaag aaccaggtga tgaacctggg ccctaactct      240
```

```
aagctgctta aggaatacaa gtctcagctg attgagctga acattgagca gttcgaggct    300
ggcataggcc tgattctggg cgatgcttac attaggtcta gggatgaggg caagacctac    360
tgcatgcagt tcgagtggaa gaacaaggct tacatggatc acgtgtgcct gctgtacgat    420
cagtgggtgc tgtctcctcc tcacaagaag gagagggtga accacttggg aaacctggtg    480
attacctggg gcgctcaaac cttcaagcac caggctttca acaagctggc taacctgttc    540
attgtgaaca acaagaagac cattcctaac aacctggtgg agaactacct gacccctatg    600
tctctggctt actggttcat ggatgatggc ggcaagtggg attacaacaa gaactctacc    660
aacaagtcta ttgtgctgaa cacccagtct ttcaccttcg aggaggtgga atacctggtg    720
aagggcctga ggaacaagtt ccagctgaac tgctacgtga agattaacaa gaacaagcct    780
attatttaca ttgattctat gtcttacctg attttctaca acctgattaa gccttacctg    840
attcctcaga tgatgtacaa gctgcctaac tga                                 873
```

<210> SEQ ID NO 50
<211> LENGTH: 304
<212> TYPE: PRT
<213> ORGANISM: Artificial Sequence
<220> FEATURE:
<223> OTHER INFORMATION: NLS - I-SceI C term mod #1 AlcR (1-60)

<400> SEQUENCE: 50

```
Met Gly Pro Lys Lys Arg Lys Val Lys Asn Ile Lys Lys Asn Gln
1               5                   10                  15

Val Met Asn Leu Gly Pro Asn Ser Lys Leu Leu Lys Glu Tyr Lys Ser
            20                  25                  30

Gln Leu Ile Glu Leu Asn Ile Glu Gln Phe Glu Ala Gly Ile Gly Leu
        35                  40                  45

Ile Leu Gly Asp Ala Tyr Ile Arg Ser Arg Asp Glu Gly Lys Thr Tyr
    50                  55                  60

Cys Met Gln Phe Glu Trp Lys Asn Lys Ala Tyr Met Asp His Val Cys
65                  70                  75                  80

Leu Leu Tyr Asp Gln Trp Val Leu Ser Pro Pro His Lys Lys Glu Arg
                85                  90                  95

Val Asn His Leu Gly Asn Leu Val Ile Thr Trp Gly Ala Gln Thr Phe
            100                 105                 110

Lys His Gln Ala Phe Asn Lys Leu Ala Asn Leu Phe Ile Val Asn Asn
        115                 120                 125

Lys Lys Thr Ile Pro Asn Asn Leu Val Glu Asn Tyr Leu Thr Pro Met
    130                 135                 140

Ser Leu Ala Tyr Trp Phe Met Asp Asp Gly Gly Lys Trp Asp Tyr Asn
145                 150                 155                 160

Lys Asn Ser Thr Asn Lys Ser Ile Val Leu Asn Thr Gln Ser Phe Thr
                165                 170                 175

Phe Glu Glu Val Glu Tyr Leu Val Lys Gly Leu Arg Asn Lys Phe Gln
            180                 185                 190

Leu Asn Cys Tyr Val Lys Ile Asn Lys Asn Lys Pro Ile Ile Tyr Ile
        195                 200                 205

Asp Ser Met Ser Tyr Leu Ile Phe Tyr Asn Leu Ile Lys Pro Tyr Leu
    210                 215                 220

Ile Pro Gln Met Met Tyr Lys Leu Pro Asn Thr Ile Lys Ser Glu Thr
225                 230                 235                 240

Phe Leu Lys Leu Met Ala Asp Thr Arg Arg Arg Gln Asn His Ser Cys
                245                 250                 255
```

```
Asp Pro Cys Arg Lys Gly Lys Arg Arg Cys Asp Ala Pro Glu Asn Arg
            260                 265                 270

Asn Glu Ala Asn Glu Asn Gly Trp Val Ser Cys Ser Asn Cys Lys Arg
        275                 280                 285

Trp Asn Lys Asp Cys Thr Phe Asn Trp Leu Ser Ser Gln Arg Ser Lys
    290                 295                 300

<210> SEQ ID NO 51
<211> LENGTH: 304
<212> TYPE: PRT
<213> ORGANISM: Artificial Sequence
<220> FEATURE:
<223> OTHER INFORMATION: NLS - I-SceI C term mod #2 AlcR (1-60)

<400> SEQUENCE: 51

Met Gly Pro Lys Lys Arg Lys Val Lys Asn Ile Lys Lys Asn Gln
1               5                   10                  15

Val Met Asn Leu Gly Pro Asn Ser Lys Leu Leu Lys Glu Tyr Lys Ser
            20                  25                  30

Gln Leu Ile Glu Leu Asn Ile Glu Gln Phe Glu Ala Gly Ile Gly Leu
        35                  40                  45

Ile Leu Gly Asp Ala Tyr Ile Arg Ser Arg Asp Glu Gly Lys Thr Tyr
    50                  55                  60

Cys Met Gln Phe Glu Trp Lys Asn Lys Ala Tyr Met Asp His Val Cys
65                  70                  75                  80

Leu Leu Tyr Asp Gln Trp Val Leu Ser Pro Pro His Lys Lys Glu Arg
                85                  90                  95

Val Asn His Leu Gly Asn Leu Val Ile Thr Trp Gly Ala Gln Thr Phe
            100                 105                 110

Lys His Gln Ala Phe Asn Lys Leu Ala Asn Leu Phe Ile Val Asn Asn
        115                 120                 125

Lys Lys Thr Ile Pro Asn Asn Leu Val Glu Asn Tyr Leu Thr Pro Met
    130                 135                 140

Ser Leu Ala Tyr Trp Phe Met Asp Asp Gly Gly Lys Trp Asp Tyr Asn
145                 150                 155                 160

Lys Asn Ser Thr Asn Lys Ser Ile Val Leu Asn Thr Gln Ser Phe Thr
                165                 170                 175

Phe Glu Glu Val Glu Tyr Leu Val Lys Gly Leu Arg Asn Lys Phe Gln
            180                 185                 190

Leu Asn Cys Tyr Val Lys Ile Asn Lys Asn Lys Pro Ile Ile Tyr Ile
        195                 200                 205

Asp Ser Met Ser Tyr Leu Ile Phe Tyr Asn Leu Ile Lys Pro Tyr Leu
    210                 215                 220

Ile Pro Gln Met Met Tyr Lys Leu Pro Asn Ala Ile Ala Asn Gln Ala
225                 230                 235                 240

Phe Leu Lys Leu Met Ala Asp Thr Arg Arg Gln Asn His Ser Cys
                245                 250                 255

Asp Pro Cys Arg Lys Gly Lys Arg Arg Cys Asp Ala Pro Glu Asn Arg
            260                 265                 270

Asn Glu Ala Asn Glu Asn Gly Trp Val Ser Cys Ser Asn Cys Lys Arg
        275                 280                 285

Trp Asn Lys Asp Cys Thr Phe Asn Trp Leu Ser Ser Gln Arg Ser Lys
    290                 295                 300

<210> SEQ ID NO 52
```

<211> LENGTH: 1065
<212> TYPE: PRT
<213> ORGANISM: Artificial Sequence
<220> FEATURE:
<223> OTHER INFORMATION: NLS - I-SceI C term mod #1 AlcR

<400> SEQUENCE: 52

```
Met Gly Pro Lys Lys Lys Arg Lys Val Lys Asn Ile Lys Lys Asn Gln
1               5                   10                  15
Val Met Asn Leu Gly Pro Asn Ser Lys Leu Leu Lys Glu Tyr Lys Ser
            20                  25                  30
Gln Leu Ile Glu Leu Asn Ile Glu Gln Phe Glu Ala Gly Ile Gly Leu
        35                  40                  45
Ile Leu Gly Asp Ala Tyr Ile Arg Ser Arg Asp Glu Gly Lys Thr Tyr
    50                  55                  60
Cys Met Gln Phe Glu Trp Lys Asn Lys Ala Tyr Met Asp His Val Cys
65                  70                  75                  80
Leu Leu Tyr Asp Gln Trp Val Leu Ser Pro Pro His Lys Lys Glu Arg
                85                  90                  95
Val Asn His Leu Gly Asn Leu Val Ile Thr Trp Gly Ala Gln Thr Phe
            100                 105                 110
Lys His Gln Ala Phe Asn Lys Leu Ala Asn Leu Phe Ile Val Asn Asn
        115                 120                 125
Lys Lys Thr Ile Pro Asn Asn Leu Val Glu Asn Tyr Leu Thr Pro Met
    130                 135                 140
Ser Leu Ala Tyr Trp Phe Met Asp Asp Gly Gly Lys Trp Asp Tyr Asn
145                 150                 155                 160
Lys Asn Ser Thr Asn Lys Ser Ile Val Leu Asn Thr Gln Ser Phe Thr
                165                 170                 175
Phe Glu Glu Val Glu Tyr Leu Val Lys Gly Leu Arg Asn Lys Phe Gln
            180                 185                 190
Leu Asn Cys Tyr Val Lys Ile Asn Lys Asn Lys Pro Ile Ile Tyr Ile
        195                 200                 205
Asp Ser Met Ser Tyr Leu Ile Phe Tyr Asn Leu Ile Lys Pro Tyr Leu
    210                 215                 220
Ile Pro Gln Met Met Tyr Lys Leu Pro Asn Thr Ile Lys Ser Glu Thr
225                 230                 235                 240
Phe Leu Lys Leu Met Ala Asp Thr Arg Arg Gln Asn His Ser Cys
                245                 250                 255
Asp Pro Cys Arg Lys Gly Lys Arg Arg Cys Asp Ala Pro Glu Asn Arg
            260                 265                 270
Asn Glu Ala Asn Glu Asn Gly Trp Val Ser Cys Ser Asn Cys Lys Arg
        275                 280                 285
Trp Asn Lys Asp Cys Thr Phe Asn Trp Leu Ser Ser Gln Arg Ser Lys
    290                 295                 300
Ala Lys Gly Ala Ala Pro Arg Ala Arg Thr Lys Lys Ala Arg Thr Ala
305                 310                 315                 320
Thr Thr Thr Ser Glu Pro Ser Thr Ser Ala Ala Thr Ile Pro Thr Pro
                325                 330                 335
Glu Ser Asp Asn His Asp Ala Pro Pro Val Ile Asn Ser His Asp Ala
            340                 345                 350
Leu Pro Ser Trp Thr Gln Gly Leu Leu Ser His Pro Gly Asp Leu Phe
        355                 360                 365
Asp Phe Ser His Ser Ala Ile Pro Ala Asn Ala Glu Asp Ala Ala Asn
    370                 375                 380
```

```
Val Gln Ser Asp Ala Pro Phe Pro Trp Asp Leu Ala Ile Pro Gly Asp
385                 390                 395                 400

Phe Ser Met Gly Gln Gln Leu Glu Lys Pro Leu Ser Pro Leu Ser Phe
            405                 410                 415

Gln Ala Val Leu Leu Pro Pro His Ser Pro Asn Thr Asp Asp Leu Ile
        420                 425                 430

Arg Glu Leu Glu Glu Gln Thr Thr Asp Pro Asp Ser Val Thr Asp Thr
            435                 440                 445

Asn Ser Val Gln Gln Val Ala Gln Asp Gly Ser Leu Trp Ser Asp Arg
        450                 455                 460

Gln Ser Pro Leu Leu Pro Glu Asn Ser Leu Cys Met Ala Ser Asp Ser
465                 470                 475                 480

Thr Ala Arg Arg Tyr Ala Arg Ser Thr Met Thr Lys Asn Leu Met Arg
                485                 490                 495

Ile Tyr His Asp Ser Met Glu Asn Ala Leu Ser Cys Trp Leu Thr Glu
            500                 505                 510

His Asn Cys Pro Tyr Ser Asp Gln Ile Ser Tyr Leu Pro Pro Lys Gln
        515                 520                 525

Arg Ala Glu Trp Gly Pro Asn Trp Ser Asn Arg Met Cys Ile Arg Val
530                 535                 540

Cys Arg Leu Asp Arg Val Ser Thr Ser Leu Arg Gly Arg Ala Leu Ser
545                 550                 555                 560

Ala Glu Glu Asp Lys Ala Ala Arg Ala Leu His Leu Ala Ile Val
                565                 570                 575

Ala Phe Ala Ser Gln Trp Thr Gln His Ala Gln Arg Gly Ala Gly Leu
                580                 585                 590

Asn Val Pro Ala Asp Ile Ala Asp Glu Arg Ser Ile Arg Arg Asn
        595                 600                 605

Ala Trp Asn Glu Ala Arg His Ala Leu Gln His Thr Thr Gly Ile Pro
610                 615                 620

Ser Phe Arg Val Ile Phe Ala Asn Ile Ile Phe Ser Leu Thr Gln Ser
625                 630                 635                 640

Val Leu Asp Asp Asp Glu Gln His Gly Met Gly Ala Arg Leu Asp Lys
                645                 650                 655

Leu Leu Glu Asn Asp Gly Ala Pro Val Phe Leu Glu Thr Ala Asn Arg
            660                 665                 670

Gln Leu Tyr Thr Phe Arg His Lys Phe Ala Arg Met Gln Arg Arg Gly
        675                 680                 685

Lys Ala Phe Asn Arg Leu Pro Gly Gly Ser Val Ala Ser Thr Phe Ala
        690                 695                 700

Gly Ile Phe Glu Thr Pro Thr Pro Ser Ser Glu Ser Pro Gln Leu Asp
705                 710                 715                 720

Pro Val Val Ala Ser Glu Glu His Arg Ser Thr Leu Ser Leu Met Phe
                725                 730                 735

Trp Leu Gly Ile Met Phe Asp Thr Leu Ser Ala Ala Met Tyr Gln Arg
            740                 745                 750

Pro Leu Val Val Ser Asp Glu Asp Ser Gln Ile Ser Ser Ala Ser Pro
        755                 760                 765

Pro Arg Arg Gly Ala Glu Thr Pro Ile Asn Leu Asp Cys Trp Glu Pro
        770                 775                 780

Pro Arg Gln Val Pro Ser Asn Gln Glu Lys Ser Asp Val Trp Gly Asp
785                 790                 795                 800
```

```
Leu Phe Leu Arg Thr Ser Asp Ser Leu Pro Asp His Glu Ser His Thr
                805                 810                 815

Gln Ile Ser Gln Pro Ala Ala Arg Trp Pro Cys Thr Tyr Glu Gln Ala
            820                 825                 830

Ala Ala Ala Leu Ser Ser Ala Thr Pro Val Lys Val Leu Leu Tyr Arg
            835                 840                 845

Arg Val Thr Gln Leu Gln Thr Leu Leu Tyr Arg Gly Ala Ser Pro Ala
        850                 855                 860

Arg Leu Glu Ala Ala Ile Gln Arg Thr Leu Tyr Val Tyr Asn His Trp
865                 870                 875                 880

Thr Ala Lys Tyr Gln Pro Phe Met Gln Asp Cys Val Ala Asn His Glu
                885                 890                 895

Leu Leu Pro Ser Arg Ile Gln Ser Trp Tyr Val Ile Leu Asp Gly His
            900                 905                 910

Trp His Leu Ala Ala Met Leu Leu Ala Asp Val Leu Glu Ser Ile Asp
        915                 920                 925

Arg Asp Ser Tyr Ser Asp Ile Asn His Ile Asp Leu Val Thr Lys Leu
    930                 935                 940

Arg Leu Asp Asn Ala Leu Ala Val Ser Ala Leu Ala Arg Ser Ser Leu
945                 950                 955                 960

Arg Gly Gln Glu Leu Asp Pro Gly Lys Ala Ser Pro Met Tyr Arg His
                965                 970                 975

Phe His Asp Ser Leu Thr Glu Val Ala Phe Leu Val Glu Pro Trp Thr
            980                 985                 990

Val Val Leu Ile His Ser Phe Ala Lys Ala Ala Tyr Ile Leu Leu Asp
        995                 1000                1005

Cys Leu Asp Leu Asp Gly Gln Gly Asn Ala Leu Ala Gly Tyr Leu
    1010                1015                1020

Gln Leu Arg Gln Asn Cys Asn Tyr Cys Ile Arg Ala Leu Gln Phe
    1025                1030                1035

Leu Gly Arg Lys Ser Asp Met Ala Ala Leu Val Ala Lys Asp Leu
    1040                1045                1050

Glu Arg Gly Leu Asn Gly Lys Val Asp Ser Phe Leu
    1055                1060                1065

<210> SEQ ID NO 53
<211> LENGTH: 1065
<212> TYPE: PRT
<213> ORGANISM: Artificial Sequence
<220> FEATURE:
<223> OTHER INFORMATION: NLS - I-SceI C term mod #2 AlcR

<400> SEQUENCE: 53

Met Gly Pro Lys Lys Lys Arg Lys Val Lys Asn Ile Lys Asn Gln
1               5                   10                  15

Val Met Asn Leu Gly Pro Asn Ser Lys Leu Leu Lys Glu Tyr Lys Ser
            20                  25                  30

Gln Leu Ile Glu Leu Asn Ile Glu Gln Phe Glu Ala Gly Ile Gly Leu
        35                  40                  45

Ile Leu Gly Asp Ala Tyr Ile Arg Ser Arg Asp Glu Gly Lys Thr Tyr
    50                  55                  60

Cys Met Gln Phe Glu Trp Lys Asn Lys Ala Tyr Met Asp His Val Cys
65                  70                  75                  80

Leu Leu Tyr Asp Gln Trp Val Leu Ser Pro Pro His Lys Lys Glu Arg
                85                  90                  95
```

Val Asn His Leu Gly Asn Leu Val Ile Thr Trp Gly Ala Gln Thr Phe
            100                 105                 110

Lys His Gln Ala Phe Asn Lys Leu Ala Asn Leu Phe Ile Val Asn Asn
        115                 120                 125

Lys Lys Thr Ile Pro Asn Asn Leu Val Glu Asn Tyr Leu Thr Pro Met
    130                 135                 140

Ser Leu Ala Tyr Trp Phe Met Asp Asp Gly Lys Trp Asp Tyr Asn
145                 150                 155                 160

Lys Asn Ser Thr Asn Lys Ser Ile Val Leu Asn Thr Gln Ser Phe Thr
                165                 170                 175

Phe Glu Glu Val Glu Tyr Leu Val Lys Gly Leu Arg Asn Lys Phe Gln
                180                 185                 190

Leu Asn Cys Tyr Val Lys Ile Asn Lys Asn Lys Pro Ile Ile Tyr Ile
            195                 200                 205

Asp Ser Met Ser Tyr Leu Ile Phe Tyr Asn Leu Ile Lys Pro Tyr Leu
        210                 215                 220

Ile Pro Gln Met Met Tyr Lys Leu Pro Asn Ala Ile Ala Asn Gln Ala
225                 230                 235                 240

Phe Leu Lys Leu Met Ala Asp Thr Arg Arg Gln Asn His Ser Cys
                245                 250                 255

Asp Pro Cys Arg Lys Gly Lys Arg Arg Cys Asp Ala Pro Glu Asn Arg
            260                 265                 270

Asn Glu Ala Asn Glu Asn Gly Trp Val Ser Cys Ser Asn Cys Lys Arg
        275                 280                 285

Trp Asn Lys Asp Cys Thr Phe Asn Trp Leu Ser Ser Gln Arg Ser Lys
290                 295                 300

Ala Lys Gly Ala Ala Pro Arg Ala Arg Thr Lys Lys Ala Arg Thr Ala
305                 310                 315                 320

Thr Thr Thr Ser Glu Pro Ser Thr Ser Ala Ala Thr Ile Pro Thr Pro
                325                 330                 335

Glu Ser Asp Asn His Asp Ala Pro Pro Val Ile Asn Ser His Asp Ala
            340                 345                 350

Leu Pro Ser Trp Thr Gln Gly Leu Leu Ser His Pro Gly Asp Leu Phe
        355                 360                 365

Asp Phe Ser His Ser Ala Ile Pro Ala Asn Ala Glu Asp Ala Ala Asn
    370                 375                 380

Val Gln Ser Asp Ala Pro Phe Pro Trp Asp Leu Ala Ile Pro Gly Asp
385                 390                 395                 400

Phe Ser Met Gly Gln Gln Leu Glu Lys Pro Leu Ser Pro Leu Ser Phe
                405                 410                 415

Gln Ala Val Leu Leu Pro Pro His Ser Pro Asn Thr Asp Asp Leu Ile
            420                 425                 430

Arg Glu Leu Glu Glu Gln Thr Thr Asp Pro Asp Ser Val Thr Asp Thr
        435                 440                 445

Asn Ser Val Gln Gln Val Ala Gln Asp Gly Ser Leu Trp Ser Asp Arg
    450                 455                 460

Gln Ser Pro Leu Leu Pro Glu Asn Ser Leu Cys Met Ala Ser Asp Ser
465                 470                 475                 480

Thr Ala Arg Arg Tyr Ala Arg Ser Thr Met Thr Lys Asn Leu Met Arg
                485                 490                 495

Ile Tyr His Asp Ser Met Glu Asn Ala Leu Ser Cys Trp Leu Thr Glu
            500                 505                 510

His Asn Cys Pro Tyr Ser Asp Gln Ile Ser Tyr Leu Pro Pro Lys Gln

```
                515                 520                 525
Arg Ala Glu Trp Gly Pro Asn Trp Ser Asn Arg Met Cys Ile Arg Val
530                 535                 540

Cys Arg Leu Asp Arg Val Ser Thr Ser Leu Arg Gly Arg Ala Leu Ser
545                 550                 555                 560

Ala Glu Glu Asp Lys Ala Ala Arg Ala Leu His Leu Ala Ile Val
                565                 570                 575

Ala Phe Ala Ser Gln Trp Thr Gln His Ala Gln Arg Gly Ala Gly Leu
                580                 585                 590

Asn Val Pro Ala Asp Ile Ala Ala Asp Glu Arg Ser Ile Arg Arg Asn
                595                 600                 605

Ala Trp Asn Glu Ala Arg His Ala Leu Gln His Thr Thr Gly Ile Pro
610                 615                 620

Ser Phe Arg Val Ile Phe Ala Asn Ile Ile Phe Ser Leu Thr Gln Ser
625                 630                 635                 640

Val Leu Asp Asp Glu Gln His Gly Met Gly Ala Arg Leu Asp Lys
                645                 650                 655

Leu Leu Glu Asn Asp Gly Ala Pro Val Phe Leu Glu Thr Ala Asn Arg
                660                 665                 670

Gln Leu Tyr Thr Phe Arg His Lys Phe Ala Arg Met Gln Arg Arg Gly
                675                 680                 685

Lys Ala Phe Asn Arg Leu Pro Gly Gly Ser Val Ala Ser Thr Phe Ala
                690                 695                 700

Gly Ile Phe Glu Thr Pro Thr Pro Ser Ser Glu Ser Pro Gln Leu Asp
705                 710                 715                 720

Pro Val Val Ala Ser Glu His Arg Ser Thr Leu Ser Leu Met Phe
                725                 730                 735

Trp Leu Gly Ile Met Phe Asp Thr Leu Ser Ala Ala Met Tyr Gln Arg
                740                 745                 750

Pro Leu Val Val Ser Asp Glu Asp Ser Gln Ile Ser Ser Ala Ser Pro
                755                 760                 765

Pro Arg Arg Gly Ala Glu Thr Pro Ile Asn Leu Asp Cys Trp Glu Pro
770                 775                 780

Pro Arg Gln Val Pro Ser Asn Gln Glu Lys Ser Asp Val Trp Gly Asp
785                 790                 795                 800

Leu Phe Leu Arg Thr Ser Asp Ser Leu Pro Asp His Glu Ser His Thr
                805                 810                 815

Gln Ile Ser Gln Pro Ala Ala Arg Trp Pro Cys Thr Tyr Glu Gln Ala
                820                 825                 830

Ala Ala Ala Leu Ser Ser Ala Thr Pro Val Lys Val Leu Leu Tyr Arg
                835                 840                 845

Arg Val Thr Gln Leu Gln Thr Leu Leu Tyr Arg Gly Ala Ser Pro Ala
                850                 855                 860

Arg Leu Glu Ala Ala Ile Gln Arg Thr Leu Tyr Val Tyr Asn His Trp
865                 870                 875                 880

Thr Ala Lys Tyr Gln Pro Phe Met Gln Asp Cys Val Ala Asn His Glu
                885                 890                 895

Leu Leu Pro Ser Arg Ile Gln Ser Trp Tyr Val Ile Leu Asp Gly His
                900                 905                 910

Trp His Leu Ala Ala Met Leu Leu Ala Asp Val Leu Glu Ser Ile Asp
                915                 920                 925

Arg Asp Ser Tyr Ser Asp Ile Asn His Ile Asp Leu Val Thr Lys Leu
                930                 935                 940
```

```
Arg Leu Asp Asn Ala Leu Ala Val Ser Ala Leu Ala Arg Ser Ser Leu
945                 950                 955                 960

Arg Gly Gln Glu Leu Asp Pro Gly Lys Ala Ser Pro Met Tyr Arg His
            965                 970                 975

Phe His Asp Ser Leu Thr Glu Val Ala Phe Leu Val Glu Pro Trp Thr
        980                 985                 990

Val Val Leu Ile His Ser Phe Ala Lys Ala Ala Tyr Ile Leu Leu Asp
            995                1000                1005

Cys Leu Asp Leu Asp Gly Gln Gly Asn Ala Leu Ala Gly Tyr Leu
       1010                1015                1020

Gln Leu Arg Gln Asn Cys Asn Tyr Cys Ile Arg Ala Leu Gln Phe
       1025                1030                1035

Leu Gly Arg Lys Ser Asp Met Ala Ala Leu Val Ala Lys Asp Leu
       1040                1045                1050

Glu Arg Gly Leu Asn Gly Lys Val Asp Ser Phe Leu
       1055                1060                1065

<210> SEQ ID NO 54
<211> LENGTH: 286
<212> TYPE: PRT
<213> ORGANISM: Artificial Sequence
<220> FEATURE:
<223> OTHER INFORMATION: AlcR(1-60) I-SceI -C-term del

<400> SEQUENCE: 54

Met Ala Asp Thr Arg Arg Gln Asn His Ser Cys Asp Pro Cys Arg
1               5                   10                  15

Lys Gly Lys Arg Arg Cys Asp Ala Pro Glu Asn Arg Asn Glu Ala Asn
                20                  25                  30

Glu Asn Gly Trp Val Ser Cys Ser Asn Cys Lys Arg Trp Asn Lys Asp
            35                  40                  45

Cys Thr Phe Asn Trp Leu Ser Ser Gln Arg Ser Lys Gly Lys Asn Ile
        50                  55                  60

Lys Lys Asn Gln Val Met Asn Leu Gly Pro Asn Ser Lys Leu Leu Lys
65                  70                  75                  80

Glu Tyr Lys Ser Gln Leu Ile Glu Leu Asn Ile Glu Gln Phe Glu Ala
                85                  90                  95

Gly Ile Gly Leu Ile Leu Gly Asp Ala Tyr Ile Arg Ser Arg Asp Glu
            100                 105                 110

Gly Lys Thr Tyr Cys Met Gln Phe Glu Trp Lys Asn Lys Ala Tyr Met
        115                 120                 125

Asp His Val Cys Leu Leu Tyr Asp Gln Trp Val Leu Ser Pro Pro His
    130                 135                 140

Lys Lys Glu Arg Val Asn His Leu Gly Asn Leu Val Ile Thr Trp Gly
145                 150                 155                 160

Ala Gln Thr Phe Lys His Gln Ala Phe Asn Lys Leu Ala Asn Leu Phe
                165                 170                 175

Ile Val Asn Asn Lys Lys Thr Ile Pro Asn Asn Leu Val Glu Asn Tyr
            180                 185                 190

Leu Thr Pro Met Ser Leu Ala Tyr Trp Phe Met Asp Asp Gly Gly Lys
        195                 200                 205

Trp Asp Tyr Asn Lys Asn Ser Thr Asn Lys Ser Ile Val Leu Asn Thr
    210                 215                 220

Gln Ser Phe Thr Phe Glu Glu Val Glu Tyr Leu Val Lys Gly Leu Arg
225                 230                 235                 240
```

```
Asn Lys Phe Gln Leu Asn Cys Tyr Val Lys Ile Asn Lys Asn Lys Pro
                245                 250                 255

Ile Ile Tyr Ile Asp Ser Met Ser Tyr Leu Ile Phe Tyr Asn Leu Ile
            260                 265                 270

Lys Pro Tyr Leu Ile Pro Gln Met Met Tyr Lys Leu Pro Asn
        275                 280                 285
```

<210> SEQ ID NO 55
<211> LENGTH: 290
<212> TYPE: PRT
<213> ORGANISM: Artificial Sequence
<220> FEATURE:
<223> OTHER INFORMATION: AlcR(1-60) I-SceI -C-term del with one amino
      acid linker

<400> SEQUENCE: 55

```
Met Ala Asp Thr Arg Arg Gln Asn His Ser Cys Asp Pro Cys Arg
1               5                   10                  15

Lys Gly Lys Arg Arg Cys Asp Ala Pro Glu Asn Arg Asn Glu Ala Asn
                20                  25                  30

Glu Asn Gly Trp Val Ser Cys Ser Asn Cys Lys Arg Trp Asn Lys Asp
            35                  40                  45

Cys Thr Phe Asn Trp Leu Ser Ser Gln Arg Ser Lys Gly Ser Gly Ser
        50                  55                  60

Gly Lys Asn Ile Lys Lys Asn Gln Val Met Asn Leu Gly Pro Asn Ser
65                  70                  75                  80

Lys Leu Leu Lys Glu Tyr Lys Ser Gln Leu Ile Glu Leu Asn Ile Glu
                85                  90                  95

Gln Phe Glu Ala Gly Ile Gly Leu Ile Leu Gly Asp Ala Tyr Ile Arg
            100                 105                 110

Ser Arg Asp Glu Gly Lys Thr Tyr Cys Met Gln Phe Glu Trp Lys Asn
        115                 120                 125

Lys Ala Tyr Met Asp His Val Cys Leu Leu Tyr Asp Gln Trp Val Leu
    130                 135                 140

Ser Pro Pro His Lys Lys Glu Arg Val Asn His Leu Gly Asn Leu Val
145                 150                 155                 160

Ile Thr Trp Gly Ala Gln Thr Phe Lys His Gln Ala Phe Asn Lys Leu
                165                 170                 175

Ala Asn Leu Phe Ile Val Asn Asn Lys Lys Thr Ile Pro Asn Asn Leu
            180                 185                 190

Val Glu Asn Tyr Leu Thr Pro Met Ser Leu Ala Tyr Trp Phe Met Asp
        195                 200                 205

Asp Gly Gly Lys Trp Asp Tyr Asn Lys Asn Ser Thr Asn Lys Ser Ile
    210                 215                 220

Val Leu Asn Thr Gln Ser Phe Thr Phe Glu Glu Val Glu Tyr Leu Val
225                 230                 235                 240

Lys Gly Leu Arg Asn Lys Phe Gln Leu Asn Cys Tyr Val Lys Ile Asn
                245                 250                 255

Lys Asn Lys Pro Ile Ile Tyr Ile Asp Ser Met Ser Tyr Leu Ile Phe
            260                 265                 270

Tyr Asn Leu Ile Lys Pro Tyr Leu Ile Pro Gln Met Met Tyr Lys Leu
        275                 280                 285

Pro Asn
    290
```

```
<210> SEQ ID NO 56
<211> LENGTH: 292
<212> TYPE: PRT
<213> ORGANISM: Artificial Sequence
<220> FEATURE:
<223> OTHER INFORMATION: AlcR(1-60) I-SceI -C-term del

<400> SEQUENCE: 56

Met Ala Asp Thr Arg Arg Gln Asn His Ser Cys Asp Pro Cys Arg
1               5                   10                  15

Lys Gly Lys Arg Arg Cys Asp Ala Pro Glu Asn Arg Asn Glu Ala Asn
            20                  25                  30

Glu Asn Gly Trp Val Ser Cys Ser Asn Cys Lys Arg Trp Asn Lys Asp
        35                  40                  45

Cys Thr Phe Asn Trp Leu Ser Ser Gln Arg Ser Lys Gly Ser Gly Ser
    50                  55                  60

Gly Ser Gly Lys Asn Ile Lys Lys Asn Gln Val Met Asn Leu Gly Pro
65                  70                  75                  80

Asn Ser Lys Leu Leu Lys Glu Tyr Lys Ser Gln Leu Ile Glu Leu Asn
                85                  90                  95

Ile Glu Gln Phe Glu Ala Gly Ile Gly Leu Ile Leu Gly Asp Ala Tyr
            100                 105                 110

Ile Arg Ser Arg Asp Glu Gly Lys Thr Tyr Cys Met Gln Phe Glu Trp
        115                 120                 125

Lys Asn Lys Ala Tyr Met Asp His Val Cys Leu Leu Tyr Asp Gln Trp
    130                 135                 140

Val Leu Ser Pro Pro His Lys Lys Glu Arg Val Asn His Leu Gly Asn
145                 150                 155                 160

Leu Val Ile Thr Trp Gly Ala Gln Thr Phe Lys His Gln Ala Phe Asn
                165                 170                 175

Lys Leu Ala Asn Leu Phe Ile Val Asn Asn Lys Lys Thr Ile Pro Asn
            180                 185                 190

Asn Leu Val Glu Asn Tyr Leu Thr Pro Met Ser Leu Ala Tyr Trp Phe
        195                 200                 205

Met Asp Asp Gly Gly Lys Trp Asp Tyr Asn Lys Asn Ser Thr Asn Lys
    210                 215                 220

Ser Ile Val Leu Asn Thr Gln Ser Phe Thr Phe Glu Glu Val Glu Tyr
225                 230                 235                 240

Leu Val Lys Gly Leu Arg Asn Lys Phe Gln Leu Asn Cys Tyr Val Lys
                245                 250                 255

Ile Asn Lys Asn Lys Pro Ile Ile Tyr Ile Asp Ser Met Ser Tyr Leu
            260                 265                 270

Ile Phe Tyr Asn Leu Ile Lys Pro Tyr Leu Ile Pro Gln Met Met Tyr
        275                 280                 285

Lys Leu Pro Asn
    290

<210> SEQ ID NO 57
<211> LENGTH: 50
<212> TYPE: PRT
<213> ORGANISM: Artificial Sequence
<220> FEATURE:
<223> OTHER INFORMATION: from accession number C8VDU4, Aspergillus
      nidulans

<400> SEQUENCE: 57

Thr Arg Lys Leu Arg Glu Ser Cys Ile Ser Cys Ser Arg Ser Lys Val
1               5                   10                  15
```

-continued

Lys Cys Asn Lys Glu Lys Pro Thr Cys Ser Arg Cys Val Arg Arg Gly
                20                  25                  30

Leu Pro Cys Glu Tyr Met Val Ser Arg Arg Thr Gly Arg Thr Arg Val
            35                  40                  45

Ile Gly
    50

<210> SEQ ID NO 58
<211> LENGTH: 50
<212> TYPE: PRT
<213> ORGANISM: Artificial Sequence
<220> FEATURE:
<223> OTHER INFORMATION: from accession number Q8TG25, Aspergillus
      ochraceoroseus

<400> SEQUENCE: 58

Thr Arg Lys Leu Arg Glu Ser Cys Met Arg Cys Ser Gly Ser Lys Val
1               5                   10                  15

Lys Cys Asn Lys Glu Lys Pro Thr Cys Ser Arg Cys Ala Arg Arg Gly
                20                  25                  30

Leu Ser Cys Glu Tyr Thr Ile Ser Arg Arg Thr Gly Arg Thr Arg Val
            35                  40                  45

Ile Gly
    50

<210> SEQ ID NO 59
<211> LENGTH: 45
<212> TYPE: PRT
<213> ORGANISM: Artificial Sequence
<220> FEATURE:
<223> OTHER INFORMATION: from accession number C8VAC4, Aspergillus
      nidulans

<400> SEQUENCE: 59

Arg Lys Leu Arg Asp Ser Cys Ile His Cys Ala Asn Ser Lys Val Lys
1               5                   10                  15

Cys Asn Lys Glu Lys Pro Ile Cys Gly Arg Cys Val Arg Arg Arg Leu
                20                  25                  30

Pro Cys Glu Tyr Lys Val Ser Arg Arg Thr Gly Arg Thr
            35                  40                  45

<210> SEQ ID NO 60
<211> LENGTH: 45
<212> TYPE: PRT
<213> ORGANISM: Artificial Sequence
<220> FEATURE:
<223> OTHER INFORMATION: from accession number B2B6C3, Podospora
      anserina

<400> SEQUENCE: 60

Arg Lys Leu Arg Asp Ser Cys Thr Glu Cys Ala Ser Ser Lys Val Lys
1               5                   10                  15

Cys Gly Lys Glu Lys Pro Thr Cys Ser Arg Cys Val Arg Arg Gly Ala
                20                  25                  30

Lys Cys Thr Tyr Met Ala Ser Arg Arg Thr Gly Arg Thr
            35                  40                  45

<210> SEQ ID NO 61
<211> LENGTH: 44
<212> TYPE: PRT
<213> ORGANISM: Artificial Sequence
<220> FEATURE:

<223> OTHER INFORMATION: from accession number Q8TG77, Aspergillus
      nomius

<400> SEQUENCE: 61

Arg Lys Leu Arg Asp Ser Cys Thr Ser Cys Ala Ser Ser Lys Val Arg
1               5                   10                  15

Cys Thr Lys Glu Lys Pro Ala Cys Ala Arg Cys Ile Glu Arg Gly Leu
            20                  25                  30

Ala Cys Gln Tyr Met Val Ser Arg Arg Met Gly Arg
        35                  40

<210> SEQ ID NO 62
<211> LENGTH: 44
<212> TYPE: PRT
<213> ORGANISM: Artificial Sequence
<220> FEATURE:
<223> OTHER INFORMATION: from accession number Q2NNI0, Aspergillus
      parasiticus

<400> SEQUENCE: 62

Arg Lys Leu Arg Asp Ser Cys Thr Ser Cys Ala Ser Ser Lys Val Arg
1               5                   10                  15

Cys Thr Lys Glu Lys Pro Ser Cys Ala Arg Cys Ile Glu Arg Gly Leu
            20                  25                  30

Ala Cys Gln Tyr Met Val Ser Lys Arg Met Gly Arg
        35                  40

<210> SEQ ID NO 63
<211> LENGTH: 44
<212> TYPE: PRT
<213> ORGANISM: Artificial Sequence
<220> FEATURE:
<223> OTHER INFORMATION: from accession number 8TG76 Aspergillus
      pseudotamarii

<400> SEQUENCE: 63

Arg Lys Leu Arg Asp Ser Cys Thr Ser Cys Ala Ser Ser Lys Val Arg
1               5                   10                  15

Cys Thr Lys Glu Lys Pro Ala Cys Ala Arg Cys Ile Glu Arg Gly Leu
            20                  25                  30

Ala Cys Gln Tyr Met Val Ser Lys Arg Met Gly Arg
        35                  40

<210> SEQ ID NO 64
<211> LENGTH: 44
<212> TYPE: PRT
<213> ORGANISM: Artificial Sequence
<220> FEATURE:
<223> OTHER INFORMATION: from accession number Q8TG74, Aspergillus
      flavus

<400> SEQUENCE: 64

Arg Lys Leu Arg Asp Ser Cys Thr Ser Cys Ala Ser Ser Lys Val Arg
1               5                   10                  15

Cys Thr Lys Glu Lys Pro Ala Cys Ala Arg Cys Ile Glu Arg Gly Leu
            20                  25                  30

Ala Cys Gln Tyr Met Val Ser Lys Arg Met Gly Arg
        35                  40

<210> SEQ ID NO 65
<211> LENGTH: 44
<212> TYPE: PRT
<213> ORGANISM: Artificial Sequence

```
<220> FEATURE:
<223> OTHER INFORMATION: from accession number Q8TG75, Aspergillus
      pseudotamarii

<400> SEQUENCE: 65

Arg Lys Phe Arg Asp Ser Cys Thr Ser Cys Ala Ser Ser Lys Val Arg
1               5                   10                  15

Cys Thr Lys Glu Lys Pro Ala Cys Ala Arg Cys Ile Glu Arg Gly Leu
            20                  25                  30

Ala Cys Gln Tyr Met Val Ser Lys Arg Met Gly Arg
        35                  40

<210> SEQ ID NO 66
<211> LENGTH: 47
<212> TYPE: PRT
<213> ORGANISM: Artificial Sequence
<220> FEATURE:
<223> OTHER INFORMATION: from accession number B8MBB2, Talaromyces
      stipitatus

<400> SEQUENCE: 66

Thr Ser Lys Ile Arg Asp Ser Cys His Ser Cys Ala Ile Ser Lys Val
1               5                   10                  15

Arg Cys Pro Lys Glu Lys Pro Thr Cys Ala Arg Cys Met Lys Arg Gly
            20                  25                  30

Val Val Cys Glu Tyr Phe Val Thr Lys Arg Pro Gly Arg Lys Arg
        35                  40                  45

<210> SEQ ID NO 67
<211> LENGTH: 44
<212> TYPE: PRT
<213> ORGANISM: Artificial Sequence
<220> FEATURE:
<223> OTHER INFORMATION: from accession number B2VZ88, Pyrenophora
      tritici-repentis

<400> SEQUENCE: 67

Gln Lys Leu Arg Asp Cys Cys Gln Ser Cys Ala Arg Ser Lys Val Lys
1               5                   10                  15

Cys Thr Lys Glu Lys Pro Ser Cys Ser Arg Cys Glu Lys Gly Ile
            20                  25                  30

Pro Cys Arg Tyr Leu Gln Ser Lys Arg Pro Gly Arg
        35                  40

<210> SEQ ID NO 68
<211> LENGTH: 45
<212> TYPE: PRT
<213> ORGANISM: Artificial Sequence
<220> FEATURE:
<223> OTHER INFORMATION: from accession number A0ST46, Cercospora
      nicotianae

<400> SEQUENCE: 68

Lys Ile Arg Glu Ser Cys Thr His Cys Ser Ser Gln Lys Ile Arg Cys
1               5                   10                  15

Thr Lys Glu Arg Pro Ala Cys Ala Arg Cys Val Asn Lys Gly Leu Leu
            20                  25                  30

Cys Gln Tyr Asn Ile Ser Arg Arg Thr Gly Thr Arg Arg
        35                  40                  45

<210> SEQ ID NO 69
<211> LENGTH: 46
<212> TYPE: PRT
```

<213> ORGANISM: Artificial Sequence
<220> FEATURE:
<223> OTHER INFORMATION: from accession number Q0CCY1, Aspergillus terreus

<400> SEQUENCE: 69

Lys Leu Arg Gly Ser Cys His Ala Cys Ala Ser Lys Val Arg Cys
1               5                   10                  15

Ser Lys Glu Lys Pro Thr Cys Ser Arg Cys Ser Lys Arg Gly Thr Thr
            20                  25                  30

Cys Glu Tyr Leu Ile Thr Lys Arg Pro Gly Arg Lys Gln Leu
            35                  40                  45

<210> SEQ ID NO 70
<211> LENGTH: 60
<212> TYPE: PRT
<213> ORGANISM: Artificial Sequence
<220> FEATURE:
<223> OTHER INFORMATION: from accession number C8VL74, Aspergillus nidulans

<400> SEQUENCE: 70

Met Ala Asp Thr Arg Arg Gln Asn His Ser Cys Asp Pro Cys Arg
1               5                   10                  15

Lys Gly Lys Arg Arg Cys Asp Ala Pro Glu Asn Arg Asn Glu Ala Asn
            20                  25                  30

Glu Asn Gly Trp Val Ser Cys Asn Cys Lys Arg Trp Asn Lys Asp
            35                  40                  45

Cys Thr Phe Asn Trp Leu Ser Ser Gln Arg Ser Lys
            50                  55                  60

<210> SEQ ID NO 71
<211> LENGTH: 70
<212> TYPE: PRT
<213> ORGANISM: Artificial Sequence
<220> FEATURE:
<223> OTHER INFORMATION: from accession number A1CA83, Aspergillus clavatus

<400> SEQUENCE: 71

Met Asp Thr Gln Arg Arg Arg Gln His His Ser Cys Asp Pro Cys Arg
1               5                   10                  15

Lys Gly Lys Arg Ala Cys Asp Ala Pro Ala Arg Arg Asp Arg Asp
            20                  25                  30

His Thr Gly Glu Val Ser Ser Ser Asn Gln Ala Ser Ser Asp Thr Ile
            35                  40                  45

Thr Cys Ser Asn Cys Arg Lys Tyr Asn Arg Glu Cys Thr Phe Asn Trp
            50                  55                  60

Leu Ser Glu Asn Arg Ala
65                  70

<210> SEQ ID NO 72
<211> LENGTH: 69
<212> TYPE: PRT
<213> ORGANISM: Artificial Sequence
<220> FEATURE:
<223> OTHER INFORMATION: from accession number Q4WU81, Aspergillus fumigatus

<400> SEQUENCE: 72

Met Glu Ala His Arg Arg Arg Gln His His Ser Cys Asp Pro Cys Arg
1               5                   10                  15

-continued

Lys Gly Lys Arg Ala Cys Asp Ala Pro Ala Arg Arg Asp Arg His Ala
            20                  25                  30

Asp Ala Gly Ser Arg Arg Val Leu Ala Glu Ser Asn Leu Asn Ile Pro
        35                  40                  45

Cys Ser Asn Cys Arg Lys Tyr Asn Arg Glu Cys Thr Phe Asn Trp Leu
50                  55                  60

Val Glu Asn Arg Ala
65

<210> SEQ ID NO 73
<211> LENGTH: 82
<212> TYPE: PRT
<213> ORGANISM: Artificial Sequence
<220> FEATURE:
<223> OTHER INFORMATION: from accession number B0Y3Q7, Aspergillus
      fumigatus

<400> SEQUENCE: 73

Met Glu Pro His Arg Arg Gln His His Ser Cys Asp Pro Cys Arg
1               5                   10                  15

Lys Gly Lys Arg Ala Cys Asp Ala Pro Ala Arg Arg Asp Arg Gln Gly
            20                  25                  30

Ala Thr Ser Ser Val Ser Gly Ala Ser Ala Ala Arg Gln Glu Ala Gly
        35                  40                  45

Asn Arg Arg Val Leu Thr Glu Ser Asn Leu Asn Ile Pro Cys Ser Asn
50                  55                  60

Cys Arg Lys Tyr Asn Arg Glu Cys Thr Phe Asn Trp Leu Val Glu Asn
65                  70                  75                  80

Arg Ala

<210> SEQ ID NO 74
<211> LENGTH: 82
<212> TYPE: PRT
<213> ORGANISM: Artificial Sequence
<220> FEATURE:
<223> OTHER INFORMATION: from accession number A1DF77, Neosartorya
      fischeri

<400> SEQUENCE: 74

Met Glu Pro His Arg Arg Gln His His Ser Cys Asp Pro Cys Arg
1               5                   10                  15

Lys Gly Lys Arg Ala Cys Asp Ala Pro Ala Arg Arg Asp Arg Gln Gly
            20                  25                  30

Ala Thr Ser Ser Val Ser Gly Ala Ser Ala Ala Arg Gln Glu Ala Gly
        35                  40                  45

Asn Arg Arg Val Leu Thr Glu Ser Asn Leu Asn Ile Pro Cys Ser Asn
50                  55                  60

Cys Arg Lys Tyr Asn Arg Glu Cys Thr Phe Asn Trp Leu Val Glu Asn
65                  70                  75                  80

Arg Ala

<210> SEQ ID NO 75
<211> LENGTH: 50
<212> TYPE: PRT
<213> ORGANISM: Artificial Sequence
<220> FEATURE:
<223> OTHER INFORMATION: from accession number B6HNY2, Penicillium
      chrysogenum

<400> SEQUENCE: 75

```
Met Glu Asp Ser Arg Arg Gln Leu His Ser Cys Asp Pro Cys Arg
1               5                  10                  15

Lys Gly Lys Arg Gly Cys Asp Ala Pro Ser Thr Phe Thr Cys Ser
            20                  25                  30

Asn Cys Thr Arg Trp Lys Lys Glu Cys Thr Phe Asn Trp Ile Ser Ser
        35                  40                  45

Lys Arg
    50

<210> SEQ ID NO 76
<211> LENGTH: 61
<212> TYPE: PRT
<213> ORGANISM: Artificial Sequence
<220> FEATURE:
<223> OTHER INFORMATION: from accession number Q2UDT6, Aspergillus
      oryzae

<400> SEQUENCE: 76

Arg Arg Arg Gln His Arg Ser Cys Asp Gln Cys Arg Lys Gly Lys Arg
1               5                  10                  15

Ala Cys Asp Ala Leu Leu Ala Asp Glu Leu Glu Arg Ser Ser Asn Thr
            20                  25                  30

Ala Ala Arg Gln Ala Tyr Asn His Ser Cys Ser Asn Cys Arg Lys Tyr
        35                  40                  45

Lys Arg Lys Cys Thr Phe Asp Trp Leu Leu Ser His Lys
    50                  55                  60

<210> SEQ ID NO 77
<211> LENGTH: 54
<212> TYPE: PRT
<213> ORGANISM: Artificial Sequence
<220> FEATURE:
<223> OTHER INFORMATION: from accession number Q4P8J5, Ustilago maydis

<400> SEQUENCE: 77

Asp Ser Arg Arg Arg Gln Tyr Arg Ser Cys Asp Arg Cys Arg Val Gly
1               5                  10                  15

Lys Arg Ala Cys Asn Ala Glu Tyr Asp Ser Val Ala Glu Ala Ile Asn
            20                  25                  30

Asn Lys Val Ala Cys Ser Asn Cys Gln Lys Lys Gly Lys Thr Cys Ser
        35                  40                  45

Phe Gln Tyr Val Leu Ser
    50

<210> SEQ ID NO 78
<211> LENGTH: 53
<212> TYPE: PRT
<213> ORGANISM: Artificial Sequence
<220> FEATURE:
<223> OTHER INFORMATION: from accession number B8NDE7, Aspergillus
      flavus

<400> SEQUENCE: 78

Arg Arg Gln Asn His Ser Cys Asp Pro Cys Arg Leu Ala Lys Arg Gly
1               5                  10                  15

Cys Asp Leu Pro Arg Gly Val Ala Ile Cys Gly Asp Lys Pro Thr Val
            20                  25                  30

Ala Cys Thr Met Cys Ser Leu Arg Ser Met Glu Cys Thr Val Ala Trp
        35                  40                  45

Leu Ala Ser Arg Lys
    50
```

-continued

```
<210> SEQ ID NO 79
<211> LENGTH: 58
<212> TYPE: PRT
<213> ORGANISM: Artificial Sequence
<220> FEATURE:
<223> OTHER INFORMATION: from accession number Q0CCZ6, Aspergillus
      terreus

<400> SEQUENCE: 79
```

Arg Arg Gln Asn His Ser Cys Asp Gln Cys Arg Arg Ser Lys Arg Ala
1               5                   10                  15

Cys Asp Ala Gln Trp Pro Ser Gln Thr Arg Arg Ala Ser Phe Asp Asn
            20                  25                  30

Val Asp Ser Arg Arg Ser Pro Cys Ser Tyr Cys Ala Lys Thr Asn Lys
        35                  40                  45

Arg Cys Thr Met Glu Trp Ala Gln Ser Lys
    50                  55

```
<210> SEQ ID NO 80
<211> LENGTH: 77
<212> TYPE: PRT
<213> ORGANISM: Artificial Sequence
<220> FEATURE:
<223> OTHER INFORMATION: from accession number C7Z9E1, Nectria
      haematococca

<400> SEQUENCE: 80
```

Arg Arg Gln Asn Arg Ser Cys Asp Gln Cys Arg Lys Ala Lys Arg Ala
1               5                   10                  15

Cys Asp Ala Pro Ser Leu Trp Asp Ile Gln Arg Asn Ser Glu Arg Leu
            20                  25                  30

Arg Asn Gly Ala Asp Gly Ala Asn Gly Val Ser Leu Ala Glu Glu His
        35                  40                  45

Leu Asp Glu Ile Asp Ser Arg Ala Leu Arg Cys Ser Tyr Cys Leu Arg
    50                  55                  60

Thr Arg Lys Gln Cys Thr Phe His Trp Val Arg Ala Gln
65                  70                  75

```
<210> SEQ ID NO 81
<211> LENGTH: 60
<212> TYPE: PRT
<213> ORGANISM: Artificial Sequence
<220> FEATURE:
<223> OTHER INFORMATION: from accession number A4R044, Magnaporthe
      grisea

<400> SEQUENCE: 81
```

Arg Gln His Tyr Ser Cys Asp Gln Cys Arg Arg Ser Lys Arg Ala Cys
1               5                   10                  15

Asp Ala Pro Gln Leu Glu Val Pro Ala His Leu Asn Gly His Ala Ala
            20                  25                  30

Ser Ile Leu Ser Gly Asn Leu Pro Ala Pro Glu Thr Lys Gln Cys Ser
        35                  40                  45

Tyr Cys Arg Arg Thr Gly Lys Thr Cys Thr Met Asn
    50                  55                  60

```
<210> SEQ ID NO 82
<211> LENGTH: 53
<212> TYPE: PRT
<213> ORGANISM: Artificial Sequence
<220> FEATURE:
```

<223> OTHER INFORMATION: from accession number Q2U8Y1, Aspergillus
      oryzae

<400> SEQUENCE: 82

Arg Arg Gln Asn His Ser Cys Asp Pro Cys Cys Leu Ala Lys Arg Gly
1               5                   10                  15

Cys Asp Leu Pro Arg Gly Val Ala Ile Cys Gly Asp Lys Pro Thr Val
            20                  25                  30

Ala Cys Thr Met Cys Ser Leu Arg Ser Met Glu Cys Thr Val Ala Trp
        35                  40                  45

Leu Ala Ser Arg Lys
    50

<210> SEQ ID NO 83
<211> LENGTH: 53
<212> TYPE: PRT
<213> ORGANISM: Artificial Sequence
<220> FEATURE:
<223> OTHER INFORMATION: from accession number B6HLG1, Penicillium
      chrysogenum

<400> SEQUENCE: 83

Arg Arg Gln Asn His Ser Cys Asp Gln Cys Arg Ser Ser Lys Arg Ala
1               5                   10                  15

Cys Ser Leu Pro Leu Arg Val Gly Ile Ser Gly Gln Lys Pro Ser Thr
            20                  25                  30

Pro Cys Ala Thr Cys Asn Ala Arg Gly Leu Glu Cys Thr Val Ala Trp
        35                  40                  45

Leu Ala Ser Lys Lys
    50

<210> SEQ ID NO 84
<211> LENGTH: 60
<212> TYPE: PRT
<213> ORGANISM: Artificial Sequence
<220> FEATURE:
<223> OTHER INFORMATION: from accession number Q2UDT6, Aspergillus
      oryzae

<400> SEQUENCE: 84

Arg Arg Arg Gln His Arg Ser Cys Asp Gln Cys Arg Lys Gly Lys Arg
1               5                   10                  15

Ala Cys Asp Ala Leu Leu Ala Asp Glu Leu Glu Arg Ser Ser Asn Thr
            20                  25                  30

Ala Ala Arg Gln Ala Tyr Asn His Ser Cys Ser Asn Cys Arg Lys Tyr
        35                  40                  45

Lys Arg Lys Cys Thr Phe Asp Trp Leu Leu Ser His
    50                  55                  60

<210> SEQ ID NO 85
<211> LENGTH: 53
<212> TYPE: PRT
<213> ORGANISM: Artificial Sequence
<220> FEATURE:
<223> OTHER INFORMATION: from accession number B6HLG1, Penicillium
      chrysogenum

<400> SEQUENCE: 85

Arg Arg Gln Asn His Ser Cys Asp Gln Cys Arg Ser Ser Lys Arg Ala
1               5                   10                  15

Cys Ser Leu Pro Leu Arg Val Gly Ile Ser Gly Gln Lys Pro Ser Thr
            20                  25                  30

-continued

Pro Cys Ala Thr Cys Asn Ala Arg Gly Leu Glu Cys Thr Val Ala Trp
        35                  40                  45

Leu Ala Ser Lys Lys
    50

<210> SEQ ID NO 86
<211> LENGTH: 44
<212> TYPE: PRT
<213> ORGANISM: Artificial Sequence
<220> FEATURE:
<223> OTHER INFORMATION: from accession number B6JZK8,
      Schizosaccharomyces spec.

<400> SEQUENCE: 86

Arg Arg Arg Val Thr Arg Ala Cys Asp Ser Cys Arg Lys Lys Lys Ile
1               5                   10                  15

Lys Cys Asp Gly Thr Arg Pro Cys Arg Asn Cys Lys Tyr Ser Asn Thr
            20                  25                  30

Glu Cys Thr Phe Gln Phe Pro Ser Ser Arg Lys Ser
        35                  40

<210> SEQ ID NO 87
<211> LENGTH: 48
<212> TYPE: PRT
<213> ORGANISM: Artificial Sequence
<220> FEATURE:
<223> OTHER INFORMATION: from accession number Q2GSZ4, Chaetomium
      globosum

<400> SEQUENCE: 87

Arg Ser Lys Val Ser Arg Ala Cys Asp Glu Cys Arg Arg Lys Lys Ile
1               5                   10                  15

Lys Cys Asp Ala Gln Ser Glu Ala Asn Glu Ala Pro Cys Ser Asn Cys
            20                  25                  30

Arg Arg Ser Asn Ala Gln Cys Leu Phe Ser Arg Val Pro Gln Lys Arg
        35                  40                  45

<210> SEQ ID NO 88
<211> LENGTH: 48
<212> TYPE: PRT
<213> ORGANISM: Artificial Sequence
<220> FEATURE:
<223> OTHER INFORMATION: from accession number C1GS25, Paracoccidioides
      spec.

<400> SEQUENCE: 88

Arg Ser Lys Val Ser Arg Ala Cys Asp Glu Cys Arg Arg Lys Lys Ile
1               5                   10                  15

Arg Cys Asp Ala Thr Ser Glu Ala Gly Val Glu Thr Cys Ser Asn Cys
            20                  25                  30

Arg Arg Thr Asn Ala Thr Cys Glu Phe Ser Arg Val Pro Met Lys Arg
        35                  40                  45

<210> SEQ ID NO 89
<211> LENGTH: 47
<212> TYPE: PRT
<213> ORGANISM: Artificial Sequence
<220> FEATURE:
<223> OTHER INFORMATION: from accession number C5JNJ4, Ajellomyces spec.

<400> SEQUENCE: 89

Arg Ser Lys Val Ser Arg Ala Cys Asp Glu Cys Arg Arg Lys Lys Val
1               5                   10                  15

Arg Cys Asp Ala Thr Ser Glu Ala Gly Val Glu Thr Cys Ser Asn Cys
            20                  25                  30

Arg Arg Thr Asn Ala Thr Cys Glu Phe Ser Arg Val Pro Met Lys
            35                  40                  45

<210> SEQ ID NO 90
<211> LENGTH: 71
<212> TYPE: PRT
<213> ORGANISM: Artificial Sequence
<220> FEATURE:
<223> OTHER INFORMATION: from accession number B6QQE4, Penicillium
      marneffei

<400> SEQUENCE: 90

Lys Arg Lys Gln Phe His Ser Cys Asp Arg Cys Arg Gln Ser Arg Arg
1               5                   10                  15

Ala Cys Asp Ala Ala Lys Arg Gly Ile Asn Pro Phe Ser Ala Thr Asn
            20                  25                  30

Gln Gln Leu Pro Val Leu Leu Pro Pro Gly Gly Ser Ser Gly Glu Ala
            35                  40                  45

Leu Pro Pro Thr Leu Ala Cys Ser Leu Cys Glu Lys Ala Asn Lys Lys
        50                  55                  60

Cys Ser Phe Thr Trp Leu Thr
65                  70

<210> SEQ ID NO 91
<211> LENGTH: 47
<212> TYPE: PRT
<213> ORGANISM: Artificial Sequence
<220> FEATURE:
<223> OTHER INFORMATION: from accession number Q0UKN2, Phaeosphaeria
      nodorum

<400> SEQUENCE: 91

Arg Gln Arg Thr Ala Ile Ala Cys Arg Tyr Cys Arg Arg Lys Ile
1               5                   10                  15

Arg Cys Ser Gly Phe Glu Ala Thr Glu Asp Gly Arg Cys Ser Asn Cys
            20                  25                  30

Met Arg Phe Asn Gln Asp Cys Ile Phe Thr Pro Val Ser Ala Gln
            35                  40                  45

<210> SEQ ID NO 92
<211> LENGTH: 69
<212> TYPE: PRT
<213> ORGANISM: Artificial Sequence
<220> FEATURE:
<223> OTHER INFORMATION: from accession number C7ZD87, Nectria
      haematococca

<400> SEQUENCE: 92

Lys Arg Gln Thr Lys Leu Ala Cys Asp Gln Cys Arg Arg Ser Lys Arg
1               5                   10                  15

Ala Cys Asp Ala Pro Pro Leu Glu Leu Pro Asp His Asp Ser Phe Ser
            20                  25                  30

Asn Gly Thr Ile Val Leu Gly Lys Arg Pro Ala Ser Glu Thr Glu Leu
            35                  40                  45

Gln Pro Cys Ser Tyr Cys Thr Lys Thr Lys Gln Cys Thr Met Asn
        50                  55                  60

Trp Ala Trp Ser Gln
65

<210> SEQ ID NO 93
<211> LENGTH: 42
<212> TYPE: PRT
<213> ORGANISM: Artificial Sequence
<220> FEATURE:
<223> OTHER INFORMATION: from accession number B6HCV2, Penicillium
      chrysogenum

<400> SEQUENCE: 93

Arg Lys Arg Ser Arg Val Ala Cys Glu Pro Cys Arg Glu Arg Lys Arg
1               5                   10                  15

Lys Cys Asp Gly Ala Glu Pro Cys Ser Thr Cys Thr Gln Trp Gly Tyr
            20                  25                  30

Asp Cys His Tyr Gly Arg Arg Pro Arg Gln
        35                  40

<210> SEQ ID NO 94
<211> LENGTH: 48
<212> TYPE: PRT
<213> ORGANISM: Artificial Sequence
<220> FEATURE:
<223> OTHER INFORMATION: from accession number O59744,
      Schizosaccharomyces pombe

<400> SEQUENCE: 94

Val Ala Thr Arg Arg Arg Arg Val Thr Arg Ala Cys Asp Met Cys Arg
1               5                   10                  15

Arg Lys Lys Ile Lys Cys Asp Gly Leu Arg Pro Cys Lys Asn Cys Lys
            20                  25                  30

Ala Gly Lys Leu Glu Cys Thr Tyr His Met Pro Ser Ser Arg Lys Ser
        35                  40                  45

<210> SEQ ID NO 95
<211> LENGTH: 70
<212> TYPE: PRT
<213> ORGANISM: Artificial Sequence
<220> FEATURE:
<223> OTHER INFORMATION: from accession number P0CE41, Saccharomyces
      cerevisiae

<400> SEQUENCE: 95

Ser Pro Pro Leu His Met Ser Ser Asp Ser Ser Lys Ile Lys Arg Lys
1               5                   10                  15

Arg Asn Arg Ile Pro Leu Ser Cys Thr Ile Cys Arg Lys Arg Lys Val
            20                  25                  30

Lys Cys Asp Lys Leu Arg Pro His Cys Gln Gln Cys Thr Lys Thr Gly
        35                  40                  45

Val Ala His Leu Cys His Tyr Met Glu Gln Thr Trp Ala Glu Glu Ala
    50                  55                  60

Glu Lys Glu Leu Leu Lys
65              70

<210> SEQ ID NO 96
<211> LENGTH: 60
<212> TYPE: PRT
<213> ORGANISM: Artificial Sequence
<220> FEATURE:
<223> OTHER INFORMATION: from accession number A7TQE5, Vanderwaltozyma
      polyspora

<400> SEQUENCE: 96

Ser Ala Ser Asn Lys Val Lys Arg Lys Arg Asn Arg Ile Pro Leu Ser
1               5                   10                  15

```
Cys Thr Ile Cys Arg Lys Arg Lys Val Lys Cys Asp Lys Thr Arg Pro
            20                  25                  30

His Cys Asn Gln Cys Thr Lys Thr Gly Val Ala His Leu Cys His Tyr
        35                  40                  45

Met Glu Gln Ser Trp Ala Glu Glu Ala Glu Lys Glu
 50                  55                  60
```

<210> SEQ ID NO 97
<211> LENGTH: 60
<212> TYPE: PRT
<213> ORGANISM: Artificial Sequence
<220> FEATURE:
<223> OTHER INFORMATION: from accession number C5E399, Lachancea
      thermotolerans

<400> SEQUENCE: 97

```
Ala Gln Met Lys Arg Lys Arg Asn Arg Val Pro Leu Ser Cys Thr Ile
 1               5                  10                  15

Cys Arg Lys Arg Lys Val Lys Cys Asp Lys Thr Arg Pro His Cys Gln
            20                  25                  30

Gln Cys Ser Lys Thr Gly Val Ala His Leu Cys His Tyr Met Glu Gln
        35                  40                  45

Thr Trp Ala Glu Glu Ala Glu Lys Glu Leu Ser Lys
 50                  55                  60
```

<210> SEQ ID NO 98
<211> LENGTH: 65
<212> TYPE: PRT
<213> ORGANISM: Artificial Sequence
<220> FEATURE:
<223> OTHER INFORMATION: from accession number Q754F3, Ashbya gossypii

<400> SEQUENCE: 98

```
Met Ser Ser Pro Thr Ala Ser Ser Lys Arg Lys Arg Asn Arg Val Pro
 1               5                  10                  15

Leu Ser Cys Thr Ile Cys Arg Lys Arg Lys Val Lys Cys Asp Lys Thr
            20                  25                  30

Arg Pro His Cys Asn Gln Cys Thr Lys Thr Gly Val Ala His Leu Cys
        35                  40                  45

His Tyr Met Glu Gln Thr Trp Ala Gly Glu Ala Glu Lys Glu Leu Ser
 50                  55                  60

Lys
 65
```

<210> SEQ ID NO 99
<211> LENGTH: 61
<212> TYPE: PRT
<213> ORGANISM: Artificial Sequence
<220> FEATURE:
<223> OTHER INFORMATION: from accession number C5E4F0, Zygosaccharomyces
      rouxii

<400> SEQUENCE: 99

```
Ala Asn Lys Met Lys Arg Lys Arg Asn Arg Ile Pro Leu Ser Cys Thr
 1               5                  10                  15

Ile Cys Arg Lys Arg Lys Val Lys Cys Asp Lys Thr Arg Pro Asn Cys
            20                  25                  30

Glu Gln Cys Ser Lys Thr Gly Val Ala His Leu Cys His Tyr Met Glu
        35                  40                  45

Gln Thr Trp Ala Glu Glu Ala Glu Lys Glu Ile Ser Lys
```

-continued

```
               50                  55                  60
```

<210> SEQ ID NO 100
<211> LENGTH: 57
<212> TYPE: PRT
<213> ORGANISM: Artificial Sequence
<220> FEATURE:
<223> OTHER INFORMATION: from accession number Q6EWQ5, Kluyveromyces
      lactis

<400> SEQUENCE: 100

```
Lys Arg Lys Arg Asn Arg Val Pro Leu Ser Cys Thr Ile Cys Arg Lys
1               5                   10                  15

Arg Lys Val Lys Cys Asp Lys Gly Arg Pro Gln Cys Gln Gln Cys Val
            20                  25                  30

Lys Thr Gly Val Gly His Leu Cys His Tyr Met Glu Gln Thr Trp Ala
        35                  40                  45

Glu Glu Ala Glu Lys Glu Leu Ser Lys
    50                  55
```

<210> SEQ ID NO 101
<211> LENGTH: 59
<212> TYPE: PRT
<213> ORGANISM: Artificial Sequence
<220> FEATURE:
<223> OTHER INFORMATION: from accession number Q6FMR4, Candida glabrata

<400> SEQUENCE: 101

```
Lys Val Lys Arg Lys Arg Asn Arg Val Pro Leu Ser Cys Thr Ile Cys
1               5                   10                  15

Arg Arg Arg Lys Val Lys Cys Asp Lys Ser Arg Pro Asn Cys Thr Gln
            20                  25                  30

Cys Val Lys Thr Gly Val Ala His Leu Cys His Tyr Met Glu Gln Ala
        35                  40                  45

Trp Ala Glu Glu Ala Glu Lys Glu Ile Ser Lys
    50                  55
```

<210> SEQ ID NO 102
<211> LENGTH: 57
<212> TYPE: PRT
<213> ORGANISM: Artificial Sequence
<220> FEATURE:
<223> OTHER INFORMATION: from accession number Q6FXJ5, Candida glabrata

<400> SEQUENCE: 102

```
Lys Lys Lys Arg Asn Arg Ile Pro Leu Ser Cys Thr Ile Cys Arg Lys
1               5                   10                  15

Arg Lys Val Lys Cys Asp Lys Thr Arg Pro His Cys Asn Gln Cys Thr
            20                  25                  30

Lys Thr Gly Val Ala His Leu Cys His Tyr Met Glu Gln Asn Trp Ala
        35                  40                  45

Gln Asp Ala Lys Lys Glu Ile Ser Lys
    50                  55
```

<210> SEQ ID NO 103
<211> LENGTH: 57
<212> TYPE: PRT
<213> ORGANISM: Artificial Sequence
<220> FEATURE:
<223> OTHER INFORMATION: from accession number A7TJF2, Vanderwaltozyma
      polyspora

<400> SEQUENCE: 103

```
Lys Val Lys Arg Lys Asn Arg Ile Pro Leu Ser Cys Thr Ile Cys
1               5                   10                  15

Arg Lys Arg Lys Val Lys Cys Asp Lys Thr His Pro His Cys Asn Gln
            20                  25                  30

Cys Ile Lys Thr Gly Val His His Leu Cys His Tyr Met Glu Gln Ser
        35                  40                  45

Trp Ala Gly Glu Val Gly Lys Glu Met
    50                  55

<210> SEQ ID NO 104
<211> LENGTH: 55
<212> TYPE: PRT
<213> ORGANISM: Artificial Sequence
<220> FEATURE:
<223> OTHER INFORMATION: from accession number C4R144, Pichia pastoris

<400> SEQUENCE: 104

Ser Glu Arg Ile Lys Leu Lys Arg Lys Asn Arg Val Pro Val Ser
1               5                   10                  15

Cys Thr Ile Cys Arg Arg Arg Lys Val Lys Cys Asp Lys Lys Lys Pro
            20                  25                  30

Ile Cys Thr Asn Cys Lys Lys Asn Gly Val Pro His Leu Cys Tyr Tyr
        35                  40                  45

Leu Glu Pro Ser Trp Ala Lys
    50                  55

<210> SEQ ID NO 105
<211> LENGTH: 51
<212> TYPE: PRT
<213> ORGANISM: Artificial Sequence
<220> FEATURE:
<223> OTHER INFORMATION: from accession number A3LR46, Pichia stipitis

<400> SEQUENCE: 105

Lys Arg Gln Arg Gln Arg Asn Arg Val Pro Val Ser Cys Leu Asn Cys
1               5                   10                  15

Lys Lys Arg Lys Val Lys Cys Asp Lys Gly Lys Pro Ser Cys Ser Gly
            20                  25                  30

Cys Ile Lys Asn Gly Val Pro His Leu Cys Glu Tyr Leu Glu Pro Val
        35                  40                  45

Trp Ser Lys
    50

<210> SEQ ID NO 106
<211> LENGTH: 48
<212> TYPE: PRT
<213> ORGANISM: Artificial Sequence
<220> FEATURE:
<223> OTHER INFORMATION: from accession number Q6BPI3, Debaryomyces
      hansenii

<400> SEQUENCE: 106

Gln Lys Gln Arg Asn Arg Val Pro Val Ser Cys Leu Ile Cys Lys Arg
1               5                   10                  15

Arg Lys Val Lys Cys Asp Lys Ala Lys Pro Ala Cys Gly Gly Cys Val
            20                  25                  30

Lys Asn Gly Val Pro His Leu Cys Glu Tyr Val Glu Pro Ala Trp Ser
        35                  40                  45

<210> SEQ ID NO 107
```

```
<211> LENGTH: 58
<212> TYPE: PRT
<213> ORGANISM: Artificial Sequence
<220> FEATURE:
<223> OTHER INFORMATION: from accession number C5M8G2, Candida
      tropicalis

<400> SEQUENCE: 107
```

Ser Lys Val Ser Lys Pro Lys Arg Gln Arg Ser Arg Val Pro Val Ser
1               5                   10                  15

Cys Leu Ala Cys Lys Lys Arg Lys Val Lys Cys Asp Lys Gly Lys Pro
            20                  25                  30

Ala Cys Gly Gly Cys Ile Arg Asn Gly Val Gly His Leu Cys Glu Tyr
        35                  40                  45

Ile Tyr Pro His Trp Val Asp Lys Gly Gln
    50                  55

```
<210> SEQ ID NO 108
<211> LENGTH: 50
<212> TYPE: PRT
<213> ORGANISM: Artificial Sequence
<220> FEATURE:
<223> OTHER INFORMATION: from accession number C8ZE58, Saccharomyces
      cerevisiae

<400> SEQUENCE: 108
```

Arg Lys Arg Lys Phe Ala Cys Val Glu Cys Arg Gln Gln Lys Ser Lys
1               5                   10                  15

Cys Asp Ala His Glu Arg Ala Pro Glu Pro Cys Thr Lys Cys Ala Lys
            20                  25                  30

Lys Asn Val Pro Cys Ile Leu Lys Arg Asp Phe Arg Arg Thr Tyr Lys
        35                  40                  45

Arg Ala
    50

```
<210> SEQ ID NO 109
<211> LENGTH: 50
<212> TYPE: PRT
<213> ORGANISM: Artificial Sequence
<220> FEATURE:
<223> OTHER INFORMATION: from accession number C5DUV2, Zygosaccharomyces
      rouxii

<400> SEQUENCE: 109
```

Arg Ser Arg Lys Phe Ala Cys Val Glu Cys Arg Gln Gln Lys Ser Lys
1               5                   10                  15

Cys Asp Ala His Asp Arg Ala Pro Glu Pro Cys Thr Lys Cys Gln Lys
            20                  25                  30

Lys Gly Val Pro Cys Val Leu Lys Asp Phe Arg Arg Thr Tyr Lys
        35                  40                  45

Arg Ala
    50

```
<210> SEQ ID NO 110
<211> LENGTH: 48
<212> TYPE: PRT
<213> ORGANISM: Artificial Sequence
<220> FEATURE:
<223> OTHER INFORMATION: from accession number Q75D49, Ashbya gossypii

<400> SEQUENCE: 110
```

Arg Lys Lys Phe Ala Cys Val Glu Cys Arg Gln Gln Lys Ser Lys Cys
1               5                   10                  15

```
Asn Ala His Asp Arg Ala Pro Glu Pro Cys Ser Arg Cys Ala Lys Lys
             20                  25                  30

Asn Val Pro Cys Val Leu Gln Arg Asp Phe Arg Arg Thr Tyr Lys Arg
         35                  40                  45
```

```
<210> SEQ ID NO 111
<211> LENGTH: 50
<212> TYPE: PRT
<213> ORGANISM: Artificial Sequence
<220> FEATURE:
<223> OTHER INFORMATION: from accession number Q6FSH9, Candida glabrata

<400> SEQUENCE: 111

Lys Lys Lys Arg Val Ala Cys Val Glu Cys Arg Gln Gln Lys Ser Lys
1               5                   10                  15

Cys Asp Ala His Asp Lys Ala Pro Glu Pro Cys Thr Arg Cys Gln Lys
             20                  25                  30

Lys Gly Val Pro Cys Val Leu Lys Lys Asp Phe Arg Arg Thr Tyr Lys
         35                  40                  45

Arg Ala
    50
```

```
<210> SEQ ID NO 112
<211> LENGTH: 49
<212> TYPE: PRT
<213> ORGANISM: Artificial Sequence
<220> FEATURE:
<223> OTHER INFORMATION: from accession number C5DJQ9, Lachancea
      thermotolerans

<400> SEQUENCE: 112

Arg Arg Lys Lys Leu Ala Cys Val Glu Cys Arg Gln Gln Lys Ser Lys
1               5                   10                  15

Cys Asp Ala His Glu Arg Ala Pro Glu Ser Cys Thr Arg Cys Ala Lys
             20                  25                  30

Lys Asn Val Gln Cys Val Leu Gln Lys Asp Phe Arg Arg Thr Tyr Lys
         35                  40                  45

Arg
```

```
<210> SEQ ID NO 113
<211> LENGTH: 50
<212> TYPE: PRT
<213> ORGANISM: Artificial Sequence
<220> FEATURE:
<223> OTHER INFORMATION: from accession number Q6CRA6, Kluyveromyces
      lactis

<400> SEQUENCE: 113

Gln Lys Lys Lys Leu Ala Cys Val Glu Cys Arg Gln Gln Lys Ser Lys
1               5                   10                  15

Cys Asp Ala His Glu Arg Ala Pro Glu Pro Cys Ser Arg Cys Leu Lys
             20                  25                  30

Lys Gly Val Pro Cys Val Leu Gln Lys Asp Phe Arg Arg Thr Cys Lys
         35                  40                  45

Arg Ala
    50
```

```
<210> SEQ ID NO 114
<211> LENGTH: 50
<212> TYPE: PRT
<213> ORGANISM: Artificial Sequence
```

```
<220> FEATURE:
<223> OTHER INFORMATION: from accession number B9WHE2, Candida
      dubliniensis

<400> SEQUENCE: 114

Arg Ser Lys Lys Met Ala Cys Val Glu Cys Arg Gln Gln Lys Ser Arg
1               5                   10                  15

Cys Asp Ala Phe Glu Lys Gln Pro Asp Pro Cys Thr Arg Cys Ala Lys
                20                  25                  30

Lys Gly Leu Gln Cys Asp Val Lys Ser Asp Tyr Lys Arg Thr Tyr Lys
            35                  40                  45

Arg Ala
    50

<210> SEQ ID NO 115
<211> LENGTH: 50
<212> TYPE: PRT
<213> ORGANISM: Artificial Sequence
<220> FEATURE:
<223> OTHER INFORMATION: from accession number B5RTY8, Debaryomyces
      hansenii

<400> SEQUENCE: 115

Lys Thr Lys Arg Met Ala Cys Val Glu Cys Arg Gln Gln Lys Ser Arg
1               5                   10                  15

Cys Asp Ala His Glu Lys His Pro Ala Pro Cys Ser Arg Cys Ala Lys
                20                  25                  30

Lys Gly Leu Gln Cys Asn Leu Lys Ser Asp Tyr Lys Arg Thr Tyr Lys
            35                  40                  45

Arg Ala
    50

<210> SEQ ID NO 116
<211> LENGTH: 48
<212> TYPE: PRT
<213> ORGANISM: Artificial Sequence
<220> FEATURE:
<223> OTHER INFORMATION: from accession number A5E2U7, Lodderomyces
      elongisporus

<400> SEQUENCE: 116

Lys Arg Met Ala Cys Val Glu Cys Arg Gln Gln Lys Ser Arg Cys Asp
1               5                   10                  15

Ala His Glu Lys Tyr Pro Asn Pro Cys Thr Arg Cys Leu Lys Lys Gly
                20                  25                  30

Leu Gln Cys Asp Leu Lys Ser Asp Tyr Lys Arg Thr Tyr Lys Arg Ala
            35                  40                  45

<210> SEQ ID NO 117
<211> LENGTH: 50
<212> TYPE: PRT
<213> ORGANISM: Artificial Sequence
<220> FEATURE:
<223> OTHER INFORMATION: from accession number A3LVE3, Pichia stipitis

<400> SEQUENCE: 117

Lys Pro Lys Arg Ile Ala Cys Val Glu Cys Arg Gln Gln Lys Ser Arg
1               5                   10                  15

Cys Asp Ala His Glu Lys His Pro Gly Pro Cys Thr Arg Cys Ile Lys
                20                  25                  30

Lys Gly Leu Lys Cys Asp Leu Lys Ser Asp Tyr Lys Arg Thr Tyr Lys
            35                  40                  45
```

Arg Ala
    50

<210> SEQ ID NO 118
<211> LENGTH: 50
<212> TYPE: PRT
<213> ORGANISM: Artificial Sequence
<220> FEATURE:
<223> OTHER INFORMATION: from accession number A5DQ60, Pichia
      guilliermondii

<400> SEQUENCE: 118

Arg Pro Lys Arg Ile Ala Cys Val Asn Cys Arg Gln Gln Lys Ser Arg
1               5                   10                  15

Cys Asp Ser His Gln Lys His Pro Ala Pro Cys Thr Arg Cys Ala Lys
            20                  25                  30

Lys Gly Leu His Cys Thr Leu Lys Ser Asp Tyr Lys Arg Thr Tyr Lys
        35                  40                  45

Arg Ala
    50

<210> SEQ ID NO 119
<211> LENGTH: 50
<212> TYPE: PRT
<213> ORGANISM: Artificial Sequence
<220> FEATURE:
<223> OTHER INFORMATION: from accession number C4Y9T2, Clavispora
      lusitaniae

<400> SEQUENCE: 119

Lys Asn Arg Arg Leu Ala Cys Thr Cys Cys Arg Gln Gln Lys Ser Lys
1               5                   10                  15

Cys Asp Ala Ser Glu Lys His Pro Glu Pro Cys Ser Arg Cys Ala Ala
            20                  25                  30

Lys Gly Leu Thr Cys Glu Leu Arg Pro Asp Phe Lys Arg Thr Glu Lys
        35                  40                  45

Arg Ala
    50

<210> SEQ ID NO 120
<211> LENGTH: 49
<212> TYPE: PRT
<213> ORGANISM: Artificial Sequence
<220> FEATURE:
<223> OTHER INFORMATION: from accession number Q4WZZ2, Aspergillus
      fumigatus

<400> SEQUENCE: 120

Lys Arg Ala Lys Lys Ala Cys Thr Glu Cys Arg Gln Gln Lys His Lys
1               5                   10                  15

Cys Asp Ala Tyr Leu Asn Pro Glu Gln Pro Cys Thr Arg Cys Arg Lys
            20                  25                  30

Ser Gln Ile Lys Cys Val Ile Ser Asp Pro Phe Arg Arg Glu His Lys
        35                  40                  45

Arg

<210> SEQ ID NO 121
<211> LENGTH: 49
<212> TYPE: PRT
<213> ORGANISM: Artificial Sequence
<220> FEATURE:
<223> OTHER INFORMATION: from accession number A2QTW6, Aspergillus niger

<400> SEQUENCE: 121

Lys Arg Gly Lys Lys Ala Cys Thr Glu Cys Arg Gln Gln Lys Ala Lys
1               5                   10                  15

Cys Asp Ala Tyr Leu Asn Pro Ser Gln Ala Cys Ser Arg Cys Ser Lys
                20                  25                  30

Leu Asn Ile Gln Cys Ile Ile Ser Asp Pro Phe Arg Arg Glu His Lys
            35                  40                  45

Arg

<210> SEQ ID NO 122
<211> LENGTH: 235
<212> TYPE: PRT
<213> ORGANISM: Saccharomyces cerevisiae

<400> SEQUENCE: 122

Met Lys Asn Ile Lys Lys Asn Gln Val Met Asn Thr Gly Pro Asn Ser
1               5                   10                  15

Lys Leu Leu Lys Glu Tyr Lys Ser Gln Leu Ile Glu Leu Asn Ile Glu
                20                  25                  30

Gln Phe Glu Ala Gly Ile Gly Leu Ile Leu Gly Asp Ala Tyr Ile Arg
            35                  40                  45

Ser Arg Asp Glu Gly Lys Thr Tyr Cys Met Gln Phe Glu Trp Lys Asn
50                  55                  60

Lys Ala Tyr Met Asp His Val Cys Leu Leu Tyr Asp Gln Trp Val Leu
65                  70                  75                  80

Ser Pro Pro His Lys Lys Glu Arg Val Asn His Leu Gly Asn Leu Val
                85                  90                  95

Ile Thr Trp Gly Ala Gln Thr Phe Lys His Gln Ala Phe Asn Lys Leu
            100                 105                 110

Ala Asn Leu Phe Ile Val Asn Asn Lys Lys Thr Ile Pro Asn Asn Leu
        115                 120                 125

Val Glu Asn Tyr Leu Thr Pro Met Ser Thr Ala Tyr Trp Phe Met Asp
130                 135                 140

Asp Gly Gly Lys Trp Asp Tyr Asn Lys Asn Ser Thr Asn Lys Ser Ile
145                 150                 155                 160

Val Leu Asn Thr Gln Ser Phe Thr Phe Glu Glu Val Glu Tyr Leu Val
                165                 170                 175

Lys Gly Leu Arg Asn Lys Phe Gln Leu Asn Cys Tyr Val Lys Ile Asn
            180                 185                 190

Lys Asn Lys Pro Ile Ile Tyr Ile Asp Ser Met Ser Tyr Thr Ile Phe
        195                 200                 205

Tyr Asn Leu Ile Lys Pro Tyr Leu Ile Pro Gln Met Met Tyr Lys Thr
210                 215                 220

Pro Asn Thr Ile Ser Ser Glu Thr Phe Leu Lys
225                 230                 235

<210> SEQ ID NO 123
<211> LENGTH: 238
<212> TYPE: PRT
<213> ORGANISM: Zygosaccharomyces bisporus

<400> SEQUENCE: 123

Met Lys Phe Ile Lys Lys Glu Gln Ile Lys Asn Leu Gly Pro Asn Ser
1               5                   10                  15

Lys Leu Leu Lys Gln Tyr Lys Ser Gln Leu Thr Asn Leu Thr Ser Glu

```
                 20                  25                  30
Gln Leu Glu Ile Gly Val Gly Leu Leu Gly Asp Ala Tyr Ile Arg
             35                  40                  45

Ser Arg Asp Asn Gly Lys Thr Asn Cys Ile Gln Phe Glu Trp Lys Asn
 50                  55                  60

Lys Ala Tyr Ile Asp His Ile Cys Leu Lys Phe Asp Glu Trp Val Leu
 65                  70                  75                  80

Ser Pro Pro His Lys Lys Met Arg Ile Asn His Leu Gly Asn Glu Val
                 85                  90                  95

Ile Thr Trp Gly Ala Gln Thr Phe Lys His Glu Ala Phe Asn Glu Leu
                100                 105                 110

Ser Lys Leu Phe Ile Ile Asn Asn Lys Lys His Ile Ile Asn Asn Leu
                115                 120                 125

Ile Glu Asp Tyr Val Thr Pro Lys Ser Leu Ala Tyr Trp Phe Met Asp
                130                 135                 140

Asp Gly Gly Lys Trp Asp Tyr Asn Lys Gly Ser Met Asn Lys Ser Ile
145                 150                 155                 160

Val Leu Asn Thr Gln Cys Phe Thr Ile Asp Glu Val Asn Ser Leu Ile
                165                 170                 175

Asn Gly Leu Asn Thr Lys Phe Lys Leu Asn Cys Ser Met Lys Phe Asn
                180                 185                 190

Lys Asn Lys Pro Ile Ile Tyr Ile Pro His Asn Ser Tyr Asn Ile Tyr
                195                 200                 205

Tyr Glu Leu Ile Ser Pro Tyr Ile Ile Thr Glu Met Arg Tyr Lys Leu
                210                 215                 220

Pro Ser Tyr Glu Gly Thr Ser Lys Asp Tyr Asn Lys Ile His
225                 230                 235

<210> SEQ ID NO 124
<211> LENGTH: 228
<212> TYPE: PRT
<213> ORGANISM: Lachancea thermotolerans

<400> SEQUENCE: 124

Met Thr Met Lys Tyr Ile Thr Lys Gln Gln Ile Lys Asn Leu Gly Pro
 1               5                  10                  15

Asn Ser Lys Leu Leu Lys Gln Tyr Lys Ala Gln Leu Thr Arg Leu Thr
                 20                  25                  30

Thr Val Gln Leu Glu Ala Gly Val Gly Leu Ile Leu Gly Asp Ala Tyr
                 35                  40                  45

Ile Arg Ser Arg Asp Glu Gly Lys Thr Tyr Cys Met Gln Phe Glu Trp
 50                  55                  60

Lys Asn Glu Ala Tyr Ile Asn His Val Cys Lys Leu Tyr Asp Glu Trp
 65                  70                  75                  80

Val Leu Ser Ser Pro His Lys Lys Val Arg Thr Asn His Leu Gly Asn
                 85                  90                  95

Glu Val Val Thr Trp Gly Ala Gln Thr Phe Lys His Lys Ala Phe Asn
                100                 105                 110

Glu Leu Ala Glu Leu Phe Ile Ile Asn Asn Lys His Ile Asn Pro
                115                 120                 125

Asp Leu Val Asn Gln Tyr Ile Thr Pro Arg Ser Leu Ala Tyr Trp Phe
                130                 135                 140

Met Asp Asp Gly Gly Lys Trp Asp Tyr Asn Thr Asn Ser Asn Asn Lys
145                 150                 155                 160
```

Ser Ile Val Leu Asn Thr Gln Gly Phe Ser Ile Gln Glu Val Gln Tyr
165                     170                     175

Leu Ile Asp Gly Leu Asn Ile Lys Phe Asn Leu Asn Cys Ile Met Lys
        180                     185                     190

Phe Asn Lys Asn Lys Pro Ile Ile Phe Ile Pro Ser Asp Asn Tyr Lys
            195                     200                     205

His Tyr Tyr Asp Leu Ile Ile Pro Tyr Ile Ile Pro Glu Met Lys Tyr
210                     215                     220

Lys Leu Pro Thr
225

<210> SEQ ID NO 125
<211> LENGTH: 230
<212> TYPE: PRT
<213> ORGANISM: Pichia canadensis

<400> SEQUENCE: 125

Met Lys Lys Gln Ile Ile Asn Lys Lys Asp Leu Leu Gly Leu Gly Pro
1               5                   10                  15

Asn Ser Lys Leu Ile Lys Asp Tyr Lys Lys Gln Trp Thr Thr Leu Ser
            20                  25                  30

Lys Ile Gln Glu Glu Thr Leu Ile Gly Asn Ile Leu Gly Asp Val Tyr
        35                  40                  45

Ile Lys Lys Leu Lys Arg Asn Lys His Phe Leu Leu Gln Phe Glu Trp
50                  55                  60

Lys Asn Lys Ala Tyr Ile Glu His Ile Val Arg Val Phe Asp Glu Tyr
65                  70                  75                  80

Val Ile Ser Pro Pro Thr Leu Tyr Glu Arg Lys Asn His Leu Gly Asn
                85                  90                  95

Lys Val Ile Thr Trp Arg Ala Gln Thr Phe Glu His Lys Ala Phe Asp
            100                 105                 110

Lys Leu Gly Tyr Tyr Phe Met Glu Asn His Lys Lys Ile Ile Lys Pro
        115                 120                 125

Asp Leu Val Leu Asn Tyr Ile Thr Glu Arg Ser Leu Ala Tyr Trp Phe
130                 135                 140

Met Asp Asp Gly Gly Lys Trp Asp Tyr Asn Lys Lys Thr Lys Asn Lys
145                 150                 155                 160

Ser Leu Val Leu His Thr Gln Gly Phe Lys Lys Glu Glu Val Glu Ile
                165                 170                 175

Leu Ile Asn Asp Leu Asn Ile Lys Phe Asn Leu Asn Cys Ser Ile Lys
            180                 185                 190

Phe Asn Lys Asn Lys Pro Ile Ile Tyr Ile Pro Asn Lys Asp Tyr Glu
        195                 200                 205

Leu Phe Tyr Asn Leu Val Asn Pro Tyr Ile Ile Pro Glu Met Lys Tyr
    210                 215                 220

Lys Leu Leu Phe Asn Val
225                 230

<210> SEQ ID NO 126
<211> LENGTH: 163
<212> TYPE: PRT
<213> ORGANISM: Chlamydomonas reinhardtii

<400> SEQUENCE: 126

Met Asn Thr Lys Tyr Asn Lys Glu Phe Leu Leu Tyr Leu Ala Gly Phe
1               5                   10                  15

```
Val Asp Gly Asp Gly Ser Ile Ile Ala Gln Ile Lys Pro Asn Gln Ser
             20                  25                  30

Tyr Lys Phe Lys His Gln Leu Ser Leu Ala Phe Gln Val Thr Gln Lys
         35                  40                  45

Thr Gln Arg Arg Trp Phe Leu Asp Lys Leu Val Asp Glu Ile Gly Val
     50                  55                  60

Gly Tyr Val Arg Asp Arg Gly Ser Val Ser Asp Tyr Ile Leu Ser Glu
65                  70                  75                  80

Ile Lys Pro Leu His Asn Phe Leu Thr Gln Leu Gln Pro Phe Leu Lys
                 85                  90                  95

Leu Lys Gln Lys Gln Ala Asn Leu Val Leu Lys Ile Ile Trp Arg Leu
                100                 105                 110

Pro Ser Ala Lys Glu Ser Pro Asp Lys Phe Leu Glu Val Cys Thr Trp
            115                 120                 125

Val Asp Gln Ile Ala Ala Leu Asn Asp Ser Lys Thr Arg Lys Thr Thr
        130                 135                 140

Ser Glu Thr Val Arg Ala Val Leu Asp Ser Leu Ser Glu Lys Lys Lys
145                 150                 155                 160

Ser Ser Pro

<210> SEQ ID NO 127
<211> LENGTH: 171
<212> TYPE: PRT
<213> ORGANISM: Carteria lunzensis

<400> SEQUENCE: 127

Met Asn Lys Phe Thr Pro Asp Gln Leu Leu Tyr Leu Ala Gly Leu Ile
1               5                   10                  15

Asp Gly Asp Gly Ser Ile Ile Ala Gln Leu Val Ser Arg Lys Asp Tyr
             20                  25                  30

Thr Trp Glu Phe Gln Ile Arg Leu Thr Val Gln Val Thr Gln Leu Lys
         35                  40                  45

Lys Arg Arg Trp Phe Leu Glu Glu Leu Gln Lys Glu Ile Gly Ala Gly
     50                  55                  60

Ser Val Arg Asp Arg Asp Thr Val Ser Asp Tyr Ile Leu Thr Glu Thr
65                  70                  75                  80

Ser Asn Val Tyr Lys Phe Leu Lys Asp Leu Gln Pro His Leu Arg Leu
                 85                  90                  95

Lys Gln Lys Gln Ala Asn Leu Val Leu Arg Ile Ile Glu Gln Leu Pro
                100                 105                 110

Ser Ser Lys Ala Ser Lys Glu Ile Phe Leu Glu Leu Cys Asn Val Val
            115                 120                 125

Asp His Val Ala Thr Leu Asn Asp Thr Lys Arg Lys Tyr Thr Ala
        130                 135                 140

Glu Ile Val Ala Ala Lys Leu Lys Glu Leu Lys Glu Cys Val Val Pro
145                 150                 155                 160

Val Glu Thr Ser Glu Glu Thr Asn Ser Gly Ile
                165                 170

<210> SEQ ID NO 128
<211> LENGTH: 182
<212> TYPE: PRT
<213> ORGANISM: Carteria olivieri

<400> SEQUENCE: 128

Met Lys Asp Leu Gln Glu Lys Asp Leu Ile Tyr Leu Ala Gly Phe Ile
```

-continued

```
              1               5                  10                 15
            Asp Ala Asp Gly Ser Ile Phe Ala Gln Leu Ile Ser Asn Asn Asp Tyr
                        20                  25                 30

Lys Phe Asn Tyr Gln Ile Arg Val Thr Val Gln Ile Thr Gln Leu Thr
                        35                  40                 45

Lys Arg Lys Leu Phe Leu Thr His Ile Arg Asp Leu Ile Gly Val Gly
                        50                  55                 60

Thr Ile Arg Asp Arg Lys Asn Val Ser Asp Tyr Val Leu Val Glu Pro
             65                  70                  75                 80

Arg Phe Val Tyr Lys Leu Leu Thr Gln Leu Gln Pro Phe Leu Arg Leu
                        85                  90                 95

Lys Lys Lys Gln Ala Asn Leu Val Leu Lys Ile Ile Glu Gln Leu Pro
                       100                 105                110

Ser Ser Lys Asp Ser Gln Pro Glu Phe Leu Lys Leu Cys Lys Gln Val
                       115                 120                125

Asp Gln Ile Ala Ala Leu Asn Asp Ser Lys Lys Arg Lys His Thr Thr
                       130                 135                140

Ser Ser Val Val Met Ser Leu Gly His Glu Leu Pro Glu Lys Val Ser
            145                 150                 155                160

Lys Glu Val Asn Val Pro Val Glu Thr Ser Asp Leu Ile Glu Ile Glu
                       165                 170                175

Glu Asp Pro Ser Ser Ile
                       180
```

<210> SEQ ID NO 129
<211> LENGTH: 167
<212> TYPE: PRT
<213> ORGANISM: Scenedesmus obliquus

<400> SEQUENCE: 129

```
            Met Thr Asn Asn Met Gln Asn Lys Gly Met Lys Ile Ile Asp Lys
             1               5                  10                 15

Asp Glu Leu Ile Tyr Leu Ala Gly Phe Ile Asp Gly Asp Gly Ser Leu
                        20                  25                 30

Ile Ala Gln Met Val Arg Arg His Asp Tyr Lys Phe Lys Tyr Gln Ile
                        35                  40                 45

Lys Cys Thr Val Gln Ile Thr Gln Leu Lys Lys Arg Arg His Phe Leu
                        50                  55                 60

Glu Lys Ile Gln Glu Ser Ile Gly Tyr Gly Ile Ile Arg Asp Arg Gly
             65                  70                  75                 80

Thr Ile Ser Asp Tyr Val Leu Val Glu Pro Lys Cys Val Tyr Trp Leu
                        85                  90                 95

Leu Lys Gln Leu Ser Pro Phe Leu Arg Leu Lys Lys Gln Ala Asp
                       100                 105                110

Leu Ile Ile Arg Ile Ile Glu Gln Leu Thr Ser Ser Lys Asn Ser Ala
                       115                 120                125

Val Leu Phe Val Gln Leu Cys Arg Leu Thr Asp Gln Val Ala Leu Leu
                       130                 135                140

Asn Asp Ser Lys Ser Arg Thr Ile Thr Ala Glu Val Val Glu Thr Thr
            145                 150                 155                160

Leu Arg Glu Leu Gly Leu Ile
                       165
```

<210> SEQ ID NO 130
<211> LENGTH: 166

<212> TYPE: PRT
<213> ORGANISM: Haematococcus lacustris

<400> SEQUENCE: 130

Met Lys Asn Ile Asn Ser Thr Arg Phe Ser His Leu Thr Asn Glu Gln
1               5                   10                  15

Lys Ala Tyr Leu Ala Gly Phe Ile Asp Cys Asp Gly Ser Leu Met Ala
            20                  25                  30

Gln Ile Val Arg Lys Pro Asp Tyr Ala Tyr Lys Phe Gln Ile Arg Val
        35                  40                  45

Thr Ile Gln Leu Ser Gln Arg Thr Ser Arg Ile His Phe Leu Lys Glu
    50                  55                  60

Ile Ala Ser Glu Val Gly Tyr Gly Tyr Val Val Ser Arg Asn Asn Met
65                  70                  75                  80

Ser Asp Tyr Val Ile Thr Gln Ala Asn Ile Val Tyr Glu Leu Leu Ser
                85                  90                  95

Leu Leu Leu Pro Tyr Leu Arg Met Lys Val Lys Gln Ala Asn Leu Ile
            100                 105                 110

Leu Lys Ile Ile Gln Glu Leu Pro Ser Ala Lys Val Ser Lys Asp Lys
        115                 120                 125

Phe Ile Glu Leu Cys Ile Leu Ala Asn Gln Val Ser Ile Leu Asn Thr
    130                 135                 140

Pro Asn Lys Ile Leu Lys Asn Thr Trp Gln Val Val Lys Ala Glu Leu
145                 150                 155                 160

Glu Ser Glu Asp Leu Gln
                165

<210> SEQ ID NO 131
<211> LENGTH: 218
<212> TYPE: PRT
<213> ORGANISM: Chlamydomonas moewusii

<400> SEQUENCE: 131

Met Ser Asn Phe Ile Leu Lys Pro Gly Glu Lys Leu Pro Gln Asp Lys
1               5                   10                  15

Leu Glu Glu Leu Lys Lys Ile Asn Asp Ala Val Lys Lys Thr Lys Asn
            20                  25                  30

Phe Ser Lys Tyr Leu Ile Asp Leu Arg Lys Leu Phe Gln Ile Asp Glu
        35                  40                  45

Val Gln Val Thr Ser Glu Ser Lys Leu Phe Leu Ala Gly Phe Leu Glu
    50                  55                  60

Gly Glu Ala Ser Leu Asn Ile Ser Thr Lys Lys Leu Ala Thr Ser Lys
65                  70                  75                  80

Phe Gly Leu Val Val Asp Pro Glu Phe Asn Val Thr Gln His Val Asn
                85                  90                  95

Gly Val Lys Val Leu Tyr Leu Ala Leu Glu Val Phe Lys Thr Gly Arg
            100                 105                 110

Ile Arg His Lys Ser Gly Ser Asn Ala Thr Leu Val Leu Thr Ile Asp
        115                 120                 125

Asn Arg Gln Ser Leu Glu Glu Lys Val Ile Pro Phe Tyr Glu Gln Tyr
    130                 135                 140

Val Val Ala Phe Ser Ser Pro Glu Lys Val Lys Arg Val Ala Asn Phe
145                 150                 155                 160

Lys Ala Leu Leu Glu Leu Phe Asn Asn Asp Ala His Gln Asp Leu Glu
                165                 170                 175

```
Gln Leu Val Asn Lys Ile Leu Pro Ile Trp Asp Gln Met Arg Lys Gln
                180                 185                 190

Gln Gly Gln Ser Asn Glu Gly Phe Pro Asn Leu Glu Ala Ala Gln Asp
            195                 200                 205

Phe Ala Arg Asn Tyr Lys Lys Gly Ile Lys
        210                 215

<210> SEQ ID NO 132
<211> LENGTH: 213
<212> TYPE: PRT
<213> ORGANISM: Chlorococcum echinozygotum

<400> SEQUENCE: 132

Met Gln Asn Tyr Thr Leu Lys Pro Gly Glu Val Leu Pro Ala Asn Val
1               5                   10                  15

Ser Gln Gln Leu Ala Lys Ile Asn Asn Asp Phe Ser Lys Ser Ser Asp
            20                  25                  30

Phe Ala Lys Tyr Leu Ser Asn Leu Arg Gln Leu Phe Gln Ile Glu Pro
        35                  40                  45

Ile Gln Val Thr Ser Glu Ala Lys Leu Tyr Leu Ala Gly Phe Val Glu
    50                  55                  60

Gly Glu Gly Ser Leu Asn Ile Ser Ala Lys Lys Thr Arg His Ala Arg
65                  70                  75                  80

Phe Gly Val Val Val Asp Pro Glu Phe Ser Ile Thr Gln His Val Asn
                85                  90                  95

Gly Phe Lys Pro Val Tyr Leu Ala Leu Glu Val Phe Lys Thr Gly Arg
            100                 105                 110

Ile Arg His Lys Gly Gly Ser Asn Ala Thr Met Val Leu Thr Ile Asp
        115                 120                 125

Asn Arg Lys Ser Leu Glu Glu Lys Val Ile Pro Phe Tyr Glu Gln Tyr
    130                 135                 140

Val Ala Gly Phe Ser Ser Ser Lys Asn Asn Arg Val Thr Lys Phe
145                 150                 155                 160

Lys Thr Leu Leu Asp Leu Phe Asn Lys Gly Ser His Lys Asp Lys Asp
                165                 170                 175

Leu Leu Ile Asn Asp Ile Leu Pro Ile Trp Asp Glu Leu Arg Gln Gln
            180                 185                 190

Lys Gly Gln Lys Asn Gln Ala Phe Lys Asp Leu Asn Glu Ala Ala Thr
        195                 200                 205

Tyr Ile Arg Gln Lys
    210

<210> SEQ ID NO 133
<211> LENGTH: 229
<212> TYPE: PRT
<213> ORGANISM: Chlorogonium elongatum

<400> SEQUENCE: 133

Met Asn Ser Ser Ser Glu Asn Arg Lys Phe Phe Leu Asn Pro Gly
1               5                   10                  15

Glu Lys Leu Pro Glu Asp Ile Val Thr Lys Leu Lys Gln Ile Asn Asp
            20                  25                  30

Ser Phe Ser Lys His Ser Asp Phe Ser Arg Tyr Lys Arg Glu Ile Lys
        35                  40                  45

Glu Leu Phe Gln Ile Ala His Ile Phe Val Thr Glu Asp Ser Lys Arg
    50                  55                  60
```

```
Phe Leu Gly Gly Phe Leu Glu Gly Glu Ala Ser Leu Asn Val Ser Ala
 65                  70                  75                  80

Lys Lys Leu Thr Asn Ala Lys Phe Gly Leu Leu Ile Asp Pro Glu Phe
                 85                  90                  95

Ser Ile Thr Gln His Val Asn Gly Ile Ser Asn Leu Tyr Leu Ala Leu
            100                 105                 110

Glu Val Phe Gln Thr Gly Arg Ile Ser Leu Lys Asn Gly Ser Asn Ala
        115                 120                 125

Thr Met Val Phe Lys Ile Asp Asn Arg Gln Asn Leu Gln Gln Lys Val
    130                 135                 140

Val Pro Phe Tyr Glu Thr Tyr Val Asn Arg Tyr Gly Ser Pro Asn Lys
145                 150                 155                 160

Lys Ala Arg Val Val Leu Phe Leu Gln Leu Leu Asp Leu Phe Asn Gln
                165                 170                 175

Lys Gly His Glu Asn Leu Gln Val Phe Val Glu Lys Met Leu Pro Ile
            180                 185                 190

Trp Asp Lys Met Arg Met Gln Lys Gly Gln Ser Asn Glu Ala Phe Pro
        195                 200                 205

Asp Leu Asp Thr Ala Gln Arg Tyr Val Lys Asn Phe Trp His Asn Lys
    210                 215                 220

Asn Asn Asn Leu Thr
225

<210> SEQ ID NO 134
<211> LENGTH: 244
<212> TYPE: PRT
<213> ORGANISM: Ankistrodesmus stipitatus

<400> SEQUENCE: 134

Met Gln Ile Lys Pro Leu Asp Ile Thr Ile Val Gln Ser Gly Ile Phe
1               5                   10                  15

Leu Lys Pro Gly Glu Lys Ile Ser Gln Glu Ile Leu Glu Lys Leu Arg
            20                  25                  30

Lys Ile Asn Lys Lys Tyr Ser Glu Thr Lys Asn Phe Pro Glu Tyr Glu
        35                  40                  45

Arg Ser Val Arg Glu Leu Phe Lys Leu Lys Pro Val Gln Ile Lys Glu
 50                 55                  60

Lys Thr Met Gln Phe Leu Ala Gly Phe Cys Glu Gly Glu Ala Ser Met
 65                 70                  75                  80

Ser Ala Gly Ala Lys Lys Asn Ser Thr Ser His Phe Lys Val Tyr Ile
                85                  90                  95

Asp Pro Glu Phe Asn Leu Thr Gln His Val Asn Gly Ile Ser Asn Leu
            100                 105                 110

Tyr Leu Ala Leu Val Ser Phe Lys Thr Gly Arg Ile Arg His Lys Ile
        115                 120                 125

Ser Ser Asn Ala Thr Phe Val Phe Thr Ile Asp Asn Arg Gln Asn Leu
    130                 135                 140

Lys Glu Lys Val Leu Pro Phe Tyr Glu Lys Tyr Val His Pro Phe Gly
145                 150                 155                 160

Ser Pro Val Lys Val Arg Arg Thr Glu Met Leu Lys Leu Leu Ser
                165                 170                 175

Leu Phe Asp Glu Lys Ala His Leu Asn Ser Asp Arg Met Ile Asn Glu
            180                 185                 190

Val Leu Pro Leu Trp Asp Ala Met Arg Ile Gln Val Gly Gln Ser Asn
        195                 200                 205
```

Glu Thr Phe Gln Ser Leu Gly Glu Ala Gln Asp Tyr Ile Arg Asn Ala
    210                 215                 220

Val Arg Pro Leu Ser Ser Gln Gly Leu Val Leu Lys His Lys Gln Lys
225                 230                 235                 240

Gly Asp Gly Asn

<210> SEQ ID NO 135
<211> LENGTH: 216
<212> TYPE: PRT
<213> ORGANISM: Chlamydomonas monadina

<400> SEQUENCE: 135

Met Ile Ile Lys Ser Gly Glu Lys Ile Pro Asp Asn Ile Leu Lys Glu
1               5                   10                  15

Leu Gln Gly Ile Asn Glu Lys Tyr Thr Lys Asp Arg Asp Phe Asn Ile
            20                  25                  30

Tyr Leu Asp Arg Leu Gly Lys Leu Phe Asn Ile Ser Lys Gln Asn Ile
            35                  40                  45

Arg Thr Glu Lys Lys Leu Phe Leu Ala Gly Tyr Leu Glu Gly Glu Gly
    50                  55                  60

Ser Leu Ser Phe Ser Ile Lys Lys Asn Leu Asn Ala Lys Tyr Gly Val
65                  70                  75                  80

Thr Leu Asp Pro Glu Phe Asn Val Thr Gln His Ile Asn Gly Val Glu
                85                  90                  95

Gln Leu Tyr Thr Tyr Leu Gln Ile Phe Gln Thr Gly Arg Ile Thr Tyr
            100                 105                 110

Lys Ser Gly Ser Asn Ala Thr Leu Val Phe Lys Ile Ser Asn Arg Arg
        115                 120                 125

Ser Leu Glu Glu Lys Val Ile Pro Phe Trp Asn Met Tyr Val Ala Pro
    130                 135                 140

Tyr Ala Thr Gln Ala Lys Gln Gln Arg Phe Leu Lys Phe Gln Lys Val
145                 150                 155                 160

Leu Glu Leu Phe Arg Glu Asp Cys His Thr Lys Leu Asp Cys Leu Thr
                165                 170                 175

Cys Glu Met Leu Pro Leu Trp Asp Ser Met Arg Ile Gln Lys Gly Gln
            180                 185                 190

Ser Asn Glu Ser Phe Pro Asp Leu Gln Ser Ala Val Asp Tyr Val Gln
        195                 200                 205

Thr Phe Val Lys Lys Ser Lys Lys
    210                 215

<210> SEQ ID NO 136
<211> LENGTH: 218
<212> TYPE: PRT
<213> ORGANISM: Chlamydomonas humicola

<400> SEQUENCE: 136

Met Ser Leu Thr Gln Gln Gln Lys Asp Leu Ile Phe Gly Ser Leu Leu
1               5                   10                  15

Gly Asp Gly Asn Leu Gln Thr Gly Ser Val Gly Arg Thr Trp Arg Tyr
            20                  25                  30

Arg Ala Leu His Lys Ser Glu His Gln Thr Tyr Leu Phe His Lys Tyr
            35                  40                  45

Glu Ile Leu Lys Pro Leu Cys Gly Glu Asn Thr Leu Pro Thr Glu Ser
    50                  55                  60

```
Ile Val Phe Asp Glu Arg Thr Asn Lys Glu Val Lys Arg Trp Phe Phe
65                  70                  75                  80

Asn Thr Leu Thr Asn Pro Ser Leu Lys Phe Phe Ala Asp Met Phe Tyr
                85                  90                  95

Thr Tyr Asp Gln Asn Thr Gln Lys Trp Val Lys Asp Val Pro Val Lys
            100                 105                 110

Val Gln Thr Phe Leu Thr Pro Gln Ala Leu Ala Tyr Phe Tyr Ile Asp
            115                 120                 125

Asp Gly Ala Leu Lys Trp Leu Asn Lys Ser Asn Ala Met Gln Ile Cys
            130                 135                 140

Thr Glu Ser Phe Ser Gln Gly Gly Thr Ile Arg Ile Gln Lys Ala Leu
145                 150                 155                 160

Lys Thr Leu Tyr Asn Ile Asp Thr Thr Leu Thr Lys Lys Thr Leu Gln
                165                 170                 175

Asp Gly Arg Ile Gly Tyr Arg Ile Ala Ile Pro Glu Ala Ser Ser Gly
            180                 185                 190

Ala Phe Arg Glu Val Ile Lys Pro Phe Leu Val Asp Cys Met Arg Tyr
            195                 200                 205

Lys Val Ser Asp Gly Asn Lys Gly His Leu
            210                 215
```

<210> SEQ ID NO 137
<211> LENGTH: 218
<212> TYPE: PRT
<213> ORGANISM: Chlamydomonas zebra

<400> SEQUENCE: 137

```
Met Ser Leu Thr Gln Gln Lys Asp Leu Ile Phe Gly Ser Leu Leu
1               5                   10                  15

Gly Asp Gly Asn Leu Gln Thr Gly Ser Val Gly Arg Thr Trp Arg Tyr
                20                  25                  30

Arg Ala Leu His Lys Ser Glu His Gln Thr Tyr Leu Phe His Lys Tyr
            35                  40                  45

Glu Ile Leu Lys Pro Leu Cys Gly Glu Asn Thr Leu Pro Thr Glu Ser
50                  55                  60

Ile Val Phe Asp Glu Arg Thr Asn Lys Glu Val Lys Arg Trp Phe Phe
65                  70                  75                  80

Asn Thr Leu Thr Asn Pro Ser Leu Lys Phe Phe Ala Asp Met Phe Tyr
                85                  90                  95

Thr Tyr Asp Gln Asn Thr Gln Lys Trp Val Lys Asp Val Pro Val Lys
            100                 105                 110

Val Gln Thr Phe Leu Thr Pro Gln Ala Leu Ala Tyr Phe Tyr Ile Asp
            115                 120                 125

Asp Gly Ala Leu Lys Trp Leu Asn Lys Ser Asn Ala Met Gln Ile Cys
            130                 135                 140

Thr Glu Ser Phe Ser Gln Gly Gly Thr Ile Arg Ile Gln Lys Ala Leu
145                 150                 155                 160

Lys Thr Leu Tyr Asn Ile Asp Thr Thr Leu Thr Lys Lys Thr Leu Gln
                165                 170                 175

Asp Gly Arg Ile Gly Tyr Arg Ile Ala Ile Pro Glu Ala Ser Ser Gly
            180                 185                 190

Ala Phe Arg Glu Val Ile Lys Pro Phe Leu Val Asp Cys Met Arg Tyr
            195                 200                 205

Lys Val Ser Asp Gly Asn Lys Gly His Leu
            210                 215
```

<210> SEQ ID NO 138
<211> LENGTH: 222
<212> TYPE: PRT
<213> ORGANISM: Chlamydomonas monadina

<400> SEQUENCE: 138

Met Leu Thr Gln His Ser Phe Ala Met Leu Glu Gln Arg Asn Leu Ile
1               5                   10                  15

Phe Gly Ser Leu Leu Gly Asp Gly Asn Leu Gln Thr Gly Ser Asn Gly
                20                  25                  30

Arg Thr Trp Arg Tyr Arg Ala Ile Gln Gln Lys His Gln Ala Tyr
            35                  40                  45

Leu Phe His Lys Tyr Gln Ile Leu Ser Pro Leu Cys Asn Thr Pro Pro
    50                  55                  60

Ala Phe Ser Gln Thr Phe Asp Pro Arg Thr Asn Asn Thr Ser Ser Arg
65                  70                  75                  80

Tyr Thr Phe Asn Thr Leu Val Ser Pro Cys Leu Asp Leu Tyr Ala Gln
                85                  90                  95

Met Phe Tyr Thr Tyr Asp Pro Ser Gln Gly Thr Trp Lys Lys Asp Val
                100                 105                 110

Pro Ser Asp Ile Tyr Leu Asp Lys His Leu Thr Pro Glu Ala Ile Ala
            115                 120                 125

Tyr Trp Tyr Met Asp Asp Gly Ala Leu Lys Trp Phe Asn Lys Ser Asn
    130                 135                 140

Ala Met Arg Ile Cys Thr Glu Ser Phe Ser Leu Gly Gly Val Met Arg
145                 150                 155                 160

Leu Lys Arg Val Leu Leu Glu Arg Tyr Asn Ile Val Thr Arg Leu Asn
                165                 170                 175

Val Lys Lys Leu Gln Asn Ser Ile Ser Tyr Arg Ile Ala Ile Pro Glu
            180                 185                 190

Ile Ser Ser Glu Ala Phe Arg Asp Leu Ile Arg Pro Tyr Leu Val Asp
    195                 200                 205

Cys Met Arg Tyr Lys Val Ser Asp Gly Tyr Arg Gly His Leu
210                 215                 220

<210> SEQ ID NO 139
<211> LENGTH: 242
<212> TYPE: PRT
<213> ORGANISM: Ankistrodesmus stipitatus

<400> SEQUENCE: 139

Met Thr Leu Thr Gln His Gln Lys Glu Leu Leu Val Gly Thr Leu Leu
1               5                   10                  15

Gly Asp Gly Asn Leu Gln Thr Glu Thr Arg Gly Arg Thr Trp Arg Tyr
                20                  25                  30

Arg Ala Ile Gln Lys Ala Glu His Lys Asp Tyr Leu Phe His Lys Tyr
            35                  40                  45

Glu Ile Leu Lys Glu Phe Cys Ser Thr Glu Pro Gln Leu Ser Arg Val
    50                  55                  60

Ala Asp Val Arg Thr Asn Lys Thr Tyr Glu Arg Trp Met Phe Ser Thr
65                  70                  75                  80

Lys Val His Asp Ser Leu Arg Phe Tyr Gly Asn Leu Phe Tyr Thr Tyr
                85                  90                  95

Asp Asn Lys Thr Gln Arg Met Val Lys Asp Ile Pro Val Asn Ile Glu
            100                 105                 110

```
Lys Phe Leu Thr Pro Ala Thr Val Ala Tyr Trp Tyr Met Asp Asp Gly
            115                 120                 125

Ser Leu Lys Tyr Pro Gly Lys Ser Asn Ala Leu Arg Ile Cys Thr Glu
        130                 135                 140

Ser Phe Ser Asp Asp Gly Val Arg Arg Leu Gln Arg Ala Leu Lys Asn
145                 150                 155                 160

Leu Tyr Gly Ile Glu Ala Ser Gln Thr Gln Lys Asn Lys Ile Val Asn
                165                 170                 175

Gly Asn Lys Leu Pro Val Gly Leu Arg Ile Ala Ile Asn Glu Arg Ala
            180                 185                 190

Ser Thr Ala Phe Arg Glu Leu Ile Glu Pro Tyr Leu Val Asp Cys Met
        195                 200                 205

Lys Tyr Lys Val Ser Asp Gly Lys Lys Gly Arg Leu Leu Val Leu Lys
    210                 215                 220

Gln Ala Asn Ser Ser Glu Asn Ile Ser Ala Glu Asn Ser Ile His Thr
225                 230                 235                 240

Glu Gly

<210> SEQ ID NO 140
<211> LENGTH: 222
<212> TYPE: PRT
<213> ORGANISM: Neochloris aquatica

<400> SEQUENCE: 140

Met Thr Thr Phe Asp Gln Leu Ser Trp Asn Gln Gln Gln Val Asp Leu
1               5                   10                  15

Ile Val Gly Thr Leu Leu Gly Asp Gly Asn Leu Ser Ser Glu Ser Leu
            20                  25                  30

Thr Ala Gly Trp Arg Tyr Arg Ala Ala Gln Lys Thr Glu His Leu Gln
        35                  40                  45

Tyr Leu Glu His Lys Tyr Gln Ile Leu Lys Asp Ser Cys Gly Thr Ser
    50                  55                  60

Ile Asn Asn Gly Asp Tyr Tyr Asp Pro Arg Thr Asn Lys Ile Tyr Lys
65                  70                  75                  80

Arg His Tyr Phe Asn Thr Leu Val His Pro Asp Phe Lys Phe Phe Gly
                85                  90                  95

Glu Met Phe Tyr Thr Trp Asp Pro Ile Leu Gln Lys Tyr Lys Lys Asp
            100                 105                 110

Val Pro Val Asp Ile His Lys Tyr Leu Thr Pro Ala Ala Ile Ala Tyr
        115                 120                 125

Phe Tyr Met Asp Asp Gly Ala Leu Lys Trp Lys Gly Gln Ser Asn Ala
    130                 135                 140

Met Arg Ile Cys Thr Glu Ser Phe Ser Glu Glu Gly Val Lys Arg Leu
145                 150                 155                 160

Gln Ala Ala Phe Trp Cys His Tyr Lys Ile Tyr Val Ser Leu Thr Pro
                165                 170                 175

His Lys Lys Asn Gly Gln Phe Val Gly Tyr Arg Leu Phe Ile Asn Glu
            180                 185                 190

Glu Asn Ser Ser Arg Phe Arg Thr Leu Val Ala Pro His Leu Val His
        195                 200                 205

Cys Met Arg Tyr Lys Val Ser Asp Gly Asn Tyr Gly Thr Leu
    210                 215                 220

<210> SEQ ID NO 141
```

<211> LENGTH: 194
<212> TYPE: PRT
<213> ORGANISM: Desulfurococcus mobilis

<400> SEQUENCE: 141

```
Met His Asn Asn Glu Asn Val Ser Gly Ile Ser Ala Tyr Leu Leu Gly
1               5                   10                  15

Leu Ile Ile Gly Asp Gly Gly Leu Tyr Lys Leu Lys Tyr Lys Gly Asn
            20                  25                  30

Arg Ser Glu Tyr Arg Val Val Ile Thr Gln Lys Ser Glu Asn Leu Ile
        35                  40                  45

Lys Gln His Ile Ala Pro Leu Met Gln Phe Leu Ile Asp Glu Leu Asn
50                  55                  60

Val Lys Ser Lys Ile Gln Ile Val Lys Gly Asp Thr Arg Tyr Glu Leu
65                  70                  75                  80

Arg Val Ser Ser Lys Lys Leu Tyr Tyr Tyr Phe Ala Asn Met Leu Glu
                85                  90                  95

Arg Ile Arg Leu Phe Asn Met Arg Glu Gln Ile Ala Phe Ile Lys Gly
            100                 105                 110

Leu Tyr Val Ala Glu Gly Asp Lys Thr Leu Lys Arg Leu Arg Ile Trp
        115                 120                 125

Asn Lys Asn Lys Ala Leu Leu Glu Ile Val Ser Arg Trp Leu Asn Asn
130                 135                 140

Leu Gly Val Arg Asn Thr Ile His Leu Asp Asp His Arg His Gly Val
145                 150                 155                 160

Tyr Val Leu Asn Ile Ser Leu Arg Asp Arg Ile Lys Phe Val His Thr
                165                 170                 175

Ile Leu Ser Ser His Leu Asn Pro Leu Pro Pro Glu Arg Ala Gly Gly
            180                 185                 190

Tyr Thr
```

<210> SEQ ID NO 142
<211> LENGTH: 234
<212> TYPE: PRT
<213> ORGANISM: Thermoproteus sp.
<220> FEATURE:
<221> NAME/KEY: misc_feature
<222> LOCATION: (185)..(185)
<223> OTHER INFORMATION: Xaa can be any naturally occurring amino acid

<400> SEQUENCE: 142

```
Met Ser Val Ala Tyr Leu Leu Gly Leu Ile Val Gly Asp Gly Gly Leu
1               5                   10                  15

Tyr Ala Leu Arg Tyr Arg Gly Gly Arg Thr Glu Tyr Arg Val Val Ile
            20                  25                  30

Thr Gln Lys Asp Glu Arg Val Val Glu Lys Ala Val Val Met Leu Glu
        35                  40                  45

Ala Leu Leu Arg Glu Leu Gly Leu Lys Ser Arg Val Gln Val Ile Arg
50                  55                  60

Gly Arg Ser Arg Thr Glu Val Arg Val Ser Ser Lys Ala Leu Trp Gln
65                  70                  75                  80

Phe Phe Asn Asn Val Leu Ser Asn Leu Glu Gly Phe Gln Pro Ser Glu
                85                  90                  95

Arg Ala Ala Phe Ile Glu Gly Leu Tyr Asp Ala Glu Gly Asp Lys Ser
            100                 105                 110

Gly Arg Arg Ala Arg Ile Trp Asn Lys Asn Leu Arg Leu Leu Glu Leu
        115                 120                 125
```

Val Lys Asn Trp Leu Ser Glu Phe Gly Ile Glu Ser Thr Ile His Leu
    130                 135                 140

Asp Asp Lys Arg His Gly Val Tyr Val Leu Glu Val Pro Ser Pro Tyr
145                 150                 155                 160

Arg Asp Arg Phe Phe Lys Leu Ile His Pro Pro Gln Pro Pro Asp Ser
                165                 170                 175

Ser Gly Val His Glu Trp Ile Asn Xaa Val Pro Thr Val Pro Ala Arg
            180                 185                 190

Gly Pro Ala Asn Pro Pro Gly Ala Gln Ser Trp Asp Pro Arg Arg
        195                 200             205

Gly Glu Lys Ser Leu Trp Ser Phe Thr Ala Ala Cys Arg Cys Gly Gly
    210                 215                 220

Ala Gly Asp Ala Glu Arg Arg Gln Glu Gln
225                 230

<210> SEQ ID NO 143
<211> LENGTH: 234
<212> TYPE: PRT
<213> ORGANISM: Thermoproteus sp.

<400> SEQUENCE: 143

Met Ser Val Ala Tyr Leu Leu Gly Leu Ile Val Gly Asp Gly Gly Leu
1               5                   10                  15

Tyr Ala Leu Arg Tyr Arg Gly Gly Arg Thr Glu Tyr Arg Val Val Ile
            20                  25                  30

Thr Gln Lys Asp Glu Gly Val Val Glu Lys Ala Val Val Met Leu Glu
        35                  40                  45

Ala Leu Leu Arg Glu Leu Gly Leu Lys Ser Arg Val Gln Val Ile Arg
    50                  55                  60

Gly Arg Ser Arg Thr Glu Val Arg Val Ser Ser Lys Ala Leu Trp Gln
65                  70                  75                  80

Phe Phe Asn Asn Val Leu Ser Asn Leu Glu Gly Phe Gln Pro Ser Glu
                85                  90                  95

Arg Ala Ala Phe Ile Glu Gly Leu Tyr Asp Ala Glu Gly Asp Lys Ser
            100                 105                 110

Gly Arg Arg Ala Arg Ile Trp Asn Lys Asn Leu Gln Leu Leu Glu Leu
        115                 120                 125

Val Lys Asn Trp Leu Ser Glu Phe Gly Ile Glu Ser Thr Ile Tyr Leu
    130                 135                 140

Asp Asp Lys Arg His Gly Val Tyr Val Leu Glu Val Pro Ser Pro Tyr
145                 150                 155                 160

Arg Asp Arg Phe Phe Lys Leu Ile His Pro Pro Gln Pro Pro Asp Ser
                165                 170                 175

Ser Gly Val His Glu Trp Ile Asn Glu Val Pro Thr Val Pro Ala Arg
            180                 185                 190

Gly Pro Ala Asn Pro Pro Gly Ala Gln Ser Trp Asp Pro Arg Arg
        195                 200             205

Gly Glu Lys Ser Leu Trp Ser Phe Thr Ala Ala Cys Arg Cys Gly Gly
    210                 215                 220

Ala Gly Asp Ala Glu Arg Arg Gln Glu Gln
225                 230

<210> SEQ ID NO 144
<211> LENGTH: 235
<212> TYPE: PRT

<213> ORGANISM: Pyrobaculum calidifontis

<400> SEQUENCE: 144

| Met | Ser | Ser | Val | Ala | Tyr | Leu | Leu | Gly | Leu | Ile | Val | Gly | Asp | Gly | Gly |
|---|---|---|---|---|---|---|---|---|---|---|---|---|---|---|---|
| 1 | | | | 5 | | | | | 10 | | | | | 15 | |

Leu Tyr Leu Leu Arg Tyr Lys Gly Gly Arg Thr Glu Tyr Arg Val Val
          20                  25                  30

Val Thr Gln Lys Asp Ala Ala Ile Ala Glu Asn Ala Ala Lys Met Phe
         35                  40                  45

His Ser Leu Leu Lys Glu Leu Gly Leu Gly Ser Lys Val Gln Val Ile
 50                  55                  60

Ser Gly Arg Thr Arg Val Glu Val Arg Val Ser Ser Lys Arg Leu Trp
 65                  70                  75                  80

Gln Leu Phe Asn Asp Lys Leu Ala Asn Leu Glu Gly Leu Ala Pro Asp
              85                  90                  95

Glu Arg Ile Ala Phe Ile Arg Gly Leu Tyr Asp Ala Glu Gly Asp Lys
             100                 105                 110

Thr Gly Arg Arg Ala Arg Leu Trp Asn Lys Asn Arg Arg Leu Leu Asp
             115                 120                 125

Leu Val Gly Ser Trp Leu Arg Glu Leu Gly Ile Glu Ser Arg Val Tyr
        130                 135                 140

Leu Asp Asp Lys Arg His Gly Val Tyr Val Leu Glu Val Pro Ser Pro
145                 150                 155                 160

Tyr Arg Arg Arg Phe Phe Glu Leu Leu Tyr Pro Pro Gln Pro Pro Asp
                165                 170                 175

Ser Ser Gly Val His Glu Trp Ile Asn Glu Val Pro Thr Val Pro Ala
            180                 185                 190

Arg Gly Pro Ala Asn Pro Pro Gly Ala Gln Ser Trp Asp Pro Arg
        195                 200                 205

Arg Gly Glu Lys Ser Leu Trp Ser Phe Thr Ala Ala Cys Arg Cys Gly
    210                 215                 220

Gly Ala Gly Gly Ala Glu Arg Arg Trp Glu Arg
225                 230                 235

<210> SEQ ID NO 145
<211> LENGTH: 1071
<212> TYPE: PRT
<213> ORGANISM: Saccharomyces cerevisiae

<400> SEQUENCE: 145

Met Ala Gly Ala Ile Glu Asn Ala Arg Lys Glu Ile Lys Arg Ile Ser
1               5                   10                  15

Leu Glu Asp His Ala Glu Ser Glu Tyr Gly Ala Ile Tyr Ser Val Ser
            20                  25                  30

Gly Pro Val Val Ile Ala Glu Asn Met Ile Gly Cys Ala Met Tyr Glu
        35                  40                  45

Leu Val Lys Val Gly His Asp Asn Leu Val Gly Glu Val Ile Arg Ile
    50                  55                  60

Asp Gly Asp Lys Ala Thr Ile Gln Val Tyr Glu Glu Thr Ala Gly Leu
65                  70                  75                  80

Thr Val Gly Asp Pro Val Leu Arg Thr Gly Lys Pro Leu Ser Val Glu
                85                  90                  95

Leu Gly Pro Gly Leu Met Glu Thr Ile Tyr Asp Gly Ile Gln Arg Pro
            100                 105                 110

Leu Lys Ala Ile Lys Glu Glu Ser Gln Ser Ile Tyr Ile Pro Arg Gly

-continued

```
            115                 120                 125
Ile Asp Thr Pro Ala Leu Asp Arg Thr Ile Lys Trp Gln Phe Thr Pro
130                 135                 140

Gly Lys Phe Gln Val Gly Asp His Ile Ser Gly Asp Ile Tyr Gly
145                 150                 155                 160

Ser Val Phe Glu Asn Ser Leu Ile Ser Ser His Lys Ile Leu Leu Pro
                165                 170                 175

Pro Arg Ser Arg Gly Thr Ile Thr Trp Ile Ala Pro Ala Gly Glu Tyr
            180                 185                 190

Thr Leu Asp Glu Lys Ile Leu Glu Val Glu Phe Asp Gly Lys Lys Ser
            195                 200                 205

Asp Phe Thr Leu Tyr His Thr Trp Pro Val Arg Val Pro Arg Pro Val
210                 215                 220

Thr Glu Lys Leu Ser Ala Asp Tyr Pro Leu Leu Thr Gly Gln Arg Val
225                 230                 235                 240

Leu Asp Ala Leu Phe Pro Cys Val Gln Gly Gly Thr Thr Cys Ile Pro
                245                 250                 255

Gly Ala Phe Gly Cys Gly Lys Thr Val Ile Ser Gln Ser Leu Ser Lys
                260                 265                 270

Tyr Ser Asn Ser Asp Ala Ile Ile Tyr Val Gly Cys Phe Ala Lys Gly
        275                 280                 285

Thr Asn Val Leu Met Ala Asp Gly Ser Ile Glu Cys Ile Glu Asn Ile
290                 295                 300

Glu Val Gly Asn Lys Val Met Gly Lys Asp Gly Arg Pro Arg Glu Val
305                 310                 315                 320

Ile Lys Leu Pro Arg Gly Arg Glu Thr Met Tyr Ser Val Val Gln Lys
                325                 330                 335

Ser Gln His Arg Ala His Lys Ser Asp Ser Ser Arg Glu Val Pro Glu
            340                 345                 350

Leu Leu Lys Phe Thr Cys Asn Ala Thr His Glu Leu Val Val Arg Thr
            355                 360                 365

Pro Arg Ser Val Arg Arg Leu Ser Arg Thr Ile Lys Gly Val Glu Tyr
        370                 375                 380

Phe Glu Val Ile Thr Phe Glu Met Gly Gln Lys Lys Ala Pro Asp Gly
385                 390                 395                 400

Arg Ile Val Glu Leu Val Lys Glu Val Ser Lys Ser Tyr Pro Ile Ser
                405                 410                 415

Glu Gly Pro Glu Arg Ala Asn Glu Leu Val Glu Ser Tyr Arg Lys Ala
            420                 425                 430

Ser Asn Lys Ala Tyr Phe Glu Trp Thr Ile Glu Ala Arg Asp Leu Ser
        435                 440                 445

Leu Leu Gly Ser His Val Arg Lys Ala Thr Tyr Gln Thr Tyr Ala Pro
    450                 455                 460

Ile Leu Tyr Glu Asn Asp His Phe Phe Asp Tyr Met Gln Lys Ser Lys
465                 470                 475                 480

Phe His Leu Thr Ile Glu Gly Pro Lys Val Leu Ala Tyr Leu Leu Gly
                485                 490                 495

Leu Trp Ile Gly Asp Gly Leu Ser Asp Arg Ala Thr Phe Ser Val Asp
            500                 505                 510

Ser Arg Asp Thr Ser Leu Met Glu Arg Val Thr Glu Tyr Ala Glu Lys
        515                 520                 525

Leu Asn Leu Cys Ala Glu Tyr Lys Asp Arg Lys Glu Pro Gln Val Ala
    530                 535                 540
```

```
Lys Thr Val Asn Leu Tyr Ser Lys Val Val Arg Gly Asn Gly Ile Arg
545                 550                 555                 560

Asn Asn Leu Asn Thr Glu Asn Pro Leu Trp Asp Ala Ile Val Gly Leu
                565                 570                 575

Gly Phe Leu Lys Asp Gly Val Lys Asn Ile Pro Ser Phe Leu Ser Thr
            580                 585                 590

Asp Asn Ile Gly Thr Arg Glu Thr Phe Leu Ala Gly Leu Ile Asp Ser
            595                 600                 605

Asp Gly Tyr Val Thr Asp Glu His Gly Ile Lys Ala Thr Ile Lys Thr
            610                 615                 620

Ile His Thr Ser Val Arg Asp Gly Leu Val Ser Leu Ala Arg Ser Leu
625                 630                 635                 640

Gly Leu Val Val Ser Val Asn Ala Glu Pro Ala Lys Val Asp Met Asn
                645                 650                 655

Gly Thr Lys His Lys Ile Ser Tyr Ala Ile Tyr Met Ser Gly Gly Asp
            660                 665                 670

Val Leu Leu Asn Val Leu Ser Lys Cys Ala Gly Ser Lys Lys Phe Arg
            675                 680                 685

Pro Ala Pro Ala Ala Phe Ala Arg Glu Cys Arg Gly Phe Tyr Phe
690                 695                 700

Glu Leu Gln Glu Leu Lys Glu Asp Asp Tyr Tyr Gly Ile Thr Leu Ser
705                 710                 715                 720

Asp Asp Ser Asp His Gln Phe Leu Leu Ala Asn Gln Val Val His
                725                 730                 735

Asn Cys Gly Glu Arg Gly Asn Glu Met Ala Glu Val Leu Met Glu Phe
            740                 745                 750

Pro Glu Leu Tyr Thr Glu Met Ser Gly Thr Lys Glu Pro Ile Met Lys
            755                 760                 765

Arg Thr Thr Leu Val Ala Asn Thr Ser Asn Met Pro Val Ala Ala Arg
770                 775                 780

Glu Ala Ser Ile Tyr Thr Gly Ile Thr Leu Ala Glu Tyr Phe Arg Asp
785                 790                 795                 800

Gln Gly Lys Asn Val Ser Met Ile Ala Asp Ser Ser Ser Arg Trp Ala
                805                 810                 815

Glu Ala Leu Arg Glu Ile Ser Gly Arg Leu Gly Glu Met Pro Ala Asp
            820                 825                 830

Gln Gly Phe Pro Ala Tyr Leu Gly Ala Lys Leu Ala Ser Phe Tyr Glu
            835                 840                 845

Arg Ala Gly Lys Ala Val Ala Leu Gly Ser Pro Asp Arg Thr Gly Ser
850                 855                 860

Val Ser Ile Val Ala Ala Val Ser Pro Ala Gly Gly Asp Phe Ser Asp
865                 870                 875                 880

Pro Val Thr Thr Ala Thr Leu Gly Ile Thr Gln Val Phe Trp Gly Leu
                885                 890                 895

Asp Lys Lys Leu Ala Gln Arg Lys His Phe Pro Ser Ile Asn Thr Ser
            900                 905                 910

Val Ser Tyr Ser Lys Tyr Thr Asn Val Leu Asn Lys Phe Tyr Asp Ser
            915                 920                 925

Asn Tyr Pro Glu Phe Pro Val Leu Arg Asp Arg Met Lys Glu Ile Leu
            930                 935                 940

Ser Asn Ala Glu Glu Leu Glu Gln Val Val Gln Leu Val Gly Lys Ser
945                 950                 955                 960
```

Ala Leu Ser Asp Ser Asp Lys Ile Thr Leu Asp Val Ala Thr Leu Ile
                965                 970                 975

Lys Glu Asp Phe Leu Gln Gln Asn Gly Tyr Ser Thr Tyr Asp Ala Phe
            980                 985                 990

Cys Pro Ile Trp Lys Thr Phe Asp Met Met Arg Ala Phe Ile Ser Tyr
        995                1000                1005

His Asp Glu Ala Gln Lys Ala Val Ala Asn Gly Ala Asn Trp Ser
   1010                1015                1020

Lys Leu Ala Asp Ser Thr Gly Asp Val Lys His Ala Val Ser Ser
   1025                1030                1035

Ser Lys Phe Phe Glu Pro Ser Arg Gly Glu Lys Glu Val His Gly
   1040                1045                1050

Glu Phe Glu Lys Leu Leu Ser Thr Met Gln Glu Arg Phe Ala Glu
   1055                1060                1065

Ser Thr Asp
   1070

<210> SEQ ID NO 146
<211> LENGTH: 1022
<212> TYPE: PRT
<213> ORGANISM: Saccharomyces cerevisiae
<220> FEATURE:
<221> NAME/KEY: misc_feature
<222> LOCATION: (318)..(318)
<223> OTHER INFORMATION: Xaa can be any naturally occurring amino acid

<400> SEQUENCE: 146

Gly Ala Ile Tyr Ser Val Ser Gly Pro Val Val Ile Ala Glu Asn Met
1               5                  10                  15

Ile Gly Cys Ala Met Tyr Glu Leu Val Lys Val Gly His Asp Asn Leu
            20                  25                  30

Val Gly Glu Val Ile Arg Ile Asp Gly Asp Lys Ala Thr Ile Gln Val
        35                  40                  45

Tyr Glu Glu Thr Ala Gly Leu Thr Val Gly Asp Pro Val Leu Arg Thr
    50                  55                  60

Gly Lys Pro Leu Ser Val Glu Leu Gly Pro Gly Leu Met Glu Thr Ile
65                  70                  75                  80

Tyr Asp Gly Ile Gln Arg Pro Leu Lys Ala Ile Lys Glu Glu Ser Gln
                85                  90                  95

Ser Ile Tyr Ile Pro Arg Gly Ile Asp Thr Pro Ala Leu Asp Arg Thr
            100                 105                 110

Ile Lys Trp Gln Phe Thr Pro Gly Lys Phe Gln Val Gly Asp His Ile
        115                 120                 125

Ser Gly Gly Asp Ile Tyr Gly Ser Val Phe Glu Asn Ser Leu Ile Ser
    130                 135                 140

Ser His Lys Ile Leu Leu Pro Pro Arg Ser Arg Gly Thr Ile Thr Trp
145                 150                 155                 160

Ile Ala Pro Ala Gly Glu Tyr Thr Leu Asp Glu Lys Ile Leu Glu Val
                165                 170                 175

Glu Phe Asp Gly Lys Lys Ser Asp Phe Thr Leu Tyr His Thr Trp Pro
            180                 185                 190

Val Arg Val Pro Arg Pro Val Thr Glu Lys Leu Ser Ala Asp Tyr Pro
        195                 200                 205

Leu Leu Thr Gly Gln Arg Val Leu Asp Ala Leu Phe Pro Cys Val Gln
    210                 215                 220

Gly Gly Thr Thr Cys Ile Pro Gly Ala Phe Gly Cys Gly Lys Thr Val

```
                225                 230                 235                 240
        Ile Ser Gln Ser Leu Ser Lys Tyr Ser Asn Ser Asp Ala Ile Ile Tyr
                        245                 250                 255

Val Gly Cys Phe Ala Lys Gly Thr Asn Val Leu Met Ala Asp Gly Ser
                        260                 265                 270

Ile Glu Cys Ile Glu Asn Ile Glu Val Gly Asn Lys Val Met Gly Lys
                        275                 280                 285

Asp Gly Arg Pro Arg Glu Val Ile Lys Leu Pro Arg Gly Arg Glu Thr
                        290                 295                 300

Met Tyr Ser Val Val Gln Lys Ser Gln His Arg Ala His Xaa Ser Asp
        305                 310                 315                 320

Ser Ser Arg Glu Val Pro Glu Leu Leu Lys Phe Thr Cys Asn Ala Thr
                        325                 330                 335

His Glu Leu Val Val Arg Thr Pro Arg Ser Val Arg Arg Leu Ser Arg
                        340                 345                 350

Thr Ile Lys Gly Val Glu Tyr Phe Glu Val Ile Thr Phe Glu Met Gly
                        355                 360                 365

Gln Lys Lys Ala Pro Asp Gly Arg Ile Val Glu Leu Val Lys Glu Val
                        370                 375                 380

Ser Lys Ser Tyr Pro Ile Ser Glu Gly Pro Glu Arg Ala Asn Glu Leu
        385                 390                 395                 400

Val Glu Ser Tyr Arg Lys Ala Ser Asn Lys Ala Tyr Phe Glu Trp Thr
                        405                 410                 415

Ile Glu Ala Arg Asp Leu Ser Leu Leu Gly Ser His Val Arg Lys Ala
                        420                 425                 430

Thr Tyr Gln Thr Tyr Ala Pro Ile Leu Tyr Glu Asn Asp His Phe Phe
                        435                 440                 445

Asp Tyr Met Gln Lys Ser Lys Phe His Leu Thr Ile Glu Gly Pro Lys
                        450                 455                 460

Val Leu Ala Tyr Leu Leu Gly Leu Trp Ile Gly Asp Gly Leu Ser Asp
        465                 470                 475                 480

Arg Ala Thr Phe Ser Val Asp Ser Arg Asp Thr Ser Leu Met Glu Arg
                        485                 490                 495

Val Thr Glu Tyr Ala Glu Lys Leu Asn Leu Cys Ala Glu Tyr Lys Asp
                        500                 505                 510

Arg Lys Glu Pro Gln Val Ala Lys Thr Val Asn Leu Tyr Ser Lys Val
                        515                 520                 525

Val Arg Gly Asn Gly Ile Arg Asn Asn Leu Asn Thr Glu Asn Pro Leu
        530                 535                 540

Trp Asp Ala Ile Val Gly Leu Gly Phe Leu Lys Asp Gly Val Lys Asn
        545                 550                 555                 560

Ile Pro Ser Phe Leu Ser Thr Asp Asn Ile Gly Thr Arg Glu Thr Phe
                        565                 570                 575

Leu Ala Gly Leu Ile Asp Ser Asp Gly Tyr Val Thr Asp Glu His Gly
                        580                 585                 590

Ile Lys Ala Thr Ile Lys Thr Ile His Thr Ser Val Arg Asp Gly Leu
                        595                 600                 605

Val Ser Leu Ala Arg Ser Leu Gly Leu Val Val Ser Val Asn Ala Glu
                        610                 615                 620

Pro Ala Lys Val Asp Val Asn Gly Thr Lys His Lys Ile Ser Tyr Ala
        625                 630                 635                 640

Ile Tyr Met Ser Gly Gly Asp Val Leu Leu Asn Val Leu Ser Lys Cys
                        645                 650                 655
```

Ala Gly Ser Lys Lys Phe Arg Pro Ala Pro Ala Ala Phe Ala Arg
                660                 665                 670

Glu Cys Arg Gly Phe Tyr Phe Glu Leu Gln Glu Leu Lys Glu Asp Asp
            675                 680                 685

Tyr Tyr Gly Ile Thr Leu Ser Asp Asp Ser Asp His Gln Phe Leu Leu
        690                 695                 700

Ala Asn Gln Val Val His Asn Cys Gly Glu Arg Gly Asn Glu Met
705                 710                 715                 720

Ala Glu Val Leu Met Glu Phe Pro Glu Leu Tyr Thr Glu Met Ser Gly
                725                 730                 735

Thr Lys Glu Pro Ile Met Lys Arg Thr Thr Leu Val Ala Asn Thr Ser
            740                 745                 750

Asn Met Pro Val Ala Ala Arg Glu Ala Ser Ile Tyr Thr Gly Ile Thr
        755                 760                 765

Leu Ala Glu Tyr Phe Arg Asp Gln Gly Lys Asn Val Ser Met Ile Ala
    770                 775                 780

Asp Ser Ser Ser Arg Trp Ala Glu Ala Leu Arg Glu Ile Ser Gly Arg
785                 790                 795                 800

Leu Gly Glu Met Pro Ala Asp Gln Gly Phe Pro Ala Tyr Leu Gly Ala
                805                 810                 815

Lys Leu Ala Ser Phe Tyr Glu Arg Ala Gly Lys Ala Val Ala Leu Gly
            820                 825                 830

Ser Pro Asp Arg Thr Gly Ser Val Ser Ile Val Ala Ala Val Ser Pro
        835                 840                 845

Ala Gly Gly Asp Phe Ser Asp Pro Val Thr Thr Ala Thr Leu Gly Ile
    850                 855                 860

Thr Gln Val Phe Trp Gly Leu Asp Lys Lys Leu Ala Gln Arg Lys His
865                 870                 875                 880

Phe Pro Ser Ile Asn Thr Ser Val Ser Tyr Ser Lys Tyr Thr Asn Val
                885                 890                 895

Leu Asn Lys Phe Tyr Asp Ser Asn Tyr Pro Glu Phe Pro Val Leu Arg
            900                 905                 910

Asp Arg Met Lys Glu Ile Leu Ser Asn Ala Glu Leu Glu Gln Val
        915                 920                 925

Val Gln Leu Val Gly Lys Ser Ala Leu Ser Asp Ser Asp Lys Ile Thr
    930                 935                 940

Leu Asp Val Ala Thr Leu Ile Lys Glu Asp Phe Leu Gln Gln Asn Gly
945                 950                 955                 960

Tyr Ser Thr Tyr Asp Ala Phe Cys Pro Ile Trp Lys Thr Phe Asp Met
                965                 970                 975

Met Arg Ala Phe Ile Ser Tyr His Asp Glu Ala Gln Lys Ala Val Ala
            980                 985                 990

Asn Gly Ala Asn Trp Ser Lys Leu Ala Asp Ser Thr Gly Asp Val Lys
        995                 1000                1005

His Ala Val Ser Ser Ser Lys Phe Phe Glu Pro Ser Arg Gly
    1010                1015                1020

<210> SEQ ID NO 147
<211> LENGTH: 1045
<212> TYPE: PRT
<213> ORGANISM: Saccharomyces pastorianus

<400> SEQUENCE: 147

Ile Ser Leu Glu Asp His Ala Glu Ser Glu Tyr Gly Ala Ile Tyr Ser

-continued

```
1               5                   10                  15
Val Ser Gly Pro Val Ile Ala Glu Asn Met Ile Gly Cys Ala Met
            20                  25                  30
Tyr Glu Leu Val Lys Val Gly His Asp Asn Leu Val Gly Glu Val Ile
            35                  40                  45
Arg Ile Asp Gly Asp Lys Ala Thr Ile Gln Val Tyr Glu Glu Thr Ala
50                  55                  60
Gly Leu Thr Val Gly Asp Pro Val Leu Arg Thr Gly Lys Pro Leu Ser
65                  70                  75                  80
Val Glu Leu Gly Pro Gly Leu Met Glu Thr Ile Tyr Asp Gly Ile Gln
            85                  90                  95
Arg Pro Leu Lys Ala Ile Lys Glu Glu Ser Gln Ser Ile Tyr Ile Pro
            100                 105                 110
Arg Gly Ile Asp Thr Pro Ala Leu Asp Arg Thr Ile Lys Trp Gln Phe
            115                 120                 125
Thr Pro Gly Lys Phe Gln Val Gly Asp His Ile Ser Gly Asp Ile
            130                 135                 140
Tyr Gly Ser Val Phe Glu Asn Ser Leu Ile Ser Ser His Lys Ile Leu
145                 150                 155                 160
Leu Pro Pro Arg Ser Arg Gly Thr Ile Thr Trp Ile Ala Pro Ala Gly
            165                 170                 175
Glu Tyr Thr Leu Asp Glu Lys Ile Leu Glu Val Glu Phe Asp Gly Lys
            180                 185                 190
Lys Ser Asp Phe Thr Leu Tyr His Thr Trp Pro Gly Arg Val Pro Arg
            195                 200                 205
Pro Val Thr Glu Lys Leu Ser Ala Asp Tyr Pro Leu Leu Thr Gly Gln
            210                 215                 220
Arg Val Leu Asp Ala Leu Phe Pro Cys Val Gln Gly Gly Thr Thr Cys
225                 230                 235                 240
Ile Pro Gly Ala Phe Gly Cys Gly Lys Thr Val Ile Ser Gln Ser Leu
            245                 250                 255
Ser Lys Tyr Ser Asn Ser Asp Ala Ile Ile Tyr Val Gly Cys Phe Ala
            260                 265                 270
Lys Gly Thr Asn Val Leu Met Ala Asp Gly Ser Ile Glu Cys Ile Glu
            275                 280                 285
Asn Ile Glu Val Gly Asn Lys Val Met Gly Lys Asp Gly Arg Pro Arg
            290                 295                 300
Glu Val Ile Lys Leu Pro Arg Gly Ser Glu Thr Met Tyr Ser Val Val
305                 310                 315                 320
Gln Lys Ser Gln His Arg Ala His Lys Ser Asp Ser Ser Arg Glu Met
            325                 330                 335
Pro Glu Leu Leu Lys Phe Thr Cys Asn Ala Thr His Glu Leu Val Val
            340                 345                 350
Arg Thr Pro Arg Ser Val Arg Arg Leu Ser Arg Thr Ile Lys Gly Val
            355                 360                 365
Glu Tyr Phe Glu Val Ile Thr Phe Glu Met Gly Gln Lys Lys Ala Pro
            370                 375                 380
Asp Gly Arg Ile Val Glu Leu Val Lys Glu Val Ser Lys Ser Tyr Pro
385                 390                 395                 400
Val Ser Glu Gly Pro Glu Arg Ala Asn Glu Leu Val Glu Ser Tyr Arg
            405                 410                 415
Lys Ala Ser Asn Lys Ala Tyr Phe Glu Trp Thr Ile Glu Ala Arg Asp
            420                 425                 430
```

Leu Ser Leu Leu Gly Ser His Val Arg Lys Ala Thr Tyr Gln Thr Tyr
            435                 440                 445

Ala Pro Ile Leu Tyr Glu Asn Asp His Phe Phe Asp Tyr Met Gln Lys
450                 455                 460

Ser Lys Phe His Leu Thr Ile Glu Gly Pro Lys Val Leu Ala Tyr Leu
465                 470                 475                 480

Leu Gly Leu Trp Ile Gly Asp Gly Leu Ser Asp Arg Ala Thr Phe Ser
                485                 490                 495

Val Asp Ser Arg Asp Thr Ser Leu Met Glu Arg Val Thr Glu Tyr Ala
            500                 505                 510

Glu Lys Leu Asn Leu Cys Ala Glu Tyr Lys Asp Arg Lys Glu Pro Gln
            515                 520                 525

Val Ala Lys Thr Val Asn Leu Tyr Ser Lys Val Arg Gly Asn Gly
            530                 535                 540

Val Arg Asn Asn Leu Asn Thr Glu Asn Pro Leu Trp Asp Ala Ile Ile
545                 550                 555                 560

Gly Leu Gly Phe Leu Lys Asp Gly Val Lys Asn Ile Pro Ser Phe Leu
                565                 570                 575

Ser Thr Asp Asn Ile Gly Thr Arg Glu Thr Phe Leu Ala Gly Leu Ile
            580                 585                 590

Asp Ser Asp Gly Tyr Val Thr Asp Glu His Gly Ile Lys Ala Thr Ile
            595                 600                 605

Lys Thr Ile His Thr Ser Val Arg Asp Gly Leu Val Ser Leu Ala Arg
610                 615                 620

Ser Leu Gly Leu Val Ala Ser Val Asn Ala Glu Pro Ala Lys Val Asp
625                 630                 635                 640

Met Asn Gly Thr Lys His Lys Ile Ser Tyr Ala Ile Tyr Met Ser Gly
                645                 650                 655

Gly Asp Val Leu Leu Asn Val Leu Ser Lys Cys Ala Gly Ser Lys Lys
            660                 665                 670

Phe Arg Pro Ala Pro Val Ala Thr Phe Val Arg Glu Cys Gln Gly Phe
            675                 680                 685

Tyr Phe Glu Leu Gln Glu Leu Lys Glu Asn Asp Tyr Tyr Gly Ile Thr
            690                 695                 700

Leu Ser Asp Asp Ser Asp His Gln Phe Leu Leu Ala Asn Gln Val Val
705                 710                 715                 720

Val His Asn Cys Gly Glu Arg Gly Asn Glu Met Ala Glu Val Leu Met
                725                 730                 735

Glu Phe Pro Glu Leu Tyr Thr Glu Met Ser Gly Thr Lys Glu Pro Ile
            740                 745                 750

Met Lys Arg Thr Thr Leu Val Ala Asn Thr Ser Asn Met Pro Val Ala
            755                 760                 765

Ala Arg Glu Ala Ser Ile Tyr Thr Gly Ile Thr Leu Ala Glu Tyr Phe
770                 775                 780

Arg Asp Gln Gly Lys Asn Val Ser Met Ile Ala Asp Ser Ser Ser Arg
785                 790                 795                 800

Trp Ala Glu Ala Leu Arg Glu Ile Ser Gly Arg Leu Gly Glu Met Pro
                805                 810                 815

Ala Asp Gln Gly Phe Pro Ala Tyr Leu Gly Ala Lys Leu Ala Ser Phe
            820                 825                 830

Tyr Glu Arg Ala Gly Lys Ala Val Ala Leu Gly Ser Pro Asp Arg Thr
            835                 840                 845

```
Gly Ser Val Ser Ile Val Ala Ala Val Ser Pro Ala Gly Gly Asp Phe
        850                 855                 860

Ser Asp Pro Val Thr Thr Ala Thr Leu Gly Ile Thr Gln Val Phe Trp
865                 870                 875                 880

Gly Leu Asp Lys Lys Leu Ala Gln Arg Lys His Phe Pro Ser Ile Asn
                885                 890                 895

Thr Ser Val Ser Tyr Ser Lys Tyr Thr Asn Val Leu Asn Lys Phe Tyr
            900                 905                 910

Asp Ser Asn Tyr Pro Glu Phe Pro Val Leu Arg Asp Arg Met Lys Glu
                915                 920                 925

Ile Leu Ser Asn Ala Glu Glu Leu Gly Gln Val Gln Leu Val Gly
        930                 935                 940

Lys Ser Ala Leu Ser Asp Asp Lys Ile Thr Leu Asp Val Ala Thr Leu
945                 950                 955                 960

Ile Lys Glu Asp Phe Leu Gln Gln Asn Gly Tyr Ser Thr Tyr Asp Ala
                965                 970                 975

Phe Cys Pro Ile Trp Lys Thr Phe Asp Met Met Arg Ala Phe Ile Ser
                980                 985                 990

Tyr His Asp Glu Ala Gln Lys Ala  Val Ala Asn Gly Ala  Asn Trp Ser
            995                 1000                 1005

Lys Leu  Ala Asp Ser Thr Gly  Asp Val Lys His Ala  Val Ser Ser
    1010                 1015                 1020

Ser Lys  Phe Phe Glu Pro Ser  Arg Gly Glu Lys Glu  Val His Gly
    1025                 1030                 1035

Glu Phe  Glu Lys Leu Leu Ser
    1040                 1045

<210> SEQ ID NO 148
<211> LENGTH: 545
<212> TYPE: PRT
<213> ORGANISM: Saccharomyces cariocanus
<220> FEATURE:
<221> NAME/KEY: misc_feature
<222> LOCATION: (291)..(291)
<223> OTHER INFORMATION: Xaa can be any naturally occurring amino acid

<400> SEQUENCE: 148

Ile Ser Gln Ser Leu Ser Lys Tyr Ser Asn Ser Asp Ala Ile Ile Tyr
1               5                   10                  15

Val Gly Cys Phe Ala Lys Gly Thr Thr Val Leu Met Ala Asp Gly Ser
                20                  25                  30

Ile Glu Cys Ile Glu Asn Ile Lys Ile Gly Asp Lys Val Met Gly Lys
            35                  40                  45

Asp Gly Lys Pro Arg Glu Val Ile Lys Leu Pro Arg Gly Asn Glu Thr
    50                  55                  60

Met Tyr Ser Val Val Gln Lys Ser Gln His Arg Ala His Lys Thr Asp
65                  70                  75                  80

Ser Ser Arg Glu Val Pro Asp Leu Leu Lys Phe Thr Cys Asn Ser Thr
                85                  90                  95

His Glu Leu Val Val Arg Thr Pro Arg Ser Val Arg Arg Val Ser Arg
                100                 105                 110

Thr Met Lys Gly Val Glu Tyr Phe Glu Val Ile Ser Phe Glu Met Val
            115                 120                 125

Gln Lys Lys Val Pro Asp Gly Arg Ile Ile Glu Leu Val Lys Glu Val
    130                 135                 140

Ser Lys Ser Tyr Pro Ala Ser Glu Gly Pro Glu Arg Ala Asp Glu Leu
```

```
            145                 150                 155                 160
        Val Glu Ser Tyr Arg Lys Ala Ser Thr Lys Pro Tyr Phe Glu Trp Thr
                        165                 170                 175

Val Glu Ala Arg Asp Leu Ser Leu Leu Gly Ser His Val Arg Lys Ala
                        180                 185                 190

Thr Tyr Gln Thr Tyr Ala Pro Ile Leu Tyr Glu Asn Asp Tyr Phe Phe
                        195                 200                 205

Asn Tyr Met Glu Asn Ser Lys Phe His Pro Thr Ile Glu Ala Pro Lys
        210                 215                 220

Val Leu Ala Tyr Phe Leu Gly Leu Trp Ile Gly Asp Gly Leu Thr Asp
        225                 230                 235                 240

Arg Thr Thr Phe Ser Ile Asp Ser Arg Asp Thr Ser Leu Met Glu Arg
                        245                 250                 255

Val Thr Glu Tyr Ala Glu Lys Leu Asp Leu Cys Ala Glu Tyr Lys Asp
                        260                 265                 270

Arg Lys Glu Pro Lys Val Ala Lys Thr Val Asn Leu Tyr Ser Lys Ser
                        275                 280                 285

Val Arg Xaa Asn Gly Ile Arg Asn Asn Leu Asn Thr Glu Asn Pro Leu
        290                 295                 300

Trp Asp Ala Ile Val Gly Leu Gly Phe Leu Lys Asp Gly Val Lys Asn
        305                 310                 315                 320

Ile Pro Ser Phe Leu Ser Thr Asp Asn Ile Gly Thr Arg Glu Thr Phe
                        325                 330                 335

Leu Ala Gly Leu Ile Asp Ser Asp Gly Tyr Val Thr Asp Glu His Gly
                        340                 345                 350

Ile Thr Ala Thr Val Lys Thr Ile His Thr Ser Val Arg Asp Gly Leu
                        355                 360                 365

Val Ser Val Ala Arg Ser Gly Leu Val Ile Ser Val Asn Ala Glu
        370                 375                 380

Pro Ala Lys Ile Asp Met Ser Gly Thr Ser His Lys Met Cys Tyr Ala
        385                 390                 395                 400

Ile Tyr Met Ser Gly Gly Asp Ile Leu Leu Asn Val Leu Ser Lys Cys
                        405                 410                 415

Ala Ser Phe Lys Lys Phe Arg Pro Ala Pro Val Ala Pro Val Arg
                        420                 425                 430

Glu Cys Arg Gly Phe Tyr Phe Glu Leu Gln Glu Leu Glu Glu Asp Asp
                        435                 440                 445

Tyr Tyr Gly Ile Thr Leu Ser Asp Asp Ser Asp His Gln Phe Leu Leu
                        450                 455                 460

Ala Asn Gln Val Val His Asn Cys Gly Glu Arg Gly Asn Glu Met
        465                 470                 475                 480

Ala Glu Val Leu Met Glu Phe Pro Glu Leu Tyr Thr Glu Met Ser Gly
                        485                 490                 495

Thr Lys Glu Pro Ile Met Lys Arg Thr Thr Leu Val Ala Asn Thr Ser
                        500                 505                 510

Asn Met Pro Val Ala Ala Arg Glu Ala Ser Ile Tyr Thr Gly Ile Thr
                        515                 520                 525

Leu Ala Glu Tyr Phe Arg Asp Gln Gly Lys Asn Val Ser Met Ile Ala
                        530                 535                 540

Asp
        545

<210> SEQ ID NO 149
```

```
<211> LENGTH: 547
<212> TYPE: PRT
<213> ORGANISM: Zygosaccharomyces bailii
<220> FEATURE:
<221> NAME/KEY: misc_feature
<222> LOCATION: (185)..(185)
<223> OTHER INFORMATION: Xaa can be any naturally occurring amino acid

<400> SEQUENCE: 149
```

| | | | | | | | | | | | | | | | |
|---|---|---|---|---|---|---|---|---|---|---|---|---|---|---|---|
| Ile | Ser | Gln | Ser | Leu | Ser | Lys | Tyr | Ser | Asn | Ser | Asp | Ala | Ile | Ile | Tyr |
| 1 | | | | 5 | | | | | 10 | | | | | 15 | |
| Val | Gly | Cys | Phe | Ala | Lys | Gly | Thr | Glu | Val | Met | Met | His | Asp | Gly | Ser |
| | | | 20 | | | | | 25 | | | | | 30 | | |
| Val | Lys | Ala | Ile | Glu | Thr | Ile | Glu | Ala | Gly | Glu | Ala | Val | Met | Gly | Thr |
| | | 35 | | | | | 40 | | | | | 45 | | | |
| Asp | Gly | Gln | Pro | Arg | Lys | Val | Val | Gly | Leu | Pro | Arg | Gly | Arg | Glu | Val |
| | 50 | | | | | 55 | | | | | 60 | | | | |
| Met | Tyr | Lys | Val | Ser | Gln | Lys | Thr | Ala | His | Arg | Val | His | Lys | Thr | Asp |
| 65 | | | | | 70 | | | | | 75 | | | | | 80 |
| Glu | Thr | Arg | Ala | Ala | Pro | Val | Ala | Leu | Phe | Glu | Tyr | Asn | Cys | Asn | Ala |
| | | | | 85 | | | | | 90 | | | | | 95 | |
| Thr | His | Lys | Leu | Val | Val | Arg | Thr | Pro | Arg | Ser | Cys | Arg | Ser | Ile | Thr |
| | | | 100 | | | | | 105 | | | | | 110 | | |
| Arg | Lys | Met | Gln | Gly | Val | Asp | Tyr | Asn | Glu | Val | Ile | Phe | Phe | Asp | Leu |
| | | 115 | | | | | 120 | | | | | 125 | | | |
| Lys | Lys | Lys | Lys | Leu | Glu | Asp | Gly | Arg | Glu | Ile | Glu | Ile | Val | Lys | Glu |
| 130 | | | | | 135 | | | | | 140 | | | | | |
| Val | Ser | Arg | Ser | Tyr | Pro | Ala | Ala | Glu | Gly | Ala | Glu | Lys | Ala | Ala | Gln |
| 145 | | | | | 150 | | | | | 155 | | | | | 160 |
| Met | Val | Lys | Asp | Tyr | Tyr | Asp | Ala | Ala | Arg | Gly | Lys | Glu | Phe | Phe | Glu |
| | | | | 165 | | | | | 170 | | | | | 175 | |
| Trp | Thr | Ile | Glu | Ala | Arg | Asp | Val | Xaa | Glu | Leu | Gly | Ala | His | Val | Arg |
| | | | 180 | | | | | 185 | | | | | 190 | | |
| Lys | Ala | Thr | His | Gln | Val | Tyr | Ala | Pro | Val | Leu | Tyr | Glu | Ser | Asp | Phe |
| | | 195 | | | | | 200 | | | | | 205 | | | |
| Phe | Phe | His | Tyr | Val | Lys | Asn | Ser | Lys | Phe | Ala | Leu | Arg | Ser | Glu | Ala |
| | 210 | | | | | 215 | | | | | 220 | | | | |
| Ser | Thr | Ala | Leu | Ala | Tyr | Leu | Leu | Gly | Leu | Trp | Val | Gly | Asp | Gly | Leu |
| 225 | | | | | 230 | | | | | 235 | | | | | 240 |
| Ser | Asp | Arg | Ala | Val | Leu | Ser | Val | Asp | Ser | Glu | Asp | Ser | Ser | Leu | Leu |
| | | | | 245 | | | | | 250 | | | | | 255 | |
| Glu | Arg | Ile | Thr | Gly | Tyr | Ala | Asp | Ile | Leu | Asp | Leu | Ser | Ala | Glu | Tyr |
| | | | 260 | | | | | 265 | | | | | 270 | | |
| Lys | Asp | Arg | Glu | Ile | Pro | Lys | Arg | Ala | Lys | Thr | Val | Cys | Leu | Tyr | Pro |
| | | 275 | | | | | 280 | | | | | 285 | | | |
| Lys | Thr | Ile | Arg | Gly | Asn | Asp | Ile | Arg | Arg | Asn | Leu | Asn | Thr | Asp | Asn |
| 290 | | | | | 295 | | | | | 300 | | | | | |
| Pro | Val | Trp | Asn | Ala | Ile | Val | Asp | Leu | Gly | Tyr | Leu | Lys | Asp | Gly | Val |
| 305 | | | | | 310 | | | | | 315 | | | | | 320 |
| Lys | Asn | Val | Pro | Ser | Tyr | Leu | Phe | Ser | Asp | Ser | Ile | Cys | His | Arg | Glu |
| | | | | 325 | | | | | 330 | | | | | 335 | |
| Val | Phe | Leu | Ala | Gly | Leu | Ile | Asp | Ser | Asp | Gly | His | Val | Arg | Gly | Asp |
| | | | 340 | | | | | 345 | | | | | 350 | | |
| Asp | Gly | Leu | Ser | Val | Thr | Ile | Lys | Thr | Ile | His | Lys | Thr | Val | Met | Glu |
| | | 355 | | | | | 360 | | | | | 365 | | | |

```
Gly Thr Val Ala Val Ala Arg Ser Leu Gly Leu Ile Val Ser Val Asn
            370                 375                 380

Thr Glu Glu Ala Lys Ile Asp Lys Asn Asp Val Asn His Arg Phe Val
385                 390                 395                 400

Tyr Ala Ile Tyr Ile Ser Gly Asp Ala Leu Leu Ser Val Leu Ala
                405                 410                 415

His Cys Ala Ala Ala Lys Lys Phe Arg Ala Pro Pro Ser Asn Glu Val
            420                 425                 430

Val Arg Gly Leu Lys Lys Val Phe Phe Glu Met Glu Glu Leu Lys Glu
            435                 440                 445

Asp Asp Tyr Tyr Gly Ile Thr Leu Ala Lys Glu Ser Asp His Gln Phe
450                 455                 460

Leu Leu Ala Asn Gln Leu Val Val His Asn Cys Gly Glu Arg Gly Asn
465                 470                 475                 480

Glu Met Ala Glu Val Leu Met Glu Phe Pro Glu Leu Phe Thr Glu Lys
                485                 490                 495

Asn Gly Arg Lys Glu Pro Ile Met Lys Arg Thr Thr Leu Val Ala Asn
            500                 505                 510

Thr Ser Asn Met Pro Val Ala Ala Arg Glu Ala Ser Ile Tyr Thr Gly
            515                 520                 525

Ile Thr Leu Ala Glu Tyr Phe Arg Asp Gln Gly Lys Asn Ile Ser Met
            530                 535                 540

Ile Ala Asp
545

<210> SEQ ID NO 150
<211> LENGTH: 170
<212> TYPE: PRT
<213> ORGANISM: Monomastix spec.

<400> SEQUENCE: 150

Met Thr Thr Lys Asn Thr Leu Gln Pro Thr Glu Ala Ala Tyr Ile Ala
1               5                   10                  15

Gly Phe Leu Asp Gly Asp Gly Ser Ile Tyr Ala Lys Leu Ile Pro Arg
            20                  25                  30

Pro Asp Tyr Lys Asp Ile Lys Tyr Gln Val Ser Leu Ala Ile Ser Phe
        35                  40                  45

Ile Gln Arg Lys Asp Lys Phe Pro Tyr Leu Gln Asp Ile Tyr Asp Gln
50                  55                  60

Leu Gly Lys Arg Gly Asn Leu Arg Lys Asp Arg Gly Asp Gly Ile Ala
65                  70                  75                  80

Asp Tyr Thr Ile Ile Gly Ser Thr His Leu Ser Ile Ile Leu Pro Asp
                85                  90                  95

Leu Val Pro Tyr Leu Arg Ile Lys Lys Gln Ala Asn Arg Ile Leu
            100                 105                 110

His Ile Ile Asn Leu Tyr Pro Gln Ala Gln Lys Asn Pro Ser Lys Phe
        115                 120                 125

Leu Asp Leu Val Lys Ile Val Asp Val Gln Asn Leu Asn Lys Arg
130                 135                 140

Ala Asp Glu Leu Lys Ser Thr Asn Tyr Asp Arg Leu Leu Glu Glu Phe
145                 150                 155                 160

Leu Lys Ala Gly Lys Ile Glu Ser Ser Pro
            165                 170

<210> SEQ ID NO 151
```

```
<211> LENGTH: 167
<212> TYPE: PRT
<213> ORGANISM: Monomastix spec.

<400> SEQUENCE: 151

Met Lys Thr Leu Glu Ser Thr Leu Ala Ala Tyr Ile Ala Gly Phe Leu
1               5                   10                  15

Asp Gly Asp Gly Ser Ile Tyr Ala Lys Val Ile Ser Arg Pro Asp Tyr
            20                  25                  30

Ala Val Ile Lys Tyr Gln Ile Ser Val Ser Leu Ser Phe Cys Gln Arg
        35                  40                  45

Lys Asp Arg Tyr Thr Tyr Leu Gln Asp Ile Tyr Glu Ala Leu Asp Lys
    50                  55                  60

Cys Gly Ser Leu Arg Lys Asp Arg Gly Asp Gly Ile Ala Asp Tyr Thr
65                  70                  75                  80

Ile Thr Gly Pro Ala His Leu Ser Ile Val Leu Pro His Leu Leu Pro
                85                  90                  95

Tyr Leu Arg Ile Lys Lys Lys Gln Ala Asn Leu Val Leu His Ile Ile
            100                 105                 110

Asn Gln Tyr Pro Ala Ala Lys Lys Asn His Leu Glu Phe Leu Ser Leu
        115                 120                 125

Val Lys Leu Val Asp Gln Ile Gln Asn Leu Asn Lys Lys Pro Asp Glu
    130                 135                 140

Pro Lys Ala Thr Asn Tyr Gln Ser Leu Leu Glu Glu Phe Gln Thr Ala
145                 150                 155                 160

Gly Arg Ile Gln Ser Ser Pro
                165

<210> SEQ ID NO 152
<211> LENGTH: 15
<212> TYPE: PRT
<213> ORGANISM: Artificial Sequence
<220> FEATURE:
<223> OTHER INFORMATION: sequence fragment comprised in I-SceI

<400> SEQUENCE: 152

His Val Cys Leu Leu Tyr Asp Gln Trp Val Leu Ser Pro Pro His
1               5                   10                  15

<210> SEQ ID NO 153
<211> LENGTH: 11
<212> TYPE: PRT
<213> ORGANISM: Artificial Sequence
<220> FEATURE:
<223> OTHER INFORMATION: sequence motive comprised in I-SceI

<400> SEQUENCE: 153

Leu Ala Tyr Trp Phe Met Asp Asp Gly Gly Lys
1               5                   10

<210> SEQ ID NO 154
<211> LENGTH: 27
<212> TYPE: PRT
<213> ORGANISM: Artificial Sequence
<220> FEATURE:
<223> OTHER INFORMATION: sequence motive comprised in I-SceI

<400> SEQUENCE: 154

Lys Thr Ile Pro Asn Asn Leu Val Glu Asn Tyr Leu Thr Pro Met Ser
1               5                   10                  15

Leu Ala Tyr Trp Phe Met Asp Asp Gly Gly Lys
```

<210> SEQ ID NO 155
<211> LENGTH: 19
<212> TYPE: PRT
<213> ORGANISM: Artificial Sequence
<220> FEATURE:
<223> OTHER INFORMATION: sequence motive comprised in I-SceI

<400> SEQUENCE: 155

Lys Pro Ile Ile Tyr Ile Asp Ser Met Ser Tyr Leu Ile Phe Tyr Asn
 1               5                  10                  15
Leu Ile Lys

<210> SEQ ID NO 156
<211> LENGTH: 13
<212> TYPE: PRT
<213> ORGANISM: Artificial Sequence
<220> FEATURE:
<223> OTHER INFORMATION: sequence motive comprised in I-SceI

<400> SEQUENCE: 156

Lys Leu Pro Asn Thr Ile Ser Ser Glu Thr Phe Leu Lys
 1               5                  10

<210> SEQ ID NO 157
<211> LENGTH: 30
<212> TYPE: DNA
<213> ORGANISM: Artificial Sequence
<220> FEATURE:
<223> OTHER INFORMATION: DNA recognition site of I-CreI

<400> SEQUENCE: 157
ctgggttcaa aacgtcgtga cagtttgg                                     30

<210> SEQ ID NO 158
<211> LENGTH: 22
<212> TYPE: DNA
<213> ORGANISM: Artificial Sequence
<220> FEATURE:
<223> OTHER INFORMATION: DNA recognition site of I-CeuI

<400> SEQUENCE: 158
ataacggtcc taaggtagcg aa                                           22

<210> SEQ ID NO 159
<211> LENGTH: 30
<212> TYPE: DNA
<213> ORGANISM: Artificial Sequence
<220> FEATURE:
<223> OTHER INFORMATION: DNA recognition site of I-DmoI

<400> SEQUENCE: 159
atgccttgcc gggtaagttc cggcgcgcat                                   30

<210> SEQ ID NO 160
<211> LENGTH: 31
<212> TYPE: DNA
<213> ORGANISM: Artificial Sequence
<220> FEATURE:
<223> OTHER INFORMATION: cutting site of I-AniI

<400> SEQUENCE: 160
gcgcgctgag gaggtttctc tgtaaagcgc a                                 31

```
<210> SEQ ID NO 161
<211> LENGTH: 254
<212> TYPE: PRT
<213> ORGANISM: Emericella nidulans

<400> SEQUENCE: 161

Gly Ser Asp Leu Thr Tyr Ala Tyr Leu Val Gly Leu Phe Glu Gly Asp
1               5                   10                  15

Gly Tyr Phe Ser Ile Thr Lys Lys Gly Lys Tyr Leu Thr Tyr Glu Leu
            20                  25                  30

Gly Ile Glu Leu Ser Ile Lys Asp Val Gln Leu Ile Tyr Lys Ile Lys
        35                  40                  45

Lys Ile Leu Gly Ile Gly Ile Val Ser Phe Arg Lys Ile Asn Glu Ile
50                  55                  60

Glu Met Val Ala Leu Arg Ile Arg Asp Lys Asn His Leu Lys Ser Phe
65                  70                  75                  80

Ile Leu Pro Ile Phe Glu Lys Tyr Pro Met Phe Ser Asn Lys Gln Tyr
                85                  90                  95

Asp Tyr Leu Arg Phe Arg Asn Ala Leu Leu Ser Gly Ile Ile Ser Leu
            100                 105                 110

Glu Asp Leu Pro Asp Tyr Thr Arg Ser Asp Glu Pro Leu Asn Ser Ile
        115                 120                 125

Glu Ser Ile Ile Asn Thr Ser Tyr Phe Ser Ala Trp Leu Val Gly Phe
130                 135                 140

Ile Glu Ala Glu Gly Cys Phe Ser Val Tyr Lys Leu Asn Lys Asp Asp
145                 150                 155                 160

Asp Tyr Leu Ile Ala Ser Phe Asp Ile Ala Gln Arg Asp Gly Asp Ile
                165                 170                 175

Leu Ile Ser Ala Ile Arg Lys Tyr Leu Ser Phe Thr Thr Lys Val Tyr
            180                 185                 190

Leu Asp Lys Thr Asn Cys Ser Lys Leu Lys Val Thr Ser Val Arg Ser
        195                 200                 205

Val Glu Asn Ile Ile Lys Phe Leu Gln Asn Ala Pro Val Lys Leu Leu
210                 215                 220

Gly Asn Lys Lys Leu Gln Tyr Leu Leu Trp Leu Lys Gln Leu Arg Lys
225                 230                 235                 240

Ile Ser Arg Tyr Ser Glu Lys Ile Lys Ile Pro Ser Asn Tyr
                245                 250

<210> SEQ ID NO 162
<211> LENGTH: 22
<212> TYPE: DNA
<213> ORGANISM: Artificial Sequence
<220> FEATURE:
<223> OTHER INFORMATION: cutting site of I-MsoI

<400> SEQUENCE: 162
cagaacgtcg tgagacagtt cc                                           22

<210> SEQ ID NO 163
<211> LENGTH: 30
<212> TYPE: DNA
<213> ORGANISM: Artificial Sequence
<220> FEATURE:
<223> OTHER INFORMATION: cutting site of Pi-SceI

<400> SEQUENCE: 163
atctatgtcg ggtgcggaga aagaggtaat                                   30
```

<210> SEQ ID NO 164
<211> LENGTH: 11
<212> TYPE: DNA
<213> ORGANISM: Artificial Sequence
<220> FEATURE:
<223> OTHER INFORMATION: binding site of transcription factor AflR
<220> FEATURE:
<221> NAME/KEY: misc_feature
<222> LOCATION: (4)..(8)
<223> OTHER INFORMATION: n is a, c, g, or t

<400> SEQUENCE: 164
tcgnnnnncg a                                                            11

<210> SEQ ID NO 165
<211> LENGTH: 238
<212> TYPE: PRT
<213> ORGANISM: Artificial Sequence
<220> FEATURE:
<223> OTHER INFORMATION: I-SceI comprising a deletion of 5 amino acids
      at the C-terminus

<400> SEQUENCE: 165

Met Gly Pro Lys Lys Arg Lys Val Lys Asn Ile Lys Lys Asn Gln
1               5                   10                  15

Val Met Asn Leu Gly Pro Asn Ser Lys Leu Leu Lys Glu Tyr Lys Ser
            20                  25                  30

Gln Leu Ile Glu Leu Asn Ile Glu Gln Phe Glu Ala Gly Ile Gly Leu
        35                  40                  45

Ile Leu Gly Asp Ala Tyr Ile Arg Ser Arg Asp Glu Gly Lys Thr Tyr
    50                  55                  60

Cys Met Gln Phe Glu Trp Lys Asn Lys Ala Tyr Met Asp His Val Cys
65                  70                  75                  80

Leu Leu Tyr Asp Gln Trp Val Leu Ser Pro Pro His Lys Lys Glu Arg
                85                  90                  95

Val Asn His Leu Gly Asn Leu Val Ile Thr Trp Gly Ala Gln Thr Phe
            100                 105                 110

Lys His Gln Ala Phe Asn Lys Leu Ala Asn Leu Phe Ile Val Asn Asn
        115                 120                 125

Lys Lys Thr Ile Pro Asn Asn Leu Val Glu Asn Tyr Leu Thr Pro Met
    130                 135                 140

Ser Leu Ala Tyr Trp Phe Met Asp Asp Gly Gly Lys Trp Asp Tyr Asn
145                 150                 155                 160

Lys Asn Ser Thr Asn Lys Ser Ile Val Leu Asn Thr Gln Ser Phe Thr
                165                 170                 175

Phe Glu Glu Val Glu Tyr Leu Val Lys Gly Leu Arg Asn Lys Phe Gln
            180                 185                 190

Leu Asn Cys Tyr Val Lys Ile Asn Lys Asn Lys Pro Ile Ile Tyr Ile
        195                 200                 205

Asp Ser Met Ser Tyr Leu Ile Phe Tyr Asn Leu Ile Lys Pro Tyr Leu
    210                 215                 220

Ile Pro Gln Met Met Tyr Lys Leu Pro Asn Thr Ile Ser Ser
225                 230                 235

<210> SEQ ID NO 166
<211> LENGTH: 455
<212> TYPE: PRT
<213> ORGANISM: Fusarium solani

<400> SEQUENCE: 166

```
Gly Asp Ser Pro Ser Asn Pro Leu Val Ser Ala Pro Thr Thr Ser
1               5                   10                  15

Pro Ser Leu Ala Pro Ile Ala Ala Ser Ala Ala Pro Pro Ala Tyr Ala
            20                  25                  30

Ala Ser Ser Ala Pro Val Ala Ala Asp Thr Thr Leu Pro Ser Leu
        35                  40                  45

Ala Ala Ala Ile Ala Gly Thr Ser Ser Thr Pro Pro Asp Asn Pro
    50                  55                  60

Thr Ala Ser Thr Ala Ser Ala Ala Leu Pro Ser Ala Pro Val Pro Ala
65                  70                  75                  80

Ala Asp His Asp Val Thr Ala Ala Ser Ser Ala Pro Thr Ser Thr Pro
                85                  90                  95

Ala Ser Ala Ala Ala Val Ser Ala Ala Pro Ser Ala Val Pro Gln Gln
                100                 105                 110

Asn Gly Asp Ser Arg Ala Ser Glu Gly Ala Ser Thr Pro Ser Ser Asn
                115                 120                 125

Pro Glu Met Ser Asn Gln His Pro Gly Ala Pro His Gly Gln Pro Val
        130                 135                 140

Ser Tyr Pro Gly Pro Ser Thr Pro Tyr Ala Thr Thr Val Gly Ala Thr
145                 150                 155                 160

Thr Ala Gln Tyr Ala Ser Tyr Pro Ala Val Thr Ser Gln Gln Gln Met
            165                 170                 175

Asp Ala Tyr Arg Pro Asn Pro Met Pro Val Gly Ser Asn Val Met Ser
            180                 185                 190

Leu Pro Ser Met Arg Thr Ile Asp Pro Val Pro Gln Gln Pro Gly Pro
        195                 200                 205

Ser Val Thr Asn Pro Gln Gly Met Gln Met Ser Met Pro Met Ala Pro
210                 215                 220

Val Ser Gly Gly Leu Pro Tyr Tyr Gly His His Gly Met Pro Met Ala
225                 230                 235                 240

Ala Gly Tyr Gly Ile Pro Ser Asp Pro Met Ser Arg Tyr Ala Leu Pro
            245                 250                 255

His Asp Pro Arg Leu Leu Gly His Arg Gly Pro Lys Lys Glu Ile Lys
            260                 265                 270

Arg Arg Thr Lys Thr Gly Cys Leu Thr Cys Arg Lys Arg Arg Ile Lys
        275                 280                 285

Cys Asp Glu Thr His Pro Thr Cys Asn Asn Cys Lys Lys Ser Lys Arg
        290                 295                 300

Glu Cys Leu Gly Tyr Asp Pro Ile Phe Arg Gln Gln Pro Gly Gly Gln
305                 310                 315                 320

Ser Ser Ser Asn Ile Gln Pro Ala Pro Ser Ser Gln Arg Thr Pro Pro
            325                 330                 335

Ala Ile Pro Ser Ser Ile Pro Ser Thr Ile Pro Ser Ser Ile Ala Thr
            340                 345                 350

Asn Pro Gly Leu Pro Ala Arg Ala Thr Asn Ser Tyr Gly Ser Gln Pro
        355                 360                 365

Ser Met Leu Pro Ser Ser Tyr Ala Thr Ala His Ala Thr Thr Ala Ser
        370                 375                 380

Pro Asn Pro Ser Ile Thr Ser Leu Ser Tyr Glu Ser Ser Leu Ser Thr
385                 390                 395                 400

Val Ala Ser Pro Pro Ile Lys Ser Glu Ser Gly Tyr Glu Tyr Ser Ser
                405                 410                 415
```

```
Ala Ile Asp Pro Ala Leu Gln Ser Leu Ala Ser Ser Ala Ile Gln Asp
            420                 425                 430

Gly Ser Arg Pro Val Asp Gln Lys Pro Leu Asp Asn Asn Leu His Leu
            435                 440                 445

Arg Gly Gly Ala Pro Tyr Phe
    450                 455

<210> SEQ ID NO 167
<211> LENGTH: 517
<212> TYPE: PRT
<213> ORGANISM: Candida albicans

<400> SEQUENCE: 167

Met Ser Asp Asp His Ser Ile His Ser His Thr Gln Gly Leu His His
1               5                   10                  15

Ile Lys Lys Lys Arg Val Gly Lys Ala Cys Asp Ser Cys Arg Ile Lys
            20                  25                  30

Lys Thr Lys Cys Asp Gly Lys Lys Pro Cys Asn Arg Cys Thr Leu Asp
            35                  40                  45

Asn Lys Ile Cys Val Phe Thr Glu Lys Lys Thr Lys Glu Lys Lys
    50                  55                  60

His Pro Ser Gly Tyr Val Glu Leu Leu Glu Ala Arg Leu Asp Ile Leu
65              70                  75                  80

Thr Arg Ser Leu Glu Lys Leu Ile Glu Leu Ser Arg Pro His Leu Gln
                85                  90                  95

Phe Ile Asp Asp Ile Ile Thr Glu Glu Lys Ser Val Asp Gln Glu Lys
            100                 105                 110

Ser Ser Pro Ala Ser Ser Thr Pro Asn Ser Ser Ser Asp His His
            115                 120                 125

Asp Asp Val Glu Glu Gln Asn Ser Thr Gly Val Val Ala Pro Ile Asn
    130                 135                 140

Lys Val Val Ser Tyr Leu Ile Lys Glu Gln Gly Leu Leu Lys Asn Ile
145                 150                 155                 160

Pro Leu Glu Trp Glu Gln Gly Thr Glu Ile Ala Ala Asn Phe Asp Pro
                165                 170                 175

Asn Arg Asn Leu Lys Ser Ser Ser Arg Leu Phe Ala Glu His Lys Gly
            180                 185                 190

Glu Ala Phe Ile Gly Ser Pro Val Thr Ser Pro Gln Gln Met Pro Thr
            195                 200                 205

Ser Asn Pro Phe Arg Arg Thr Ser Met Phe Lys Glu Glu Leu Glu Ser
    210                 215                 220

Pro Ser Ser Asp His Tyr Asn Glu Ser Ile Phe Ser Gln Ser Val Asp
225                 230                 235                 240

Glu Pro Tyr Ile Lys Lys Glu Pro Asn Ser Ala Gln Phe Ser Lys Gly
                245                 250                 255

Thr Phe Ser Pro Gln Gln Gln Leu Gln Gln Gln Gln Met Leu
            260                 265                 270

Asn Gln Phe Ser Leu Asn Thr Ser Arg Asp Ile Ser Asp Ile Glu Ser
    275                 280                 285

Asp Ser Ser Asn Lys Glu Asp Gly Leu Asn Ser Gly Ser Val Ser Pro
    290                 295                 300

Pro Thr Ser Asn Tyr Arg Ser Phe Ser Leu Phe Ser Asp Ser Asn Gly
305                 310                 315                 320

Glu Pro Ile Leu Gly Lys Thr Ser Ser Leu Thr Ser Leu Thr Asn Lys
                325                 330                 335
```

```
Tyr Glu Asn His Ser Leu Ser Ser Pro Gln Thr Ala Ile Asn Pro Val
            340                 345                 350

Phe Asn Asn Ser Thr Thr Gly Pro Ile Leu Thr Thr Leu Arg Arg Asn
            355                 360                 365

Ser Ser Ser His Ser Gln Lys Thr Leu Gly Ser Ile Gln Leu Gln Gln
            370                 375                 380

Lys Pro Arg Gly Ser Val His Lys Pro Val Arg Asn His Ser Arg Val
385                 390                 395                 400

Ser Ser Phe Asp Lys Arg Met Glu Ser Thr Ala Thr Ala Ala Ala Thr
                405                 410                 415

Val Ala Ala Val Ser Gly Ser Val Gln Leu Ser Gln Asn Thr Thr Pro
            420                 425                 430

Gln Asn Leu Pro His Leu Asp Asn Ser Gln Asn Asn Asn Tyr Leu Arg
            435                 440                 445

Asp Asn Gly Met Asn Asn Ile Gly Ala Gly Ser Val Gly Gly Gly Leu
            450                 455                 460

Thr Phe Gly Ala Pro Ser Phe Thr Gln Pro Leu Ser Pro Ser Asp Asp
465                 470                 475                 480

Ala Ile Val Tyr Pro Thr Asn Gln Phe Thr Asn Arg Pro Ala Thr Val
                485                 490                 495

Ser Thr Phe Gly Gly Gly Leu Asp Val Leu Val Asp Asn Ser Leu Asp
            500                 505                 510

Pro Phe Phe Asn Ile
            515

<210> SEQ ID NO 168
<211> LENGTH: 865
<212> TYPE: PRT
<213> ORGANISM: Neurospora crassa

<400> SEQUENCE: 168

Met Pro Gly Ile Leu Pro Met Lys Val Ile Lys Val Gly Asn Ser Ser
1               5                   10                  15

Gln Ser Arg Ile Ala Gln Ala Cys Asp Arg Cys Arg Ser Lys Lys Ile
            20                  25                  30

Arg Cys Asp Gly Ile Arg Pro Cys Cys Ser Gln Cys Ala Asn Val Gly
            35                  40                  45

Phe Glu Cys Lys Thr Ser Asp Lys Leu Ser Arg Arg Ala Phe Pro Arg
            50                  55                  60

Gly Tyr Thr Glu Ser Leu Glu Glu Arg Val Arg Ala Leu Glu Ala Glu
65                  70                  75                  80

Ile Arg Glu Leu Lys Asp Leu Leu Asp Glu Lys Asp Glu Lys Leu Asp
                85                  90                  95

Met Leu Ser Lys Met His Ser Asn Arg Ser Arg Ser Ala Glu Pro Pro
            100                 105                 110

Arg Ser Thr Pro Ala Ala Glu Ile Lys Arg Asp Ser Gly Thr Pro Ala
            115                 120                 125

Lys Glu Asp Thr Phe Arg Val Gln Ala Ser Pro Leu Gly Ala Ser Lys
130                 135                 140

Gly Arg Ser Phe Ile Glu Thr Phe Lys Arg Lys Ile Gln Glu Asn Gly
145                 150                 155                 160

Lys Ser Cys Thr Asp Phe Asn Pro Glu Ala Phe Leu His Ile Gln Gly
                165                 170                 175

Cys Tyr Pro Leu Ser Thr Lys Leu Ala Pro Gln Ser Met Arg Ile Pro
```

```
                180             185             190
Pro Arg Leu Ser Pro Asp Arg Cys Val Asn Val Tyr Phe Gln Glu Trp
            195             200             205

Ala Pro Leu Phe Pro Val Leu His Lys Pro Ala Phe Leu Arg Val Tyr
        210             215             220

Glu Glu Phe Val Ala Asp Pro Glu Lys Ile Lys Asn Asn His Lys Leu
225             230             235             240

Thr Gln Leu Tyr Leu Val Phe Ser Ile Ala Gly Leu Ser Ser Glu Gln
            245             250             255

Pro Asp Phe Gln Gln Leu Ala Ala Cys Glu Thr Gln Trp His Lys Ser
        260             265             270

Leu Glu Ala Val Leu Met Asp Asn Thr Met Leu Thr Leu Gln Cys Leu
    275             280             285

Ile Leu Ala Leu Met Tyr Cys Thr Val Arg Ala Asp Tyr Lys Arg Leu
    290             295             300

Gln Tyr Tyr Lys Gly Ile Ala Val Gly Leu Ser His Arg Leu Gly Leu
305             310             315             320

His Gln Ser Gln Lys Arg Phe Ser Phe Gly Ala Leu Thr Ile Glu Thr
            325             330             335

Arg Lys Lys Val Phe Trp Thr Leu Tyr Thr Leu Asp Cys Phe Ser Ala
        340             345             350

Ala Ile Leu Gly Leu Pro Lys Leu Leu Lys Asp Glu Asp Val His Ala
    355             360             365

Glu Phe Pro Ser Asp Thr Asp Asp Glu Asn Val Thr Glu Lys Gly Phe
    370             375             380

Gln Pro Ser Leu Pro Gly Glu Pro Thr Arg Ile Ser Ser Ala Leu Ala
385             390             395             400

Leu Phe Arg Gly Ser Arg Ile Leu Gly Lys Val Leu Glu Lys Ile Tyr
            405             410             415

Pro Ala Ala Thr Ser Tyr Glu Leu Ser Leu His Gln Met Ser Ser Leu
        420             425             430

Glu Gly Glu Leu Thr Glu Trp Phe Glu Asn Leu Pro Gln His Leu Lys
    435             440             445

Leu Asn Phe Lys Gln Asp Lys Pro Ser Thr Asp Val Thr Gly Ser Arg
    450             455             460

Ser Pro Leu Leu Ala Leu Ala Tyr Tyr Tyr Thr Arg Ile Leu Ile Tyr
465             470             475             480

Arg Pro Ala Ile Ala Pro Ser Leu Gly Pro Lys Ala Ala Pro Ala Leu
            485             490             495

Met Ser Val Ala Glu Ser Ser Lys Ser Ile Val Gln Ile Val Gln Leu
        500             505             510

Leu Glu Glu Arg Ser Met Ser Phe Ser Phe Cys Leu Asn Lys Ala Asp
    515             520             525

Ile Leu Ile Val Cys Gly Met Ala Leu Leu Tyr Gln Thr Leu Gly Leu
    530             535             540

Lys His Asp Ser Lys Val Leu Lys Asp Asn Glu Lys Leu Val Asn Ser
545             550             555             560

Val Val Lys Ile Val Thr Lys Val Asn Ala Pro Gly Tyr Asp Phe
            565             570             575

Lys Arg Ile Ala Gly Met Leu Val Thr Val Glu Glu Ser Leu Pro Gln
        580             585             590

Ser Leu Pro Thr Pro Pro Arg Gln Ser Pro Glu Ala Cys Met Pro Thr
    595             600             605
```

Pro Pro Ala Gln Gln Gly Ser Pro Ser Pro Ser Ala Val Asp Arg Gly
610                 615                 620

Ala Gln Pro Asn Leu Ala Arg Gln Ser Ser Ala Ser Leu Ser Glu Thr
625                 630                 635                 640

Asp Leu Ile Val Gln Arg Asp Lys Leu Leu Gly Met Ala Val Thr Pro
                645                 650                 655

Gln His Gln Gln Tyr Gln His Gln Gln Leu Gln Gln Gln His Lys Asn
            660                 665                 670

Glu Leu Ser Arg Ala Arg Ser Gln Thr Ser Phe Asp Asn Leu Arg Gln
        675                 680                 685

Lys Ala Gln Gln Met Arg Pro His His Arg His Ser Leu Ser His Ala
    690                 695                 700

Gln Val Ala Gln Ala Ala Leu Met Gly Arg Thr Ser Thr Gly Thr Gln
705                 710                 715                 720

Ser Thr Pro Asn Leu Asp Tyr Leu Ser Leu Ser Ser Pro Gln Ser Pro
                725                 730                 735

Val Ser Pro Val Gln Met Arg Ser Gln Pro His Gln Leu Gln Gln Gln
            740                 745                 750

Gln Gln Gln Gln Pro Gln Pro Gln Gln Gln Gln Gln His Gln Arg
        755                 760                 765

Ser Ser Ile Ala Ser Ser His Ser Gln Gln Gly Gln Met Phe Pro Gln
770                 775                 780

Lys Thr Ser Thr Gly Met Ser Thr Ala Glu Trp Glu Ala Leu Val Arg
785                 790                 795                 800

Ser Leu Asp Gly Gly Pro Val Ser Leu Tyr Thr Ala Ile Tyr Gly Gly
                805                 810                 815

Pro Ala Leu Ala Pro Leu Glu Thr Pro Ser Ser Ala Thr Gln Ser Ser
            820                 825                 830

Ala Thr Ala Trp Gly Gln Asp Pro Trp Asp Met Ser Ser Phe Asn Leu
        835                 840                 845

Gly Asp Phe Val Pro Gly Ala Pro Thr Ser Thr Glu Arg Ser Gln Phe
    850                 855                 860

Glu
865

<210> SEQ ID NO 169
<211> LENGTH: 595
<212> TYPE: PRT
<213> ORGANISM: Neurospora crassa

<400> SEQUENCE: 169

Met Ala Leu Lys Lys Met Pro Pro Lys Pro Tyr His Gln Lys Ala
1               5                   10                  15

Ser Lys Thr Lys Ala Cys Tyr Asn Cys His Arg Lys Arg Leu Arg Cys
            20                  25                  30

Asp Lys Ser Leu Pro Ala Cys Leu Lys Cys Ser Ile Asn Gly Glu Glu
        35                  40                  45

Cys Leu Gly Tyr Gly Ile Val Leu Arg Trp Ala Ala Cys Asn Ser Pro
    50                  55                  60

Thr Ser Thr Ile Thr Thr Arg Thr Thr Asn Lys Thr Asn Phe Asn Gly
65                  70                  75                  80

Thr Asn Thr Thr Thr Pro Arg Thr Val Lys Ser Ser Thr Pro Thr Gln
                85                  90                  95

Ala Pro Thr Pro Ser Asp Ser Pro Arg Gln Leu Asp Thr Asp Val Thr

```
            100                 105                 110
Ser Ser Ser Ala Pro Ser His Thr Cys Ser Arg Ser Thr Thr Thr Ser
            115                 120                 125
Thr Thr Thr Thr Arg Ile Ser Ser Pro Thr Leu Glu Glu Thr Ile Asp
            130                 135                 140
Ser Phe Thr Val Glu Thr Pro Ile Asp Asn Asn Val Asp Pro Leu Pro
145                 150                 155                 160
Arg Ala Pro Asp Asp Asn Pro Asp Pro Ser Ser Gln Ile Ile Lys Arg
                    165                 170                 175
Pro Val Asn Leu Ile Lys Ile Pro Leu Thr Asp Pro Leu Leu Asn Gly
                    180                 185                 190
Leu Ser Thr Lys Ala Arg Trp Tyr Met His His Val Ala Thr Ile Val
                    195                 200                 205
Cys Arg Asp Leu Val Ser Ile Asp Gln Lys Glu Arg Asn Pro Phe Arg
                    210                 215                 220
Ala Ile Ile Pro Leu Val Arg Lys Phe Asp Tyr Leu Gln Ser Val Val
225                 230                 235                 240
Leu Ala Thr Ala Ala Met His Leu Ser Thr Ile His Lys Tyr Gln Gly
                    245                 250                 255
Arg Ser Leu Pro Ser Glu Ser Ala Leu Val Asp Ala Leu Met Leu Lys
                    260                 265                 270
Ser Arg Ala Leu His Leu Leu Arg Ala Ala Ile Asn Asp Asn Thr Leu
                    275                 280                 285
Thr Asp Lys Ala Met Ile Leu Ser Ala Ile Val Phe Leu Val Lys Leu
                    290                 295                 300
Asp Leu Ile Asp Ser Gly Arg Gly Gly Trp Lys Ala His Val Gly Ala
305                 310                 315                 320
Ala Arg Arg Leu Ile Ser Ser Leu Tyr Leu Thr Lys Ala His Leu Asp
                    325                 330                 335
Gly Ala Ile Ala Pro Leu Val Asn Ala Ile Ala Ala Asp Cys Leu Thr
                    340                 345                 350
Tyr Arg Ile Tyr Gly Ser Thr Ile Ser Gly Asn Thr Ser Ser Trp Ser
                    355                 360                 365
Asp Asn Thr Ile Asp Asp Gly Val Val Leu Pro Tyr Ile Leu Gln Asn
                    370                 375                 380
Ala Glu Ala Tyr Ser Tyr His Cys Ala Pro Pro Ala Ile Leu Gln Ile
385                 390                 395                 400
Ile Leu Ser Ala Ser Gln Leu Cys Ser Gly Ser Ser Thr Thr Leu Glu
                    405                 410                 415
Thr Asp Gly Gly Ala Gly Arg Ile Val Thr Ala Ala Ala Leu Leu His
                    420                 425                 430
Lys Ala Arg Asn Phe Asp Val Gln Thr Trp Val Tyr Asn Ile Lys Gly
                    435                 440                 445
Leu Pro Pro Asp Asp Asp Leu Glu Ala Arg Val Ser Val Ala Ser Ala
                    450                 455                 460
His Arg Ala Ala Ala Cys Leu Phe Val Leu Leu Ser Val Pro Glu Thr
465                 470                 475                 480
Gly Leu Leu Glu Ile Pro Leu Leu Glu Pro Lys Asp Leu Val Gln Glu
                    485                 490                 495
Ile Leu Gly His Leu Ser Cys Ile Pro Asp Asn His Val His Leu Lys
                    500                 505                 510
Gly Thr Val Trp Pro Thr Phe Val Val Gly Ala Glu Thr Asp Asp Leu
                    515                 520                 525
```

Ser Glu Arg Ala Trp Cys Leu Glu Arg Leu Val Ala Val Trp Thr Lys
530                 535                 540

Asn Pro Trp Thr Tyr Pro Trp Gly Tyr Val His Thr Ala Met Glu Met
545                 550                 555                 560

Leu Gln Glu Ile Trp Arg Leu Lys Asp Leu Ala Ala Gln Gln Gly Asp
            565                 570                 575

Asp Gly Ile Asn Trp Leu Gln Arg Leu Lys Ala Thr Glu Asn Ser Cys
            580                 585                 590

Leu Ile Val
        595

<210> SEQ ID NO 170
<211> LENGTH: 491
<212> TYPE: PRT
<213> ORGANISM: Aspergillus parasiticus

<400> SEQUENCE: 170

Met Val Arg Arg Arg Ala Cys Asp Gly Cys Ser Leu Arg Lys Thr Arg
1               5                   10                  15

Cys Ser Gly Gly Gln Pro Cys Gln Pro Cys Ala Gln Ser Gly Phe Glu
            20                  25                  30

Cys Ser Tyr Leu Lys Pro Ala Ala Lys Pro Gly Pro Lys Gly Pro Arg
        35                  40                  45

Ala Glu Thr Tyr Ile Arg Ile Asn Arg Arg Leu Gln Ser Met Arg Asp
    50                  55                  60

Arg Ala Pro Arg Gly Ala Thr Glu Thr Ala Ser Pro Ala Asn Ile Arg
65                  70                  75                  80

Ala Gly Leu Ala Glu Ala Thr Asp Ser Ser Arg Val Ile Pro Ala Val
                85                  90                  95

Glu Val Ala Gly Ala Glu Gln Met Pro Ile Leu Thr Glu Trp Pro Ser
            100                 105                 110

Gln Leu Pro Leu Ala Asp Val Leu Gly His Leu Glu Ala Tyr Glu His
        115                 120                 125

Arg Met Tyr Pro Val Trp Pro Val Val Asp Val Ala Arg Leu Arg Asp
    130                 135                 140

Ser Leu Met Leu Asp Met Asn Asn Val Glu Leu Arg Ser Leu Ala Phe
145                 150                 155                 160

Ala Val Cys Ala Ala Thr Cys Ala Gln Leu Gln Cys His Pro Asp Asn
                165                 170                 175

Gln Gly Thr Gln Met Phe Gly Val Gly Thr Cys Ala Leu Ala Asp Tyr
            180                 185                 190

Phe Ala Lys Glu Ser Glu Tyr Cys Arg Thr Met Tyr Asp Tyr Arg Glu
        195                 200                 205

Ser Gly Thr Phe Glu Ala Val Leu Val Pro Leu Phe Leu His Phe Tyr
    210                 215                 220

Tyr Gly Ala Thr Asn Lys Met Ala Thr Ala Ser Leu Leu Leu Arg Glu
225                 230                 235                 240

Ser Val Thr Leu Cys Gln Leu Gln Gly Leu Asp Ser Glu Asp Thr Tyr
                245                 250                 255

Gln Asp Met Ala Val Glu Glu Asp Thr Tyr Arg Arg Ala Phe Trp
            260                 265                 270

Leu Leu Tyr Val Thr Glu Arg Gly His Ala Ile Gln His Gly Ile Asn
        275                 280                 285

Thr Cys Leu Lys Asn Ser Ile Arg Leu Pro Thr Arg Asp Cys Ser Asp

```
    290                 295                 300

Glu Leu His Leu Val Glu Ala Phe Asp Ser Leu Val Gly Leu Phe Ile
305                 310                 315                 320

Ser Val Glu Gly Val Leu Leu Gly Pro Gly Gly Ser Pro Arg Gly Pro
                325                 330                 335

Asn Thr Ile Ile Cys Ser Lys Asp Met Leu Cys Arg Leu Gln Ser Gln
            340                 345                 350

Leu Arg Gln Arg Leu Gln Trp Pro Thr Ala Tyr His Ala Leu Gln Arg
        355                 360                 365

Thr Asp Ile Ala Ile Thr Gln Gln Trp Leu Arg Val Leu Leu Trp Gln
    370                 375                 380

Leu Ser Leu Lys Asn Ile Phe Leu Ser Ser Ala Ser Ala Asp Asp Ser
385                 390                 395                 400

Met Lys Leu Thr Tyr Pro Val His Val Ala Arg Asp Ala Ile Val Leu
                405                 410                 415

Ile Ser Asn Val Pro Pro Gly Tyr Ile Tyr Gly Thr Cys Leu Leu Asn
            420                 425                 430

Pro Gly Asn Gln Thr Leu Arg Asn His Lys Tyr Pro Thr Gly Cys Asp
        435                 440                 445

Ser Leu Cys Ser Leu Pro Cys Ala Pro Gln Pro Ser Trp Asp Ile Arg
    450                 455                 460

His Ser Pro Pro Phe Met Leu Phe Thr Val Ile Ser Glu Pro Pro Thr
465                 470                 475                 480

Ile Trp Thr Arg Val Thr Ala Glu Glu Ile Arg
                485                 490

<210> SEQ ID NO 171
<211> LENGTH: 974
<212> TYPE: PRT
<213> ORGANISM: Pyricularia grisea

<400> SEQUENCE: 171

Met Phe Cys Ala Tyr Cys Gly Gln Lys Phe Thr Arg Lys Glu His Leu
1               5                   10                  15

Glu Arg His Ile Pro Thr His Thr Asn Val Lys Pro His Arg Cys Thr
            20                  25                  30

Ala Cys Gly Ile Ser Phe Gly Arg Ser Arg Asp Leu Leu Thr Arg His
        35                  40                  45

Tyr Gln Ala Tyr His Glu Ala Arg Asp Pro Met Glu Pro Ile Pro Gly
    50                  55                  60

Ser Ala Pro Pro Val Ala Gly Arg Thr Pro Ile Ala Cys Gln Asn Cys
65                  70                  75                  80

Ala Asn Ala Lys Thr Gly Cys Asp Lys Arg Val Pro Cys Ser Arg Cys
                85                  90                  95

Ala Glu Lys Asn Leu Asp Cys Ala Ala Arg Tyr Ala Arg Arg Ser Ser
            100                 105                 110

Lys Ala Ala Val Arg Ala Ala Gln Ala Ser Ala Ala Phe His Asn Ser
        115                 120                 125

Gln Ile Pro Asn Pro Thr Thr Thr Met His His Gln Pro His Pro His
    130                 135                 140

His His Asn His Val Gln Val Val Asn Pro Ala Met Met Glu Ile Asp
145                 150                 155                 160

Pro Val Met Pro Lys Gln Glu Ser Leu Val Gln Thr Pro Glu Gly Val
                165                 170                 175
```

```
Glu Pro Gln Ala Leu Met Glu Thr Ser Arg Leu His Thr Ser Pro Gln
            180                 185                 190

Gln Lys Ser Pro Leu Thr Ser His His Gln Ser Pro Leu Glu Phe Pro
        195                 200                 205

Ser Pro His Pro Arg Gln Glu Gly Met Glu Asp Phe Met His Leu Ser
    210                 215                 220

Thr Glu Phe Pro Gly Thr Glu Ser His Tyr Asn Asp Leu Met Ile Trp
225                 230                 235                 240

Pro Asp Tyr Pro Leu Asp Leu Glu Met Tyr Pro Ser Gln Ile Pro Met
                245                 250                 255

Thr Arg Pro Asp Leu Ala Val Gln Pro Phe Ala Asp Leu Gly Ser Glu
            260                 265                 270

Ile Ser Ser Thr Ser Glu Pro Met Ala Thr Ser Ser Arg Gly Ser
        275                 280                 285

Thr His Thr Arg Gly Thr Ser Ile Leu Ser Ser Ala Glu Phe Glu Thr
    290                 295                 300

Ser Met Lys Pro Ala Asp Leu Ala Ala Ile Asn Thr Pro Ala Gly
305                 310                 315                 320

Ser Ser Ile Ala Glu Phe Glu Val Val Ile Ala Ala Glu Ala Ala Trp
                325                 330                 335

Pro Leu Ala Arg Cys Asn Pro Pro Ile Tyr Ser Asn Thr Cys Pro Arg
            340                 345                 350

Thr Ala Ile Val His Leu Glu Cys Leu Glu Gln Lys Ser Lys Val Glu
        355                 360                 365

Gly Thr Trp Ser Ser Leu Glu Lys Tyr Met Glu Gln Val Asp Trp Asp
    370                 375                 380

Ala Ala Asp Leu Ser Ser Val Val Pro Ile Thr Ser Arg Thr Arg Asp
385                 390                 395                 400

Lys Met Leu Ala Ile Thr Gln Gly Phe Leu His Lys Ala Leu Asp Ile
                405                 410                 415

His Arg Gly Gly Ile Thr Gly Phe Ser Asn Gln Gly His His Arg Pro
            420                 425                 430

Gly Asp Phe Asn Phe Ile Val Leu Pro Pro Thr Lys Ile Leu Glu Tyr
        435                 440                 445

Phe Leu Arg Ser Tyr Ile Arg Thr Leu Ser Pro Tyr Tyr Ser Leu Ser
    450                 455                 460

Leu Gly Ser Cys Val Asp Pro Asn Glu Met Leu Arg Asp Asn His Ala
465                 470                 475                 480

Ser Thr Leu Leu Val Leu Leu Met Ile Ala Gln Gly Ala Ala Ala Val
                485                 490                 495

Pro Met Ala Glu Ala Arg Tyr Leu Ser Thr Gly Leu Val Glu Thr Cys
            500                 505                 510

Arg Ile Ser Leu Phe Asp Ile Ile Glu Lys Asn Val Glu Leu Ser Ala
        515                 520                 525

Asp Pro Thr Ala Leu Arg Cys Ala Leu Leu Phe Thr Leu Leu Gly Ala
    530                 535                 540

Trp Ser Gly Asp Lys Trp Leu Met Asp Ile Ser Met Gly Gln Arg Gly
545                 550                 555                 560

Met Tyr Met Ser Met Val Lys His Ala Gly Met Met Asp Ser Gln Pro
                565                 570                 575

Pro Met Ile Pro Val Phe Thr Asn Ser Thr Ser Thr Glu Leu Glu Trp
            580                 585                 590

Arg Ala Trp Cys His Arg Glu Ser Gln Asn Arg Leu Val Tyr Asn Trp
```

595                 600                 605
Val Met Met Asp Gln Glu Leu Ser Leu Phe His Asp Thr Ala Pro Leu
610                 615                 620

Ile Ser Ile Ser Asp Leu Leu Cys Pro Leu Pro Gly Pro Asp Glu Leu
625                 630                 635                 640

Trp Thr Ala Pro Asn Ser Glu Val Trp Leu Ser Ser Val Gln Ser Leu
                645                 650                 655

Tyr Gly Gly Asn Asn Val Asn Val Asn Pro Gln Leu Leu Ser Thr Pro
                660                 665                 670

Ser Pro Thr Pro Ser Leu Ser Asp Leu Phe Gln Asn Phe Leu His Asp
                675                 680                 685

Asn Leu Thr Pro Gly Lys Asn Ser Leu Ser Pro Gln His Leu Arg Leu
690                 695                 700

Leu Leu His Pro Leu Gln Ser Leu Leu Cys His Leu Arg Gln Met Leu
705                 710                 715                 720

Ser Cys Phe Pro Asp Ile Pro Ser Thr Arg Arg Thr Thr Thr Arg Thr
                725                 730                 735

Val Thr Arg Ala Ser Thr Leu Ser Arg Leu Glu Glu Val Gln Ala Leu
                740                 745                 750

Leu Gln Lys Trp Tyr Glu Leu Ser Met Glu Phe Ser Lys Glu Ser Pro
                755                 760                 765

Asp Cys Pro Ile Thr Arg Cys Asn Met Val Leu Tyr His Leu Ile Ser
770                 775                 780

Leu Asn Ala Val Thr Asn Phe Pro Glu Val Glu Arg Leu Ala Arg Arg
785                 790                 795                 800

Glu Gly Phe Asp Gly Ser Tyr Trp Glu Leu Ser Met Arg His Lys Met
                805                 810                 815

Cys Ile Tyr Gln Arg Glu Glu Ala Val Phe His Cys Gly Gln Val Leu
                820                 825                 830

Arg Leu Val Arg Ser Met Pro Gln Asp Arg Arg Pro Val Trp Trp Ser
                835                 840                 845

Ala Ala Val Tyr Arg Ala Val Leu Ile Leu Trp Ala Asp Ser Met Ala
850                 855                 860

Arg Leu Asp Pro Thr Leu Lys Arg Glu Asp Thr Val Gly Pro Ser Ser
865                 870                 875                 880

Thr Pro Ala Ala Ala Thr Pro Gly Pro Leu Val Pro Val Asp Gln
                885                 890                 895

Val Thr Pro Glu Asn Pro Ala Val Ile Ala Tyr Leu Trp Asn Arg Glu
                900                 905                 910

Gly Val Ala Leu Leu Thr Arg Asn Asp Gly Arg Ser Val Ser Leu Asp
                915                 920                 925

Asn Pro Ala Glu Val Leu Ala Tyr Gly Val Lys Glu Ile Glu Glu Ala
                930                 935                 940

Val Ser Ile Arg Phe Ser Asp Gly Ile Lys Arg Lys Leu Ala Ala Leu
945                 950                 955                 960

Ala Gln Asn Trp Ser Val Gly Ser Pro Leu Ala Gly Ser Ser
                965                 970

<210> SEQ ID NO 172
<211> LENGTH: 437
<212> TYPE: PRT
<213> ORGANISM: Aspergillus flavus

<400> SEQUENCE: 172

```
Met Val Asp His Ile Ser Pro Arg Ala Ser Pro Gly Pro Ile Arg Ser
1               5                   10                  15

Ser Gln Thr Arg Arg Ala Arg Lys Leu Arg Asp Ser Cys Thr Ser Cys
            20                  25                  30

Ala Ser Ser Lys Val Arg Cys Thr Lys Glu Lys Pro Ala Cys Ala Arg
            35                  40                  45

Cys Ile Glu Arg Gly Leu Ala Cys Gln Tyr Met Val Ser Lys Arg Met
50                  55                  60

Gly Arg Asn Pro Arg Ala Pro Ser Pro Leu Asp Ser Thr Arg Arg Pro
65                  70                  75                  80

Ser Glu Ser Leu Pro Ser Ala Arg Ser Glu Gln Gly Leu Pro Ala His
            85                  90                  95

Asn Thr Tyr Ser Thr Pro His Ala His Thr Gln Ala His Thr His Ala
            100                 105                 110

His Ser His Pro Gln Pro His Pro Gln Ser His Pro Gln Ser Asn Gln
            115                 120                 125

Pro Pro His Ala Leu Pro Thr Pro Asn Gly Ser Ser Val Ser Ala
            130                 135                 140

Ile Phe Ser His Gln Ser Pro Pro Pro Val Glu Thr Gln Gly Leu
145                 150                 155                 160

Gly Gly Asp Leu Ala Gly Gln Glu Gln Ser Thr Leu Ser Ser Leu Thr
            165                 170                 175

Val Asp Ser Glu Phe Gly Ser Leu Gln Ser Met Glu His Gly Asn
            180                 185                 190

His Val Asp Phe Leu Ala Glu Ser Thr Gly Ser Leu Phe Asp Ala Phe
            195                 200                 205

Leu Glu Val Gly Thr Pro Met Ile Asp Pro Phe Leu Glu Ser Ala Pro
210                 215                 220

Leu Pro Pro Phe Gln Ala Arg Tyr Cys Cys Phe Ser Leu Ala Leu Gln
225                 230                 235                 240

Thr Leu Thr His Leu Phe Pro His Ala Pro Leu Gly Cys Gln Leu Arg
            245                 250                 255

Leu Thr Asp Gly Glu Asp Ser Ser Cys Asn Leu Met Thr Thr Asp Met
            260                 265                 270

Val Ile Ser Gly Asn Lys Arg Ala Thr Asp Ala Val Arg Lys Ile Leu
            275                 280                 285

Gly Cys Ser Cys Ala Gln Asp Gly Tyr Leu Leu Ser Met Val Val Leu
            290                 295                 300

Ile Val Leu Lys Val Leu Ala Trp Tyr Ala Ala Ala Gly Thr Gln
305                 310                 315                 320

Cys Thr Ser Thr Ala Ala Gly Gly Glu Thr Asn Ser Gly Ser Cys Ser
            325                 330                 335

Asn Ser Pro Ala Thr Val Ser Ser Gly Cys Leu Thr Glu Glu Arg Val
            340                 345                 350

Leu His Leu Pro Ser Met Met Gly Glu Asp Cys Val Asp Glu Asp
            355                 360                 365

Gln Pro Arg Val Ala Ala Gln Leu Val Leu Ser Glu Leu His Arg Val
370                 375                 380

Gln Ser Leu Val Asn Leu Leu Ala Lys Arg Leu Gln Glu Gly Gly Asp
385                 390                 395                 400

Asp Ala Ala Gly Ile Pro Ala His His Pro Ala Ser Pro Phe Ser Leu
                405                 410                 415

Leu Gly Phe Ser Gly Leu Glu Ala Asn Leu Ala Thr Ala Trp Arg Arg
```

Val Leu Arg His Tyr
          435

<210> SEQ ID NO 173
<211> LENGTH: 433
<212> TYPE: PRT
<213> ORGANISM: Aspergillus nidulans

<400> SEQUENCE: 173

Met Glu Pro Pro Ala Ile Ser Gln Gln Ser Thr Pro Thr Ala Pro Gly
1               5                   10                  15

Gly Thr Gln Gly Thr Arg Lys Leu Arg Glu Ser Cys Ile Ser Cys Ser
            20                  25                  30

Arg Ser Lys Val Lys Cys Asn Lys Glu Lys Pro Thr Cys Ser Arg Cys
        35                  40                  45

Val Arg Arg Gly Leu Pro Cys Glu Tyr Met Val Ser Arg Arg Thr Gly
    50                  55                  60

Arg Thr Arg Val Ile Gly Val Glu Gln Pro Lys Thr Ala Pro Ser Pro
65                  70                  75                  80

Thr Thr Pro Thr Asn Thr Thr Ala Ala Thr Thr Ala Thr Lys Ala Gly
                85                  90                  95

Pro Pro Val Thr Thr Asp Ser Ala Val His Thr Pro Val Ile Thr Thr
            100                 105                 110

Ala Pro Ser Pro Lys Pro Val Gln Ile Gln Ser Pro Ala Glu Pro
        115                 120                 125

Asp Leu Trp Gly Ala Ile Leu Ser Pro Asn Thr Ser Thr Ser Thr Asp
    130                 135                 140

Leu Ser Ser Leu Leu Ser Val Asn Thr Asn Phe Ser Gln Leu Phe Ala
145                 150                 155                 160

Ser Leu Ser Pro Ser Leu Leu Glu Gly Met Asp Gly Met Asp Ala Glu
                165                 170                 175

Met His Ala Pro Glu Leu Gly Ala Leu Ser Val Ala Asp Pro Ser Ser
            180                 185                 190

Ser Met Met Gln Gly Leu Glu Ala Pro Asn Ala Ala Gln Pro Pro Ser
        195                 200                 205

Ser Asn Thr Thr Ser His Ser Tyr Cys Leu Ser Ile Cys Leu Asp Thr
    210                 215                 220

Leu Met Arg Leu Phe Pro Asn Ala Gly Ala Asn Cys Glu Arg Pro Gly
225                 230                 235                 240

His Glu Ser Asn Pro Gly Lys Leu Phe Thr Ile Glu Ser Val Ile Glu
                245                 250                 255

Asp Asn Lys Gln Ile Leu Asp Thr Ala Gln Thr Ile Leu Ala Cys Arg
            260                 265                 270

Cys Ala Glu Asp Glu Tyr Val Val Thr Leu Val Ser Leu Ile Val Phe
        275                 280                 285

Lys Val Leu Gly Trp Tyr Val Ala Ala Ala Arg Asp Arg Ser Ser Asp
    290                 295                 300

Pro Gly Arg Glu Glu Asp Phe Asn Trp Ser Thr Ala Gln Asp Ser Arg
305                 310                 315                 320

Arg Gly Ser Val Ser Ser Phe Glu Glu Gln Val Leu His Leu Pro Thr
                325                 330                 335

Val Val Gly Thr Tyr Cys Ile Asp Gly His His Gln Ser Arg Met Ala
            340                 345                 350

```
Ala Gln Leu Val Leu Ser Glu Leu Tyr Arg Val Gln Arg Leu Val Thr
            355                 360                 365

Gln Val Ser Arg Arg Leu Glu Ser Ile Arg Arg Ser Ser Ser Ser
370                 375                 380

Ser Ser Ser Ala Ser Ser Asn Thr Thr Asp Ser Asp Gly Gly Met Ser
385                 390                 395                 400

Thr Pro Leu Ser Ser Thr Thr Leu Val His Leu Glu Asp Asp Leu Arg
                405                 410                 415

Lys Arg Leu Arg Ala Val Ser Ser Glu Thr Ile Ser Ile Leu Arg His
            420                 425                 430

Ala

<210> SEQ ID NO 174
<211> LENGTH: 384
<212> TYPE: PRT
<213> ORGANISM: Aspergillus oryzae

<400> SEQUENCE: 174

Met Val Asp His Ile Ser Pro Arg Ala Ser Pro Gly Pro Ile Arg Ser
1               5                   10                  15

Ser Gln Thr Arg Arg Ala Arg Lys Leu Arg Asp Ser Cys Thr Ser Cys
            20                  25                  30

Ala Ser Ser Lys Val Arg Cys Thr Lys Glu Lys Pro Ala Cys Ala Arg
        35                  40                  45

Cys Ile Glu Arg Gly Leu Ala Cys Gln Tyr Met Val Ser Lys Arg Met
    50                  55                  60

Gly Arg Asn Pro Arg Ala Pro Ser Pro Leu Asp Ser Thr Arg Arg Pro
65                  70                  75                  80

Ser Glu Ser Leu Pro Ser Ala Gly Ser Glu Gln Gly Leu Pro Ala His
                85                  90                  95

Asn Thr Tyr Ser Thr Pro His Ala His Thr Gln Ala His Thr His Ala
            100                 105                 110

His Ala His Ser His Pro Gln Pro His Pro Gln Ser His Pro Gln Ser
        115                 120                 125

Asn Gln Pro Pro His Ala Leu Pro Thr Pro Asn Gly Ser Ser Ser Val
    130                 135                 140

Ser Ala Ile Phe Ser His Gln Ser Pro Pro Leu Val Glu Thr Gln
145                 150                 155                 160

Gly Leu Gly Gly Asp Leu Ala Gly Gln Ala Gln Ser Thr Leu Ser Ser
                165                 170                 175

Leu Thr Val Asp Ser Glu Phe Gly Ser Leu Gln Ser Met Glu His
            180                 185                 190

Gly Asn His Ala Asp Phe Leu Ala Glu Ser Thr Gly Ser Leu Phe Asp
        195                 200                 205

Ala Phe Leu Glu Val Gly Thr Pro Met Ile Asp Pro Phe Leu Glu Ser
    210                 215                 220

Ala Pro Leu Pro Pro Phe Gln Ala Arg Tyr Cys Cys Phe Ser Leu Ala
225                 230                 235                 240

Leu Gln Thr Leu Thr Cys Leu Phe Pro His Ala Pro Leu Gly Cys Gln
                245                 250                 255

Leu Arg Leu Thr Asp Gly Glu Asp Ser Ser Cys Asn Leu Met Thr Thr
            260                 265                 270

Asp Met Val Ile Ser Gly Asn Lys Lys Ala Thr Asp Ala Val Arg Lys
        275                 280                 285
```

Ile Leu Gly Cys Ser Cys Ala Gln Asp Gly Tyr Leu Leu Ser Met Val
            290                 295                 300

Val Leu Ile Val Leu Lys Val Leu Gly Trp Tyr Ala Ala Ala Ala Gly
305                 310                 315                 320

Thr Gln Cys Thr Ser Thr Ala Ala Gly Gly Glu Thr Asn Ser Gly Ser
                325                 330                 335

Cys Ser Asn Ser Pro Ala Thr Val Ser Ser Gly Cys Leu Thr Glu Glu
                340                 345                 350

Arg Val Leu His His Pro Ser Met Val Gly Glu Asp Cys Val Asp Glu
                355                 360                 365

Glu Asp Gln Pro Arg Val Ala Ala Gln Leu Val Leu Ser Glu Leu His
370                 375                 380

<210> SEQ ID NO 175
<211> LENGTH: 444
<212> TYPE: PRT
<213> ORGANISM: Aspergilluls parasiticus

<400> SEQUENCE: 175

Met Val Asp His Ile Ser Pro Arg Ala Ser Gly Pro Ile Arg Ser
1               5                   10                  15

Ser Gln Thr Arg Arg Ala Arg Lys Leu Arg Asp Ser Cys Thr Ser Cys
                20                  25                  30

Ala Ser Ser Lys Val Arg Cys Thr Lys Glu Lys Pro Ala Cys Ala Arg
                35                  40                  45

Cys Ile Glu Arg Gly Leu Ala Cys Gln Tyr Met Val Ser Lys Arg Met
            50                  55                  60

Gly Arg Asn Pro Arg Ala Pro Ser Pro Leu Asp Ser Thr Arg Arg Pro
65                  70                  75                  80

Ser Glu Ser Leu Pro Ser Ala Gly Ser Glu Gln Gly Leu Pro Ala His
                85                  90                  95

Asn Thr Tyr Ser Thr Pro His Ala His Thr Gln Ala His Thr His Ala
                100                 105                 110

His Ser His Pro Gln Pro His Pro Gln Ser His Pro Gln Ser Asn Gln
            115                 120                 125

Pro Pro His Ala Leu Pro Thr Pro Asn Gly Ser Ser Ser Val Ser Ala
130                 135                 140

Ile Phe Ser His Gln Ser Pro Pro Leu Val Glu Thr Gln Gly Leu
145                 150                 155                 160

Gly Gly Asp Leu Ala Gly Gln Ala Gln Ser Thr Leu Ser Ser Leu Thr
                165                 170                 175

Val Asp Ser Glu Phe Gly Gly Ser Leu Gln Ser Met Glu His Gly Asn
                180                 185                 190

His Ala Asp Phe Leu Ala Glu Ser Thr Gly Ser Leu Phe Asp Ala Phe
            195                 200                 205

Leu Glu Val Gly Thr Pro Met Ile Asp Pro Phe Leu Glu Ser Ala Pro
210                 215                 220

Leu Pro Pro Phe Gln Ala Arg Tyr Cys Cys Phe Ser Leu Ala Leu Gln
225                 230                 235                 240

Thr Leu Thr Cys Leu Phe Pro His Ala Pro Leu Gly Cys Gln Leu Arg
                245                 250                 255

Leu Thr Asp Gly Glu Asp Ser Ser Cys Asn Leu Met Thr Thr Asp Met
                260                 265                 270

Val Ile Ser Gly Asn Lys Lys Ala Thr Asp Ala Val Arg Lys Ile Leu
            275                 280                 285

```
Gly Cys Ser Cys Ala Gln Asp Gly Tyr Leu Leu Ser Met Val Val Leu
        290                 295                 300

Ile Val Leu Lys Val Leu Gly Trp Tyr Ala Ala Ala Gly Thr Gln
305                 310                 315                 320

Cys Thr Ser Thr Ala Ala Gly Gly Glu Thr Asn Ser Gly Ser Cys Ser
                325                 330                 335

Asn Ser Pro Ala Thr Val Ser Ser Gly Cys Leu Thr Glu Glu Arg Val
                340                 345                 350

Leu His His Pro Ser Met Val Gly Glu Asp Cys Val Asp Glu Glu Asp
                355                 360                 365

Gln Pro Arg Val Ala Ala Gln Leu Val Leu Ser Glu Leu His Arg Val
370                 375                 380

Gln Ser Leu Val Asn Leu Leu Ala Lys Arg Leu Gln Glu Gly Gly Asp
385                 390                 395                 400

Asp Ala Ala Gly Ile Pro Ala His His Pro Ala Ser Pro Phe Ser Leu
                405                 410                 415

Leu Gly Phe Ser Gly Leu Glu Ala Asn Leu Arg His Arg Leu Arg Ala
                420                 425                 430

Val Ser Ser Asp Ile Ile Asp Tyr Leu His Arg Glu
                435                 440

<210> SEQ ID NO 176
<211> LENGTH: 821
<212> TYPE: PRT
<213> ORGANISM: Aspergillus nidulans

<400> SEQUENCE: 176

Met Ala Asp Thr Arg Arg Gln Asn His Ser Cys Asp Pro Cys Arg
1               5                   10                  15

Lys Gly Lys Arg Arg Cys Asp Ala Pro Glu Asn Arg Asn Glu Ala Asn
                20                  25                  30

Glu Asn Gly Trp Val Ser Cys Ser Asn Cys Lys Arg Trp Asn Lys Asp
                35                  40                  45

Cys Thr Phe Asn Trp Leu Ser Ser Gln Arg Ser Lys Ala Lys Gly Ala
50                  55                  60

Ala Pro Arg Ala Arg Thr Lys Lys Ala Arg Thr Ala Thr Thr Thr Ser
65                  70                  75                  80

Glu Pro Ser Thr Ser Ala Ala Thr Ile Pro Thr Pro Glu Ser Asp Asn
                85                  90                  95

His Asp Ala Pro Pro Val Ile Asn Ser His Asp Ala Leu Pro Ser Trp
                100                 105                 110

Thr Gln Gly Leu Leu Ser His Pro Gly Asp Leu Phe Asp Phe Ser His
                115                 120                 125

Ser Ala Ile Pro Ala Asn Ala Glu Asp Ala Ala Asn Val Gln Ser Asp
                130                 135                 140

Ala Pro Phe Pro Trp Asp Leu Ala Ile Pro Gly Asp Phe Ser Met Gly
145                 150                 155                 160

Gln Gln Leu Glu Lys Pro Leu Ser Pro Leu Ser Phe Gln Ala Val Leu
                165                 170                 175

Leu Pro Pro His Ser Pro Asn Thr Asp Asp Leu Ile Arg Glu Leu Glu
                180                 185                 190

Glu Gln Thr Thr Asp Pro Asp Ser Val Thr Asp Thr Asn Ser Val Gln
                195                 200                 205

Gln Val Ala Gln Asp Gly Ser Leu Trp Ser Asp Arg Gln Ser Pro Leu
```

-continued

```
            210                 215                 220
Leu Pro Glu Asn Ser Leu Cys Met Ala Ser Asp Ser Thr Ala Arg Arg
225                 230                 235                 240

Tyr Ala Arg Ser Thr Met Thr Lys Asn Leu Met Arg Ile Tyr His Asp
                245                 250                 255

Ser Met Glu Asn Ala Leu Ser Cys Trp Leu Thr Glu His Asn Cys Pro
                260                 265                 270

Tyr Ser Asp Gln Ile Ser Tyr Leu Pro Pro Lys Gln Arg Ala Glu Trp
            275                 280                 285

Gly Pro Asn Trp Ser Asn Arg Met Cys Ile Arg Val Cys Arg Leu Asp
        290                 295                 300

Arg Val Ser Thr Ser Leu Arg Gly Arg Ala Leu Ser Ala Glu Glu Asp
305                 310                 315                 320

Lys Ala Ala Ala Arg Ala Leu His Leu Ala Ile Val Ala Phe Ala Ser
                325                 330                 335

Gln Trp Thr Gln His Ala Gln Arg Gly Ala Gly Leu Asn Val Pro Ala
                340                 345                 350

Asp Ile Ala Ala Asp Glu Arg Ser Ile Arg Arg Asn Ala Trp Asn Glu
            355                 360                 365

Ala Arg His Ala Leu Gln His Thr Thr Gly Ile Pro Ser Phe Arg Val
        370                 375                 380

Ile Phe Ala Asn Ile Ile Phe Ser Leu Thr Gln Ser Val Leu Asp Asp
385                 390                 395                 400

Asp Glu Gln His Gly Met Gly Ala Arg Leu Asp Lys Leu Leu Glu Asn
                405                 410                 415

Asp Gly Ala Pro Val Phe Leu Glu Thr Ala Asn Arg Gln Leu Tyr Thr
            420                 425                 430

Phe Arg His Lys Phe Ala Arg Met Gln Arg Arg Gly Lys Ala Phe Asn
        435                 440                 445

Arg Leu Pro Gly Gly Ser Val Ala Ser Thr Phe Ala Gly Ile Phe Glu
    450                 455                 460

Thr Pro Thr Pro Ser Ser Glu Ser Pro Gln Leu Asp Pro Val Val Ala
465                 470                 475                 480

Ser Glu Glu His Arg Ser Thr Leu Ser Leu Met Phe Trp Leu Gly Ile
                485                 490                 495

Met Phe Asp Thr Leu Ser Ala Ala Met Tyr Gln Arg Pro Leu Val Val
            500                 505                 510

Ser Asp Glu Asp Ser Gln Ile Ser Ser Ala Ser Pro Pro Arg Arg Gly
        515                 520                 525

Ala Glu Thr Pro Ile Asn Leu Asp Cys Trp Glu Pro Pro Arg Gln Val
    530                 535                 540

Pro Ser Asn Gln Glu Lys Ser Asp Val Trp Gly Asp Leu Phe Leu Arg
545                 550                 555                 560

Thr Ser Asp Ser Leu Pro Asp His Glu Ser His Thr Gln Ile Ser Gln
                565                 570                 575

Pro Ala Ala Arg Trp Pro Cys Thr Tyr Glu Gln Ala Ala Ala Ala Leu
            580                 585                 590

Ser Ser Ala Thr Pro Val Lys Val Leu Leu Tyr Arg Arg Val Thr Gln
        595                 600                 605

Leu Gln Thr Leu Leu Tyr Arg Gly Ala Ser Pro Ala Arg Leu Glu Ala
    610                 615                 620

Ala Ile Gln Arg Thr Leu Tyr Val Tyr Asn His Trp Thr Ala Lys Tyr
625                 630                 635                 640
```

```
Gln Pro Phe Met Gln Asp Cys Val Ala Asn His Glu Leu Leu Pro Ser
                645                 650                 655

Arg Ile Gln Ser Trp Tyr Val Ile Leu Asp Gly His Trp His Leu Ala
            660                 665                 670

Ala Met Leu Leu Ala Asp Val Leu Glu Ser Ile Asp Arg Asp Ser Tyr
        675                 680                 685

Ser Asp Ile Asn His Ile Asp Leu Val Thr Lys Leu Arg Leu Asp Asn
    690                 695                 700

Ala Leu Ala Val Ser Ala Leu Ala Arg Ser Ser Leu Arg Gly Gln Glu
705                 710                 715                 720

Leu Asp Pro Gly Lys Ala Ser Pro Met Tyr Arg His Phe His Asp Ser
                725                 730                 735

Leu Thr Glu Val Ala Phe Leu Val Glu Pro Trp Thr Val Val Leu Ile
            740                 745                 750

His Ser Phe Ala Lys Ala Ala Tyr Ile Leu Leu Asp Cys Leu Asp Leu
        755                 760                 765

Asp Gly Gln Gly Asn Ala Leu Ala Gly Tyr Leu Gln Leu Arg Gln Asn
    770                 775                 780

Cys Asn Tyr Cys Ile Arg Ala Leu Gln Phe Leu Gly Arg Lys Ser Asp
785                 790                 795                 800

Met Ala Ala Leu Val Ala Lys Asp Leu Glu Arg Gly Leu Asn Gly Lys
                805                 810                 815

Val Asp Ser Phe Leu
            820

<210> SEQ ID NO 177
<211> LENGTH: 765
<212> TYPE: PRT
<213> ORGANISM: Aspergillus nidulans

<400> SEQUENCE: 177

Met Ser Ser Thr Ala His Pro Thr Asn Leu Ala Pro Ser Gly Asn Gly
1               5                   10                  15

Ser Ala Ala Cys Val His Cys His Arg Arg Lys Val Arg Cys Asp Ala
            20                  25                  30

Arg Leu Val Gly Leu Pro Cys Ser Asn Cys Arg Ser Ala Gly Lys Thr
        35                  40                  45

Asp Cys Gln Ile His Glu Lys Lys Lys Leu Ala Val Arg Ser Ile
    50                  55                  60

Leu Asp Pro Val Pro Ile Arg Cys Arg Pro Asn Pro Glu Glu Ala
65                  70                  75                  80

Pro Lys Pro Ile Ser Ser Leu Ser Pro Ser Glu Pro Pro Asn Ala
                85                  90                  95

Phe Thr Thr Ala Leu Arg Ala Val Gln Ser Asp Ile Thr Ala Pro Ser
            100                 105                 110

Gly Val Ala Asn Arg Val Ala His Ile Arg Ser Arg Ser Ser Gln Tyr
        115                 120                 125

Asp Thr Lys Gly Thr Arg Ser Asn Asn Asn Ser Gly Asn Asn Thr Gln
    130                 135                 140

Tyr Gln Asn Val Leu Pro Glu Pro Asp Ser Pro Tyr Ser Arg Pro
145                 150                 155                 160

Ala Ala Ser Asp Pro Ser Glu Gly Glu Ser Arg Ala Asp Ile Glu Lys
                165                 170                 175

Arg Leu Val Asn Leu Ile Asp Gly Glu Ala Ser Asp Ser Arg Ala Ile
```

```
                    180                 185                 190
Gln Arg Gly Val Arg Ala Ile Tyr Val Gly His Glu Leu Ser Asn Met
                195                 200                 205
Ser Phe Leu Ile Arg Gln Gln Arg Asp Thr Gly Asp Asp Val Tyr His
            210                 215                 220
Phe Ala Gly Asn Glu Ile Pro Arg Arg Gln Leu Arg Thr Gly His Asp
225                 230                 235                 240
Gln Leu Leu Met Asp Ala Leu Thr Leu Pro Glu Pro Ala Leu Ala Asp
                245                 250                 255
Glu Leu Val His Ala Tyr Phe Ala Gln Val Asn Pro Gly Tyr Pro Ile
            260                 265                 270
Val Glu Glu Glu Leu Phe Met Ser Gln Tyr Arg Asn Arg Asp Pro Ala
                275                 280                 285
Asp Ala Pro Pro Ile Leu Leu Gln Thr Ile Leu Leu Val Gly Ala
            290                 295                 300
His Val Thr Arg Pro Lys Ser Glu Arg Asp Thr Leu Lys Asp Ile Phe
305                 310                 315                 320
Phe Arg Arg Ala Lys Trp Leu Phe Asp Asn Arg Ile Glu Arg Asn Arg
                325                 330                 335
Asp Ile Leu Val Gln Ala Ala Leu Leu Leu Thr Trp His Ser Asp Leu
            340                 345                 350
Ala Asp Asp Asp Val Ser Ala Asn Ala His Tyr Trp Ile Gly Ile Ala
            355                 360                 365
Ala Arg Ile Ala Thr Gly Leu Gly Met His Arg Asn Pro Val Cys Thr
        370                 375                 380
Leu Asn Leu Glu Asp Ser Asp Val Ser Pro Leu Thr Phe Ser Asp Phe
385                 390                 395                 400
Glu Gly Cys Gly Ala Arg Val Gln Ala Asp Phe Val Ile His Phe Ser
                405                 410                 415
Glu Leu Cys Thr Met Ile Ser Tyr Ile Val Arg Glu Arg Phe Gly Leu
            420                 425                 430
Arg Ile Ser Ala Glu Arg Arg Lys Ala Ala Leu Leu Glu Ala Asp Glu
        435                 440                 445
Ala Leu Ala Asn Trp Ser Leu Arg Leu Pro Asp Arg Leu Arg Leu Arg
            450                 455                 460
Ala Ser Asp Met Asp Pro Trp Ser Ala Met Leu His Leu Thr Tyr Asn
465                 470                 475                 480
Asn Phe Leu Ile Leu Leu His Arg Pro His Pro Arg Ala Ser Ala Tyr
                485                 490                 495
Ser Asp Asp Tyr Gly Pro His Asp Ala Glu Ile Cys Ser Ala Ala Ala
            500                 505                 510
Gly Val Ile Ala Ser Ile Phe Glu Glu Leu Arg Ile His Asp Arg Leu
        515                 520                 525
Lys Leu Leu Trp Tyr Ser Gly Val His Thr Leu Phe Thr Ala Met Ile
        530                 535                 540
Gln Val Arg Val Glu Leu Arg Phe Ser Asn Pro Val Leu Ala Ile Asn
545                 550                 555                 560
Ala Leu Arg Arg Phe Asp Ser Ala Ser Tyr Ser Leu Arg Glu Leu Ala
                565                 570                 575
Gln Tyr Trp Ser His Ala Ser Thr Ile Leu Arg Leu Phe Glu Glu Ser
            580                 585                 590
Arg Arg Leu Gln Glu Asp Leu Arg Thr Thr Thr Ser Asp Arg Pro Arg
            595                 600                 605
```

```
Arg Phe Ser Asn Leu Ser Asn Ser Thr Asn Ser Pro Ala Ser Gln
        610                 615                 620

Gln Lys Asn Thr Ser Gly Ile Pro His Leu Ala Asn Ile Asn Ser Ser
625                 630                 635                 640

Asp Ala Thr Pro Pro Ser Ala Pro Ser Ile Pro Pro Leu Gln Pro Ser
                645                 650                 655

Ser Gln Leu Ser Tyr Glu Val Pro Thr Thr Glu Ser Ala His His Asn
                660                 665                 670

Pro Arg Ser Gln Pro Thr Leu Ser Ala His Thr His Thr Tyr Thr Thr
        675                 680                 685

Gln Pro Phe Asp Thr Trp Ile Pro Ser Asn Asn Leu Thr Pro Met Asp
        690                 695                 700

Thr Val Asp Asn Ser Arg Glu Met Leu Asp Trp Arg Gln Leu Phe Ser
705                 710                 715                 720

Phe Thr Asp Leu Glu Gly Pro Val Leu Pro Ser Thr Met Glu Gly Ile
                725                 730                 735

Thr Glu Leu Glu Asp Glu Trp Arg Gln Ile Tyr Trp Gln Glu Thr Pro
                740                 745                 750

Met Ser Asp Leu Leu Gln Asp Gly Gly Trp Met His Gly
        755                 760                 765

<210> SEQ ID NO 178
<211> LENGTH: 735
<212> TYPE: PRT
<213> ORGANISM: Aspergillus oryzae

<400> SEQUENCE: 178

Met Ser Ser Thr Ala His Asn Ser Gln Pro Ser Thr Gly Asn Gly Ser
1               5                   10                  15

Ala Ala Cys Ile His Cys His Arg Arg Lys Val Arg Cys Asp Ala Arg
                20                  25                  30

Ile Val Gly Leu Pro Cys Ser Asn Cys Arg Ser Ala Gly Lys Ala Asp
                35                  40                  45

Cys Arg Ile His Glu Lys Lys Lys Arg Leu Ala Val Arg Ser Ile Leu
50                  55                  60

Asp Pro Val Pro Ile Arg Cys Arg Pro Pro Asp Ser Asp Ser Thr
65                  70                  75                  80

Pro Lys Leu Leu Pro Ser Thr Pro Ile Gln Pro Asn Ala Phe Thr Thr
                85                  90                  95

Ala Phe Arg Gly Val Gln Pro Asp Val Thr Ser Pro Val Ala Ala Gly
                100                 105                 110

Ala Gln Ile Ile Gln Ser Pro His Ser Ser Tyr Thr Asn Gly Asn His
            115                 120                 125

Leu Ser Asn Asn Arg Gly Ser Gln Pro Ile Thr Glu Thr Gln Thr Phe
    130                 135                 140

Thr Arg Gln Pro Gly Ala Asp Arg Ser Met Glu Leu Glu Asn Asn Ala
145                 150                 155                 160

Asp Leu Glu Lys Arg Leu Val Lys Leu Ile Asp Glu Glu Ser Gly
                165                 170                 175

Ser Arg Glu Ile Gln Arg Gly Val Arg Ala Ile Tyr Val Gly His Glu
                180                 185                 190

Leu Ser Asn Met Ser Phe Leu Ile Arg Gln Gln Arg Asp Lys Asp Asp
            195                 200                 205

Asp Val Tyr His Phe Ala Gly Asn Glu Ile Pro Arg Arg Gln Leu Arg
```

```
              210                 215                 220
Thr Gly His Asp Gln Leu Leu Met Asp Ala Leu Thr Leu Pro Glu Pro
225                 230                 235                 240

Ala Leu Ala Asp Glu Leu Val Glu Ala Tyr Phe Met His Val Asn Pro
                245                 250                 255

Gly Tyr Pro Ile Ile Glu Glu Asp Leu Phe Met Thr Gln Tyr Arg Asn
                260                 265                 270

Arg Asp Pro Ala Asp Pro Pro Ile Leu Leu Leu Gln Ala Ile Leu
            275                 280                 285

Leu Val Gly Ala His Val Thr Arg Pro Lys Ala Glu Arg Asp Ala Leu
        290                 295                 300

Lys Glu Ile Phe Phe Arg Arg Val Lys Trp Leu Phe Asp Ser Arg Ile
305                 310                 315                 320

Glu Arg Asn Arg Asp Ile Met Val Gln Ala Ala Leu Leu Met Thr Trp
                325                 330                 335

His Ser Asp Ser Ala Asp Asp Val Ala Ala Asn Ala His Tyr Trp
            340                 345                 350

Val Gly Val Ala Ala Arg Ile Ala Thr Gly Leu Gly Met His Arg Asn
        355                 360                 365

Pro Val Ser Thr Ile Asn Leu Glu Asp Ser Asp Val Ser Pro Leu Thr
                370                 375                 380

Pro Ser Asp Phe Glu Gly Cys Gly Ser Arg Val Gln Ala Glu Tyr Val
385                 390                 395                 400

Ile His Phe Ser Glu Leu Cys Thr Met Ile Pro Tyr Ile Val Arg Glu
                405                 410                 415

Arg Phe Gly Leu Arg Val Ser Ala Glu Arg Lys Ala Ala Leu Gln
            420                 425                 430

Glu Ala Asp Glu Ala Leu Ala Asn Trp Ser Leu Lys Leu Pro Asp Ser
        435                 440                 445

Leu Arg Leu Arg Ala Ser Asp Met Asp Pro Trp Ser Ala Met Leu His
450                 455                 460

Leu Thr Tyr Asn Asn Phe Leu Ile Leu Leu His Arg Pro His Pro Arg
465                 470                 475                 480

Ala Ser Ala Tyr Ser Asp Asp Tyr Gly Pro His Asp Ala Glu Ile Cys
                485                 490                 495

Ser Ala Ala Gly Val Ile Ala Ser Ile Phe Glu Glu Leu Arg Leu
            500                 505                 510

Asn Asp Arg Leu Lys Phe Leu Trp Tyr Ser Gly Val His Thr Leu Phe
        515                 520                 525

Thr Ala Met Ile Gln Val Arg Val Glu Leu Arg Phe Ser Asn Pro Val
530                 535                 540

Leu Ala Ile Asn Ala Leu Arg Arg Phe Asp Ser Ala Ser Tyr Ser Leu
545                 550                 555                 560

Arg Glu Leu Ala Glu Tyr Trp Ser His Ala Asn Thr Ile Leu Arg Leu
                565                 570                 575

Phe Gln Asp Ser Lys Arg Leu Gln Glu Asp Leu Arg Met Ala Thr Ser
            580                 585                 590

Glu Arg Pro Arg Arg Phe Ser Thr His Asp Gln Asn Lys Asn Thr Thr
        595                 600                 605

Asn Pro Ser Asn Pro His Pro Thr Pro Thr Pro Asn Leu Asn Ser Asn
610                 615                 620

Thr Thr Ile Gln Ser Ala Gln Thr Glu Pro Arg Pro Pro Tyr Glu Val
625                 630                 635                 640
```

```
Pro Thr Pro Glu Ser Pro Arg Met Pro Thr Thr Met Ser Pro His
                645                 650                 655

Gln Asn Gln Pro Phe Asp Ser Trp Ile Pro Ser Ser His Leu Ala Ser
            660                 665                 670

Val Asp Pro Ile Asp Gln Pro Arg Glu Phe Leu Asp Trp Arg Pro Val
            675                 680                 685

Phe Ser Phe Thr Asp Pro Asp Gln Ser Val Leu Pro Val Pro Met Glu
        690                 695                 700

Gly Leu Pro Glu Leu Glu Asp Glu Trp Arg Gln Ile Tyr Trp Gln Glu
705                 710                 715                 720

Thr Pro Met Ser Asp Leu Leu Gln Asp Gly Gly Trp Met His Gly
                725                 730                 735

<210> SEQ ID NO 179
<211> LENGTH: 579
<212> TYPE: PRT
<213> ORGANISM: Aspergillus niger

<400> SEQUENCE: 179

Met Asp Ser His Pro Ser Pro Thr Lys Gln Lys Ala Ser Lys Gln Ala
1               5                   10                  15

Cys Asp Asn Cys Arg Arg Arg Lys Ile Lys Cys Ser Arg Glu Leu Pro
            20                  25                  30

Cys Asp Lys Cys Arg Arg Leu Leu Ser Cys Ser Tyr Ser Asp Val
        35                  40                  45

Leu Arg Arg Lys Gly Pro Lys Phe Arg Thr Leu Tyr Pro Leu Ala Pro
    50                  55                  60

Ile His Pro Leu Val Ser Arg Gln Gln Asn Thr Tyr Gln Gln Asn Ser
65                  70                  75                  80

Ser Gln Asn Pro Leu Asn Lys Gln Trp Thr Ala Asp Val Gly Tyr
            85                  90                  95

Pro Leu Ser Ser Leu Met Ser Pro Ser Phe Thr Val Ala Asp Pro Gln
            100                 105                 110

Tyr Leu Pro His Asp Ala Pro Glu Pro Phe Ser Gln Phe Pro Pro Pro
            115                 120                 125

Glu Leu Val Ser Ser Pro Asp Ser Thr Asn Ser Leu Ser Asp Ser Ser
    130                 135                 140

Met Ala Leu Val Arg Pro Tyr Ala Arg Arg Leu Ser Ala Pro Val Leu
145                 150                 155                 160

Leu Ala His Val Asn Val Tyr Leu Lys Tyr Leu Phe Pro Ile Met Pro
                165                 170                 175

Val Val Arg Lys Glu Glu Leu Gln Gln Asp Cys His Gln Pro Glu Arg
            180                 185                 190

Leu Ser Pro Gln Arg Tyr Ala Phe Leu Val Ala Leu Cys Ala Ala Thr
        195                 200                 205

His Ile Gln Leu Lys Leu Asp Gly Thr Ala Ser Val Pro Glu Pro Ser
    210                 215                 220

His Leu Gln Ala Gly Ile Asp Gly His Ser Trp Met Ser Gly Glu Glu
225                 230                 235                 240

Leu Leu Ala Glu Ala Val Arg Ala Arg Lys Asp Cys Asp Pro Val Asp
                245                 250                 255

Gly Met Asn Ile Glu Ser Leu Leu Thr Ser Phe Phe Leu Phe Ala Ser
            260                 265                 270

Tyr Gly Asn Leu Asp Lys Gln Asp His Ala Trp Phe Tyr Leu Cys Gln
```

```
            275                 280                 285
Ala Thr Ser Met Val Phe Thr Leu Ala Leu His Arg Glu Ser Ser Tyr
        290                 295                 300
Val Asp Leu Ser Thr Glu Glu Ala Glu Glu Arg Arg Lys Val Phe Trp
305                 310                 315                 320
Leu Leu Phe Val Thr Glu Arg Gly Tyr Ala Leu Gln Gln Ser Lys Pro
                325                 330                 335
Val Met Leu Arg Asn Ser Ile Arg Lys Pro Gln Val Leu Cys Ser Glu
            340                 345                 350
Asp Pro Ile Leu Ala Tyr Gly Phe Ile Asn Leu Ile Ser Ile Phe Glu
                355                 360                 365
Lys Leu Thr Val Asn Leu Tyr Asp Trp Val Ser Ala Gly Gly Met Asp
        370                 375                 380
Gly Ser Ser Glu Met Pro Pro Thr Ser Ala Ile Gln Ser Ser Leu Cys
385                 390                 395                 400
Asn Ala Ile Ser Val Asp Gly Val Ser Glu Ile Gln Lys Val Asp Ile
                405                 410                 415
Leu Ile Thr Gln Gln Trp Leu Gln Thr Val Met Trp Lys Leu Ser Met
            420                 425                 430
Thr Arg Ala Thr Gln Pro Gly Ser Arg Asp Glu Ala Val Leu Pro Phe
                435                 440                 445
His Leu Pro Val Leu Val Gly Lys Ala Val Met Asn Val Ile Gly Ala
        450                 455                 460
Ala Ser Gln Gly Ala Val Asp Val His Gly Ile Gly Met Glu Gln Lys
465                 470                 475                 480
Leu Phe Asp Leu Gly Ser Ser Val Ala Asp Val Ala Arg Ser Leu Asn
                485                 490                 495
Ser Lys Ala Ala His Arg Leu Thr Glu Ala Ala Val Asp Pro Arg Glu
            500                 505                 510
Leu Leu Trp Gly Ile Leu Thr Thr Leu Ser Arg Ile Arg Gly Ser Gln
                515                 520                 525
Ser Tyr Leu Phe Pro Ser Leu Leu Glu Arg Cys Lys Gly Ala Leu Asp
        530                 535                 540
Phe Thr Ser Pro Thr Ser Met Gly Asn Phe Leu Pro Pro Leu Ser Thr
545                 550                 555                 560
Ala Ser Thr Trp Gly Arg Gly Asn Gly Ala Arg Arg Gly Phe Cys Pro
                565                 570                 575
Gly Glu Ser

<210> SEQ ID NO 180
<211> LENGTH: 662
<212> TYPE: PRT
<213> ORGANISM: Aspergillus nidulans

<400> SEQUENCE: 180

Met Ala Ser Pro Ala Ala Pro Lys His Lys Pro Phe Lys Gln Ala Cys
1               5                   10                  15
Asp Asn Cys Arg Arg Arg Lys Ile Lys Cys Ser Arg Glu Leu Pro Cys
            20                  25                  30
Asp Lys Cys Gln Arg Leu Leu Leu Ser Cys Ser Tyr Ser Asp Val Leu
        35                  40                  45
Arg Arg Lys Gly Pro Lys Phe Arg Thr Leu Tyr Pro Leu Ala Pro Ile
    50                  55                  60
His Pro Leu Val Ala Arg Asp Arg Gln Ile Leu Gln Tyr Asp Pro Pro
```

```
                65                  70                  75                  80
Arg Phe Ser Ala Glu Arg Glu Trp Tyr Ala Glu Pro Thr Ser Tyr Pro
                    85                  90                  95

Val Gly Gly Ser Pro Thr Ser Pro Pro Phe Met Glu Pro Gln Tyr
                100                 105                 110

Leu Pro Pro Glu His Pro Asp Ser Phe Ser Arg Leu Pro Pro Glu
                115                 120                 125

Leu Val Ser Ser Pro Asp Ser Leu Asn Ser Leu Ser Asp Ser Pro Thr
130                 135                 140

Ala Val Leu Phe Arg Ser Pro Arg Ile Leu Thr Ala Pro Val Leu Leu
145                 150                 155                 160

Ala His Val Asn Val Tyr Leu Lys Tyr Met Phe Pro Ile Met Pro Val
                    165                 170                 175

Val Arg Arg Glu Glu Leu Gln Gln Asp Cys His His Pro Glu Arg Leu
                180                 185                 190

Thr Pro Gln Arg Tyr Ala Phe Leu Ala Ser Leu Cys Ala Ala Thr His
                195                 200                 205

Ile Gln Leu Lys Leu Asp Gly Ala Thr Pro Val Ala Asp Pro Ser His
            210                 215                 220

Phe Gln Ala Gly Glu Asn Ser Ser Met Ser Gly Glu Glu Leu Leu Ala
225                 230                 235                 240

Glu Ala Val Arg Ala Arg Lys Asp Cys Asp Pro Ile Glu Asp Met Asn
                245                 250                 255

Val Glu Ser Leu Leu Thr Ser Phe Phe Leu Phe Ala Ser Tyr Gly Asn
                260                 265                 270

Leu Asp Arg Gln Asp His Ala Trp Phe Tyr Leu Cys Gln Ala Thr Ser
            275                 280                 285

Met Val Phe Ala Leu Gly Leu His Arg Glu Ser Thr Tyr Ala Glu Leu
                290                 295                 300

Asn Thr Glu Glu Ala Glu Gln Lys Arg Arg Val Phe Trp Leu Leu Phe
305                 310                 315                 320

Ile Thr Glu Arg Gly Tyr Ala Leu Gln Gln Ala Lys Pro Val Met Leu
                325                 330                 335

Arg Asn Ser Ile His Lys Pro Gln Val Leu Cys Ser Asp Asp Pro Ile
                340                 345                 350

Leu Ala Tyr Gly Phe Ile Asn Leu Ile Gly Val Phe Glu Ser Leu Ser
                355                 360                 365

Val Asn Leu Tyr Asp Trp Val Ser Ala Gly Ser Val Ser Gly Gly
                370                 375                 380

Gly Asn Asn Arg Asp Gly Ser Ser Glu Met Pro Pro Thr Ser Ala Ile
385                 390                 395                 400

Gln Ala Thr Leu Ser Lys Pro Ile Ser Leu Glu Gly Val Ser Glu Ile
                405                 410                 415

Gln Lys Val Asp Ile Leu Ile Thr Gln Gln Trp Leu Gln Ala Met Met
                420                 425                 430

Trp Lys Leu Ser Met Thr Arg Ala Ser Gln Pro Gly Ser Arg Asn Glu
                435                 440                 445

Thr Val Leu Pro Phe His Leu Pro Val Met Val Gly Lys Ala Val Met
                450                 455                 460

Ser Val Ile Ala Glu Ala Ser Gln Gly Ala Val Asp Ala His Gly Ile
465                 470                 475                 480

Gly Met Glu Gln Lys Leu Phe Asp Leu Gly Thr Ser Ile Ala Asp Val
                485                 490                 495
```

```
Ser Arg Ser Leu Ser Thr Lys Ala Ala Asn Ser Leu Ala Glu Ser Thr
            500                 505                 510

Val Asp Pro Arg Glu Leu Leu Trp Gly Ile Leu Ser Thr Leu Ser Arg
            515                 520                 525

Ile Arg Gly Ser Gln Ser Tyr Leu Phe Pro Ser Leu Leu Glu Arg Cys
        530                 535                 540

Lys Gly Thr Leu Gly Phe Asp Ser Pro Thr Pro Leu Ser Ile Ser Asp
545                 550                 555                 560

Phe His Gln Ile Asn Pro Pro Leu Leu Asn Ser Ala Ser Ser Ser Ser
                565                 570                 575

Ile Ala Ser Glu Thr Leu Asp Ile Ser Gly Pro Trp Pro Ala Ala Asp
            580                 585                 590

Asp Asn Thr Met Asp Ser Ser Thr Gly Ser Arg Thr Thr Asn Ser Cys
            595                 600                 605

Ala Trp Glu Ile Thr Ser Gly Asp Thr Asn Asp Gln Asn Gln Thr Ser
        610                 615                 620

Asp Gln Pro Pro Ser Leu Ser Gly Ser Ser Ser Val Pro Leu Ser Val
625                 630                 635                 640

Ser Arg Met His Ser Ser Thr Ser Met Ala Ala Glu Leu Ser Phe Gln
                645                 650                 655

Ala Gly Arg Leu Leu Thr
            660

<210> SEQ ID NO 181
<211> LENGTH: 604
<212> TYPE: PRT
<213> ORGANISM: Aspergillus oryzae

<400> SEQUENCE: 181

Met Ser His Ser Pro Thr Asp Ile Pro Ser Thr Ser Glu Lys Glu Met
1               5                   10                  15

Glu Ser Thr Pro Glu Lys Pro Pro Lys Gln Ala Cys Asp Asn Cys Arg
            20                  25                  30

Arg Arg Lys Ile Lys Cys Ser Arg Glu Leu Pro Cys Asp Lys Cys Gln
        35                  40                  45

Arg Leu Leu Leu Ser Cys Ser Tyr Ser Asp Val Leu Arg Arg Lys Gly
    50                  55                  60

Pro Lys Phe Arg Thr Leu Tyr Pro Leu Ala Pro Ile His Pro Leu Ala
65              70                  75                  80

Ser Arg Pro Arg Pro Leu Thr Lys Glu Trp Leu Pro Asn Pro Gly
                85                  90                  95

Ala Cys His Leu Ala Ser Pro Thr Ser Pro Ser Thr Val Ala Asp
            100                 105                 110

Ala Gln Tyr Leu His Pro Asp Phe Ser Glu Ser Phe Thr Arg Leu Pro
        115                 120                 125

Pro Pro Asp Leu Val Ser Ser Pro Asp Ser Thr Asn Ser Leu Phe Asp
    130                 135                 140

Ser Ser Thr Ile Gly Ala Leu Pro Ala Pro Arg Arg Leu Ser Thr Pro
145                 150                 155                 160

Asn Leu Leu Ala His Val Asn Val Phe Leu Lys Tyr Leu Phe Pro Ile
                165                 170                 175

Met Pro Val Val Arg Gln Asp Gln Leu Gln Gln Asp Cys His Gln Pro
            180                 185                 190

Glu Arg Leu Ser Pro Gln Arg Tyr Ala Phe Ile Ala Ala Leu Cys Ala
```

-continued

```
            195                 200                 205

Ala Thr His Ile Gln Leu Lys Leu Asp Gly Ala Ala Pro Gly Pro Glu
            210                 215                 220

Ala Ala Ser Ala Arg Ala Ser Leu Asp Gly His Pro Met Leu Ser Gly
225                 230                 235                 240

Glu Glu Leu Leu Ala Glu Ala Val Arg Ala Arg Lys Glu Tyr Asn Val
                245                 250                 255

Val Asp Glu Ile Asn Met Glu Asn Leu Leu Thr Ser Phe Phe Leu Phe
            260                 265                 270

Ala Ala Tyr Gly Asn Leu Asp Arg Gln Asp Gln Ala Trp Phe Tyr Leu
            275                 280                 285

Cys Gln Thr Thr Ser Met Val Phe Thr Leu Gly Leu Gln Arg Glu Ser
290                 295                 300

Thr Tyr Ser Lys Leu Ser Val Glu Glu Ala Glu Glu Lys Arg Arg Val
305                 310                 315                 320

Phe Trp Leu Leu Phe Val Thr Glu Arg Gly Tyr Ala Leu Gln Gln Ala
                325                 330                 335

Lys Pro Val Met Leu Arg Asn Ser Ile His Lys Pro Gln Val Leu Cys
            340                 345                 350

Ser Asp Asp Pro Ile Leu Ala Tyr Gly Phe Ile Asn Leu Ile Asn Val
            355                 360                 365

Phe Glu Lys Leu Ser Pro Asn Leu Tyr Asp Trp Val Ser Ala Gly Gly
370                 375                 380

Ser Ser Ala Asp Gly Asp Pro Pro Thr Ser Ser Ile Gln Ser Ser
385                 390                 395                 400

Leu Ala Lys Gln Ile Ser Leu Glu Gly Val Ser Glu Ile Gln Lys Val
                405                 410                 415

Asp Ile Leu Ile Thr Gln Gln Trp Leu Gln Thr Met Met Trp Lys Leu
            420                 425                 430

Ser Met Thr His Val Thr Gln Pro Gly Ser Arg Asp Asp Ala Val Leu
            435                 440                 445

Pro Phe His Leu Pro Val Leu Val Gly Lys Ala Val Met Gly Val Ile
450                 455                 460

Ala Ala Ala Ser Gln Gly Ala Val Asp Ala His Gly Ile Gly Met Glu
465                 470                 475                 480

Gln Lys Leu Tyr Asp Leu Gly Thr Ser Val Ala Asp Val Ser Arg Ser
                485                 490                 495

Leu Ser Thr Lys Ala Ala His His Leu Ala Glu Ser Thr Ile Asp Pro
            500                 505                 510

Arg Glu Leu Leu Trp Gly Ile Leu Thr Thr Leu Ser Arg Ile Arg Gly
            515                 520                 525

Ser Gln Ser Tyr Leu Phe Pro Ala Leu Val Glu Gln Ser Arg Gly Ile
530                 535                 540

Ile Ser Phe Asp Cys Ser Leu Ser Ile Ser Asp Phe Leu Pro Ser Phe
545                 550                 555                 560

Gly Gly Pro Pro Ala Ile Met Trp Arg Thr Gly Glu Ser Gly Phe Asp
                565                 570                 575

Leu Leu Gly Ile Ala Asp Asp Leu Gln Glu Arg Glu Asn Glu Gly Gly
            580                 585                 590

Glu Gly Ile Val Val Ala Gly Glu Glu Ile Ser Phe
            595                 600

<210> SEQ ID NO 182
```

<211> LENGTH: 311
<212> TYPE: PRT
<213> ORGANISM: Aspergillus nidulans

<400> SEQUENCE: 182

Met Thr Ala Arg Gln Ser Thr Pro Ser Asp Asn Ser His Ser Asp
1               5                   10                  15

Ser Gly Val Arg Lys Arg Val Cys Lys Ala Cys Asp Arg Cys Arg Leu
            20                  25                  30

Lys Lys Ser Lys Cys Asp Gly Ala Lys Pro Cys Gly Arg Cys Arg Ala
        35                  40                  45

Asp Asn Thr Leu Cys Val Phe Gly Glu Arg Lys Lys Ala His Asp Lys
50                  55                  60

Val Tyr Pro Lys Gly Tyr Val Glu Met Leu Glu Gln Gln Gln Thr Trp
65                  70                  75                  80

Leu Val Asn Gly Leu Gln Glu Leu Tyr Arg Arg Leu Leu Glu Gly Asp
                85                  90                  95

Gly Trp Pro Gly Glu Pro Leu Lys Cys Glu Ala Asn Gly Gln Pro Leu
            100                 105                 110

Thr His Asp Leu Leu Thr Gln Leu Gly Ala Leu Asp Thr Ser Lys His
        115                 120                 125

Glu Arg Phe Glu Glu His Ala Glu Val Met Gln Gln Glu Leu Trp Lys
130                 135                 140

Arg Asn Ala Gly His Met Gln Arg Gln Asp Ser Ser Asp Thr Ser Ser
145                 150                 155                 160

Glu Ser Pro Gln Ser Pro Val Met Pro Ser Gln Phe Ser Asp Pro Phe
                165                 170                 175

Ser Val Arg Thr Val Pro Gln Thr Pro Thr Thr Ile Ser Pro Asn Thr
            180                 185                 190

Thr Leu Arg Ile Asp Val Pro Gln Ser Ala Thr Lys Ser Glu Pro Gln
        195                 200                 205

Met Thr Ser Pro Asn Ser Ile Tyr Thr Thr Ala Val Ser Met Pro Arg
210                 215                 220

Val Val Asp Pro Ser Glu Leu Gln Ser Ala Gln Ile Ala Asn Pro Gln
225                 230                 235                 240

Trp Pro Ser Pro Gly Phe Gly Gly Tyr Asp Glu Met Asp Leu Met Ser
                245                 250                 255

Gly Gln Tyr Asn Gly Leu Pro Tyr Glu Asp Ala Ile Ser Ser Pro Met
            260                 265                 270

Phe Asn Arg Pro Met Pro Met Gly Cys Leu Ile Pro Gly Ser Tyr Gly
        275                 280                 285

Asn Leu Asp Asn Lys Asn Asp Phe Glu Asp Ile Asn Gln Phe Leu Asn
290                 295                 300

Thr Gln Leu Glu Ile Thr Ser
305                 310

<210> SEQ ID NO 183
<211> LENGTH: 880
<212> TYPE: PRT
<213> ORGANISM: Saccharomyces cerevisiae

<400> SEQUENCE: 183

Met Gly Ile Ser Ser Lys Asn Gly Pro Lys Lys Met Gly Arg Ala Lys
1               5                   10                  15

Thr Phe Thr Gly Cys Trp Thr Cys Arg Gly Arg Lys Val Lys Cys Asp
            20                  25                  30

```
Leu Arg His Pro His Cys Gln Arg Cys Glu Lys Ser Asn Leu Pro Cys
        35                  40                  45

Gly Gly Tyr Asp Ile Lys Leu Arg Trp Ser Lys Pro Met Gln Phe Asp
        50                  55                  60

Pro Tyr Gly Val Pro Ile Pro Gln Asn Ser Pro Ala Thr Thr Thr Asn
65                  70                  75                  80

Leu Ser Gly Ser Val Asp Glu Pro Gln Tyr Gln Arg Arg Asn Ile Asp
                85                  90                  95

Phe Val Arg Tyr Asp Glu Glu Tyr Val Tyr His Glu Asp Met Asp Asp
                100                 105                 110

Glu Leu Thr Met Leu His Thr Pro Pro Ile Glu Lys Ile Ser Asp Asn
            115                 120                 125

Lys Thr Trp Ile Ile Lys Lys Phe Gly Val Phe Lys Gly Thr Asp Lys
        130                 135                 140

Ile Asp Lys Gln Tyr Ala Pro Arg Lys Lys Arg Asn Arg Lys Arg Val
145                 150                 155                 160

Ala Lys Ser Leu Glu Ser Ser Ala Ser Ile Ser Leu Ser Ser Leu Pro
                165                 170                 175

Ser Ser Ser Thr Ile Ser Phe Pro Ile Arg His Ile Glu Asp Lys Leu
                180                 185                 190

Arg Asn Lys Gly His Val Lys Thr Gly Ile Leu Ser Ala Asn Asp Gly
            195                 200                 205

Val Pro Pro Thr Pro Asn Leu Leu Asp Tyr Asp Trp Asn Asn Leu Asn
        210                 215                 220

Ile Thr Gly Tyr Glu Trp Ile Ser Ser Glu Leu Arg Asp Asp Ala Leu
225                 230                 235                 240

Leu Ser Ala Val Thr Leu Gln Gly His His Leu Gly His Thr Gln Pro
                245                 250                 255

Gln Glu Ile Ser Leu Glu Glu Asn Ser Asn Val Val Ser Gly Glu Glu
                260                 265                 270

His Val Asn Ala Lys Glu His Gly Cys Ala Phe Glu Ala Asp Asn Gln
            275                 280                 285

Gly Ser Ser Thr Leu Pro Asn Lys Ala Ala Ser Ala Asn Asp Lys Leu
        290                 295                 300

Tyr Gln Gln Asn Leu Lys Leu Leu Phe Gln Lys Asn Ser Ser Asn Ser
305                 310                 315                 320

Glu Glu Pro Asp Pro Gln Ala Leu Ile Asp Asp Val Phe Val Asn Ile
                325                 330                 335

Glu Pro Arg Ser Leu Pro Ala Ser Asp Leu Asn Lys Ile Thr Leu Ala
            340                 345                 350

Pro Pro Asn Glu Glu Ser Arg Met Pro Lys Ser Met Leu Glu Leu Thr
        355                 360                 365

Ser Tyr Ser Ser Asp Leu Pro Pro Glu Leu Val Asp Ile Ile Pro Lys
370                 375                 380

Thr Asp Leu Thr Val His Gly Leu Ala Arg Phe Leu Leu Asn His Tyr
385                 390                 395                 400

Phe Asn Asn Val Ala Asp Lys Met Thr Val Val Leu Glu Lys Asn
                405                 410                 415

Pro Trp Lys Thr Leu Tyr Phe Pro Arg Ala Leu Met Ala Leu Gly Asp
            420                 425                 430

Leu Ala Gly Leu Gly Gln Ser Ser Asn Ser Arg Asn Ala Leu Leu Asn
        435                 440                 445
```

```
Ala Leu Leu Ala Val Ser Cys Phe His Leu Gln Ser Lys Tyr Pro Arg
450                 455                 460

Asn Tyr Lys Leu Gln Lys Tyr Phe Leu Gly Leu Gly Ile Glu Leu Arg
465                 470                 475                 480

Asn Gln Ala Ser Asn Phe Leu Arg Leu Cys Leu Asn Thr Lys Ser Ser
                485                 490                 495

Ile Pro Glu Lys Tyr Lys Asp Val Leu Thr Ala Ile Leu Ser Met Asn
            500                 505                 510

Ser Ile Asp Val Val Trp Gly Thr Met Ala Asp Cys Gln Asp His Leu
        515                 520                 525

Ala Leu Cys Glu Asp Phe Val Glu Ser Arg Met Lys Leu Arg Pro Asn
530                 535                 540

Ile Ser Glu Lys Thr Lys Thr Leu His Arg Ile Phe Ser Phe Leu Lys
545                 550                 555                 560

Leu Ile Gln Asp Ser Thr Ala Leu Asp Lys Val Arg Ala Lys Glu Ile
                565                 570                 575

Val Ile Leu Pro Ser Glu Glu Asp Asp Asn Tyr Lys Pro Leu Asp Thr
            580                 585                 590

Ser Asn Ala Thr Thr Ser Ser Ser Glu Pro Arg Val Asp Val Val Gln
        595                 600                 605

Glu Gly Leu Phe Arg Glu Ala Leu Asn Glu Asn Asp Gly Lys Ile His
610                 615                 620

Ile Glu Phe Val Lys Glu Pro Ile Thr Asn Val Ser Ala Asp Ser Thr
625                 630                 635                 640

Pro Ser Ser Thr Thr Pro Pro Ile Phe Thr Asn Ile Ala Thr Glu Ser
                645                 650                 655

Tyr Tyr Asn Lys Ser Asp Ile Ser Lys Leu Val Ser Lys Thr Asp Glu
            660                 665                 670

Asn Ile Ile Gly Thr Asp Ser Leu Tyr Gly Leu Pro Asn Ser Leu Ile
        675                 680                 685

Leu Leu Phe Ser Asp Cys Val Arg Ile Val Arg His Asn Glu Tyr Tyr
690                 695                 700

Asn Leu Thr Tyr Leu Pro Val Pro Arg Lys Phe Asn Glu Leu Ser Leu
705                 710                 715                 720

Asn Phe Glu Lys Arg Leu Leu Lys Trp Lys Ser Glu Trp Asn Phe His
                725                 730                 735

Gln Glu Asn Ser Glu Gly Lys Ser Phe Ile Asn Ser Thr Ala Glu Ala
            740                 745                 750

Leu Tyr His His Thr Met Ser Phe Tyr Phe Ser Leu Ile Ile Tyr Tyr
        755                 760                 765

Phe Thr Met Ala Arg Ser Leu Asn Cys Gln Phe Leu Gln Asn Tyr Val
770                 775                 780

Ala Lys Val Leu Asp His Leu Asn Ala Met Glu Glu Leu Val Asp Gln
785                 790                 795                 800

Lys Lys Val Lys Ile Val Pro Leu Ile Trp Gln Gly Phe Met Ala Gly
                805                 810                 815

Cys Ala Cys Thr Asp Glu Asn Arg Gln Gln Glu Phe Arg Arg Trp Ala
            820                 825                 830

Ala Lys Leu Ala Glu Ser Gly Val Gly Ser Tyr Trp Gly Ala Arg Gln
        835                 840                 845

Val Met Leu Glu Val Trp Arg Arg Arg Lys Asp Glu Pro Gly Asp
850                 855                 860

Asn Trp Tyr Ser Val Tyr Lys Asp Trp Glu Met Asn Leu Met Leu Ser
```

<210> SEQ ID NO 184
<211> LENGTH: 879
<212> TYPE: PRT
<213> ORGANISM: Saccharomyces cerevisiae

<400> SEQUENCE: 184

Met Gly Ile Phe Ser Lys Asn Gly Pro Lys Met Gly Arg Ala Lys
1               5                   10                  15

Thr Phe Thr Gly Cys Trp Thr Cys Arg Gly Arg Lys Val Lys Cys Asp
                20                  25                  30

Leu Arg His Pro His Cys Gln Arg Cys Glu Lys Ser Asn Leu Pro Cys
            35                  40                  45

Gly Gly Tyr Asp Ile Lys Leu Arg Trp Ser Lys Pro Met Gln Phe Asp
        50                  55                  60

Pro Tyr Gly Val Pro Ile Pro Gln Asn Ser Pro Ala Thr Thr Thr Asn
65                  70                  75                  80

Leu Ser Gly Ser Val Asp Glu Pro Gln Tyr Gln Arg Arg Asn Ile Asp
                85                  90                  95

Phe Val Arg Tyr Asp Glu Glu Tyr Val Tyr His Glu Asp Met Asp Asp
                100                 105                 110

Glu Leu Thr Met Leu His Thr Pro Pro Ile Glu Lys Ile Ser Asp Asn
            115                 120                 125

Thr Trp Ile Ile Lys Lys Phe Gly Val Phe Lys Gly Thr Asp Lys Ile
130                 135                 140

Asp Lys Gln Tyr Ala Pro Arg Lys Lys Arg Asn Arg Lys Arg Val Ala
145                 150                 155                 160

Lys Ser Leu Glu Ser Ser Ala Ser Ile Ser Leu Ser Ser Leu Pro Ser
                165                 170                 175

Ser Ser Thr Ile Ser Phe Pro Ile Arg His Ile Glu Asp Lys Leu Arg
            180                 185                 190

Asn Lys Gly His Val Lys Thr Gly Ile Leu Ser Ala Asn Asp Gly Val
        195                 200                 205

Pro Pro Thr Pro Asn Leu Leu Asp Tyr Asp Trp Asn Asn Leu Asn Ile
    210                 215                 220

Thr Gly Tyr Glu Trp Ile Ser Ser Glu Leu Arg Asp Asp Ala Leu Leu
225                 230                 235                 240

Ser Ala Val Thr Leu Gln Gly His His Leu Gly His Thr Gln Pro Gln
                245                 250                 255

Glu Ile Ser Leu Glu Glu Asn Ser Asn Val Val Ser Gly Glu His
            260                 265                 270

Val Asn Ala Lys Glu His Gly Cys Ala Val Glu Ala Asp Asn Gln Gly
        275                 280                 285

Ser Ser Thr Leu Pro Asn Lys Ala Ala Ser Ala Asn Asp Lys Leu Tyr
    290                 295                 300

Gln Gln Asn Leu Lys Leu Leu Phe Gln Lys Asn Ser Ser Asn Ser Glu
305                 310                 315                 320

Glu Pro Asp Pro Gln Ala Leu Ile Asp Asp Val Phe Val Asn Ile Glu
                325                 330                 335

Pro Arg Ser Leu Pro Ala Ser Val Leu Asn Lys Ile Thr Leu Ala Pro
            340                 345                 350

Pro Asn Glu Glu Ser Arg Met Pro Lys Ser Met Leu Gln Leu Thr Ser
        355                 360                 365

-continued

Tyr Ser Ser Asp Leu Pro Pro Glu Leu Val Asp Ile Ile Pro Lys Thr
    370                 375                 380

Asp Leu Thr Val His Gly Leu Ala Arg Phe Leu Leu Asn His Tyr Phe
385                 390                 395                 400

Asn Asn Val Ala Asp Lys Met Thr Val Val Leu Glu Lys Asn Pro
                405                 410                 415

Trp Lys Thr Leu Tyr Phe Pro Arg Ala Leu Met Ala Leu Gly Asp Leu
                420                 425                 430

Ala Gly Leu Gly Gln Ser Ser Asn Ser Arg Asn Ala Leu Leu Asn Ala
            435                 440                 445

Leu Leu Ala Val Ser Cys Phe His Leu Gln Ser Lys Tyr Pro Arg Asn
450                 455                 460

Tyr Lys Leu Gln Lys Tyr Phe Leu Gly Leu Gly Ile Glu Leu Arg Asn
465                 470                 475                 480

Gln Ala Ser Asn Phe Leu Arg Leu Cys Leu Asn Thr Lys Ser Ser Ile
                485                 490                 495

Pro Glu Lys Tyr Lys Asp Val Leu Thr Ala Ile Leu Ser Met Asn Ser
            500                 505                 510

Ile Asp Val Val Trp Gly Thr Met Ala Asp Cys Gln Asp His Leu Ala
            515                 520                 525

Leu Cys Glu Asp Phe Val Glu Ser Arg Met Lys Leu Arg Pro Asn Ile
530                 535                 540

Ser Glu Lys Ala Lys Thr Leu His Arg Ile Phe Ser Phe Leu Lys Leu
545                 550                 555                 560

Ile Gln Asp Ser Thr Ala Leu Asp Lys Val Arg Ala Lys Glu Ile Val
                565                 570                 575

Ile Leu Pro Ser Glu Asp Asp Asn Tyr Lys Pro Leu Asp Thr Ser
            580                 585                 590

Asn Ala Thr Ser Ser Ser Glu Pro Arg Val Asp Val Val Gln Glu
        595                 600                 605

Gly Leu Phe Arg Glu Ala Leu Asn Glu Asn Asp Gly Lys Ile His Ile
        610                 615                 620

Glu Phe Val Lys Glu Pro Ile Thr Asn Val Ser Ala Asp Ser Thr Pro
625                 630                 635                 640

Ser Ser Thr Thr Pro Pro Ile Phe Thr Asn Ile Ala Thr Glu Ser Tyr
                645                 650                 655

Tyr Asn Lys Ser Asp Ile Ser Asn Leu Val Ser Lys Thr Asp Glu Asn
            660                 665                 670

Ile Ile Gly Thr Asp Ser Leu Tyr Gly Leu Pro Asn Ser Leu Ile Leu
        675                 680                 685

Leu Phe Ser Asp Cys Val Arg Ile Val Arg His Asn Glu Tyr Tyr Asn
690                 695                 700

Leu Thr Tyr Leu Pro Val Pro Arg Lys Phe Asn Glu Leu Ser Leu Asn
705                 710                 715                 720

Phe Glu Lys Arg Leu Leu Lys Trp Lys Ser Glu Trp Asn Phe His Gln
                725                 730                 735

Glu Asn Ser Glu Gly Lys Ser Phe Ile Asn Ser Thr Ala Glu Ala Leu
            740                 745                 750

Tyr His His Thr Met Ser Phe Tyr Phe Ser Leu Ile Ile Tyr Tyr Phe
        755                 760                 765

Thr Met Ala Arg Ser Leu Asn Cys Gln Phe Leu Gln Asn Tyr Val Ala
770                 775                 780

Lys Val Leu Asp His Leu Asn Ala Met Glu Glu Leu Val Asp Gln Lys

```
            785                 790                 795                 800
Lys Val Lys Ile Val Pro Leu Ile Trp Gln Gly Phe Met Ala Gly Cys
                805                 810                 815

Ala Cys Thr Asp Glu Asn Arg Gln Gln Glu Phe Arg Arg Trp Ala Ala
                820                 825                 830

Lys Leu Ala Glu Ser Gly Val Gly Ser Tyr Trp Gly Ala Arg Gln Val
                835                 840                 845

Met Leu Glu Val Trp Arg Arg Arg Lys Glu Asp Glu Pro Gly Asp Asn
        850                 855                 860

Trp Tyr Ser Ile Tyr Lys Asp Trp Glu Met Asn Leu Met Leu Ser
865                 870                 875

<210> SEQ ID NO 185
<211> LENGTH: 738
<212> TYPE: PRT
<213> ORGANISM: Schizosaccharomyces pombe

<400> SEQUENCE: 185

Met Gln Lys Lys Val Gln Ser Ala Ser Lys Asn Glu Glu Leu Asp
1               5                   10                  15

Pro His Tyr Lys Arg Ser Ser Val Pro Phe Pro Tyr Gly Leu Pro Asp
                20                  25                  30

Tyr Asp Ala Glu Tyr Gln Phe Ile Asn His His Met Gln Gln Leu Leu
            35                  40                  45

Thr Arg Pro Val Glu Gly Thr His Ser Ala Ser Val His Pro Ser Thr
        50                  55                  60

Ser Ser Thr Ser His Ile Ser Ser Pro Ser Ala Phe Ser Val Gln Asn
65                  70                  75                  80

Pro Asn Pro Asn Asp Ala Pro Phe Val Gly Asn Ile Gly Leu Asp Ala
                85                  90                  95

Ser Gly Phe Ser Ser Gly Gly Met Ser Glu Tyr Tyr Pro Arg Ser Val
            100                 105                 110

Ser Met Gln Gln Ser Gln Asp Val His Phe Gln Asn Thr Glu Ile Pro
        115                 120                 125

Tyr Tyr His Arg Ser Pro Ser Ser Asp Ser Phe Ser Pro Gly Val Val
    130                 135                 140

Ala Ser Val Asn Pro Asn Ser Asn Asn Ser Pro Thr Phe Tyr Ser Asn
145                 150                 155                 160

Pro Pro Ala Leu Ser Asn Ile Pro Ile Pro Leu Asn Asn Ser Pro Tyr
                165                 170                 175

Arg Pro Glu Asp Ala Tyr Phe Gln Leu Gln Gly Ala Gly Val Lys Ala
            180                 185                 190

Asp Ile Asn Pro Tyr Asn Leu Ser Pro Tyr Ser Gln Tyr Gly Pro Glu
        195                 200                 205

Gly Thr Ala Tyr Ser Asn Ala Gln Ala His His Gln Asp Gly Ala Pro
    210                 215                 220

Leu Gln Arg Val Cys Ser Ala Pro Asp Pro Lys Thr Ser Met Pro
225                 230                 235                 240

Pro Phe Gly Ser Ala Gly Ser Pro Ser Asn Arg Ser Leu Asn Val
                245                 250                 255

Ser Asn Asn Thr Thr Pro Pro Leu Ser Thr Val Asn Lys Ile Ile Lys
            260                 265                 270

Lys Pro Lys Ala Thr Thr Gly Lys Val Lys Lys Arg Leu Pro Gln Ala
        275                 280                 285
```

-continued

```
Lys Arg Ala Cys Ala Lys Cys Gln Lys Asp Asn Lys Lys Cys Asp Asp
    290                 295                 300
Ala Arg Pro Cys Gln Arg Cys Ile Lys Ala Lys Thr Asp Cys Ile Asp
305                 310                 315                 320
Leu Pro Arg Lys Lys Arg Pro Thr Gly Val Arg Arg Gly Pro Tyr Lys
                325                 330                 335
Lys Leu Ser Asp Thr Ser Asn Asn Thr Lys Ser Thr Thr Ala Ser Ser
            340                 345                 350
Gly His Ser Thr Gln Asp Ser Leu Ser Ser Lys Met Leu Asp Pro Ser
        355                 360                 365
Ser Asp Asn Gln Phe Ala Met Ser Ser Arg Gln Met Asp Glu Asn Gly
370                 375                 380
Met Ala Gln Tyr Pro Ser Ser Ala Ile Lys Gln Glu Leu Asn Leu Gln
385                 390                 395                 400
Pro Gln Ile Leu Val Ser Ser Ala Ser Lys Asn Phe Gln Pro Asn Val
                405                 410                 415
Thr Pro Pro Phe Ala Val His His Asp His Phe Asn Ser Thr Ser Met
            420                 425                 430
Asp Gly Val Ala Val Ser Asn Met Asp Glu Thr Gly Thr Ser Ser Ala
        435                 440                 445
Gly Ser Lys Pro Phe Asn Arg Lys Ser Arg Asn Arg Ser Phe Thr Asn
450                 455                 460
Pro Val Gly Met Thr Glu Glu His Phe Leu Arg Glu Tyr Ala Gln His
465                 470                 475                 480
Ser Val Ala Asn Pro Ser Leu Leu Ile His Gln Ile His Gly Leu Pro
                485                 490                 495
Ser Glu Gln Val His Gly Leu Leu Ser His Thr Glu Leu Gly Asn Ala
            500                 505                 510
Met His Asn Gln Pro Thr Tyr Asn Glu Ser Ser Ile Ala Ala Glu Asn
        515                 520                 525
Val Asn Asn Trp Met Leu Glu Thr Asn Asp His Glu Asn Leu Ser Met
530                 535                 540
Gln Ser His Phe Glu Val Pro Asp Leu Lys Met Asn His His Asp Ser
545                 550                 555                 560
Ser Phe Phe Asp Arg His Ile Asp Gln Thr Ala Met Pro Gly Gln Asn
                565                 570                 575
Gln His Gly Thr Val Lys Asn Met Glu Thr Met His His Phe Tyr Pro
            580                 585                 590
Asp Val His Asn Ser Glu Phe Pro Ala Ala Pro Asn Pro Val Lys Ser
        595                 600                 605
Gln Val Pro Tyr Tyr Gln Ser Gln Ala Ala Asp Glu Glu Glu
610                 615                 620
Asp Val Pro Asp His Gln Pro Ser Trp Arg Gly Arg Ile His Ser Phe
625                 630                 635                 640
Ser Ile Ala Thr Asp Ser Ser Gln His Val Glu Arg Pro Cys Ile
                645                 650                 655
His Ser Leu Arg Gly Ile His Gly Gln Gln Asp Gly Leu Glu Gln
            660                 665                 670
His Asp Gly Asp His Val Asn Met Leu Pro Asp Thr His Ala Glu Glu
        675                 680                 685
Leu Ala Tyr Thr Ser Met Leu Leu Phe His Asp Ile Pro Thr Arg Asp
690                 695                 700
Ile Arg Pro Asp Phe Asn Val His Glu Leu Val Asp His Gly Thr Tyr
```

```
                705                 710                 715                 720
Pro Asn Phe His Gln Asn Gln Ala Asp Ser Phe Lys Asn His Pro Phe
                725                 730                 735

Arg Gln

<210> SEQ ID NO 186
<211> LENGTH: 18
<212> TYPE: DNA
<213> ORGANISM: Artificial Sequence
<220> FEATURE:
<223> OTHER INFORMATION: wt target site of I-SceI

<400> SEQUENCE: 186
attaccctgt tatcccta                                                          18

<210> SEQ ID NO 187
<211> LENGTH: 31
<212> TYPE: DNA
<213> ORGANISM: Artificial Sequence
<220> FEATURE:
<223> OTHER INFORMATION: #55 target site

<400> SEQUENCE: 187
attaccctgt tatccctagc ggatccgcac g                                           31

<210> SEQ ID NO 188
<211> LENGTH: 29
<212> TYPE: PRT
<213> ORGANISM: Artificial Sequence
<220> FEATURE:
<223> OTHER INFORMATION: I-SceI#1-AlcR(1-60) sequence fusion

<400> SEQUENCE: 188

Pro Tyr Leu Ile Pro Gln Met Met Tyr Lys Leu Pro Asn Thr Ile Lys
1               5                   10                  15

Ser Glu Thr Phe Leu Lys Leu Met Ala Asp Thr Arg Arg
            20                  25

<210> SEQ ID NO 189
<211> LENGTH: 29
<212> TYPE: PRT
<213> ORGANISM: Artificial Sequence
<220> FEATURE:
<223> OTHER INFORMATION: I-SceI#2-AlcR (1-60) sequence fusion

<400> SEQUENCE: 189

Pro Tyr Leu Ile Pro Gln Met Met Tyr Lys Leu Pro Asn Ala Ile Ala
1               5                   10                  15

Asn Gln Ala Phe Leu Lys Leu Met Ala Asp Thr Arg Arg
            20                  25

<210> SEQ ID NO 190
<211> LENGTH: 229
<212> TYPE: PRT
<213> ORGANISM: Artificial Sequence
<220> FEATURE:
<223> OTHER INFORMATION: consensus sequence of Figure 3
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: misc_feature
<222> LOCATION: (28)..(28)
<223> OTHER INFORMATION: Xaa can be any naturally occurring amino acid
<220> FEATURE:
```

<220> FEATURE:
<221> NAME/KEY: misc_feature
<222> LOCATION: (31)..(31)
<223> OTHER INFORMATION: Xaa can be any naturally occurring amino acid
<220> FEATURE:
<221> NAME/KEY: misc_feature
<222> LOCATION: (34)..(34)
<223> OTHER INFORMATION: Xaa can be any naturally occurring amino acid
<220> FEATURE:
<221> NAME/KEY: misc_feature
<222> LOCATION: (95)..(95)
<223> OTHER INFORMATION: Xaa can be any naturally occurring amino acid
<220> FEATURE:
<221> NAME/KEY: misc_feature
<222> LOCATION: (107)..(107)
<223> OTHER INFORMATION: Xaa can be any naturally occurring amino acid
<220> FEATURE:
<221> NAME/KEY: misc_feature
<222> LOCATION: (114)..(114)
<223> OTHER INFORMATION: Xaa can be any naturally occurring amino acid
<220> FEATURE:
<221> NAME/KEY: misc_feature
<222> LOCATION: (123)..(123)
<223> OTHER INFORMATION: Xaa can be any naturally occurring amino acid
<220> FEATURE:
<221> NAME/KEY: misc_feature
<222> LOCATION: (125)..(125)
<223> OTHER INFORMATION: Xaa can be any naturally occurring amino acid
<220> FEATURE:
<221> NAME/KEY: misc_feature
<222> LOCATION: (156)..(156)
<223> OTHER INFORMATION: Xaa can be any naturally occurring amino acid
<220> FEATURE:
<221> NAME/KEY: misc_feature
<222> LOCATION: (166)..(166)
<223> OTHER INFORMATION: Xaa can be any naturally occurring amino acid
<220> FEATURE:
<221> NAME/KEY: misc_feature
<222> LOCATION: (169)..(169)
<223> OTHER INFORMATION: Xaa can be any naturally occurring amino acid
<220> FEATURE:
<221> NAME/KEY: misc_feature
<222> LOCATION: (177)..(177)
<223> OTHER INFORMATION: Xaa can be any naturally occurring amino acid
<220> FEATURE:
<221> NAME/KEY: misc_feature
<222> LOCATION: (181)..(181)
<223> OTHER INFORMATION: Xaa can be any naturally occurring amino acid
<220> FEATURE:
<221> NAME/KEY: misc_feature
<222> LOCATION: (188)..(188)
<223> OTHER INFORMATION: Xaa can be any naturally occurring amino acid
<220> FEATURE:
<221> NAME/KEY: misc_feature
<222> LOCATION: (203)..(203)
<223> OTHER INFORMATION: Xaa can be any naturally occurring amino acid
<220> FEATURE:
<221> NAME/KEY: misc_feature
<222> LOCATION: (206)..(206)
<223> OTHER INFORMATION: Xaa can be any naturally occurring amino acid
<220> FEATURE:
<221> NAME/KEY: misc_feature
<222> LOCATION: (213)..(213)
<223> OTHER INFORMATION: Xaa can be any naturally occurring amino acid
<220> FEATURE:
<221> NAME/KEY: misc_feature
<222> LOCATION: (225)..(226)
<223> OTHER INFORMATION: Xaa can be any naturally occurring amino acid
<220> FEATURE:
<221> NAME/KEY: misc_feature
<222> LOCATION: (228)..(228)
<223> OTHER INFORMATION: Xaa can be any naturally occurring amino acid

<400> SEQUENCE: 190

Met Lys Xaa Ile Lys Lys Asn Gln Ile Met Asn Leu Gly Pro Asn Ser
1               5                   10                  15

Lys Leu Leu Lys Glu Tyr Lys Ser Gln Leu Thr Xaa Leu Thr Xaa Glu
            20                  25                  30

```
Gln Xaa Glu Ala Gly Ile Gly Leu Ile Leu Gly Asp Ala Tyr Ile Arg
     35                  40                  45

Ser Arg Asp Glu Gly Lys Thr Tyr Cys Met Gln Phe Glu Trp Lys Asn
 50                  55                  60

Lys Ala Tyr Ile Asp His Val Cys Leu Leu Tyr Asp Glu Trp Val Leu
 65                  70                  75                  80

Ser Pro Pro His Lys Lys Glu Arg Val Asn His Leu Gly Asn Xaa Val
                 85                  90                  95

Ile Thr Trp Gly Ala Gln Thr Phe Lys His Xaa Ala Phe Asn Lys Leu
                100                 105                 110

Ala Xaa Leu Phe Ile Ile Asn Asn Lys Xaa Ile Xaa Asn Asn Leu
        115                 120                 125

Val Glu Asn Tyr Ile Thr Pro Arg Ser Leu Ala Tyr Trp Phe Met Asp
130                 135                 140

Asp Gly Gly Lys Trp Asp Tyr Asn Lys Asn Ser Xaa Asn Lys Ser Ile
145                 150                 155                 160

Val Leu Asn Thr Gln Xaa Phe Thr Xaa Glu Glu Val Glu Tyr Leu Ile
                165                 170                 175

Xaa Gly Leu Asn Xaa Lys Phe Asn Leu Asn Cys Xaa Met Lys Phe Asn
            180                 185                 190

Lys Asn Lys Pro Ile Ile Tyr Ile Pro Ser Xaa Ser Tyr Xaa Ile Phe
            195                 200                 205

Tyr Asn Leu Ile Xaa Pro Tyr Ile Ile Pro Glu Met Lys Tyr Leu Pro
            210                 215                 220

Xaa Xaa Ile Xaa Ser
225

<210> SEQ ID NO 191
<211> LENGTH: 155
<212> TYPE: PRT
<213> ORGANISM: Artificial Sequence
<220> FEATURE:
<223> OTHER INFORMATION: consensus sequence of Figure 4
<220> FEATURE:
<221> NAME/KEY: misc_feature
<222> LOCATION: (2)..(3)
<223> OTHER INFORMATION: Xaa can be any naturally occurring amino acid
<220> FEATURE:
<221> NAME/KEY: misc_feature
<222> LOCATION: (5)..(6)
<223> OTHER INFORMATION: Xaa can be any naturally occurring amino acid
<220> FEATURE:
<221> NAME/KEY: misc_feature
<222> LOCATION: (8)..(8)
<223> OTHER INFORMATION: Xaa can be any naturally occurring amino acid
<220> FEATURE:
<221> NAME/KEY: misc_feature
<222> LOCATION: (28)..(28)
<223> OTHER INFORMATION: Xaa can be any naturally occurring amino acid
<220> FEATURE:
<221> NAME/KEY: misc_feature
<222> LOCATION: (30)..(30)
<223> OTHER INFORMATION: Xaa can be any naturally occurring amino acid
<220> FEATURE:
<221> NAME/KEY: misc_feature
<222> LOCATION: (52)..(52)
<223> OTHER INFORMATION: Xaa can be any naturally occurring amino acid
<220> FEATURE:
<221> NAME/KEY: misc_feature
<222> LOCATION: (56)..(56)
<223> OTHER INFORMATION: Xaa can be any naturally occurring amino acid
<220> FEATURE:
<221> NAME/KEY: misc_feature
<222> LOCATION: (58)..(58)
<223> OTHER INFORMATION: Xaa can be any naturally occurring amino acid
```

```
<220> FEATURE:
<221> NAME/KEY: misc_feature
<222> LOCATION: (63)..(63)
<223> OTHER INFORMATION: Xaa can be any naturally occurring amino acid
<220> FEATURE:
<221> NAME/KEY: misc_feature
<222> LOCATION: (65)..(65)
<223> OTHER INFORMATION: Xaa can be any naturally occurring amino acid
<220> FEATURE:
<221> NAME/KEY: misc_feature
<222> LOCATION: (70)..(70)
<223> OTHER INFORMATION: Xaa can be any naturally occurring amino acid
<220> FEATURE:
<221> NAME/KEY: misc_feature
<222> LOCATION: (80)..(80)
<223> OTHER INFORMATION: Xaa can be any naturally occurring amino acid
<220> FEATURE:
<221> NAME/KEY: misc_feature
<222> LOCATION: (82)..(82)
<223> OTHER INFORMATION: Xaa can be any naturally occurring amino acid
<220> FEATURE:
<221> NAME/KEY: misc_feature
<222> LOCATION: (85)..(85)
<223> OTHER INFORMATION: Xaa can be any naturally occurring amino acid
<220> FEATURE:
<221> NAME/KEY: misc_feature
<222> LOCATION: (98)..(98)
<223> OTHER INFORMATION: Xaa can be any naturally occurring amino acid
<220> FEATURE:
<221> NAME/KEY: misc_feature
<222> LOCATION: (116)..(116)
<223> OTHER INFORMATION: Xaa can be any naturally occurring amino acid
<220> FEATURE:
<221> NAME/KEY: misc_feature
<222> LOCATION: (118)..(118)
<223> OTHER INFORMATION: Xaa can be any naturally occurring amino acid
<220> FEATURE:
<221> NAME/KEY: misc_feature
<222> LOCATION: (120)..(120)
<223> OTHER INFORMATION: Xaa can be any naturally occurring amino acid
<220> FEATURE:
<221> NAME/KEY: misc_feature
<222> LOCATION: (126)..(126)
<223> OTHER INFORMATION: Xaa can be any naturally occurring amino acid
<220> FEATURE:
<221> NAME/KEY: misc_feature
<222> LOCATION: (133)..(133)
<223> OTHER INFORMATION: Xaa can be any naturally occurring amino acid
<220> FEATURE:
<221> NAME/KEY: misc_feature
<222> LOCATION: (137)..(137)
<223> OTHER INFORMATION: Xaa can be any naturally occurring amino acid
<220> FEATURE:
<221> NAME/KEY: misc_feature
<222> LOCATION: (140)..(140)
<223> OTHER INFORMATION: Xaa can be any naturally occurring amino acid
<220> FEATURE:
<221> NAME/KEY: misc_feature
<222> LOCATION: (143)..(143)
<223> OTHER INFORMATION: Xaa can be any naturally occurring amino acid
<220> FEATURE:
<221> NAME/KEY: misc_feature
<222> LOCATION: (149)..(149)
<223> OTHER INFORMATION: Xaa can be any naturally occurring amino acid
<220> FEATURE:
<221> NAME/KEY: misc_feature
<222> LOCATION: (151)..(151)
<223> OTHER INFORMATION: Xaa can be any naturally occurring amino acid
<220> FEATURE:
<221> NAME/KEY: misc_feature
<222> LOCATION: (153)..(154)
<223> OTHER INFORMATION: Xaa can be any naturally occurring amino acid

<400> SEQUENCE: 191

Met Xaa Xaa Leu Xaa Xaa Asp Xaa Leu Thr Tyr Leu Ala Gly Phe Ile
1               5                   10                  15

Asp Gly Asp Gly Ser Ile Ile Ala Gln Ile Val Xaa Arg Xaa Asp Tyr
```

```
                    20                  25                  30
Lys Phe Lys Phe Gln Ile Arg Leu Thr Val Gln Ile Thr Gln Leu Thr
                35                  40                  45

Lys Arg Arg Xaa Phe Leu Glu Xaa Ile Xaa Asp Glu Ile Gly Xaa Gly
            50                  55                  60

Xaa Val Arg Asp Arg Xaa Thr Val Ser Asp Tyr Val Leu Thr Glu Xaa
65                  70                  75                  80

Lys Xaa Val Tyr Xaa Leu Leu Thr Gln Leu Gln Pro Phe Leu Arg Leu
                85                  90                  95

Lys Xaa Lys Gln Ala Asn Leu Val Leu Lys Ile Ile Glu Gln Leu Pro
            100                 105                 110

Ser Ser Lys Xaa Ser Xaa Asp Xaa Phe Leu Glu Leu Cys Xaa Leu Val
            115                 120                 125

Asp Gln Val Ala Xaa Leu Asn Asp Xaa Ser Lys Xaa Arg Lys Xaa Thr
            130                 135                 140

Ala Glu Val Val Xaa Ala Xaa Leu Xaa Xaa Leu
145                 150                 155

<210> SEQ ID NO 192
<211> LENGTH: 1024
<212> TYPE: PRT
<213> ORGANISM: Artificial Sequence
<220> FEATURE:
<223> OTHER INFORMATION: consensus seequence of Figure 5
<220> FEATURE:
<221> NAME/KEY: misc_feature
<222> LOCATION: (136)..(136)
<223> OTHER INFORMATION: Xaa can be any naturally occurring amino acid
<220> FEATURE:
<221> NAME/KEY: misc_feature
<222> LOCATION: (193)..(193)
<223> OTHER INFORMATION: Xaa can be any naturally occurring amino acid
<220> FEATURE:
<221> NAME/KEY: misc_feature
<222> LOCATION: (328)..(328)
<223> OTHER INFORMATION: Xaa can be any naturally occurring amino acid
<220> FEATURE:
<221> NAME/KEY: misc_feature
<222> LOCATION: (347)..(347)
<223> OTHER INFORMATION: Xaa can be any naturally occurring amino acid
<220> FEATURE:
<221> NAME/KEY: misc_feature
<222> LOCATION: (411)..(411)
<223> OTHER INFORMATION: Xaa can be any naturally occurring amino acid
<220> FEATURE:
<221> NAME/KEY: misc_feature
<222> LOCATION: (671)..(671)
<223> OTHER INFORMATION: Xaa can be any naturally occurring amino acid
<220> FEATURE:
<221> NAME/KEY: misc_feature
<222> LOCATION: (942)..(942)
<223> OTHER INFORMATION: Xaa can be any naturally occurring amino acid

<400> SEQUENCE: 192

Gly Ala Ile Tyr Ser Val Ser Gly Pro Val Val Ile Ala Glu Asn Met
1               5                   10                  15

Ile Gly Cys Ala Met Tyr Glu Leu Val Lys Val Gly His Asp Asn Leu
                20                  25                  30

Val Gly Glu Val Ile Arg Ile Asp Gly Asp Lys Ala Thr Ile Gln Val
            35                  40                  45

Tyr Glu Glu Thr Ala Gly Leu Thr Val Gly Asp Pro Val Leu Arg Thr
        50                  55                  60

Gly Lys Pro Leu Ser Val Glu Leu Gly Pro Gly Leu Met Glu Thr Ile
65                  70                  75                  80
```

```
Tyr Asp Gly Ile Gln Arg Pro Leu Lys Ala Ile Lys Glu Glu Ser Gln
            85                  90                  95
Ser Ile Tyr Ile Pro Arg Gly Ile Asp Thr Pro Ala Leu Asp Arg Thr
        100                 105                 110
Ile Lys Trp Gln Phe Thr Pro Gly Lys Phe Gln Val Gly Asp His Ile
        115                 120                 125
Ser Gly Gly Asp Ile Tyr Gly Xaa Val Phe Glu Asn Ser Leu Ile Ser
130                 135                 140
Ser His Lys Ile Leu Leu Pro Pro Arg Ser Arg Gly Thr Ile Thr Trp
145                 150                 155                 160
Ile Ala Pro Ala Gly Glu Tyr Thr Leu Asp Glu Lys Ile Leu Glu Val
                165                 170                 175
Glu Phe Asp Gly Lys Lys Ser Asp Phe Thr Leu Tyr His Thr Trp Pro
        180                 185                 190
Xaa Arg Val Pro Arg Pro Val Thr Glu Lys Leu Ser Ala Asp Tyr Pro
        195                 200                 205
Leu Leu Thr Gly Gln Arg Val Leu Asp Ala Leu Phe Pro Cys Val Gln
        210                 215                 220
Gly Gly Thr Thr Cys Ile Pro Gly Ala Phe Gly Cys Gly Lys Thr Val
225                 230                 235                 240
Ile Ser Gln Ser Leu Ser Lys Tyr Ser Asn Ser Asp Ala Ile Ile Tyr
                245                 250                 255
Val Gly Cys Phe Ala Lys Gly Thr Asn Val Leu Met Ala Asp Gly Ser
                260                 265                 270
Ile Glu Cys Ile Glu Asn Ile Glu Val Gly Asn Lys Val Met Gly Lys
        275                 280                 285
Asp Gly Arg Pro Arg Glu Val Ile Lys Leu Pro Arg Gly Arg Glu Thr
        290                 295                 300
Met Tyr Ser Val Val Gln Lys Ser Gln His Arg Ala His Lys Ser Asp
305                 310                 315                 320
Ser Ser Arg Glu Val Pro Glu Xaa Leu Leu Lys Phe Thr Cys Asn Ala
                325                 330                 335
Thr His Glu Leu Val Val Arg Thr Pro Arg Xaa Val Arg Arg Leu Ser
                340                 345                 350
Arg Thr Ile Lys Gly Val Glu Tyr Phe Glu Val Ile Thr Phe Glu Met
        355                 360                 365
Gly Gln Lys Lys Ala Pro Asp Gly Arg Ile Val Glu Leu Val Lys Glu
        370                 375                 380
Val Ser Lys Ser Tyr Pro Ile Ser Glu Gly Pro Glu Arg Ala Asn Glu
385                 390                 395                 400
Leu Val Glu Ser Tyr Arg Lys Ala Ser Asn Xaa Lys Ala Tyr Phe Glu
                405                 410                 415
Trp Thr Ile Glu Ala Arg Asp Leu Ser Leu Leu Gly Ser His Val Arg
        420                 425                 430
Lys Ala Thr Tyr Gln Thr Tyr Ala Pro Ile Leu Tyr Glu Asn Asp His
        435                 440                 445
Phe Phe Asp Tyr Met Gln Lys Ser Lys Phe His Leu Thr Ile Glu Gly
        450                 455                 460
Pro Lys Val Leu Ala Tyr Leu Leu Gly Leu Trp Ile Gly Asp Gly Leu
465                 470                 475                 480
Ser Asp Arg Ala Thr Phe Ser Val Asp Ser Arg Asp Thr Ser Leu Met
                485                 490                 495
Glu Arg Val Thr Glu Tyr Ala Glu Lys Leu Asn Leu Cys Ala Glu Tyr
```

```
                500             505             510
Lys Asp Arg Lys Glu Pro Gln Val Ala Lys Thr Val Asn Leu Tyr Ser
            515             520             525
Lys Val Val Arg Gly Asn Gly Ile Arg Asn Asn Leu Asn Thr Glu Asn
            530             535             540
Pro Leu Trp Asp Ala Ile Val Gly Leu Gly Phe Leu Lys Asp Gly Val
545             550             555             560
Lys Asn Ile Pro Ser Phe Leu Ser Thr Asp Asn Ile Gly Thr Arg Glu
            565             570             575
Thr Phe Leu Ala Gly Leu Ile Asp Ser Asp Gly Tyr Val Thr Asp Glu
            580             585             590
His Gly Ile Lys Ala Thr Ile Lys Thr Ile His Thr Ser Val Arg Asp
            595             600             605
Gly Leu Val Ser Leu Ala Arg Ser Leu Gly Leu Val Val Ser Val Asn
            610             615             620
Ala Glu Pro Ala Lys Val Asp Met Asn Gly Thr Lys His Lys Ile Ser
625             630             635             640
Tyr Ala Ile Tyr Met Ser Gly Gly Asp Val Leu Leu Asn Asx Leu Ser
            645             650             655
Lys Cys Ala Gly Ser Lys Lys Phe Arg Pro Ala Pro Ala Ala Xaa Phe
            660             665             670
Asx Arg Glu Cys Arg Gly Phe Tyr Phe Glu Leu Gln Glu Leu Lys Glu
            675             680             685
Asp Asp Tyr Tyr Gly Ile Thr Leu Ser Asp Asp Ser Asp His Gln Phe
            690             695             700
Leu Leu Ala Asn Gln Val Val His Asn Cys Gly Glu Arg Gly Asn
705             710             715             720
Glu Met Ala Glu Val Leu Met Glu Phe Pro Glu Leu Tyr Thr Glu Met
            725             730             735
Ser Gly Thr Lys Glu Pro Ile Met Lys Arg Thr Thr Leu Val Ala Asn
            740             745             750
Thr Ser Asn Met Pro Val Ala Ala Arg Glu Ala Ser Ile Tyr Thr Gly
            755             760             765
Ile Thr Leu Ala Glu Tyr Phe Arg Asp Gln Gly Lys Asn Val Ser Met
            770             775             780
Ile Ala Asp Ser Ser Ser Arg Trp Ala Glu Ala Leu Arg Glu Ile Ser
785             790             795             800
Gly Arg Leu Gly Glu Met Pro Ala Asp Gln Gly Phe Pro Ala Tyr Leu
            805             810             815
Gly Ala Lys Leu Ala Ser Phe Tyr Glu Arg Ala Gly Lys Ala Val Ala
            820             825             830
Leu Gly Ser Pro Asp Arg Thr Gly Ser Val Ser Ile Val Ala Ala Val
            835             840             845
Ser Pro Ala Gly Gly Asp Phe Ser Asp Pro Val Thr Thr Ala Thr Leu
            850             855             860
Gly Ile Thr Gln Val Phe Trp Gly Leu Asp Lys Lys Leu Ala Gln Arg
865             870             875             880
Lys His Phe Pro Ser Ile Asn Thr Ser Val Ser Tyr Ser Lys Tyr Thr
            885             890             895
Asn Val Leu Asn Lys Phe Tyr Asp Ser Asn Tyr Pro Glu Phe Pro Val
            900             905             910
Leu Arg Asp Arg Met Lys Glu Ile Leu Ser Asn Ala Glu Glu Leu Glu
            915             920             925
```

```
Gln Val Val Gln Leu Val Gly Lys Ser Ala Leu Ser Asp Xaa Asp Lys
    930                 935                 940

Ile Thr Leu Asp Val Ala Thr Leu Ile Lys Glu Asp Phe Leu Gln Gln
945                 950                 955                 960

Asn Gly Tyr Ser Thr Tyr Asp Ala Phe Cys Pro Ile Trp Lys Thr Phe
                965                 970                 975

Asp Met Met Arg Ala Phe Ile Ser Tyr His Asp Glu Ala Gln Lys Ala
            980                 985                 990

Val Ala Asn Gly Ala Asn Trp Ser Lys Leu Ala Asp Ser Thr Gly Asp
        995                 1000                1005

Val Lys His Ala Val Ser Ser Ser Lys Phe Phe Glu Pro Ser Arg
    1010                1015                1020

Gly

<210> SEQ ID NO 193
<211> LENGTH: 211
<212> TYPE: PRT
<213> ORGANISM: Artificial Sequence
<220> FEATURE:
<223> OTHER INFORMATION: consensus sequence of Figure 6
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (11)..(11)
<223> OTHER INFORMATION: Xaa can be any naturally occurring amino acid
<220> FEATURE:
<221> NAME/KEY: misc_feature
<222> LOCATION: (15)..(16)
<223> OTHER INFORMATION: Xaa can be any naturally occurring amino acid
<220> FEATURE:
<221> NAME/KEY: misc_feature
<222> LOCATION: (23)..(23)
<223> OTHER INFORMATION: Xaa can be any naturally occurring amino acid
<220> FEATURE:
<221> NAME/KEY: misc_feature
<222> LOCATION: (35)..(36)
<223> OTHER INFORMATION: Xaa can be any naturally occurring amino acid
<220> FEATURE:
<221> NAME/KEY: misc_feature
<222> LOCATION: (39)..(39)
<223> OTHER INFORMATION: Xaa can be any naturally occurring amino acid
<220> FEATURE:
<221> NAME/KEY: misc_feature
<222> LOCATION: (44)..(45)
<223> OTHER INFORMATION: Xaa can be any naturally occurring amino acid
<220> FEATURE:
<221> NAME/KEY: misc_feature
<222> LOCATION: (73)..(75)
<223> OTHER INFORMATION: Xaa can be any naturally occurring amino acid
<220> FEATURE:
<221> NAME/KEY: misc_feature
<222> LOCATION: (96)..(96)
<223> OTHER INFORMATION: Xaa can be any naturally occurring amino acid
<220> FEATURE:
<221> NAME/KEY: misc_feature
<222> LOCATION: (114)..(114)
<223> OTHER INFORMATION: Xaa can be any naturally occurring amino acid
<220> FEATURE:
<221> NAME/KEY: misc_feature
<222> LOCATION: (140)..(140)
<223> OTHER INFORMATION: Xaa can be any naturally occurring amino acid
<220> FEATURE:
<221> NAME/KEY: misc_feature
<222> LOCATION: (143)..(144)
<223> OTHER INFORMATION: Xaa can be any naturally occurring amino acid
<220> FEATURE:
<221> NAME/KEY: misc_feature
<222> LOCATION: (149)..(149)
```

<223> OTHER INFORMATION: Xaa can be any naturally occurring amino acid
<220> FEATURE:
<221> NAME/KEY: misc_feature
<222> LOCATION: (151)..(152)
<223> OTHER INFORMATION: Xaa can be any naturally occurring amino acid
<220> FEATURE:
<221> NAME/KEY: misc_feature
<222> LOCATION: (155)..(156)
<223> OTHER INFORMATION: Xaa can be any naturally occurring amino acid
<220> FEATURE:
<221> NAME/KEY: misc_feature
<222> LOCATION: (159)..(159)
<223> OTHER INFORMATION: Xaa can be any naturally occurring amino acid
<220> FEATURE:
<221> NAME/KEY: misc_feature
<222> LOCATION: (166)..(167)
<223> OTHER INFORMATION: Xaa can be any naturally occurring amino acid
<220> FEATURE:
<221> NAME/KEY: misc_feature
<222> LOCATION: (170)..(171)
<223> OTHER INFORMATION: Xaa can be any naturally occurring amino acid
<220> FEATURE:
<221> NAME/KEY: misc_feature
<222> LOCATION: (184)..(184)
<223> OTHER INFORMATION: Xaa can be any naturally occurring amino acid
<220> FEATURE:
<221> NAME/KEY: misc_feature
<222> LOCATION: (200)..(201)
<223> OTHER INFORMATION: Xaa can be any naturally occurring amino acid
<220> FEATURE:
<221> NAME/KEY: misc_feature
<222> LOCATION: (210)..(210)
<223> OTHER INFORMATION: Xaa can be any naturally occurring amino acid

<400> SEQUENCE: 193

```
Phe Xaa Lys Leu Pro Gly Glu Lys Leu Pro Xaa Asp Ile Leu Xaa Xaa
1               5                   10                  15

Leu Lys Lys Ile Asn Asp Xaa Phe Ser Lys Thr Lys Asp Phe Ser Lys
            20                  25                  30

Tyr Leu Xaa Xaa Leu Arg Xaa Leu Phe Gln Ile Xaa Xaa Ile Gln Val
        35                  40                  45

Thr Ser Glu Ser Lys Leu Phe Leu Ala Gly Phe Leu Glu Gly Glu Ala
    50                  55                  60

Ser Leu Asn Ile Ser Ala Lys Lys Xaa Xaa Xaa Ala Lys Phe Gly Val
65                  70                  75                  80

Val Ile Asp Pro Glu Phe Asn Ile Thr Gln His Val Asn Gly Ile Xaa
                85                  90                  95

Asn Leu Tyr Leu Ala Leu Glu Val Phe Lys Thr Gly Arg Ile Arg His
            100                 105                 110

Lys Xaa Gly Ser Asn Ala Thr Leu Val Gly Thr Ile Asp Asn Arg Gln
        115                 120                 125

Ser Leu Glu Glu Lys Val Ile Pro Phe Tyr Glu Xaa Tyr Val Xaa Xaa
    130                 135                 140

Phe Ser Ser Pro Xaa Lys Xaa Xaa Arg Val Xaa Xaa Phe Lys Xaa Leu
145                 150                 155                 160

Leu Asp Leu Phe Asn Xaa Xaa Ala His Xaa Xaa Leu Asp Leu Ile Asn
                165                 170                 175

Glu Ile Leu Pro Ile Trp Asp Xaa Met Arg Ile Gln Lys Gly Gln Ser
            180                 185                 190

Asn Glu Ala Phe Pro Asp Leu Xaa Ala Gln Asp Tyr Ile Arg Asn
        195                 200                 205

Phe Xaa Lys
    210
```

```
<210> SEQ ID NO 194
<211> LENGTH: 224
<212> TYPE: PRT
<213> ORGANISM: Artificial Sequence
<220> FEATURE:
<223> OTHER INFORMATION: consensus sequence of Figure 7
<220> FEATURE:
<221> NAME/KEY: misc_feature
<222> LOCATION: (42)..(42)
<223> OTHER INFORMATION: Xaa can be any naturally occurring amino acid
<220> FEATURE:
<221> NAME/KEY: misc_feature
<222> LOCATION: (57)..(58)
<223> OTHER INFORMATION: Xaa can be any naturally occurring amino acid
<220> FEATURE:
<221> NAME/KEY: misc_feature
<222> LOCATION: (60)..(60)
<223> OTHER INFORMATION: Xaa can be any naturally occurring amino acid
<220> FEATURE:
<221> NAME/KEY: misc_feature
<222> LOCATION: (62)..(63)
<223> OTHER INFORMATION: Xaa can be any naturally occurring amino acid
<220> FEATURE:
<221> NAME/KEY: misc_feature
<222> LOCATION: (65)..(65)
<223> OTHER INFORMATION: Xaa can be any naturally occurring amino acid
<220> FEATURE:
<221> NAME/KEY: misc_feature
<222> LOCATION: (69)..(69)
<223> OTHER INFORMATION: Xaa can be any naturally occurring amino acid
<220> FEATURE:
<221> NAME/KEY: misc_feature
<222> LOCATION: (74)..(75)
<223> OTHER INFORMATION: Xaa can be any naturally occurring amino acid
<220> FEATURE:
<221> NAME/KEY: misc_feature
<222> LOCATION: (85)..(85)
<223> OTHER INFORMATION: Xaa can be any naturally occurring amino acid
<220> FEATURE:
<221> NAME/KEY: misc_feature
<222> LOCATION: (101)..(101)
<223> OTHER INFORMATION: Xaa can be any naturally occurring amino acid
<220> FEATURE:
<221> NAME/KEY: misc_feature
<222> LOCATION: (111)..(112)
<223> OTHER INFORMATION: Xaa can be any naturally occurring amino acid
<220> FEATURE:
<221> NAME/KEY: misc_feature
<222> LOCATION: (114)..(114)
<223> OTHER INFORMATION: Xaa can be any naturally occurring amino acid
<220> FEATURE:
<221> NAME/KEY: misc_feature
<222> LOCATION: (116)..(116)
<223> OTHER INFORMATION: Xaa can be any naturally occurring amino acid
<220> FEATURE:
<221> NAME/KEY: misc_feature
<222> LOCATION: (122)..(122)
<223> OTHER INFORMATION: Xaa can be any naturally occurring amino acid
<220> FEATURE:
<221> NAME/KEY: misc_feature
<222> LOCATION: (137)..(137)
<223> OTHER INFORMATION: Xaa can be any naturally occurring amino acid
<220> FEATURE:
<221> NAME/KEY: misc_feature
<222> LOCATION: (152)..(152)
<223> OTHER INFORMATION: Xaa can be any naturally occurring amino acid
<220> FEATURE:
<221> NAME/KEY: misc_feature
<222> LOCATION: (164)..(164)
<223> OTHER INFORMATION: Xaa can be any naturally occurring amino acid
<220> FEATURE:
<221> NAME/KEY: misc_feature
<222> LOCATION: (174)..(174)
<223> OTHER INFORMATION: Xaa can be any naturally occurring amino acid
<220> FEATURE:
<221> NAME/KEY: misc_feature
<222> LOCATION: (176)..(176)
<223> OTHER INFORMATION: Xaa can be any naturally occurring amino acid
<220> FEATURE:
```

```
<221> NAME/KEY: misc_feature
<222> LOCATION: (179)..(185)
<223> OTHER INFORMATION: Xaa can be any naturally occurring amino acid
<220> FEATURE:
<221> NAME/KEY: misc_feature
<222> LOCATION: (195)..(195)
<223> OTHER INFORMATION: Xaa can be any naturally occurring amino acid
<220> FEATURE:
<221> NAME/KEY: misc_feature
<222> LOCATION: (198)..(198)
<223> OTHER INFORMATION: Xaa can be any naturally occurring amino acid

<400> SEQUENCE: 194
```

Met Ser Leu Thr Gln Gln Lys Asp Leu Ile Phe Gly Ser Leu Leu
1               5                   10                  15

Gly Asp Gly Asn Leu Gln Thr Gly Ser Val Gly Arg Thr Trp Arg Tyr
                20                  25                  30

Arg Ala Ile Gln Lys Ser Glu His Gln Xaa Tyr Leu Phe His Lys Tyr
            35                  40                  45

Glu Ile Leu Lys Pro Leu Cys Gly Xaa Xaa Thr Xaa Pro Xaa Xaa Ser
        50                  55                  60

Xaa Val Phe Asp Xaa Arg Thr Asn Lys Xaa Xaa Lys Arg Trp Phe Phe
65                  70                  75                  80

Asn Thr Leu Val Xaa Pro Ser Leu Lys Phe Phe Ala Asp Met Phe Tyr
                85                  90                  95

Thr Tyr Asp Gln Xaa Thr Gln Lys Trp Val Lys Asp Val Pro Xaa Xaa
            100                 105                 110

Val Xaa Ile Xaa Lys Phe Leu Thr Pro Xaa Ala Ile Ala Tyr Phe Tyr
        115                 120                 125

Met Asp Asp Gly Ala Leu Lys Trp Xaa Asn Lys Ser Asn Ala Met Arg
    130                 135                 140

Ile Cys Thr Glu Ser Phe Ser Xaa Gly Gly Val Ile Arg Leu Gln Lys
145                 150                 155                 160

Ala Leu Lys Xaa Leu Tyr Asn Ile Asp Thr Ser Leu Thr Xaa Lys Xaa
                165                 170                 175

Leu Gln Xaa Xaa Xaa Xaa Xaa Xaa Ile Gly Tyr Arg Ile Ala Ile
            180                 185                 190

Pro Glu Xaa Ser Ser Xaa Ala Phe Arg Glu Leu Ile Lys Pro Phe Leu
        195                 200                 205

Val Asp Cys Met Arg Tyr Lys Val Ser Asp Gly Asn Lys Gly His Leu
    210                 215                 220

```
<210> SEQ ID NO 195
<211> LENGTH: 235
<212> TYPE: PRT
<213> ORGANISM: Artificial Sequence
<220> FEATURE:
<223> OTHER INFORMATION: consensus sequence of Figure 8
<220> FEATURE:
<221> NAME/KEY: misc_feature
<222> LOCATION: (46)..(46)
<223> OTHER INFORMATION: Xaa can be any naturally occurring amino acid

<400> SEQUENCE: 195
```

Met Ser Val Ala Tyr Leu Leu Gly Leu Ile Val Gly Asp Gly Leu
1               5                   10                  15

Tyr Ala Leu Arg Tyr Lys Gly Gly Arg Thr Glu Tyr Arg Val Val Ile
                20                  25                  30

Thr Gln Lys Asp Glu Ala Val Val Glu Lys Ala Val Val Xaa Met Leu
            35                  40                  45

-continued

```
Glu Ala Leu Leu Arg Glu Leu Gly Leu Lys Ser Lys Val Gln Val Ile
 50                  55                  60

Arg Gly Arg Ser Arg Thr Glu Val Arg Val Ser Ser Lys Ala Leu Trp
 65                  70                  75                  80

Gln Phe Phe Asn Asn Val Leu Ser Asn Leu Glu Gly Phe Gln Pro Ser
                 85                  90                  95

Glu Arg Ile Ala Phe Ile Glu Gly Leu Tyr Asp Ala Glu Gly Asp Lys
            100                 105                 110

Ser Gly Arg Arg Ala Arg Ile Trp Asn Lys Asn Leu Arg Leu Leu Glu
        115                 120                 125

Leu Val Lys Asn Trp Leu Ser Glu Leu Gly Ile Glu Ser Thr Ile His
130                 135                 140

Leu Asp Asp Lys Arg His Gly Val Tyr Val Leu Glu Val Pro Ser Pro
145                 150                 155                 160

Tyr Arg Asp Arg Phe Phe Lys Leu Ile His Pro Pro Gln Pro Pro Asp
                165                 170                 175

Ser Ser Gly Val His Glu Trp Ile Asn Glu Val Pro Thr Asx Pro Ala
            180                 185                 190

Arg Gly Pro Ala Asn Pro Pro Gly Ala Gln Ser Trp Asp Pro Arg
        195                 200                 205

Arg Gly Glu Lys Ser Leu Trp Ser Phe Thr Ala Ala Cys Arg Cys Gly
210                 215                 220

Gly Ala Gly Asp Ala Glu Arg Arg Gln Glu Gln
225                 230                 235

<210> SEQ ID NO 196
<211> LENGTH: 165
<212> TYPE: PRT
<213> ORGANISM: Artificial Sequence
<220> FEATURE:
<223> OTHER INFORMATION: consensus sequence of Figure 9
<220> FEATURE:
<221> NAME/KEY: misc_feature
<222> LOCATION: (3)..(4)
<223> OTHER INFORMATION: Xaa can be any naturally occurring amino acid
<220> FEATURE:
<221> NAME/KEY: misc_feature
<222> LOCATION: (6)..(6)
<223> OTHER INFORMATION: Xaa can be any naturally occurring amino acid
<220> FEATURE:
<221> NAME/KEY: misc_feature
<222> LOCATION: (26)..(26)
<223> OTHER INFORMATION: Xaa can be any naturally occurring amino acid
<220> FEATURE:
<221> NAME/KEY: misc_feature
<222> LOCATION: (31)..(32)
<223> OTHER INFORMATION: Xaa can be any naturally occurring amino acid
<220> FEATURE:
<221> NAME/KEY: misc_feature
<222> LOCATION: (44)..(44)
<223> OTHER INFORMATION: Xaa can be any naturally occurring amino acid
<220> FEATURE:
<221> NAME/KEY: misc_feature
<222> LOCATION: (51)..(51)
<223> OTHER INFORMATION: Xaa can be any naturally occurring amino acid
<220> FEATURE:
<221> NAME/KEY: misc_feature
<222> LOCATION: (59)..(59)
<223> OTHER INFORMATION: Xaa can be any naturally occurring amino acid
<220> FEATURE:
<221> NAME/KEY: misc_feature
<222> LOCATION: (61)..(61)
<223> OTHER INFORMATION: Xaa can be any naturally occurring amino acid
<220> FEATURE:
<221> NAME/KEY: misc_feature
<222> LOCATION: (63)..(63)
<223> OTHER INFORMATION: Xaa can be any naturally occurring amino acid
```

```
<220> FEATURE:
<221> NAME/KEY: misc_feature
<222> LOCATION: (65)..(65)
<223> OTHER INFORMATION: Xaa can be any naturally occurring amino acid
<220> FEATURE:
<221> NAME/KEY: misc_feature
<222> LOCATION: (80)..(80)
<223> OTHER INFORMATION: Xaa can be any naturally occurring amino acid
<220> FEATURE:
<221> NAME/KEY: misc_feature
<222> LOCATION: (82)..(83)
<223> OTHER INFORMATION: Xaa can be any naturally occurring amino acid
<220> FEATURE:
<221> NAME/KEY: misc_feature
<222> LOCATION: (91)..(91)
<223> OTHER INFORMATION: Xaa can be any naturally occurring amino acid
<220> FEATURE:
<221> NAME/KEY: misc_feature
<222> LOCATION: (105)..(105)
<223> OTHER INFORMATION: Xaa can be any naturally occurring amino acid
<220> FEATURE:
<221> NAME/KEY: misc_feature
<222> LOCATION: (112)..(112)
<223> OTHER INFORMATION: Xaa can be any naturally occurring amino acid
<220> FEATURE:
<221> NAME/KEY: misc_feature
<222> LOCATION: (115)..(115)
<223> OTHER INFORMATION: Xaa can be any naturally occurring amino acid
<220> FEATURE:
<221> NAME/KEY: misc_feature
<222> LOCATION: (117)..(117)
<223> OTHER INFORMATION: Xaa can be any naturally occurring amino acid
<220> FEATURE:
<221> NAME/KEY: misc_feature
<222> LOCATION: (120)..(122)
<223> OTHER INFORMATION: Xaa can be any naturally occurring amino acid
<220> FEATURE:
<221> NAME/KEY: misc_feature
<222> LOCATION: (125)..(125)
<223> OTHER INFORMATION: Xaa can be any naturally occurring amino acid
<220> FEATURE:
<221> NAME/KEY: misc_feature
<222> LOCATION: (132)..(132)
<223> OTHER INFORMATION: Xaa can be any naturally occurring amino acid
<220> FEATURE:
<221> NAME/KEY: misc_feature
<222> LOCATION: (140)..(140)
<223> OTHER INFORMATION: Xaa can be any naturally occurring amino acid
<220> FEATURE:
<221> NAME/KEY: misc_feature
<222> LOCATION: (143)..(143)
<223> OTHER INFORMATION: Xaa can be any naturally occurring amino acid
<220> FEATURE:
<221> NAME/KEY: misc_feature
<222> LOCATION: (149)..(150)
<223> OTHER INFORMATION: Xaa can be any naturally occurring amino acid
<220> FEATURE:
<221> NAME/KEY: misc_feature
<222> LOCATION: (156)..(157)
<223> OTHER INFORMATION: Xaa can be any naturally occurring amino acid
<220> FEATURE:
<221> NAME/KEY: misc_feature
<222> LOCATION: (162)..(162)
<223> OTHER INFORMATION: Xaa can be any naturally occurring amino acid

<400> SEQUENCE: 196

Thr Leu Xaa Xaa Thr Xaa Ala Ala Tyr Ile Ala Gly Phe Leu Asp Gly
1               5                   10                  15

Asp Gly Ser Ile Tyr Ala Lys Leu Ile Xaa Arg Pro Asp Tyr Xaa Xaa
                20                  25                  30

Ile Lys Tyr Gln Ile Ser Leu Ala Ile Ser Phe Xaa Gln Arg Lys Asp
            35                  40                  45

Lys Phe Xaa Tyr Leu Gln Asp Ile Tyr Asp Xaa Leu Xaa Lys Xaa Gly
    50                  55                  60
```

```
Xaa Leu Arg Lys Asp Arg Gly Asp Gly Ile Ala Asp Tyr Thr Ile Xaa
 65                 70                  75                  80

Gly Xaa Xaa His Leu Ser Ile Ile Leu Pro Xaa Leu Leu Pro Tyr Leu
                85                  90                  95

Arg Ile Lys Lys Lys Gln Ala Asn Xaa Ile Leu His Ile Ile Asn Xaa
            100                 105                 110

Tyr Pro Xaa Ala Xaa Lys Asn Xaa Xaa Xaa Phe Leu Xaa Leu Val Lys
        115                 120                 125

Ile Val Asp Xaa Ile Gln Asn Leu Asn Lys Lys Xaa Asp Glu Xaa Lys
        130                 135                 140

Ala Thr Asn Tyr Xaa Xaa Leu Leu Glu Glu Phe Xaa Xaa Ala Gly Lys
145                 150                 155                 160

Ile Xaa Ser Ser Pro
                165
```

<210> SEQ ID NO 197
<211> LENGTH: 21
<212> TYPE: PRT
<213> ORGANISM: Artificial Sequence
<220> FEATURE:
<223> OTHER INFORMATION: consensus sequence I of Figure 10
<220> FEATURE:
<221> NAME/KEY: misc_feature
<222> LOCATION: (5)..(5)
<223> OTHER INFORMATION: Xaa can be any naturally occurring amino acid
<220> FEATURE:
<221> NAME/KEY: misc_feature
<222> LOCATION: (10)..(10)
<223> OTHER INFORMATION: Xaa can be any naturally occurring amino acid
<220> FEATURE:
<221> NAME/KEY: misc_feature
<222> LOCATION: (14)..(14)
<223> OTHER INFORMATION: Xaa can be any naturally occurring amino acid

<400> SEQUENCE: 197

```
Arg Arg Arg Gln Xaa His Ser Cys Asp Xaa Cys Arg Lys Xaa Lys Arg
1               5                   10                  15

Ala Cys Asp Ala Pro
                20
```

<210> SEQ ID NO 198
<211> LENGTH: 20
<212> TYPE: PRT
<213> ORGANISM: Artificial Sequence
<220> FEATURE:
<223> OTHER INFORMATION: consensus sequence II of Figure 10
<220> FEATURE:
<221> NAME/KEY: misc_feature
<222> LOCATION: (7)..(8)
<223> OTHER INFORMATION: Xaa can be any naturally occurring amino acid
<220> FEATURE:
<221> NAME/KEY: misc_feature
<222> LOCATION: (14)..(14)
<223> OTHER INFORMATION: Xaa can be any naturally occurring amino acid
<220> FEATURE:
<221> NAME/KEY: misc_feature
<222> LOCATION: (17)..(17)
<223> OTHER INFORMATION: Xaa can be any naturally occurring amino acid
<220> FEATURE:
<221> NAME/KEY: misc_feature
<222> LOCATION: (19)..(19)
<223> OTHER INFORMATION: Xaa can be any naturally occurring amino acid

<400> SEQUENCE: 198

```
Cys Ser Asn Cys Arg Lys Xaa Xaa Lys Glu Cys Thr Phe Xaa Trp Leu
1               5                   10                  15

Xaa Ser Xaa Arg
```

```
<210> SEQ ID NO 199
<211> LENGTH: 44
<212> TYPE: PRT
<213> ORGANISM: Artificial Sequence
<220> FEATURE:
<223> OTHER INFORMATION: consensus sequence of Figure 11
<220> FEATURE:
<221> NAME/KEY: misc_feature
<222> LOCATION: (29)..(29)
<223> OTHER INFORMATION: Xaa can be any naturally occurring amino acid
<220> FEATURE:
<221> NAME/KEY: misc_feature
<222> LOCATION: (33)..(33)
<223> OTHER INFORMATION: Xaa can be any naturally occurring amino acid
<220> FEATURE:
<221> NAME/KEY: misc_feature
<222> LOCATION: (35)..(35)
<223> OTHER INFORMATION: Xaa can be any naturally occurring amino acid
<220> FEATURE:
<221> NAME/KEY: misc_feature
<222> LOCATION: (42)..(42)
<223> OTHER INFORMATION: Xaa can be any naturally occurring amino acid

<400> SEQUENCE: 199

Arg Lys Leu Arg Asp Ser Cys Thr Ser Cys Ala Ser Ser Lys Val Arg
1               5                   10                  15

Cys Thr Lys Glu Lys Pro Thr Cys Arg Cys Ile Xaa Arg Gly Leu
            20                  25                  30

Xaa Cys Xaa Tyr Met Val Ser Lys Arg Xaa Gly Arg
        35                  40

<210> SEQ ID NO 200
<211> LENGTH: 59
<212> TYPE: PRT
<213> ORGANISM: Artificial Sequence
<220> FEATURE:
<223> OTHER INFORMATION: consensus sequence of Figure 12
<220> FEATURE:
<221> NAME/KEY: misc_feature
<222> LOCATION: (29)..(29)
<223> OTHER INFORMATION: Xaa can be any naturally occurring amino acid
<220> FEATURE:
<221> NAME/KEY: misc_feature
<222> LOCATION: (34)..(34)
<223> OTHER INFORMATION: Xaa can be any naturally occurring amino acid
<220> FEATURE:
<221> NAME/KEY: misc_feature
<222> LOCATION: (58)..(58)
<223> OTHER INFORMATION: Xaa can be any naturally occurring amino acid

<400> SEQUENCE: 200

Lys Val Lys Arg Lys Arg Asn Arg Val Pro Leu Ser Cys Thr Ile Cys
1               5                   10                  15

Arg Lys Arg Lys Val Lys Cys Asp Lys Thr Arg Pro Xaa Cys Asn Gln
            20                  25                  30

Cys Xaa Lys Thr Gly Val Ala His Leu Cys His Tyr Met Glu Gln Thr
        35                  40                  45

Trp Ala Glu Glu Ala Glu Lys Glu Leu Xaa Lys
    50                  55

<210> SEQ ID NO 201
<211> LENGTH: 50
<212> TYPE: PRT
<213> ORGANISM: Artificial Sequence
<220> FEATURE:
<223> OTHER INFORMATION: consensus sequence of Figure 13
<220> FEATURE:
```

```
<221> NAME/KEY: misc_feature
<222> LOCATION: (23)..(23)
<223> OTHER INFORMATION: Xaa can be any naturally occurring amino acid
<220> FEATURE:
<221> NAME/KEY: misc_feature
<222> LOCATION: (36)..(36)
<223> OTHER INFORMATION: Xaa can be any naturally occurring amino acid
<220> FEATURE:
<221> NAME/KEY: misc_feature
<222> LOCATION: (41)..(41)
<223> OTHER INFORMATION: Xaa can be any naturally occurring amino acid

<400> SEQUENCE: 201

Lys Arg Lys Lys Leu Ala Cys Val Glu Cys Arg Gln Gln Lys Ser Lys
1               5                   10                  15

Cys Asp Ala His Glu Lys Xaa Pro Glu Pro Cys Thr Arg Cys Ala Lys
                20                  25                  30

Lys Gly Leu Xaa Cys Val Leu Lys Xaa Asp Phe Arg Arg Thr Tyr Lys
            35                  40                  45

Arg Ala
    50

<210> SEQ ID NO 202
<211> LENGTH: 10
<212> TYPE: PRT
<213> ORGANISM: Artificial Sequence
<220> FEATURE:
<223> OTHER INFORMATION: I-SceI mutant C-terminus

<400> SEQUENCE: 202

Thr Ile Lys Ser Glu Glu Thr Phe Leu Lys
1               5                   10

<210> SEQ ID NO 203
<211> LENGTH: 18
<212> TYPE: DNA
<213> ORGANISM: Artificial Sequence
<220> FEATURE:
<223> OTHER INFORMATION: I-SceI DNA cutting site first strand

<400> SEQUENCE: 203
ttaccctgtt atccctag                                                 18

<210> SEQ ID NO 204
<211> LENGTH: 18
<212> TYPE: DNA
<213> ORGANISM: Artificial Sequence
<220> FEATURE:
<223> OTHER INFORMATION: I-SceI DNA cutting site second strand

<400> SEQUENCE: 204
aatgggacaa tagggatc                                                 18

<210> SEQ ID NO 205
<211> LENGTH: 7
<212> TYPE: PRT
<213> ORGANISM: Artificial Sequence
<220> FEATURE:
<223> OTHER INFORMATION: KEN-box motif
<220> FEATURE:
<221> NAME/KEY: misc_feature
<222> LOCATION: (4)..(6)
<223> OTHER INFORMATION: Xaa can be any naturally occurring amino acid
<220> FEATURE:
<221> NAME/KEY: MISC_FEATURE
<222> LOCATION: (7)..(7)
<223> OTHER INFORMATION: Xaa is Asn or Asp
```

<400> SEQUENCE: 205

Lys Glu Asn Xaa Xaa Xaa Xaa
1               5

<210> SEQ ID NO 206
<211> LENGTH: 15
<212> TYPE: PRT
<213> ORGANISM: Artificial Sequence
<220> FEATURE:
<223> OTHER INFORMATION: A-box motif
<220> FEATURE:
<221> NAME/KEY: misc_feature
<222> LOCATION: (4)..(4)
<223> OTHER INFORMATION: Xaa can be any naturally occurring amino acid
<220> FEATURE:
<221> NAME/KEY: misc_feature
<222> LOCATION: (6)..(7)
<223> OTHER INFORMATION: Xaa can be any naturally occurring amino acid
<220> FEATURE:
<221> NAME/KEY: misc_feature
<222> LOCATION: (9)..(11)
<223> OTHER INFORMATION: Xaa can be any naturally occurring amino acid

<400> SEQUENCE: 206

Ala Gln Arg Xaa Leu Xaa Xaa Ser Xaa Xaa Xaa Gln Arg Val Leu
1               5                   10                  15

<210> SEQ ID NO 207
<211> LENGTH: 4
<212> TYPE: PRT
<213> ORGANISM: Artificial Sequence
<220> FEATURE:
<223> OTHER INFORMATION: O-box motif
<220> FEATURE:
<221> NAME/KEY: misc_feature
<222> LOCATION: (2)..(3)
<223> OTHER INFORMATION: Xaa can be any naturally occurring amino acid

<400> SEQUENCE: 207

Arg Xaa Xaa Leu
1

<210> SEQ ID NO 208
<211> LENGTH: 15
<212> TYPE: PRT
<213> ORGANISM: Artificial Sequence
<220> FEATURE:
<223> OTHER INFORMATION: I-SceI motif 1

<400> SEQUENCE: 208

His Val Cys Leu Leu Tyr Asp Gln Trp Val Leu Ser Pro Pro His
1               5                   10                  15

<210> SEQ ID NO 209
<211> LENGTH: 11
<212> TYPE: PRT
<213> ORGANISM: Artificial Sequence
<220> FEATURE:
<223> OTHER INFORMATION: I-SceI motif 2

<400> SEQUENCE: 209

Leu Ala Tyr Trp Phe Met Asp Asp Gly Gly Lys
1               5                   10

<210> SEQ ID NO 210
<211> LENGTH: 27
<212> TYPE: PRT
<213> ORGANISM: Artificial Sequence
<220> FEATURE:

```
<223> OTHER INFORMATION: I-SceI motif 3

<400> SEQUENCE: 210

Lys Thr Ile Pro Asn Asn Leu Val Glu Asn Tyr Leu Thr Pro Met Ser
1               5                   10                  15

Leu Ala Tyr Trp Phe Met Asp Asp Gly Gly Lys
            20                  25

<210> SEQ ID NO 211
<211> LENGTH: 19
<212> TYPE: PRT
<213> ORGANISM: Artificial Sequence
<220> FEATURE:
<223> OTHER INFORMATION: I-SceI motif 4

<400> SEQUENCE: 211

Lys Pro Ile Ile Tyr Ile Asp Ser Met Ser Tyr Leu Leu Phe Tyr Asn
1               5                   10                  15

Leu Leu Lys

<210> SEQ ID NO 212
<211> LENGTH: 13
<212> TYPE: PRT
<213> ORGANISM: Artificial Sequence
<220> FEATURE:
<223> OTHER INFORMATION: I-SceI motif 5

<400> SEQUENCE: 212

Lys Leu Pro Asn Thr Ile Ser Ser Glu Thr Phe Leu Lys
1               5                   10

<210> SEQ ID NO 213
<211> LENGTH: 8
<212> TYPE: PRT
<213> ORGANISM: Artificial Sequence
<220> FEATURE:
<223> OTHER INFORMATION: I-SceI C-term deletion 1

<400> SEQUENCE: 213

Thr Ile Ser Ser Glu Thr Phe Leu
1               5

<210> SEQ ID NO 214
<211> LENGTH: 7
<212> TYPE: PRT
<213> ORGANISM: Artificial Sequence
<220> FEATURE:
<223> OTHER INFORMATION: I-SceI C-term deletion 2

<400> SEQUENCE: 214

Thr Ile Ser Ser Glu Thr Phe
1               5

<210> SEQ ID NO 215
<211> LENGTH: 6
<212> TYPE: PRT
<213> ORGANISM: Artificial Sequence
<220> FEATURE:
<223> OTHER INFORMATION: I-SceI C-term deletion 3

<400> SEQUENCE: 215

Thr Ile Ser Ser Glu Thr
1               5

<210> SEQ ID NO 216
```

-continued

```
<211> LENGTH: 5
<212> TYPE: PRT
<213> ORGANISM: Artificial Sequence
<220> FEATURE:
<223> OTHER INFORMATION: I-SceI C-term deletion 4

<400> SEQUENCE: 216

Thr Ile Ser Ser Glu
1               5

<210> SEQ ID NO 217
<211> LENGTH: 4
<212> TYPE: PRT
<213> ORGANISM: Artificial Sequence
<220> FEATURE:
<223> OTHER INFORMATION: I-SceI C-term deletion 5

<400> SEQUENCE: 217

Thr Ile Ser Ser
1

<210> SEQ ID NO 218
<211> LENGTH: 94
<212> TYPE: PRT
<213> ORGANISM: Artificial Sequence
<220> FEATURE:
<223> OTHER INFORMATION: Zn2C6 zinc finger sequence motif
<220> FEATURE:
<221> NAME/KEY: misc_feature
<222> LOCATION: (2)..(3)
<223> OTHER INFORMATION: Xaa can be any naturally occurring amino acid
<220> FEATURE:
<221> NAME/KEY: misc_feature
<222> LOCATION: (5)..(10)
<223> OTHER INFORMATION: Xaa can be any naturally occurring amino acid
<220> FEATURE:
<221> NAME/KEY: misc_feature
<222> LOCATION: (12)..(16)
<223> OTHER INFORMATION: Xaa can be any naturally occurring amino acid
<220> FEATURE:
<221> NAME/KEY: misc_feature
<222> LOCATION: (17)..(52)
<223> OTHER INFORMATION: Xaa can be any naturally occurring amino acid
      or no amino acid
<220> FEATURE:
<221> NAME/KEY: misc_feature
<222> LOCATION: (54)..(55)
<223> OTHER INFORMATION: Xaa can be any naturally occurring amino acid
<220> FEATURE:
<221> NAME/KEY: misc_feature
<222> LOCATION: (57)..(62)
<223> OTHER INFORMATION: Xaa can be any naturally occurring amino acid
<220> FEATURE:
<221> NAME/KEY: misc_feature
<222> LOCATION: (63)..(64)
<223> OTHER INFORMATION: Xaa can be any naturally occurring amino acid
      or no amino acid
<220> FEATURE:
<221> NAME/KEY: misc_feature
<222> LOCATION: (67)..(68)
<223> OTHER INFORMATION: Xaa can be any naturally occurring amino acid
<220> FEATURE:
<221> NAME/KEY: misc_feature
<222> LOCATION: (70)..(75)
<223> OTHER INFORMATION: Xaa can be any naturally occurring amino acid
<220> FEATURE:
<221> NAME/KEY: misc_feature
<222> LOCATION: (77)..(81)
<223> OTHER INFORMATION: Xaa can be any naturally occurring amino acid
<220> FEATURE:
<221> NAME/KEY: misc_feature
<222> LOCATION: (83)..(84)
<223> OTHER INFORMATION: Xaa can be any naturally occurring amino acid
<220> FEATURE:
<221> NAME/KEY: misc_feature
```

<222> LOCATION: (86)..(93)
<223> OTHER INFORMATION: Xaa can be any naturally occurring amino acid

<400> SEQUENCE: 218

Cys Xaa Xaa Cys Xaa Xaa Xaa Xaa Xaa Cys Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa
                20                  25                  30

Xaa Xaa Xaa Xaa Xaa Xaa Xaa Xaa Xaa Xaa Xaa Xaa Xaa Xaa Xaa
            35                  40                  45

Xaa Xaa Xaa Xaa Cys Xaa Xaa Cys Xaa Xaa Xaa Xaa Xaa Xaa Xaa
        50                  55                  60

Cys Cys Xaa Xaa Cys Xaa Xaa Xaa Xaa Xaa Cys Xaa Xaa Xaa Xaa
65                  70                  75                  80

Xaa Cys Xaa Xaa Cys Xaa Xaa Xaa Xaa Xaa Xaa Xaa Cys
            85                  90

<210> SEQ ID NO 219
<211> LENGTH: 9
<212> TYPE: PRT
<213> ORGANISM: Artificial Sequence
<220> FEATURE:
<223> OTHER INFORMATION: C-terminus of wildtype I-SceI

<400> SEQUENCE: 219

Thr Ile Ser Ser Glu Thr Phe Leu Lys
1               5

<210> SEQ ID NO 220
<211> LENGTH: 8
<212> TYPE: PRT
<213> ORGANISM: Artificial Sequence
<220> FEATURE:
<223> OTHER INFORMATION: I-SceI mutant C-terminus

<400> SEQUENCE: 220

Thr Ile Lys Ser Glu Thr Phe Leu
1               5

<210> SEQ ID NO 221
<211> LENGTH: 8
<212> TYPE: PRT
<213> ORGANISM: Artificial Sequence
<220> FEATURE:
<223> OTHER INFORMATION: I-SceI mutant C-terminus

<400> SEQUENCE: 221

Thr Ile Ala Ser Glu Thr Phe Leu
1               5

<210> SEQ ID NO 222
<211> LENGTH: 4
<212> TYPE: PRT
<213> ORGANISM: Artificial Sequence
<220> FEATURE:
<223> OTHER INFORMATION: Linker polypeptide

<400> SEQUENCE: 222

Gly Ser Gly Ser
1

<210> SEQ ID NO 223
<211> LENGTH: 6
<212> TYPE: PRT

```
<213> ORGANISM: Artificial Sequence
<220> FEATURE:
<223> OTHER INFORMATION: Linker polypeptide

<400> SEQUENCE: 223

Gly Ser Gly Ser Gly Ser
1               5

<210> SEQ ID NO 224
<211> LENGTH: 5
<212> TYPE: PRT
<213> ORGANISM: Artificial Sequence
<220> FEATURE:
<223> OTHER INFORMATION: Linker polypeptide

<400> SEQUENCE: 224

Gly Gly Ser Gly Gly
1               5

<210> SEQ ID NO 225
<211> LENGTH: 8
<212> TYPE: PRT
<213> ORGANISM: Artificial Sequence
<220> FEATURE:
<223> OTHER INFORMATION: Linker polypeptide

<400> SEQUENCE: 225

Gly Gly Ser Gly Gly Ser Gly Gly
1               5

<210> SEQ ID NO 226
<211> LENGTH: 8
<212> TYPE: PRT
<213> ORGANISM: Artificial Sequence
<220> FEATURE:
<223> OTHER INFORMATION: Linker polypeptide

<400> SEQUENCE: 226

Gly Ser Gly Ser Gly Gly Ser Gly
1               5
```